(12) United States Patent
Chu et al.

(10) Patent No.: US 11,517,743 B2
(45) Date of Patent: Dec. 6, 2022

(54) DEVICES AND METHODS FOR DELIVERING MECHANICAL STIMULATION TO NERVE, MECHANORECEPTOR, AND CELL TARGETS

(71) Applicant: Apex Neuro Holdings, Inc., Brooklyn, NY (US)

(72) Inventors: Zen Chu, Brookline, MA (US); Miles Thibault, Boston, MA (US); Kelsey Fafara, Watertown, MA (US); Francois Kress, New York, NY (US); Rohan Ajay Verma, Cambridge, MA (US); Alyssa Boasso, Brookline, MA (US); Sean Hagberg, Cranston, RI (US); Julia Brock, Yarmouth, ME (US)

(73) Assignee: Apex Neuro Holdings, Inc., Brooklyn, NY (US)

( * ) Notice: Subject to any disclaimer, the term of this patent is extended or adjusted under 35 U.S.C. 154(b) by 63 days.

(21) Appl. No.: 17/035,689

(22) Filed: Sep. 29, 2020

(65) Prior Publication Data
US 2021/0060330 A1 Mar. 4, 2021

Related U.S. Application Data

(63) Continuation of application No. 16/657,073, filed on Oct. 18, 2019, now Pat. No. 10,786,666, which is a (Continued)

(51) Int. Cl.
*A61N 1/04* (2006.01)
*A61N 1/375* (2006.01)
(Continued)

(52) U.S. Cl.
CPC .......... *A61N 1/0456* (2013.01); *A61H 23/00* (2013.01); *A61H 23/0218* (2013.01);
(Continued)

(58) Field of Classification Search
CPC .............. A61N 1/0456; A61N 1/36025; A61N 1/3603; A61H 23/00; A61H 23/0218; A61H 2205/027
See application file for complete search history.

(56) References Cited

U.S. PATENT DOCUMENTS

2013/0303953 A1* 11/2013 Lattner .............. A61H 23/0245
601/47
2015/0283019 A1* 10/2015 Feingold ................ A61H 1/001
601/136

* cited by examiner

*Primary Examiner* — Amanda K Hulbert
*Assistant Examiner* — Philip C Edwards
(74) *Attorney, Agent, or Firm* — Steve Hassid; Partners Law Group Inc.

(57) ABSTRACT

Presented herein are systems, methods, and devices that provide for stimulation of nerves and/or targets such as mechanoreceptors, tissue regions, mechanoresponsive proteins, and vascular targets through generation and delivery of mechanical vibrational waves. In certain embodiments, the approaches described herein utilize a stimulation device (e.g., a wearable device) for generation and delivery of the mechanical vibrational waves. As described herein, the delivered vibrational waves can be tailored based on particular targets (e.g., nerves, mechanoreceptors, vascular targets, tissue regions) to stimulate and/or to elicited particular desired responses in a subject.

19 Claims, 76 Drawing Sheets

Related U.S. Application Data continuation of application No. 16/241,224, filed on Jan. 7, 2019.

(60) Provisional application No. 62/741,758, filed on Oct. 5, 2018, provisional application No. 62/680,525, filed on Jun. 4, 2018, provisional application No. 62/623,977, filed on Jan. 30, 2018.

(51) Int. Cl.
*A61N 1/36* (2006.01)
*A61H 23/02* (2006.01)
*A61H 23/00* (2006.01)

(52) U.S. Cl.
CPC ....... *A61N 1/3603* (2017.08); *A61N 1/36025* (2013.01); *A61N 1/37518* (2017.08); *A61H 2201/0157* (2013.01); *A61H 2201/1207* (2013.01); *A61H 2201/165* (2013.01); *A61H 2201/501* (2013.01); *A61H 2201/5007* (2013.01); *A61H 2201/5084* (2013.01); *A61H 2201/5097* (2013.01); *A61H 2205/02* (2013.01); *A61H 2205/027* (2013.01); *A61H 2230/065* (2013.01); *A61H 2230/085* (2013.01); *A61H 2230/655* (2013.01)

| Level of Resolution | Target | Frequency Range | Refractory Range |
|---|---|---|---|
| Cell membrane | Piezo2 | < 100 Hz | 2 seconds |
| Cell | Merkel Cell | 5-15 Hz | |
| Nerve | Vagus | 130-180 Hz | |
| | C-Tactile Afferent | < 50 Hz | |
| Brain | Theta | 4-8 Hz | |
| | Alpha | 8-16 Hz | |
| | Beta | 16-30 Hz | |
| | Gamma | 30-60 Hz | |

Figure 3

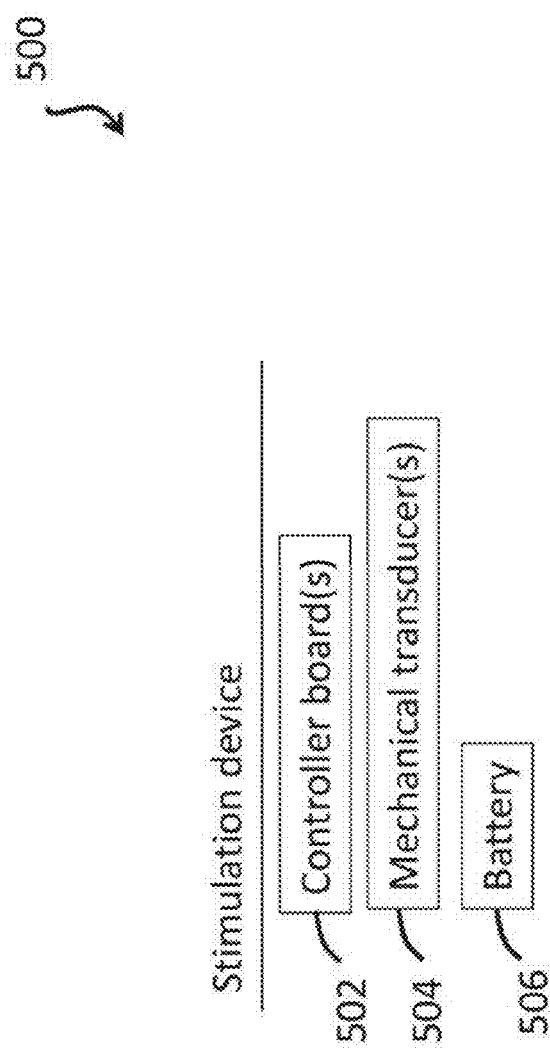

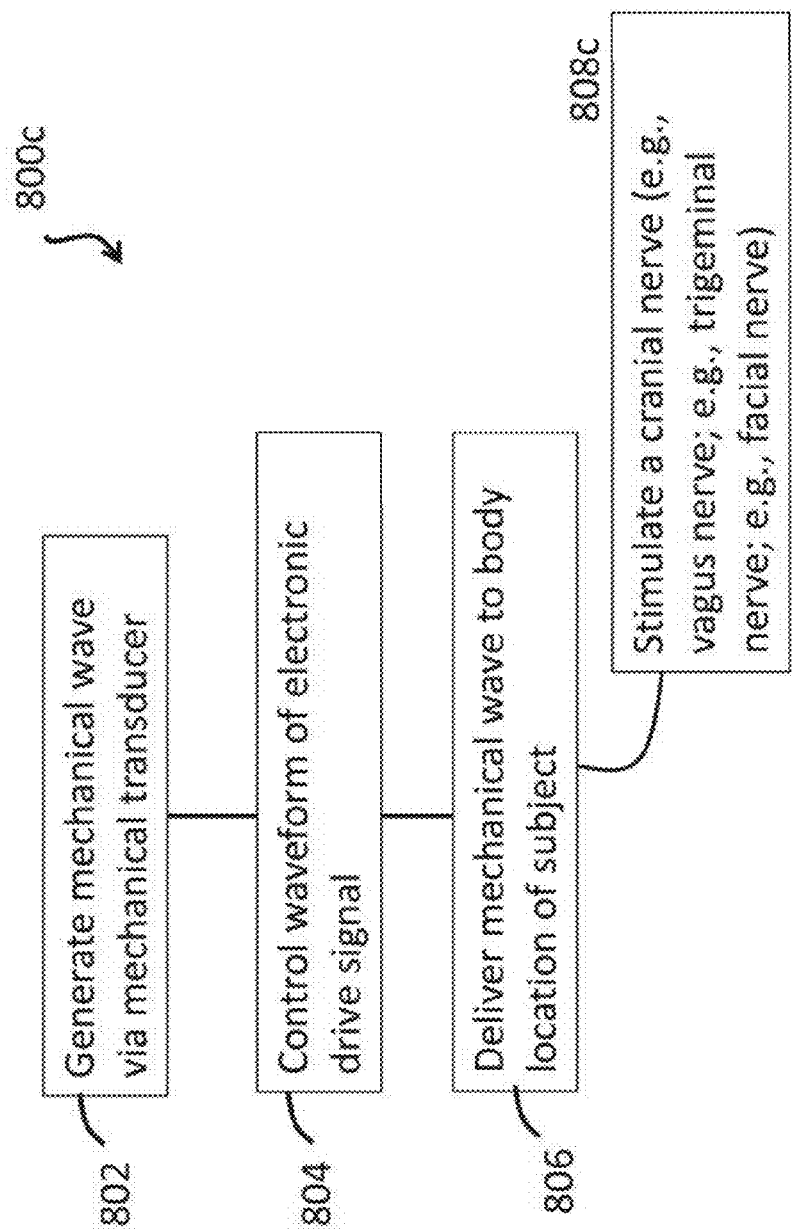

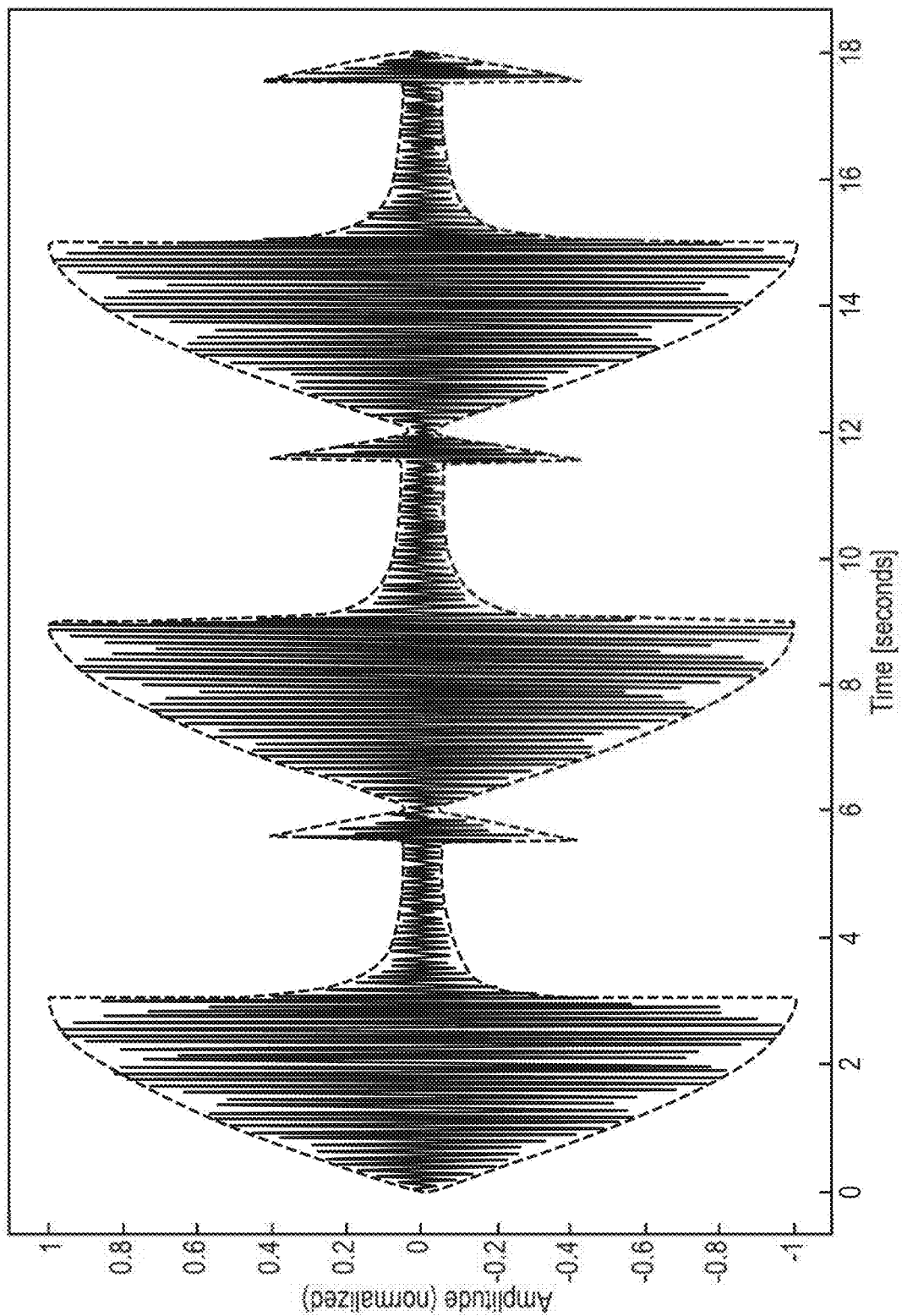

This product is intended to provide transcutaneous acoustic nerve stimulation.

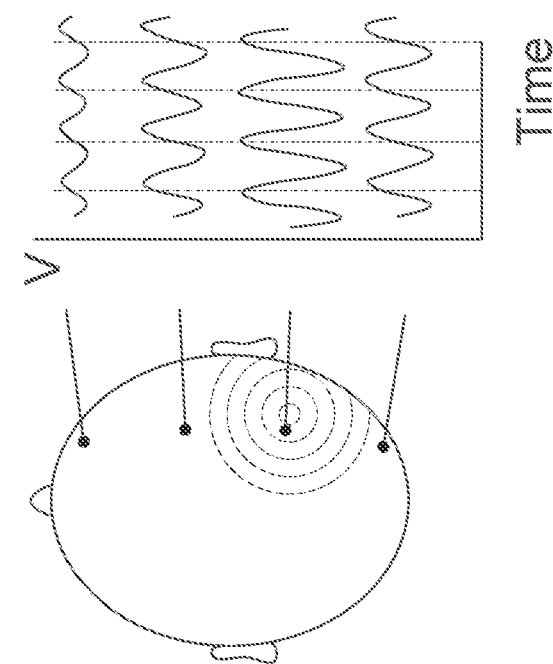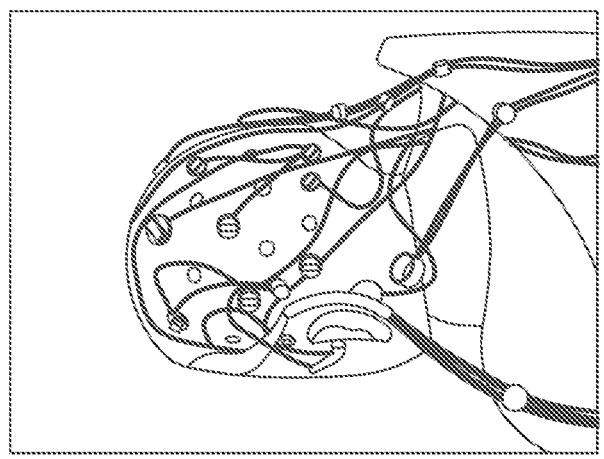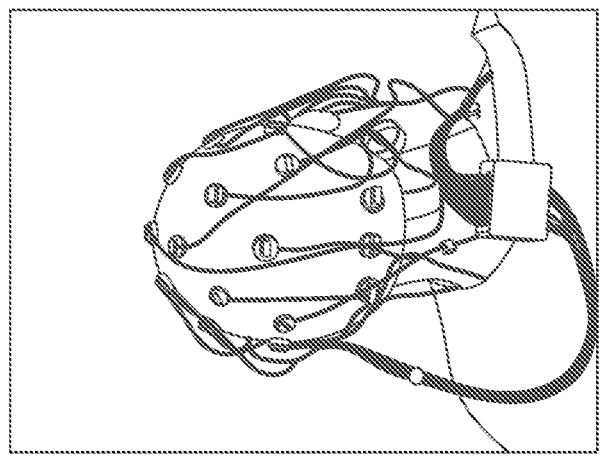
FIG. 27

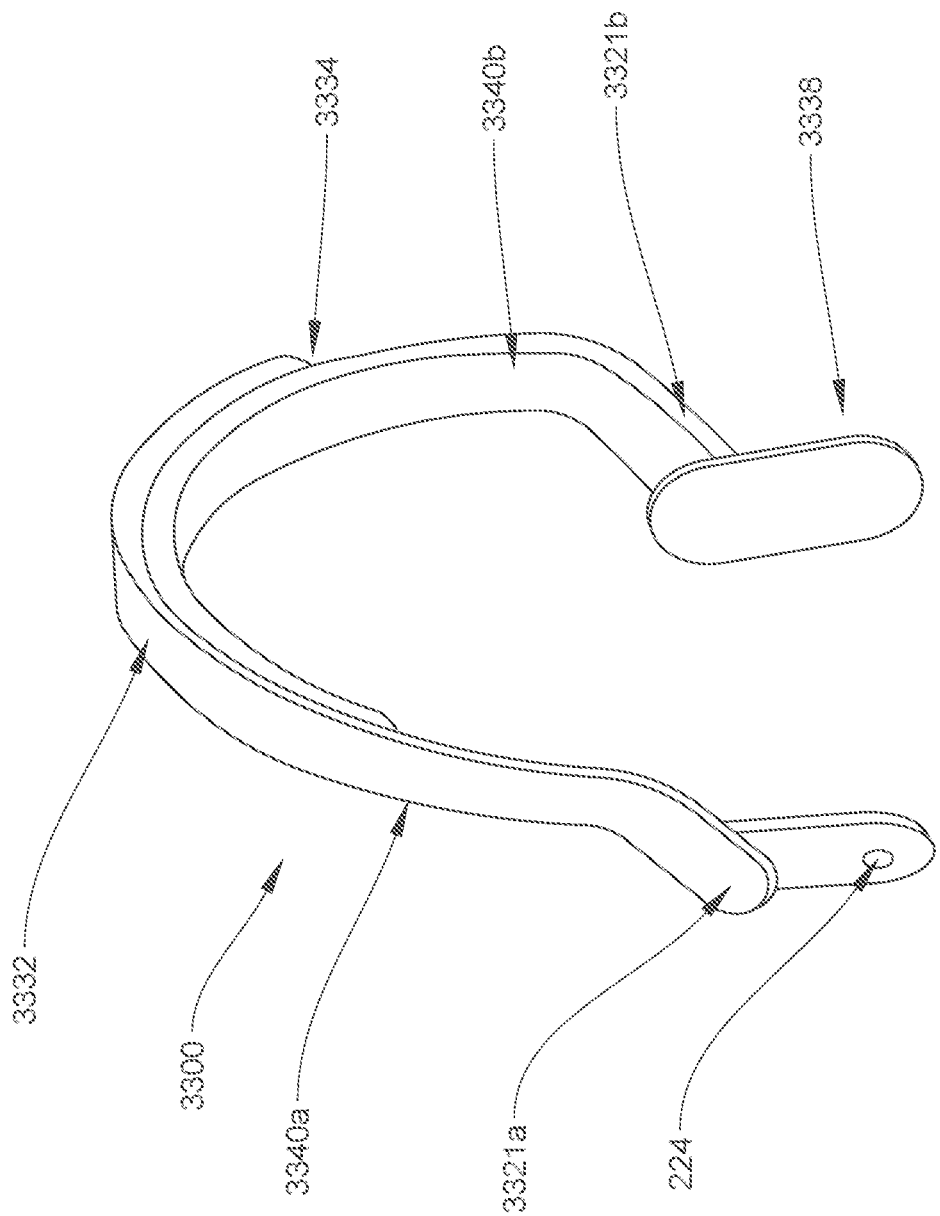

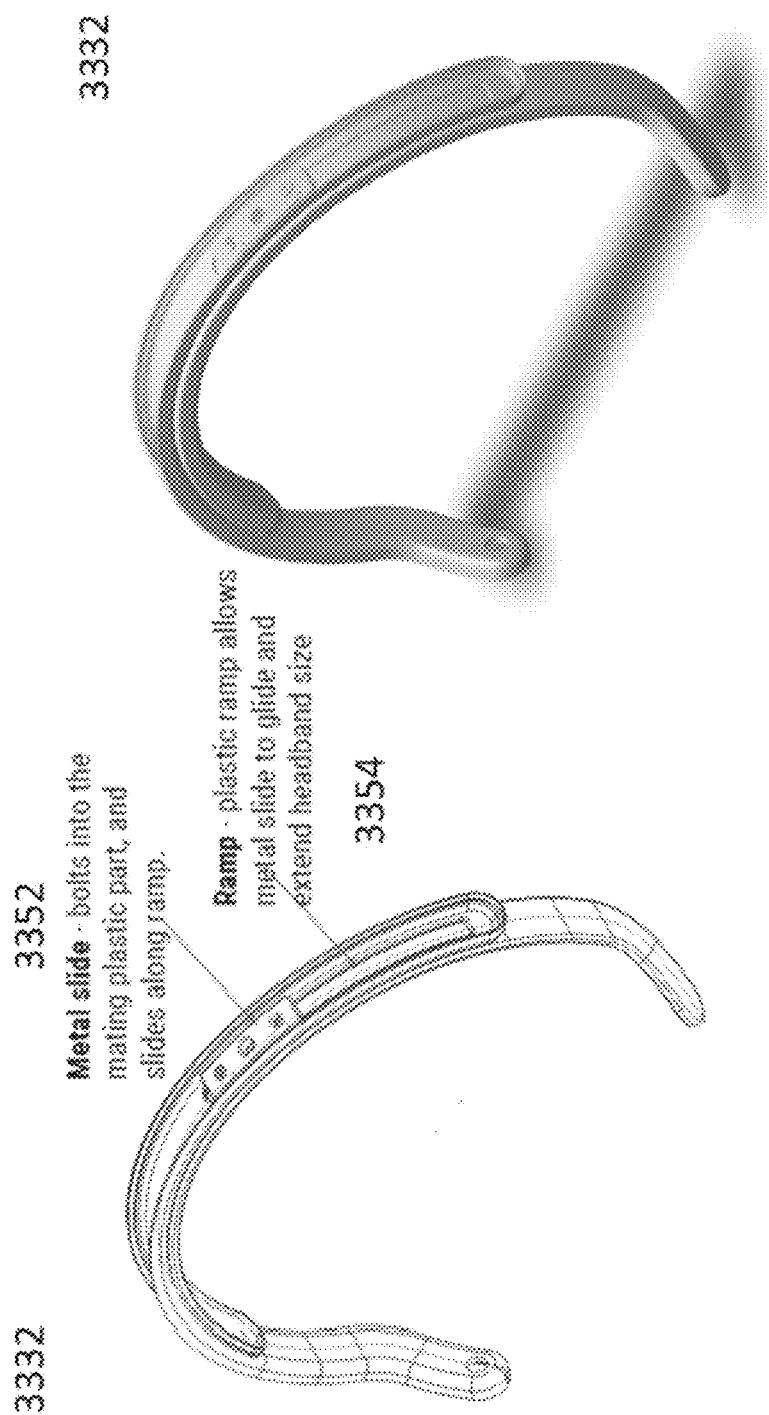

3372
POSITIONING DETENTS -
Grooves allow for controlled extension and positioning of head band. Spring steel insert in mating component creates a gentle stopping force as it slides along these grooves

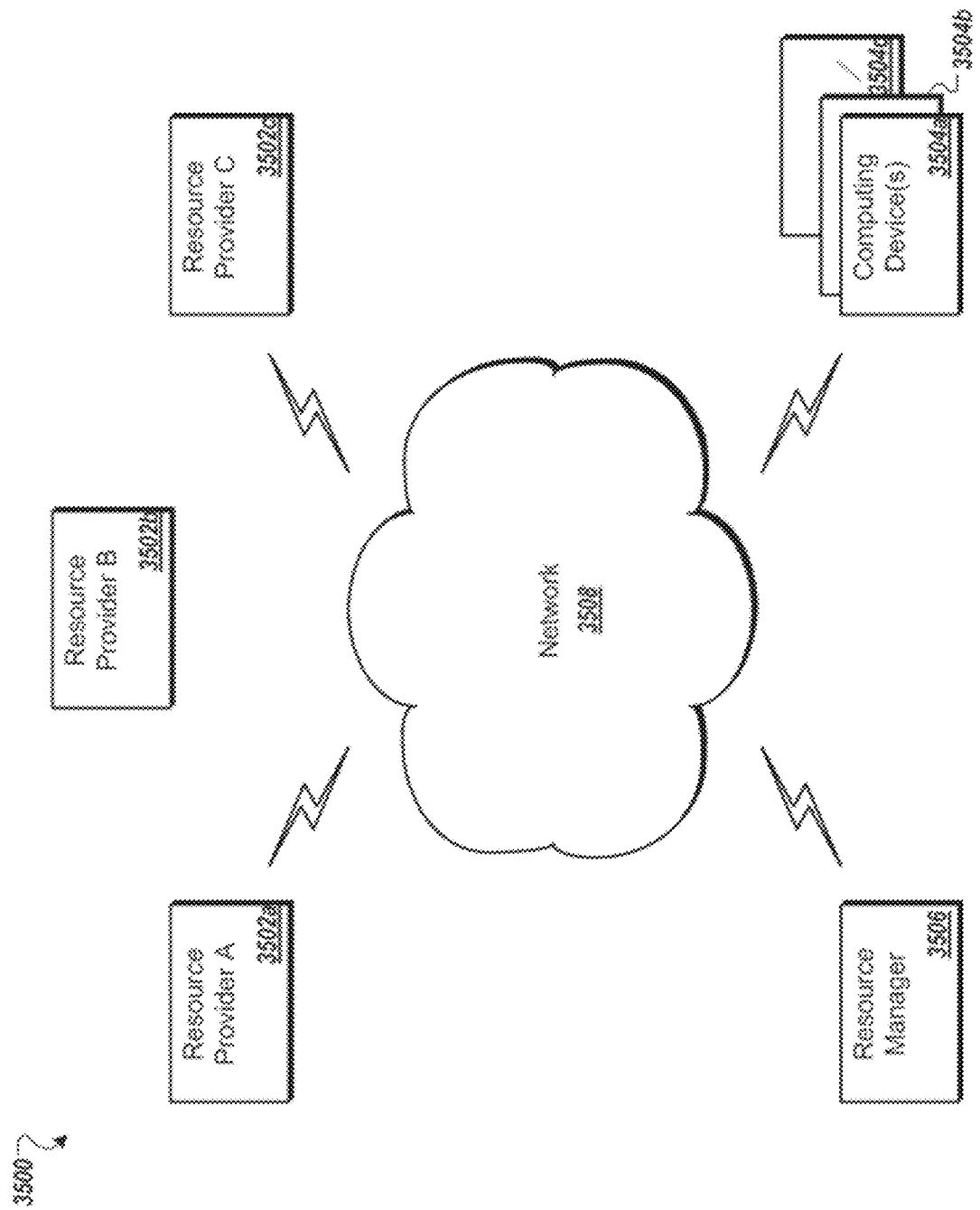

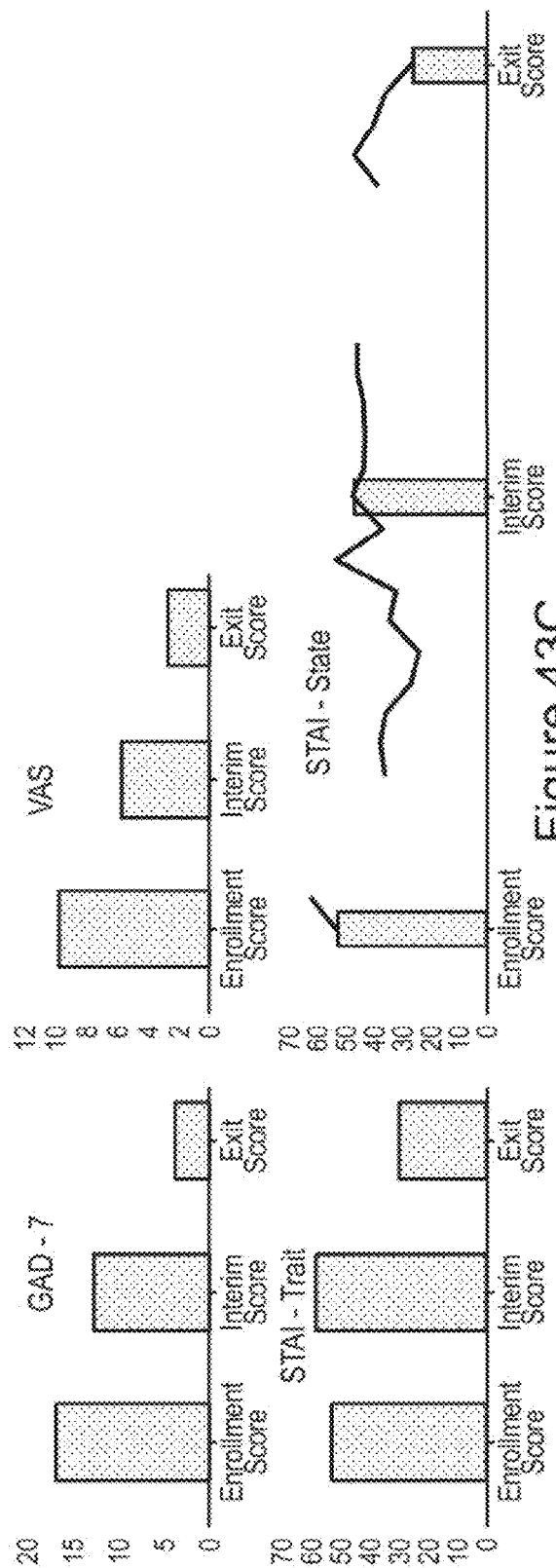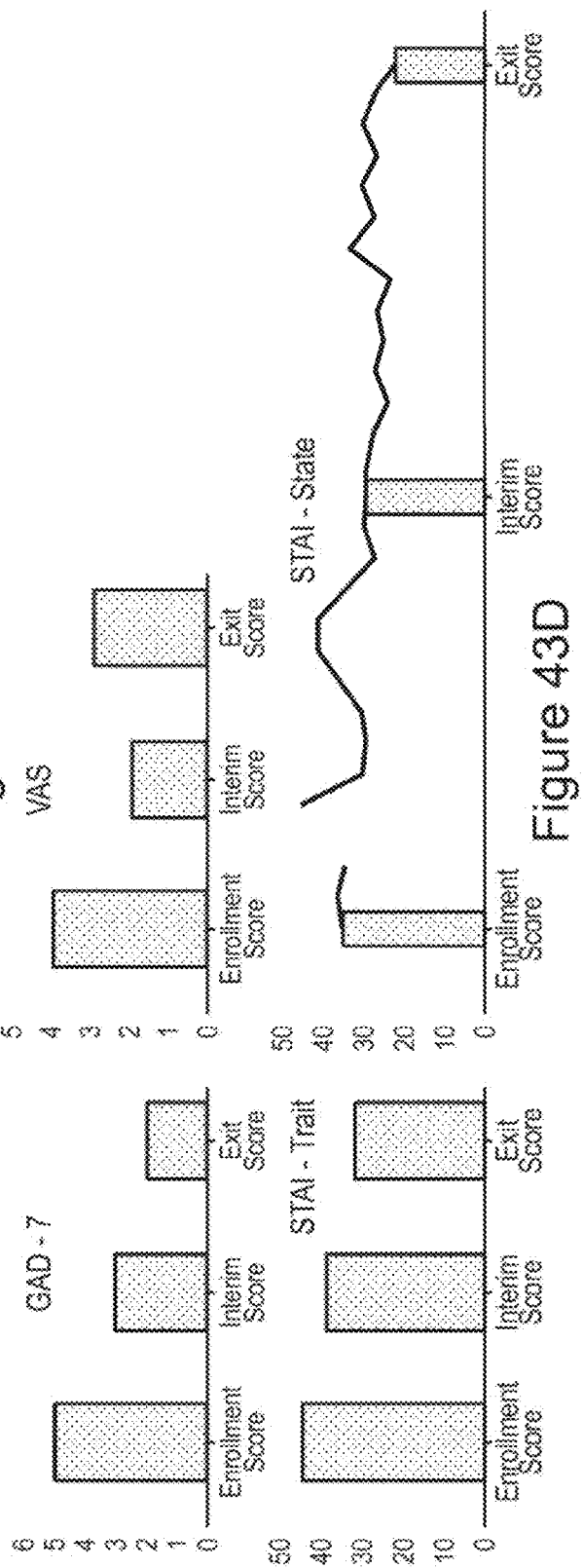
Figure 43C
Figure 43D

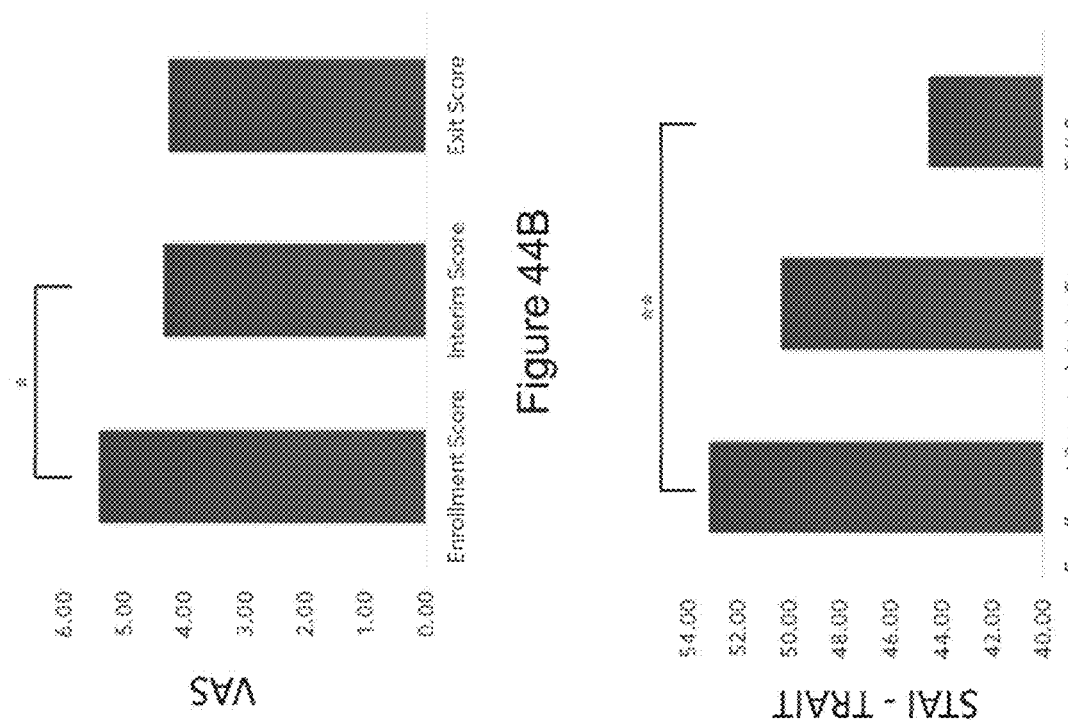
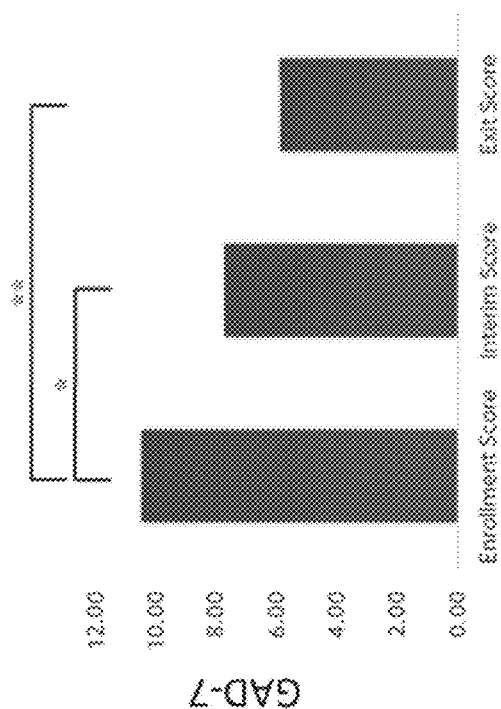
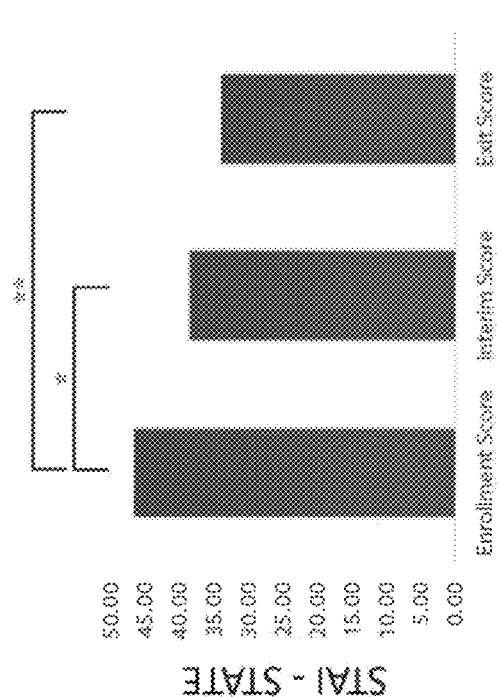
Figure 44A, Figure 44B, Figure 44C, Figure 44D

DEVICES AND METHODS FOR DELIVERING MECHANICAL STIMULATION TO NERVE, MECHANORECEPTOR, AND CELL TARGETS

CROSS REFERENCE TO RELATED APPLICATIONS

This application hereby claims priority to and benefit of U.S. Non-Provisional patent application Ser. No. 16/657,073, filed on Oct. 18, 2019, which issued as U.S. Pat. No. 10,786,666 on Aug. 29, 2020, U.S. Non-Provisional patent application Ser. No. 16/241,224, filed on Jan. 7, 2019,U.S. Provisional Patent Application No. 62/623,977, filed Jan. 30, 2018, U.S. Provisional Patent Application No. 62/680,525, filed Jun. 4, 2018 and U.S. Provisional Patent Application No. 62/741,758, filed Oct. 5, 2018, the contents of each of which are hereby incorporated by reference in their entirety.

FIELD OF THE INVENTION

The present invention relates generally to wearable neuromodulation devices for promoting nerve stimulation through mechanical vibration.

BACKGROUND

Electrical stimulation of nerves in human subjects can alter mood states, reduce the sensation of pain, and treat certain diseases. While promising in this regard, patients subjected to electrical stimulation often experience unpleasant and/or dangerous side effects, including skin irritation resulting from gels needed to maintain good contact between electrodes and the patient's skin, burns and/or rashes, and pain or irritation at the stimulation site. Such side effects are particularly problematic for applications where nerve stimulation should be applied frequently (e.g., daily), such as for stress management.

Accordingly, there is a need for systems, methods, and devices that provide for convenient, regular nerve stimulation with limited side effects and a robust safety profile. Such systems, methods, and devices are of particular relevance to the treatment of conditions where frequent nerve stimulation is desired.

SUMMARY OF THE INVENTION

Presented herein are systems, methods, and devices that provide for stimulation of nerves and/or targets such as mechanoreceptors, tissue regions, cellular mechanotransduction and vascular targets through generation and delivery of mechanical vibrational waves. In certain embodiments, the approaches described herein utilize a stimulation device (e.g., a wearable or applied device) for generation and delivery of the mechanical vibrational waves. As described herein, the delivered vibrational waves can be tailored based on particular targets (e.g., nerves, mechanoreceptors, vascular targets, tissue regions) to stimulate and/or to elicit particular desired responses in a subject. As described herein, in certain embodiments, the delivery of mechanical stimulation to a subject provides for treatment of anxiety.

In certain embodiments, the properties of mechanical waves generated are tailored by controlling a waveform of an electronic drive signal that is applied to mechanical transducers in order to generate a desired mechanical wave. By controlling and delivering various specific mechanical waves in this manner, the approaches described herein can be used to achieve a variety of health benefits in subjects, for example by promoting relaxation, preventing migraine headaches, facilitating stress management, alleviating diseases exacerbated by stress, and improving sleep.

In one aspect, the invention is directed to a transcutaneous neuromodulation device [e.g., a wearable device; e.g., a non-invasive device (e.g., not comprising any components that penetrate skin)] for promoting nerve stimulation through mechanical vibration, comprising: one or more mechanical transducers, a battery, and one or more controller boards, wherein the one or more mechanical transducers, the battery and the one or more controller boards are in communication (e.g., through one or more connectors; e.g., wirelessly), and wherein the controller board controls waveform output through the one or more mechanical transducers, thereby producing mechanical vibration, and wherein the waveform output comprises an isochronic wave.

In certain embodiments, the device promotes stimulation (e.g., wherein the waveform is selected to promote stimulation) of one or more nerves [e.g., a vagus nerve; e.g., a trigeminal nerve; e.g., peripheral nerves; e.g., a greater auricular nerve; e.g., a lesser occipital nerve; e.g., one or more cranial nerves (e.g., cranial nerve VII; e.g., cranial nerve IX; e.g., cranial nerve XI; e.g., cranial nerve XII)]. In certain embodiments, the one or more nerves comprises a vagus nerve and/or a trigeminal nerve. In certain embodiments, the one or more nerves comprises a C-tactile afferent.

In certain embodiments, the device promotes stimulation of (e.g., wherein the waveform is selected to promote stimulation of) one or more mechanoreceptors and/or cutaneous sensory receptors in the skin (e.g., to stimulate an afferent sensory pathway and use properties of receptive fields to propagate stimulation through tissue and bone). In certain embodiments, the one or more mechanoreceptors and/or cutaneous sensory receptors comprise Piezo2 protein and/or Merkel cells.

In certain embodiments, the one or more controller boards modulate the waveform output to introduce particular signal that include active or inactive pulse durations and frequencies configured to accommodate particular mechanoreceptor recovery periods, adaptation times, inactivation times, sensitization and desensitization times, or latencies.

In certain embodiments, the one or more controller boards modulate the waveform output to enhance or inhibit the expression of presynaptic molecules essential for synaptic vesicle release in neurons. In certain embodiments, the one or more controller boards modulate the waveform output to enhance or inhibit the expression of neuroactive substances that can act as fast excitatory neurotransmitters or neuromodulators.

In certain embodiments, the one or more controller boards modulates the waveform output to stimulate mechanoreceptor cells associated with Aδ-fibers and C-fibers (e.g., including C tactile fibers) in order to stimulate nociceptive, thermoceptive, interoceptive and/or other pathways modulated by these fibers.

In certain embodiments, the one or more controller boards modulate the waveform output using dynamical systems methods to produce a preferred response in neural network dynamics (e.g., via modulation of signal timing). In certain embodiments, the one or more controller boards modulates the waveform output using dynamical systems measures to assess response signals (e.g., electronic) to detect particular network responses correlated with changes in mechanical wave properties (e.g., and modulates the waveform output to target/optimally enhance particular preferred responses).

In certain embodiments, the device comprises an adhesive (e.g., a biocompatible adhesive) for adhering at least one of the one or more mechanical transducers (e.g., up to all) to a subject [e.g., skin (e.g., on a neck of; e.g., overlaying at least one mastoid process of; e.g., of an outer or posterior of at least one ear of) a human subject] (e.g., wherein the at least one mechanical transducer is embedded within the adhesive; e.g., wherein the at least one mechanical transducer is surrounded by the adhesive).

In certain embodiments, the device comprising one or more ergonomic support components, wherein the one or more transducers are supported by (e.g., housed within; e.g., mounted on) the one or more ergonomic support component(s) (e.g., collectively) and the one or more ergonomic support component(s) is/are formed (e.g., molded) to maintain the transducer in substantial proximity to one or more mastoid regions of a human subject (e.g., by maintaining substantial contact with skin overlaying the one or more mastoid regions).

In certain embodiments, the device comprises a first ergonomic support component, the first ergonomic support component comprising: (a) a first housing comprising a casing (e.g., molded casing) of sufficient size to at least partially house (i) a first transducer set comprising at least a portion (e.g., half; e.g., all) of the one or more mechanical transducers and (ii) a first controller board set comprising at least a portion (e.g., half; e.g., all) of the one or more controller boards, wherein the first transducer set is disposed adjacent to a window in the first housing [e.g., an insulated region of the first housing that contacts skin of the human subject in substantial proximity to a first mastoid region (e.g., on a first (e.g., left; e.g., right) side of head of the subject); e.g., wherein the window comprises fabric, adhesive, etc. placed in between a surface of the transducers of the first transducer set and skin of the subject so as to prevent direct contact with skin]; and (b) a first elastomeric arm comprising a resilient material and formed (e.g., molded) to engage an first ear of the subject and thereby support (e.g., fully) the first housing (e.g., and first transducer set and first controller board set housed therein), wherein the first housing is coupled to a distal end of the first elastomeric arm, wherein the distal end of the first elastomeric arm substantially aligns the window of the first housing with a first body location on the subject in substantial proximity to a first mastoid region (e.g., on a first side of the subject's head; e.g., on a left side; e.g., on a right side), and wherein the resilient material provides a force to hold the first housing against the first body location.

In certain embodiments, the device further comprises a second ergonomic support component, the second ergonomic support component comprising: (a) a second housing comprising a casing (e.g., molded casing) of sufficient size to at least partially house (i) a second transducer set comprising at least a portion (e.g., half; e.g., all) of the one or more mechanical transducers and (ii) a second controller board set comprising at least a portion (e.g., half; e.g., all) of the one or more controller boards, wherein the second transducer set is disposed adjacent to a window in the second housing [e.g., an insulated region of the second housing that contacts skin of the human subject in substantial proximity to a second mastoid region (e.g., on a second (e.g., left; e.g., right) side of head of the subject); e.g., wherein the window comprises fabric, adhesive, etc. placed in between a surface of the transducers of the second transducer set and skin of the subject so as to prevent direct contact with skin]; and (b) a second elastomeric arm comprising a resilient material and formed (e.g., molded) to engage an ear of the subject and thereby support (e.g., fully) the second housing (e.g., and second transducer set and second controller board set housed therein), wherein the second housing is coupled to a distal end of the second elastomeric arm, wherein the distal end of the second elastomeric arm substantially aligns the window of the second housing with a second body location on the subject in substantial proximity to a second mastoid region (e.g., on a second side of the subject's head; e.g., on a right side; e.g., on a left side), and wherein the resilient material provides a force to hold the second housing against the second body location.

In certain embodiments, the first and second ergonomic support components are in wireless communication with each other (e.g., via near-field magnetic induction (NFMI) e.g., so as to avoid/overcome interference from the subject's head) for synchronizing delivery of the mechanical vibration to the first and second mastoid regions of the subject (e.g., for synchronizing delivery of a first mechanical vibration produced by the first transducer set and delivery of a second mechanical vibration produced by the second transducer set).

In certain embodiments, the one or more ergonomic support components comprises: a linkage component formed to engage (e.g., wrap around a top of) a head of the subject; two housings disposed at opposite ends of the linkage component so as to be positioned on opposite sides of the head of the subject, wherein each housing comprising a casing (e.g., a molded casing) of sufficient size to at least partially house a corresponding transducer set comprising at least a portion (e.g., one; e.g., half; e.g., all) of the one or more mechanical transducers, wherein the mechanical transducers are disposed adjacent to a window in each housing; and two elastomeric hinges, each disposed at the opposite ends of the linkage component and mounted to flexibly couple a housings to the linkage component, wherein at least one of the elastomeric hinges is formed and positioned to substantially align the window of each housing with and against opposing mastoid regions on opposite sides of the head of the subject.

In certain embodiments, the linkage component comprises an adjustment mechanism comprising two partially overlaid, interlocking, and sliding curved arms (e.g., curved elastomeric arms), wherein said curved arms are maintained in alignment with each other to form an arc (e.g., approximately matching an average arc of a human head) and slide with respect to each other so as to vary an amount of overlap, thereby varying a size of the arc (e.g., to match different size human heads), and wherein the two elastomeric hinges are disposed on opposing ends of the arc formed by the two sliding arms.

In certain embodiments, the device comprises at least one transducer array comprising a plurality of (e.g., two or more) mechanical transducers maintained in a fixed spatial arrangement in relation to each other (e.g., in substantial proximity to each other; e.g., spaced along a straight or curved line segment) and wherein at least a portion of the one or more controller boards (e.g., a single controller board; e.g., two or more controller boards) are in communication with the mechanical transducers of the transducer array to control output of the mechanical transducers of the transducer array in relation to each other [e.g., wherein the at least a portion of the one or more controller boards synchronizes mechanical vibration produced by each mechanical transducer of the transducer array (e.g., such that each mechanical transducer begins and/or ends producing mechanical vibration at a particular delay with respect to one or more other mechanical transducers of the array; e.g., such that the mechanical transducers are sequentially triggered, one after the other; e.g., wherein the mechanical transducers are spaced along a straight or curved line segment and triggered sequentially along the line segment, such that an apparent source of mechanical vibration moves along the line segment to mimic a stroking motion)] [e.g., wherein a first portion of the mechanical transducers outputs a different frequency mechanical vibration from a second portion of the mechanical transducers of the transducer array (e.g., wherein each mechanical transducer of the transducer array outputs a different frequency mechanical vibration)].

In certain embodiments, the device comprises a receiver in communication with the one or more controller boards, wherein the receiver is operable to receive a signal from and/or transmit a signal (e.g., wirelessly; e.g., via a wired connection) to a personal computing device (e.g., a smart phone; e.g., a personal computer; e.g., a laptop computer; e.g., a tablet computer; e.g., a smartwatch; e.g., a fitness tracker; e.g., a smart charger)(e.g., to upload new waveforms and/or settings for waveforms).

In certain embodiments, the one or more controller boards is/are operable to modulate and/or select the waveform output in response to (e.g., based on) the signal received from the personal computing device by the receiver.

In certain embodiments, the device is non-invasive (e.g., does not comprise any components for penetrating skin).

In certain embodiments, the isochronic wave comprises a frequency component ranging from 5 to 15 Hz (e.g., ranging from approximately 7 to approximately 13 Hz; e.g., a frequency range matching an alpha brain wave frequency range; e.g., approximately 10 Hz). In certain embodiments, the isochronic wave comprises a frequency component ranging from 0 to 49 Hz (e.g., from 18 to 48 Hz; e.g., from 15 to 40 Hz; e.g. from 8 to 14 Hz).

In certain embodiments, one or more low-amplitude sub-intervals of the isochronic wave have a duration of greater than or approximately two seconds (e.g., wherein the one or more low-amplitude sub-intervals have a duration of approximately two seconds; e.g., wherein the one or more low-amplitude sub-intervals have a duration ranging from approximately two seconds to approximately 10 seconds; e.g., wherein the one or more low amplitude sub-intervals have a duration ranging from approximately two seconds to approximately 4 seconds).

In certain embodiments, the isochronic wave comprises a carrier wave [e.g., a periodic wave having a substantially constant frequency (e.g., ranging from 5 to 15 Hz; e.g., ranging from approximately 7 to approximately 13 Hz; e.g., a frequency range matching an alpha brain wave frequency range; e.g., approximately 10 Hz)] modulated by an envelope function having one or more low-amplitude sub-intervals [e.g., a periodic envelope function (e.g., a square wave; e.g., a 0.5 Hz square wave); e.g., the one or more low-amplitude sub-intervals having a duration of greater than or approximately equal to two seconds; e.g., the one or more low-amplitude sub-intervals having a duration of approximately two seconds].

In certain embodiments, the device comprises a receiver in communication with the one or more controller boards, wherein the receiver is operable to receive a signal from and/or transmit a signal to a monitoring device (e.g., directly from and/or to the monitoring device; e.g., via one or more intermediate server(s) and/or computing device(s))(e.g., a wearable monitoring device; e.g., a personal computing device; e.g., a fitness tracker; e.g., a heart-rate monitor; e.g., an electrocardiograph (EKG) monitor; e.g., an electroencephalography (EEG) monitor; e.g., an accelerometer; e.g., a blood-pressure monitor; e.g., a galvanic skin response (GSR) monitor) and wherein the one or more controller boards is/are operable to modulate and/or select the waveform output in response to (e.g., based on) the signal from the wearable monitoring device received by the receiver.

In certain embodiments, the device is operable to record usage data (e.g., parameters such as a record of when the device was used, duration of use, etc.) and/or one or more biofeedback signals for a human subject [e.g., wherein the device comprises one or more sensors, each operable to measure and record one or more biofeedback signals (e.g., a galvanic skin response (GSR) sensor; e.g., a heart-rate monitor; e.g., an accelerometer)] [e.g., wherein the device is operable to store the recorded usage data and/or biofeedback signals for further processing and/or transmission to an external computing device, e.g., for computation (e.g., using a machine learning algorithm that receives the one or more biofeedback signals as input, along with, optionally, user reported information) and display of one or more performance metrics (e.g., a stress index) to a subject using the device]. In certain embodiments, the one or more controller boards is/are operable to automatically modulate and/or select the waveform output in response to (e.g., based on) the recorded usage data and/or biofeedback signals (e.g., using a machine learning algorithm that receives the one or more biofeedback signals as input, along with, optionally, user reported information, to optimize the waveform output).

In certain embodiments, a level [e.g., amplitude (e.g., a force; e.g., a displacement)] of at least a portion of the mechanical vibration is based on activation thresholds of one or more target cells and/or proteins (e.g., mechanoreceptors (e.g., C tactile afferents); e.g., nerves; e.g., sensory thresholds corresponding to a level of tactile sensation) [e.g., wherein the one or more controller boards modulate the waveform output based on sub-activation thresholds (e.g., accounting for the response of the mechanical transducers)].

In certain embodiments, an amplitude of the mechanical vibration corresponds to a displacement ranging from 1 micron to 10 millimeters (e.g., approximately 25 microns) (e.g., wherein the amplitude is adjustable over the displacement ranging from 1 micron to 10 millimeters)[e.g., wherein the amplitude corresponds to a force of approximately 0.4N] [e.g., thereby matching the amplitude to activation thresholds of C tactile afferents].

In certain embodiments, the isochronic wave comprises one or more components (e.g., additive noise; e.g., stochastic resonance signals) that, when transduced by the transducer to produce the mechanical wave, correspond to sub-threshold signals that are below an activation threshold of one or more target cells and/or proteins (e.g., below a level of tactile sensation).

In certain embodiments, the isochronic wave comprises one or more components (e.g., additive noise; e.g., stochastic resonance signals) that, when transduced by the transducer to produce the mechanical wave, correspond to supra-threshold signals that are above an activation threshold of one or more target cells and/or proteins (e.g., above a level of tactile sensation).

In another aspect, the invention is directed to a transcutaneous neuromodulation device [e.g., a wearable device; e.g., a non-invasive device (e.g., not comprising any components that penetrate skin)] for promoting nerve stimulation through mechanical vibration, comprising: one or more mechanical transducers, a battery, and one or more controller boards, wherein the one or more mechanical transducers, the battery and the one or more controller boards are in communication (e.g., through one or more connectors; e.g., wirelessly), and wherein the one or more controller boards control waveform output through the one or more mechanical transducers, and the one or more mechanical transducers transcutaneously stimulate one or more nerves of a human subject and wherein the waveform output comprises an isochronic wave.

In another aspect, the invention is directed to a transcutaneous stimulation device [e.g., a wearable device; e.g., a non-invasive device (e.g., not comprising any components that penetrate skin)] for promoting mechanoreceptor stimulation through mechanical vibration, comprising: one or more mechanical transducers, a battery, and one or more controller boards, wherein the one or more mechanical transducers, the battery and the one or more controller boards are in communication (e.g., through one or more connectors; e.g., wirelessly), and wherein the one or more controller boards control waveform output through the transducer, and the one or more mechanical transducers transcutaneously stimulate one or more mechanoreceptors of a human subject and wherein the waveform output comprises an isochronic wave.

In another aspect, the invention is directed to a method of treating a subject by providing transcutaneous mechanical stimulation (e.g., non-invasive mechanical stimulation) to the subject via a stimulation device (e.g., a wearable device), the method comprising: generating a mechanical wave by a mechanical transducer of the stimulation device in response to an applied electronic drive signal; controlling a waveform of the electronic drive signal by a controller board (e.g., a controller board of the stimulation device; e.g., a remote controller board), wherein the waveform comprises an isochronic wave; and delivering the mechanical wave to a body location of the subject via the stimulation device, thereby providing the transcutaneous mechanical stimulation to the subject.

In certain embodiments, the mechanical wave promotes stimulation (e.g., wherein the waveform is selected to promote stimulation) of one or more nerves [e.g., a vagus nerve; e.g., a trigeminal nerve; e.g., peripheral nerves; e.g., a greater auricular nerve; e.g., a lesser occipital nerve; e.g., one or more cranial nerves (e.g., cranial nerve VII; e.g., cranial nerve IX; e.g., cranial nerve XI; e.g., cranial nerve XII)]. In certain embodiments, the one or more nerves comprises a vagus nerve and/or a trigeminal nerve. In certain embodiments, the one or more nerves comprises a C-tactile afferent.

In certain embodiments, the mechanical wave promotes stimulation of (e.g., wherein the waveform is selected to promote stimulation of) one or more mechanoreceptors and/or cutaneous sensory receptors in the skin (e.g., to stimulate an afferent sensory pathway and use properties of receptive fields to propagate stimulation through tissue and bone). In certain embodiments, the one or more mechanoreceptors and/or cutaneous sensory receptors comprise Piezo2 protein and/or Merkel cells.

In certain embodiments, the controlling the waveform of the electronic drive signal comprises modulating the waveform to introduce particular signals that include active or inactive pulse durations and frequencies configured to accommodate particular mechanoreceptor recovery periods, adaptation times, inactivation times, sensitization and desensitization times, or latencies.

In certain embodiments, the controlling the waveform of the electronic drive signal comprises modulating the waveform to enhance or inhibit the expression of presynaptic molecules essential for synaptic vesicle release in neurons.

In certain embodiments, the controlling the waveform of the electronic drive signal comprises modulating the waveform to enhance or inhibit the expression of neuroactive substances that can act as fast excitatory neurotransmitters or neuromodulators.

In certain embodiments, the controlling the waveform of the electronic drive signal comprises modulating the waveform to stimulate mechanoreceptor cells associated with Aδ-fibers and C-fibers (e.g., including C tactile fibers) in order to stimulate nociceptive, thermoceptive, interoceptive and/or other pathways modulated by these fibers.

In certain embodiments, the controlling the waveform of the electronic drive signal comprises modulating the waveform using dynamical systems methods to produce a preferred response in neural network dynamics (e.g., via modulation of signal timing).

In certain embodiments, the controlling the waveform of the electronic drive signal comprises modulating the waveform using dynamical systems measures to assess response signals (e.g., electronic) to detect particular network responses correlated with changes in mechanical wave properties (e.g., and modulates the waveform output to target/optimally enhance particular preferred responses).

In certain embodiments, the delivering the mechanical wave to the body location comprises contacting the mechanical transducer to a surface (e.g., skin) of the subject at the body location.

In certain embodiments, the contacting the mechanical transducer to the surface of the subject at the body location comprises using an adhesive (e.g., a biocompatible adhesive) for adhering at least one of the one or more mechanical transducers (e.g., up to all) to a subject [e.g., skin (e.g., on a neck of; e.g., overlaying at least one mastoid process of; e.g., of an outer or posterior of at least one ear of) a human subject] (e.g., wherein the at least one mechanical transducer is embedded within the adhesive; e.g., wherein the at least one mechanical transducer is surrounded by the adhesive).

In certain embodiments, the contacting the mechanical transducer to the surface of the subject at the body location comprises using one or more ergonomic support components, wherein the one or more transducers are supported by (e.g., housed within; e.g., mounted on) the one or more ergonomic support component(s) (e.g., collectively) and the one or more ergonomic support component(s) is/are formed (e.g., molded) to maintain the transducer in substantial proximity to one or more mastoid regions of a human subject (e.g., by maintaining substantial contact with skin overlaying the one or more mastoid regions).

In certain embodiments, the one or more ergonomic support components comprise(s) a first ergonomic support component, the first ergonomic support component comprising: (a) a first housing comprising a casing (e.g., molded casing) of sufficient size to at least partially house (i) a first transducer set comprising at least a portion (e.g., half; e.g., all) of the one or more mechanical transducers and (ii) a first controller board set comprising at least a portion (e.g., half; e.g., all) of the one or more controller boards, wherein the first transducer set is disposed adjacent to a window in the first housing [e.g., an insulated region of the first housing that contacts skin of the human subject in substantial proximity to a first mastoid region (e.g., on a first (e.g., left; e.g., right) side of head of the subject); e.g., wherein the window comprises fabric, adhesive, etc. placed in between a surface of the transducers of the first transducer set and skin of the subject so as to prevent direct contact with skin]; and (b) a first elastomeric arm comprising a resilient material and formed (e.g., molded) to engage an first ear of the subject and thereby support (e.g., fully) the first housing (e.g., and first transducer set and first controller board set housed therein), wherein the first housing is coupled to a distal end of the first elastomeric arm, wherein the distal end of the first elastomeric arm substantially aligns the window of the first housing with a first body location on the subject in substantial proximity to a first mastoid region (e.g., on a first side of the subject's head; e.g., on a left side; e.g., on a right side), and wherein the resilient material provides a force to hold the first housing against the first body location.

In certain embodiments, the one or more ergonomic support components further comprise(s) a second ergonomic support component, the second ergonomic support component comprising: (a) a second housing comprising a casing (e.g., molded casing) of sufficient size to at least partially house (i) a second transducer set comprising at least a portion (e.g., half; e.g., all) of the one or more mechanical transducers and (ii) a second controller board set comprising at least a portion (e.g., half; e.g., all) of the one or more controller boards, wherein the second transducer set is disposed adjacent to a window in the second housing [e.g., an insulated region of the second housing that contacts skin of the human subject in substantial proximity to a second mastoid region (e.g., on a second (e.g., left; e.g., right) side of head of the subject); e.g., wherein the window comprises fabric, adhesive, etc. placed in between a surface of the transducers of the second transducer set and skin of the subject so as to prevent direct contact with skin]; and (b) a second elastomeric arm comprising a resilient material and formed (e.g., molded) to engage an ear of the subject and thereby support (e.g., fully) the second housing (e.g., and second transducer set and second controller board set housed therein), wherein the second housing is coupled to a distal end of the second elastomeric arm, wherein the distal end of the second elastomeric arm substantially aligns the window of the second housing with a second body location on the subject in substantial proximity to a second mastoid region (e.g., on a second side of the subject's head; e.g., on a right side; e.g., on a left side), and wherein the resilient material provides a force to hold the second housing against the second body location.

In certain embodiments, the first and second ergonomic support components are in wireless communication with each other (e.g., via near-field magnetic induction (NFMI) e.g., so as to avoid/overcome interference from the subject's head) for synchronizing delivery of the mechanical vibration to the first and second mastoid regions of the subject (e.g., for synchronizing delivery of a first mechanical vibration produced by the first transducer set and delivery of a second mechanical vibration produced by the second transducer set).

In certain embodiments, the one or more ergonomic support components comprises: a linkage component formed to engage (e.g., wrap around a top of) a head of the subject two housings disposed at opposite ends of the linkage component so as to be positioned on opposite sides of the head of the subject, wherein each housing comprising a casing (e.g., a molded casing) of sufficient size to at least partially house a corresponding transducer set comprising at least a portion (e.g., one; e.g., half; e.g., all) of the one or more mechanical transducers, wherein the mechanical transducers are disposed adjacent to a window in each housing; two elastomeric hinges, each disposed at the opposite ends of the linkage component and mounted to flexibly couple a housings to the linkage component; wherein at least one of the elastomeric hinges is formed and positioned to substantially align the window of each housing with and against opposing mastoid regions on opposite sides of the head of the subject.

In certain embodiments, the linkage component comprises an adjustment mechanism comprising two partially overlaid, interlocking, and sliding curved arms (e.g., curved elastomeric arms), wherein said curved arms are maintained in alignment with each other to form an arc (e.g., approximately matching an average arc of a human head) and slide with respect to each other so as to vary an amount of overlap, thereby varying a size of the arc (e.g., to match different size human heads), and wherein the two elastomeric hinges are disposed on opposing ends of the arc formed by the two sliding arms.

In certain embodiments, the mechanical transducer is a member of a transducer array comprising a plurality of (e.g., two or more) mechanical transducers maintained in a fixed spatial arrangement in relation to each other (e.g., in substantial proximity to each other; e.g., spaced along a straight or curved line segment) and wherein the controller board controls output of the mechanical transducer in relation to other mechanical transducers of the array [e.g., so as to synchronize mechanical vibration produced by each mechanical transducer of the transducer array (e.g., such that each mechanical transducer begins and/or ends producing mechanical vibration at a particular delay with respect to one or more other mechanical transducers of the array; e.g., such that the mechanical transducers are sequentially triggered, one after the other; e.g., wherein the mechanical transducers are spaced along a straight or curved line segment and triggered sequentially along the line segment, such that an apparent source of mechanical vibration moves along the line segment to mimic a stroking motion)] [e.g., wherein a first portion of the mechanical transducers outputs a different frequency mechanical vibration from a second portion of the mechanical transducers of the transducer array (e.g., wherein each mechanical transducer of the transducer array outputs a different frequency mechanical vibration)].

In certain embodiments, the transducer is a linear transducer (e.g., operable to produce mechanical vibration comprising a longitudinal component (e.g., a longitudinal vibration)).

In certain embodiments, the mechanical transducer is incorporated into a headphone (e.g., an in-ear headphone; e.g., an over-the-ear headphone).

In certain embodiments, the controlling the waveform of the electronic drive signal comprises receiving (e.g., by a receiver in communication with the controller board) a signal from a personal computing device (e.g., a smart phone; e.g., a personal computer; e.g., a laptop computer; e.g., a tablet computer; e.g., a smartwatch; e.g., a fitness tracker; e.g., a smart charger)(e.g., to upload new waveforms and/or settings for waveforms).

In certain embodiments, the controlling the waveform of the electronic drive signal comprises modulating and/or selecting the waveform in response to (e.g., based on) the signal received from the personal computing device by the receiver.

In certain embodiments, the delivering the mechanical wave to the body location is performed in a non-invasive fashion (e.g., without penetrating skin of the subject).

In certain embodiments, the method comprising providing, by a secondary stimulation device, one or more external stimulus/stimuli (e.g., visual stimulus; e.g., acoustic stimulus; e.g., limbic priming; e.g., a secondary tactile signal).

In certain embodiments, the isochronic wave comprises a frequency component ranging from 5 to 15 Hz (e.g., ranging from approximately 7 to approximately 13 Hz; e.g., a frequency range matching an alpha brain wave frequency range; e.g., approximately 10 Hz). In certain embodiments, the isochronic wave comprises a frequency component ranging from 0 to 49 Hz (e.g., from 18 to 48 Hz; e.g., from 15 to 40 Hz; e.g. from 8 to 14 Hz).

In certain embodiments, one or more low-amplitude sub-intervals of the isochronic wave have a duration of greater than or approximately two seconds (e.g., wherein the one or more low-amplitude sub-intervals have a duration of approximately two seconds; e.g., wherein the one or more low-amplitude sub-intervals have a duration ranging from approximately two seconds to approximately 10 seconds; e.g., wherein the one or more low amplitude sub-intervals have a duration ranging from approximately two seconds to approximately 4 seconds).

In certain embodiments, the isochronic wave comprises a carrier wave [e.g., a periodic wave having a substantially constant frequency (e.g., ranging from 5 to 15 Hz; e.g., ranging from approximately 7 to approximately 13 Hz; e.g., a frequency range matching an alpha brain wave frequency range; e.g., approximately 10 Hz)] modulated by an envelope function having one or more low-amplitude sub-intervals [e.g., a periodic envelope function (e.g., a square wave; e.g., a 0.5 Hz square wave); e.g., the one or more low-amplitude sub-intervals having a duration of greater than or approximately equal to two seconds; e.g., the one or more low-amplitude sub-intervals having a duration of approximately two seconds].

In certain embodiments, the isochronic wave is also a transformed time-varying wave. In certain embodiments, the isochronic wave comprises a chirped wave. In certain embodiments, the waveform of the electronic drive signal comprises a transformed time-varying wave having a functional form corresponding to a carrier wave within an envelope {e.g., wherein the transformed-time varying wave is the carrier wave and is further modulated by an envelope [e.g., wherein the envelope is a sinusoidal wave; e.g., wherein the envelope has a monotonically increasing (in time) amplitude (e.g., wherein the envelope has a functional form corresponding to an increasing (in time) exponential)]; e.g., wherein the transformed time-varying wave is the envelope that modulates a carrier wave [e.g., wherein the carrier wave is a periodic wave (e.g., a sinusoidal wave; e.g., a square wave; e.g., a sawtooth wave)(e.g., having a higher frequency than the envelope)]}.

In certain embodiments, a functional form of the waveform of the electronic drive signal is based on one or more recorded natural sounds (e.g., running water; e.g., ocean waves; e.g., purring; e.g., breathing; e.g., chanting; e.g., gongs; e.g., bells).

In certain embodiments, the method comprises receiving an electronic response signal from a monitoring device (e.g., directly from and/or to the monitoring device; e.g., via one or more intermediate server(s) and/or computing device(s)) (e.g., a wearable monitoring device; e.g., a personal computing device; e.g., a fitness tracker; e.g., a heart-rate monitor; e.g., an electrocardiograph (EKG) monitor; e.g., an electroencephalography (EEG) monitor; e.g., an accelerometer; e.g., a blood-pressure monitor; e.g., a galvanic skin response (GSR) monitor) and wherein the controlling the waveform of the electronic drive signal comprises adjusting and/or selecting the waveform in response to (e.g., based on) the received electronic response signal.

In certain embodiments, the method comprises recording usage data (e.g., parameters such as a record of when the device was used, duration of use, etc.) and/or one or more biofeedback signals for a human subject [e.g., using one or more sensors, each operable to measure and record one or more biofeedback signals (e.g., a galvanic skin response (GSR) sensor; e.g., a heart-rate monitor; e.g., an accelerometer)] [e.g., storing and/or providing the recorded usage data and/or biofeedback signals for further processing and/or transmission to an external computing device, e.g., for computation (e.g., using a machine learning algorithm that receives the one or more biofeedback signals as input, along with, optionally, user reported information) and display of one or more performance metrics (e.g., a stress index) to a subject].

In certain embodiments, the method comprises automatically modulating and/or selecting the waveform of the electronic drive signal in response to (e.g., based on) the recorded usage data and/or biofeedback signals (e.g., using a machine learning algorithm that receives the one or more biofeedback signals as input, along with, optionally, user reported information, to optimize the waveform output).

In certain embodiments, a level [e.g., amplitude (e.g., a force; e.g., a displacement)] of at least a portion of the mechanical wave is (e.g., modulated and/or selected) based on activation thresholds of one or more target cells and/or proteins (e.g., mechanoreceptors (e.g., C tactile afferents); e.g., nerves; e.g., sensory thresholds corresponding to a level of tactile sensation) [e.g., wherein the one or more controller boards modulate the waveform output based on sub-activation thresholds (e.g., accounting for the response of the mechanical transducers)].

In certain embodiments, an amplitude of the mechanical wave corresponds to a displacement ranging from 1 micron to 10 millimeters (e.g., approximately 25 microns) (e.g., wherein the amplitude is adjustable over the displacement ranging from 1 micron to 10 millimeters)[e.g., wherein the amplitude corresponds to a force of approximately 0.4N] [e.g., thereby matching the amplitude to activation thresholds of C tactile afferents].

In another aspect, the invention is directed to a method of treating a subject by providing transcutaneous mechanical stimulation (e.g., non-invasive mechanical stimulation) to the subject via a stimulation device (e.g., a wearable device), the method comprising: generating a mechanical wave by a mechanical transducer of the stimulation device in response to an applied electronic drive signal; controlling a waveform of the electronic drive signal by a controller board (e.g., a controller board of the stimulation device; e.g., a remote controller board); and delivering the mechanical wave to a body location of the subject via the stimulation device, wherein the body location is in proximity to a mastoid of the subject (e.g., wherein the mastoid lies directly beneath the body location), thereby providing the transcutaneous mechanical stimulation to the subject.

In another aspect, the invention is directed to a method of treating a subject by providing transcutaneous mechanical stimulation (e.g., non-invasive mechanical stimulation) to one or more nerves of the subject via a stimulation device (e.g., a wearable device), the method comprising: generating a mechanical wave by a mechanical transducer of the stimulation device in response to an applied electronic drive signal; controlling a waveform of the electronic drive signal by a controller board (e.g., of the stimulation device; e.g., a remote controller board); and delivering the mechanical wave to a body location of the subject via the wearable stimulation device, thereby stimulating the one or more nerves, wherein the one or more nerves comprise(s) a cranial nerve (e.g., vagus nerve; e.g., trigeminal nerve; e.g., facial nerve) of the subject.

In another aspect, the invention is directed to a method of treating a subject by providing transcutaneous mechanical stimulation (e.g., non-invasive mechanical stimulation) to one or more nerves and/or mechanoreceptors of the subject via a stimulation device (e.g., a wearable device), the method comprising: generating a mechanical wave by a mechanical transducer of the stimulation device in response to an applied electronic drive signal; controlling a waveform of the electronic drive signal by a controller board (e.g., a controller board of the wearable stimulation device; e.g., a remote controller board), wherein the waveform comprises a frequency component ranging from approximately 5 Hz to 15 Hz (e.g., approximately 10 Hz; e.g., ranging from approximately 7 Hz to approximately 13 Hz; e.g., a frequency range matching an alpha brain wave frequency); and delivering the mechanical wave to a body location of the subject via the stimulation device, thereby providing the transcutaneous mechanical stimulation of the one or more nerves and/or mechanoreceptors of the subject.

In another aspect, the invention is directed to a method of treating a subject by providing transcutaneous mechanical stimulation (e.g., non-invasive mechanical stimulation) to the subject via a stimulation device (e.g., a wearable device), the method comprising: generating a mechanical wave by a mechanical transducer of the stimulation device in response to an applied electronic drive signal; receiving an electronic response signal from a monitoring device (e.g., a wearable monitoring device) operable to monitor one or more physiological signals from the subject and generate, in response to the one or more physiological signals from the subject, the electronic response signal (e.g., wherein the electronic response signal is received directly from the monitoring device; e.g., wherein the electronic response signal is received from the wearable monitoring device via one or more intermediate servers and/or processors); responsive to the receiving the electronic response signal, controlling, via a controller board (e.g., a controller board of the stimulation device; e.g., a remote controller board), a waveform of the electronic drive signal to adjust and/or select the waveform based at least in part on the received electronic response signal; and delivering the mechanical wave to a body location of the subject via the stimulation device, thereby providing the transcutaneous mechanical stimulation to the subject.

In another aspect, the invention is directed to a method of treating a subject by providing transcutaneous mechanical stimulation (e.g., non-invasive mechanical stimulation) to the subject via a stimulation device (e.g., a wearable device), the method comprising: (a) generating a mechanical wave by a mechanical transducer of the stimulation device in response to an applied electronic drive signal; (b) accessing and/or receiving [e.g., by a processor of a computing device, of and/or in communication with the stimulation device, e.g., an intermediate server and/or processor (e.g., of a mobile computing device in communication with the stimulation device)] subject response data (e.g., entered by the subjects themselves or biofeedback data recorded via sensors) and/or initialization setting data [e.g., physical characteristics of the subject (e.g., age, height, weight, gender, body-mass index (BMI), and the like); e.g., activity levels (e.g., physical activity levels); e.g., biofeedback data recorded by one or more sensors (e.g., included within the device and/or external to and in communication with the device)(e.g., a heart rate; e.g., a galvanic skin response; e.g., physical movement (e.g., recorded by an accelerometer)); e.g., results of a preliminary survey (e.g., entered by the subject themselves, e.g., via a mobile computing device, an app, and/or online portal; e.g., provided by a therapist/physician treating the subject for a disorder)]; (c) responsive to the accessed and/or received subject response data and/or initialization setting data, controlling, via a controller board (e.g., a controller board of the stimulation device; e.g., a remote controller board), a waveform of the electronic drive signal to adjust and/or select the waveform based at least in part on the subject response data and/or initialization setting data (e.g., using a machine learning algorithm that receives one or more biofeedback signals as input, along with, optionally, user reported information, to optimize the waveform output); and (d) delivering the mechanical wave to a body location of the subject via the stimulation device, thereby providing the transcutaneous mechanical stimulation to the subject.

In certain embodiments, step (b) comprises receiving and/or accessing subject response data [e.g., results of a survey recorded for the subject (e.g., entered by the subject themselves, e.g., via a mobile computing device, an app, and/or online portal; e.g., provided by a therapist/physician treating the subject for a disorder); e.g., biofeedback data recorded by one or more sensors (e.g., included within the device and/or external to and in communication with the device)(e.g., a heart rate; e.g., a galvanic skin response; e.g., physical movement (e.g., recorded by an accelerometer))] provided following their receipt of a round (e.g., a duration) of the transcutaneous mechanical stimulation provided by the stimulation device; and step (c) comprises controlling the waveform of the electronic drive signal based at least in part on the subject feedback, thereby modifying the transcutaneous mechanical stimulation provided to the subject based on subject response data.

In another aspect, the invention is directed to a method of treating a subject by providing transcutaneous mechanical stimulation (e.g., non-invasive mechanical stimulation) to the subject via a stimulation device (e.g., a wearable device), the method comprising: generating a first mechanical wave by a first mechanical transducer of the stimulation device in response to a first applied electronic drive signal; controlling a first waveform of the first electronic drive signal by a controller board (e.g., a controller board of the stimulation device; e.g., a remote controller board); and delivering the first mechanical wave to a first body location (e.g., on a right side; e.g., a location behind a right ear) of the subject via the stimulation device; generating a second mechanical wave by a second mechanical transducer of the stimulation device in response to a second applied electronic drive signal; controlling a second waveform of the second electronic drive signal by the controller board; and delivering the second mechanical wave to a second body location (e.g., on a left side; e.g., a location behind a left ear) of the subject via the stimulation device, thereby providing the transcutaneous mechanical stimulation to the subject.

In another aspect, the invention is directed to a method of treating a subject by providing transcutaneous mechanical stimulation (e.g., non-invasive mechanical stimulation) to the subject via a stimulation device (e.g., a wearable device), the method comprising: generating a first mechanical wave by a first mechanical transducer of the stimulation device in response to an applied electronic drive signal; controlling a waveform of the first electronic drive signal by a controller board (e.g., a controller board of the stimulation device; e.g., a remote controller board); and delivering the first mechanical wave to a first body location (e.g., on a right side; e.g., a location behind a right ear) of the subject via the stimulation device; generating a second mechanical wave by a second mechanical transducer of the stimulation device in response to the applied electronic drive signal; delivering the second mechanical wave to a second body location (e.g., on a left side; e.g., a location behind a left ear) of the subject via the stimulation device, thereby providing the transcutaneous mechanical stimulation to the subject.

In another aspect, the invention is directed to a method of stimulating one or more nerves and/or mechanoreceptors of a subject (e.g., a human subject), the method comprising: using any of the devices described herein, for stimulation of the one or more nerves and/or mechanoreceptors of the subject.

In another aspect, the invention is directed to a method of stimulating one or more nerves of a human subject using a transcutaneous, neuromodulation device [e.g., a wearable device; e.g., a non-invasive device (e.g., not comprising any components that penetrate skin)], the device comprising one or more transducers (e.g., mechanical transducers), a battery, connectors, and one or more controller boards, wherein the one or more controller boards control waveform output through the connectors and the one or more transducers, and wherein the transducers transcutaneously applied stimulate the one or more nerves, the method comprising: contacting the one or more transducers of the device to the human subject, generating the waveform output signal, activating the transducers using the waveform output signal (e.g., by applying the waveform output signal to the transducers to generate a mechanical wave), and stimulating the one or more nerves of the human subject, wherein the waveform output comprises an isochronic wave.

In another aspect, the invention is directed to a method of stimulating one or more mechanoreceptors of a human subject using transcutaneous stimulation device [e.g., a wearable device; e.g., a non-invasive device (e.g., not comprising any components that penetrate skin)], the device comprising one or more mechanical transducers, a battery, connectors, and one or more controller boards, wherein the one or more controller boards control waveform output through the connectors and the one or more mechanical transducers, and wherein the one or more mechanical transducers transcutaneously applied stimulate the one or more mechanoreceptors, the method comprising: contacting the one or more mechanical transducers of the device to the human subject, generating the waveform output signal, activating the mechanical transducers using the waveform output signal (e.g., by applying the waveform output signal to the transducers to generate a mechanical wave), and stimulating the one or more mechanoreceptors of the human subject, wherein the waveform output comprises an isochronic wave.

In another aspect, the invention is directed to a method of improving interoception in a subject (e.g., a human subject) [e.g., improving and/or restoring mind-body connection (e.g., mindfulness) in the subject; e.g., effortlessly to quiet mind of the subject; e.g., to improve and/or restore mindfulness without meditation], the method comprising transcutaneously delivering mechanical stimulation to the subject using a mechanical wave having a vibrational waveform selected to improve interoception in the subject upon and/or following the delivering of the mechanical wave to the subject.

In another aspect, the invention is directed to a kit comprising the device of any one of the aspects and embodiments described herein and a label indicating that the device is to be used for improving interoception [e.g., improving and/or restoring mind-body connection (e.g., mindfulness) in the subject; e.g., effortlessly to quiet mind of the subject; e.g., to improve and/or restore mindfulness without meditation].

In another aspect, the invention is directed to a method of promoting relaxation and/or reducing stress in a subject (e.g., a human subject) [e.g., to promote calm and positive emotional states; e.g., to promote and/or stimulate subject's body's own relaxation response (e.g., to lead to greater calm, clarity, and/or focus in the subject); e.g., to improve cognitive performance; e.g., to support and maintain memory, concentration, and focus; e.g., to provide long term drug free neurological benefits; e.g., to reduce fatigue and/or irritability], the method comprising transcutaneously delivering mechanical stimulation to the subject using a mechanical wave having a vibrational waveform selected to promote relaxation and/or reduce stress in the subject upon and/or following the delivering of the mechanical wave to the subject.

In another aspect, the invention is directed to a kit comprising the device of any one of the aspects or embodiments described herein and a label indicating that the device is to be used for promoting relaxation and/or managing stress [e.g., the label indicating that the device to be used as a serenity device; e.g., the label indicating that the device is to be used (e.g., as a safe, easy, and/or effective way) to promote calm and positive emotional states; e.g., to promote and/or stimulate subject's body's own relaxation response (e.g., to lead to greater calm, clarity, and/or focus in the subject); e.g., to improve cognitive performance; e.g., to support and maintain memory, concentration, and focus; e.g., to provide long term drug free neurological benefits; e.g., to reduce fatigue and/or irritability].

In another aspect, the invention is directed to a method of improving mental acuity and/or concentration in a subject (e.g., a human subject)(e.g., improving clarity and/or focus; e.g., improving cognitive performance), the method comprising transcutaneously delivering mechanical stimulation to the subject using a mechanical wave having a vibrational waveform selected to improve mental acuity and/or concentration in the subject upon and/or following the delivering of the mechanical wave to the subject.

In another aspect, the invention is directed to a kit comprising the device of any one of the aspects and embodiments described herein and a label indicating that the device is to be used for improving mental acuity and/or concentration (e.g., improving clarity and/or focus; e.g. improving cognitive performance).

In another aspect, the invention is directed to a method of enhancing learning capacity and/or memory (e.g., supporting and maintaining memory, concentration, and focus) in a subject (e.g., a human subject), the method comprising transcutaneously delivering mechanical stimulation to the subject using a mechanical wave having a vibrational waveform selected to enhance learning capacity and/or memory in the subject upon and/or following the delivering of the mechanical wave to the subject.

In another aspect, the invention is directed to a kit comprising the device of any one of the aspects and embodiments described herein and a label indicating that the device is to be used for enhancing learning capacity and/or memory e.g., supporting and maintaining memory, concentration, and focus).

In another aspect, the invention is directed to a method of managing (e.g., reducing negative effects of; e.g., provide relief from) a social phobia in a subject (e.g., a human subject), the method comprising transcutaneously delivering mechanical stimulation to the subject using a mechanical wave having a vibrational waveform selected to manage the social phobia in the subject upon and/or following the delivering of the mechanical wave to the subject.

In another aspect, the invention is directed to a kit comprising the device of any one of the aspects and embodiments described herein and a label indicating that the device is to be used for managing (e.g., reducing negative effects of; e.g., provide relief from) a social phobia.

In another aspect, the invention is directed to a method of reducing performance anxiety in a subject, the method comprising transcutaneously delivering mechanical stimulation to the subject using a mechanical wave having a vibrational waveform selected to reduce performance anxiety in the subject upon and/or following the delivering of the mechanical wave to the subject.

In another aspect, the invention is directed to a kit comprising the device of any one of the aspects or embodiments described herein and a label indicating that the device is to be used for reducing performance anxiety.

In another aspect, the invention is directed to a method of improving quality of life in a subject (e.g., a human subject) when the subject has a condition (e.g., high blood pressure; e.g., tinnitus; e.g., anxiety)(e.g., to help living well with anxiety), the method comprising transcutaneously delivering mechanical stimulation to the subject using a mechanical wave having a vibrational waveform selected to improve quality of life in the subject having the condition upon and/or following the delivering of the mechanical wave to the subject.

In another aspect, the invention is directed to a kit comprising the device of any one of the aspects or embodiments described herein and a label indicating that the device is to be used for improving quality of life in a subject (e.g., a human subject) when the subject has a condition (e.g., high blood pressure; e.g., tinnitus; e.g., anxiety)(e.g., to help living well with anxiety).

In another aspect, the invention is directed to a method of reducing (e.g., frequency of; e.g., intensity of; e.g., risk of) stress-induced headaches and/or stress headaches in a subject (e.g., a human subject), the method comprising transcutaneously delivering mechanical stimulation to the subject using a mechanical wave having a vibrational waveform selected to reduce stress induced headaches in the subject upon and/or following the delivering of the mechanical wave to the subject.

In another aspect, the invention is directed to a kit comprising the device of any one of the aspects or embodiments described herein and a label indicating that the device is to be used for reducing (e.g., frequency of; e.g., intensity of; e.g., risk of) stress induced headaches and/or stress headaches.

In another aspect, the invention is directed to a method of reducing stress-induced infertility in a subject, the method comprising transcutaneously delivering mechanical stimulation to the subject using a mechanical wave having a vibrational waveform selected to stress-induced infertility in the subject upon and/or following the delivering of the mechanical wave to the subject.

In another aspect, the invention is directed to a kit comprising the device of any one of the aspects and embodiments described herein and a label indicating that the device is to be used for reducing stress-induced infertility.

In another aspect, the invention is directed to a method of managing stress-induced blood pressure conditions (e.g., high-blood pressure; e.g., hypertension; e.g., hypotension) in a subject, the method comprising transcutaneously delivering mechanical stimulation to the subject using a mechanical wave having a vibrational waveform selected to manage stress-induced high blood pressure in the subject upon and/or following the delivering of the mechanical wave to the subject.

In another aspect, the invention is directed to a kit comprising the device of any one of the aspects or embodiments described herein and a label indicating that the device is to be used for managing stress-induced blood pressure conditions (e.g., high-blood pressure; e.g., hypertension; e.g., hypotension).

In another aspect, the invention is directed to a method of reducing (e.g., frequency of; e.g., intensity of; e.g., risk of) stress-induced diseases in a subject (e.g., a human subject), the method comprising transcutaneously delivering mechanical stimulation to the subject using a mechanical wave having a vibrational waveform selected to reduce stress induced headaches in the subject upon and/or following the delivering of the mechanical wave to the subject.

In another aspect, the invention is directed to a kit comprising the device of any one of the aspects and embodiments described herein and a label indicating that the device is to be used for reducing (e.g., frequency of; e.g., intensity of; e.g., risk of) stress induced diseases.

In another aspect, the invention is directed to a method of improving peripheral nerve sensitivity in a subject, the method comprising transcutaneously delivering mechanical stimulation to the subject using a mechanical wave having a vibrational waveform selected to improve peripheral nerve sensitivity in the subject upon and/or following the delivering of the mechanical wave to the subject.

In another aspect, the invention is directed to a kit comprising the device of any one of the aspects and embodiments described herein and a label indicating that the device is to be used for improving peripheral nerve sensitivity.

In another aspect, the invention is directed to a method of supporting immune system function in a subject, the method comprising transcutaneously delivering mechanical stimulation to the subject using a mechanical wave having a vibrational waveform selected to support immune system function in the subject upon and/or following the delivering of the mechanical wave to the subject.

In another aspect, the invention is directed to a kit comprising the device of any one of the aspects and embodiments described herein and a label indicating that the device is to be used for supporting immune system function.

In another aspect, the invention is directed to a method of managing stress-induced anger and/or mood problems (e.g., reduce fatigue and/or irritability) in a subject, the method comprising transcutaneously delivering mechanical stimulation to the subject using a mechanical wave having a vibrational waveform selected to manage stress induced anger and/or mood problems in the subject upon and/or following the delivering of the mechanical wave to the subject.

In another aspect, the invention is directed to a kit comprising the device of any one of the aspects and embodiments described herein and a label indicating that the device is to be used for managing stress induced anger and mood problems (e.g., to reduce fatigue and/or irritability).

In another aspect, the invention is directed to a method of managing stress-induced sleep problems in a subject, the method comprising transcutaneously delivering mechanical stimulation to the subject using a mechanical wave having a vibrational waveform selected to manage stress-induced sleep problems in the subject (e.g., to improve sleep quality; e.g., to provide for drug-free promotion of longer and more restful sleep) upon and/or following the delivering of the mechanical wave to the subject.

In another aspect, the invention is directed to a kit comprising the device of any one of the aspects or embodiments described herein and a label indicating that the device is to be used for managing stress-induced sleep problems (e.g., improve sleep quality; e.g., to provide for drug-free promotion of longer and more restful sleep).

In another aspect, the invention is directed to a method of reducing stress-induced menstrual cramping in a subject, the method comprising transcutaneously delivering mechanical stimulation to the subject using a mechanical wave having a vibrational waveform selected to reduce stress-induced menstrual cramping in the subject upon and/or following the delivering of the mechanical wave to the subject.

In another aspect, the invention is directed to a kit comprising the device of any one of the aspects and embodiments described herein and a label indicating that the device is to be used for reducing stress-induced menstrual cramping.

In another aspect, the invention is directed to a method of improving appetite and/or salivation in a subject, the method comprising transcutaneously delivering mechanical stimulation to the subject using a mechanical wave having a vibrational waveform selected to improve appetite and/or salivation in the subject upon and/or following the delivering of the mechanical wave to the subject.

In another aspect, the invention is directed to a kit comprising the device of any one of the aspects and embodiments described herein and a label indicating that the device is to be used for improving appetite and/or salivation.

In another aspect, the invention is directed to a method of improving balance in a subject, the method comprising transcutaneously delivering mechanical stimulation to the subject using a mechanical wave having a vibrational waveform selected to improve balance in the subject upon and/or following the delivering of the mechanical wave to the subject.

In another aspect, the invention is directed to a kit comprising the device of any one of the aspects and embodiments described herein and a label indicating that the device is to be used for improving balance.

In another aspect, the invention is directed to a method of improving immune function in a subject, the method comprising transcutaneously delivering mechanical stimulation to the subject using a mechanical wave having a vibrational waveform selected to improving immune function in the subject upon and/or following the delivering of the mechanical wave to the subject.

In another aspect, the invention is directed to a kit comprising the device of any one of the aspects and embodiments described herein and a label indicating that the device is to be used for improving immune function.

In another aspect, the invention is directed to a method of increasing (e.g., an amplitude of) alpha brain waves in a subject, the method comprising transcutaneously delivering mechanical stimulation to the subject using a mechanical wave having a vibrational waveform selected to increase alpha brain waves in the subject upon and/or following the delivering of the mechanical wave to the subject.

In another aspect, the invention is directed to a kit comprising the device of any one of the aspects and embodiments described herein and a label indicating that the device is to be used for improving alpha brain waves.

In another aspect, the invention is directed to a method of enhancing (e.g., increasing) heart rate variability in a subject (e.g., a human subject), the method comprising transcutaneously delivering mechanical stimulation to the subject using a mechanical wave having a vibrational waveform selected to enhance (e.g., increase) heart rate variability in the subject upon and/or following the delivering of the mechanical wave to the subject.

In another aspect, the invention is directed to a kit comprising the device of any one of the aspects and embodiments described herein and a label indicating that the device is to be used for enhancing (e.g., increasing) heart rate variability.

In another aspect, the invention is directed to a method of improving vagal tone in a subject, the method comprising transcutaneously delivering mechanical stimulation to the subject using a mechanical wave having a vibrational waveform selected to improve vagal tone in the subject upon and/or following the delivering of the mechanical wave to the subject.

In another aspect, the invention is directed to a kit comprising the device of any one of the aspects and embodiments described herein and a label indicating that the device is to be used for improving vagal tone.

In another aspect, the invention is directed to a method of promoting sleep management in a subject, the method comprising transcutaneously delivering mechanical stimulation to the subject using a mechanical wave having a vibrational waveform selected to promote sleep management (e.g., to provide drug-free promotion of longer and more restful sleep) in the subject upon and/or following the delivering of the mechanical wave to the subject.

In another aspect, the invention is directed to a kit comprising the device of any one of the aspects or embodiments described herein and a label indicating that the device is to be used for promoting sleep management (e.g., to provide drug-free promotion of longer and more restful sleep).

In one aspect, the invention is directed to a method of reducing stress induced ringing in ears of a subject, the method comprising transcutaneously delivering mechanical stimulation to the subject using a mechanical wave having a vibrational waveform selected to reduce stress induced ringing in the ears of the subject upon and/or following the delivering of the mechanical wave to the subject.

In another aspect, the invention is directed to a kit comprising the device of any one of the aspects and embodiments described herein and a label indicating that the device is to be used for reducing stress induced ringing in ears.

In another aspect, the invention is directed to a method of enhancing sexual function in a subject, the method comprising transcutaneously delivering mechanical stimulation to the subject using a mechanical wave having a vibrational waveform selected to enhance sexual function in the subject upon and/or following the delivering of the mechanical wave to the subject.

In another aspect, the invention is directed to a kit comprising the device of any one of the aspects and embodiments described herein and a label indicating that the device is to be used for enhancing sexual function.

In another aspect, the invention is directed to a method of enhancing libido, sexual arousal, and/or orgasm in a subject, the method comprising transcutaneously delivering mechanical stimulation to the subject using a mechanical wave having a vibrational waveform selected to enhance libido, sexual arousal, and/or orgasm in the subject upon and/or following the delivering of the mechanical wave to the subject.

In another aspect, the invention is directed to a kit comprising the device of any one of the aspects and embodiments described herein and a label indicating that the device is to be used for enhancing libido, sexual arousal, and/or orgasm.

In another aspect, the invention is directed to a method of reducing blushing in a subject, the method comprising transcutaneously delivering mechanical stimulation to the subject using a mechanical wave having a vibrational waveform selected to reduce blushing in the subject upon and/or following the delivering of the mechanical wave to the subject.

In another aspect, the invention is directed to a kit comprising the device of any one of the aspects and embodiments described herein and a label indicating that the device is to be used for reducing blushing.

In another aspect, the invention is directed to a method of adjusting (e.g., controlling) a level of a stress hormone [e.g., cortisol (e.g., reducing a cortisol level); e.g., oxytocin (e.g., increasing an oxytocin level); e.g., serotonin (e.g., increasing a serotonin level] in a subject, the method comprising transcutaneously delivering mechanical stimulation to the subject using a mechanical wave having a vibrational waveform selected to reduce the level of the stress hormone in the subject upon and/or following the delivering of the mechanical wave to the subject.

In another aspect, the invention is directed to a kit comprising the device of any one of the aspects and embodiments described herein and a label indicating that the device is to be used for reducing stress in a user as measured by a level of a stress hormone [e.g., cortisol (e.g., reducing a cortisol level); e.g., oxytocin (e.g., increasing an oxytocin level); e.g., serotonin (e.g., increasing a serotonin level)] for the subject.

In another aspect, the invention is directed to a method of a subject by providing transcutaneous mechanical stimulation (e.g., non-invasive mechanical stimulation) to one or more nerves and/or mechanoreceptors of the subject via a stimulation device (e.g., a wearable device), in combination with one or more rounds of a therapy [e.g., psychotherapy; e.g., exposure therapy (e.g., for treatment of various phobias such as fear of heights, fear of public speaking, social phobia, panic attack, fear of flying, germ phobia, and the like); e.g., cognitive behavioral therapy (CBT); e.g., acceptance and commitment therapy (ACT)] the method comprising: generating a mechanical wave by a mechanical transducer of the stimulation device in response to an applied electronic drive signal; controlling a waveform of the electronic drive signal by a controller board (e.g., a controller board of the wearable stimulation device; e.g., a remote controller board); and delivering the mechanical wave to a body location of the subject via the stimulation device at one or more times each in proximity to and/or during a round of the therapy received by the subject [e.g., prior to the round of therapy (e.g., such that the subject is in a more relaxed state prior to the round of the therapy; e.g., such that the subject is in a more responsive state prior to the round of the therapy; e.g., such that the subject is more open to an exposure; e.g., such that the subject is in a state of improved receptiveness and/or readiness to change); e.g., during the round of the therapy; e.g., following (e.g., immediately following) the round of the therapy; e.g., in between two or more rounds of therapy], thereby providing the transcutaneous mechanical stimulation of the one or more nerves and/or mechanoreceptors of the subject in combination with one or more rounds of the therapy.

In another aspect, the invention is directed to a transcutaneous neuromodulation device [e.g., a wearable device; e.g., a non-invasive device (e.g., not comprising any components that penetrate skin)] for treating anxiety and/or an anxiety related disorder in a subject by promoting nerve stimulation through mechanical vibration, comprising: one or more mechanical transducers, a battery, and one or more controller boards, wherein the one or more mechanical transducers, the battery and the one or more controller boards are in communication (e.g., through one or more connectors; e.g., wirelessly), and wherein the controller board controls waveform output through the one or more mechanical transducers, thereby producing mechanical vibration, and wherein the waveform output comprises an isochronic wave In certain embodiments, the device promotes stimulation (e.g., wherein the waveform is selected to promote stimulation) of one or more nerves [e.g., a vagus nerve; e.g., a trigeminal nerve; e.g., peripheral nerves; e.g., a greater auricular nerve; e.g., a lesser occipital nerve; e.g., one or more cranial nerves (e.g., cranial nerve VII; e.g., cranial nerve IX; e.g., cranial nerve XI; e.g., cranial nerve XII)]. In certain embodiments, the one or more nerves comprises a vagus nerve and/or a trigeminal nerve. In certain embodiments, the one or more nerves comprises a C-tactile afferent.

In certain embodiments, the device promotes stimulation of (e.g., wherein the waveform is selected to promote stimulation of) one or more mechanoreceptors and/or cutaneous sensory receptors in the skin (e.g., to stimulate an afferent sensory pathway and use properties of receptive fields to propagate stimulation through tissue and bone). In certain embodiments, the one or more mechanoreceptors and/or cutaneous sensory receptors comprise Piezo2 protein and/or Merkel cells.

In certain embodiments, the one or more controller boards modulate the waveform output to introduce particular signals that include active or inactive pulse durations and frequencies configured to accommodate particular mechanoreceptor recovery periods, adaptation times, inactivation times, sensitization and desensitization times, or latencies.

In certain embodiments, the one or more controller boards modulate the waveform output to enhance or inhibit the expression of presynaptic molecules essential for synaptic vesicle release in neurons. In certain embodiments, the one or more controller boards modulate the waveform output to enhance or inhibit the expression of neuroactive substances that can act as fast excitatory neurotransmitters or neuromodulators.

In certain embodiments, the one or more controller boards modulates the waveform output to stimulate mechanoreceptor cell associated with M-fibers and C-fibers (e.g., including C tactile fibers) in order to stimulate nociceptive, thermoceptive and other pathways modulated by these fibers.

In certain embodiments, the one or more controller boards modulate the waveform output using dynamical systems methods to produce a preferred response in neural network dynamics (e.g., via modulation of signal timing).

In certain embodiments, the one or more controller boards modulates the waveform output using dynamical systems measures to assess response signals (e.g., electronic) to detect particular network responses correlated with changes in mechanical wave properties (e.g., and modulates the waveform output to target/optimally enhance particular preferred responses).

In certain embodiments, the device comprises an adhesive (e.g., a biocompatible adhesive) for adhering at least one of the one or more mechanical transducers (e.g., up to all) to a subject [e.g., skin (e.g., on a neck of; e.g., overlaying at least one mastoid process of; e.g., of an outer or posterior of at least one ear of) a human subject] (e.g., wherein the at least one mechanical transducer is embedded within the adhesive; e.g., wherein the at least one mechanical transducer is surrounded by the adhesive).

In certain embodiments, device comprises one or more ergonomic support components, wherein the one or more transducers are supported by (e.g., housed within; e.g., mounted on) the one or more ergonomic support component(s) (e.g., collectively) and the one or more ergonomic support component(s) is/are formed (e.g., molded) to maintain the transducer in substantial proximity to one or more mastoid regions of a human subject (e.g., by maintaining substantial contact with skin overlaying the one or more mastoid regions).

In certain embodiments, the device comprises a first ergonomic support component, the first ergonomic support component comprising: (a) a first housing comprising a casing (e.g., molded casing) of sufficient size to at least partially house (i) a first transducer set comprising at least a portion (e.g., half; e.g., all) of the one or more mechanical transducers and (ii) a first controller board set comprising at least a portion (e.g., half; e.g., all) of the one or more controller boards, wherein the first transducer set is disposed adjacent to a window in the first housing [e.g., an insulated region of the first housing that contacts skin of the human subject in substantial proximity to a first mastoid region (e.g., on a first (e.g., left; e.g., right) side of head of the subject); e.g., wherein the window comprises fabric, adhesive, etc. placed in between a surface of the transducers of the first transducer set and skin of the subject so as to prevent direct contact with skin]; and (b) a first elastomeric arm comprising a resilient material and formed (e.g., molded) to engage an first ear of the subject and thereby support (e.g., fully) the first housing (e.g., and first transducer set and first controller board set housed therein), wherein the first housing is coupled to a distal end of the first elastomeric arm, wherein the distal end of the first elastomeric arm substantially aligns the window of the first housing with a first body location on the subject in substantial proximity to a first mastoid region (e.g., on a first side of the subject's head; e.g., on a left side; e.g., on a right side), and wherein the resilient material provides a force to hold the first housing against the first body location.

In certain embodiments, the device further comprises a second ergonomic support component, the second ergonomic support component comprising: (a) a second housing comprising a casing (e.g., molded casing) of sufficient size to at least partially house (i) a second transducer set comprising at least a portion (e.g., half; e.g., all) of the one or more mechanical transducers and (ii) a second controller board set comprising at least a portion (e.g., half; e.g., all) of the one or more controller boards, wherein the second transducer set is disposed adjacent to a window in the second housing [e.g., an insulated region of the second housing that contacts skin of the human subject in substantial proximity to a second mastoid region (e.g., on a second (e.g., left; e.g., right) side of head of the subject); e.g., wherein the window comprises fabric, adhesive, etc. placed in between a surface of the transducers of the second transducer set and skin of the subject so as to prevent direct contact with skin]; and (b) a second elastomeric arm comprising a resilient material and formed (e.g., molded) to engage an ear of the subject and thereby support (e.g., fully) the second housing (e.g., and second transducer set and second controller board set housed therein), wherein the second housing is coupled to a distal end of the second elastomeric arm, wherein the distal end of the second elastomeric arm substantially aligns the window of the second housing with a second body location on the subject in substantial proximity to a second mastoid region (e.g., on a second side of the subject's head; e.g., on a right side; e.g., on a left side), and wherein the resilient material provides a force to hold the second housing against the second body location.

In certain embodiments, the first and second ergonomic support components are in wireless communication with each other (e.g., via near-field magnetic induction (NFMI) e.g., so as to avoid/overcome interference from the subject's head) for synchronizing delivery of the mechanical vibration to the first and second mastoid regions of the subject (e.g., for synchronizing delivery of a first mechanical vibration produced by the first transducer set and delivery of a second mechanical vibration produced by the second transducer set).

In certain embodiments, the one or more ergonomic support components comprises: a linkage component formed to engage (e.g., wrap around a top of) a head of the subject; two housings disposed at opposite ends of the linkage component so as to be positioned on opposite sides of the head of the subject, wherein each housing comprising a casing (e.g., a molded casing) of sufficient size to at least partially house a corresponding transducer set comprising at least a portion (e.g., one; e.g., half; e.g., all) of the one or more mechanical transducers, wherein the mechanical transducers are disposed adjacent to a window in each housing; and two elastomeric hinges, each disposed at the opposite ends of the linkage component and mounted to flexibly couple a housings to the linkage component, wherein at least one of the elastomeric hinges is formed and positioned to substantially align the window of each housing with and against opposing mastoid regions on opposite sides of the head of the subject.

In certain embodiments, the linkage component comprises an adjustment mechanism comprising two partially overlaid, interlocking, and sliding curved arms (e.g., curved elastomeric arms), wherein said curved arms are maintained in alignment with each other to form an arc (e.g., approximately matching an average arc of a human head) and slide with respect to each other so as to vary an amount of overlap, thereby varying a size of the arc (e.g., to match different size human heads), and wherein the two elastomeric hinges are disposed on opposing ends of the arc formed by the two sliding arms.

In certain embodiments, the device comprises at least one transducer array comprising a plurality of (e.g., two or more) mechanical transducers maintained in a fixed spatial arrangement in relation to each other (e.g., in substantial proximity to each other; e.g., spaced along a straight or curved line segment) and wherein at least a portion of the one or more controller boards (e.g., a single controller board; e.g., two or more controller boards) are in communication with the mechanical transducers of the transducer array to control output of the mechanical transducers of the transducer array in relation to each other [e.g., wherein the at least a portion of the one or more controller boards synchronizes mechanical vibration produced by each mechanical transducer of the transducer array (e.g., such that each mechanical transducer begins and/or ends producing mechanical vibration at a particular delay with respect to one or more other mechanical transducers of the array; e.g., such that the mechanical transducers are sequentially triggered, one after the other; e.g., wherein the mechanical transducers are spaced along a straight or curved line segment and triggered sequentially along the line segment, such that an apparent source of mechanical vibration moves along the line segment to mimic a stroking motion)] [e.g., wherein a first portion of the mechanical transducers outputs a different frequency mechanical vibration from a second portion of the mechanical transducers of the transducer array (e.g., wherein each mechanical transducer of the transducer array outputs a different frequency mechanical vibration)].

In certain embodiments, the transducer is a linear transducer (e.g., operable to produce mechanical vibration comprising a longitudinal component (e.g., a longitudinal vibration)).

In certain embodiments, the device is incorporated into a headphone (e.g., an in-ear headphone; e.g., an over-the-ear headphone).

In certain embodiments, the device comprises a receiver in communication with the one or more controller boards, wherein the receiver is operable to receive a signal from and/or transmit a signal (e.g., wirelessly; e.g., via a wired connection) to a personal computing device (e.g., a smart phone; e.g., a personal computer; e.g., a laptop computer; e.g., a tablet computer; e.g., a smartwatch; e.g., a fitness tracker; e.g., a smart charger)(e.g., to upload new waveforms and/or settings for waveforms).

In certain embodiments, the one or more controller boards is/are operable to modulate and/or select the waveform output in response to (e.g., based on) the signal received from the personal computing device by the receiver.

In certain embodiments, the device is non-invasive (e.g., does not comprise any components for penetrating skin).

In certain embodiments, the device comprises a secondary stimulation device for providing one or more external stimulus/stimuli (e.g., visual stimulus; e.g., acoustic stimulus; e.g., limbic priming; e.g., a secondary tactile signal).

In certain embodiments, the isochronic wave comprises a frequency component ranging from 5 to 15 Hz (e.g., ranging from approximately 7 to approximately 13 Hz; e.g., a frequency range matching an alpha brain wave frequency range; e.g., approximately 10 Hz).

In certain embodiments, the isochronic wave comprises a frequency component ranging from 0 to 49 Hz (e.g., from 18 to 48 Hz; e.g., from 15 to 40 Hz; e.g. from 8 to 14 Hz).

In certain embodiments, one or more low-amplitude sub-intervals of the isochronic wave have a duration of greater than or approximately two seconds (e.g., wherein the one or more low-amplitude sub-intervals have a duration of approximately two seconds; e.g., wherein the one or more low-amplitude sub-intervals have a duration ranging from approximately two seconds to approximately 10 seconds; e.g., wherein the one or more low amplitude sub-intervals have a duration ranging from approximately two seconds to approximately 4 seconds).

In certain embodiments, the isochronic wave comprises a carrier wave [e.g., a periodic wave having a substantially constant frequency (e.g., ranging from 5 to 15 Hz; e.g., ranging from approximately 7 to approximately 13 Hz; e.g., a frequency range matching an alpha brain wave frequency range; e.g., approximately 10 Hz)] modulated by an envelope function having one or more low-amplitude sub-intervals [e.g., a periodic envelope function (e.g., a square wave; e.g., a 0.5 Hz square wave); e.g., the one or more low-amplitude sub-intervals having a duration of greater than or approximately equal to two seconds; e.g., the one or more low-amplitude sub-intervals having a duration of approximately two seconds].

In certain embodiments, the isochronic wave is also a transformed time-varying wave. In certain embodiments, the isochronic wave comprises a chirped wave. In certain embodiments, the waveform output comprises a transformed time-varying wave having a functional form corresponding to a carrier wave within an envelope {e.g., wherein the transformed-time varying wave is the carrier wave and is further modulated by an envelope [e.g., wherein the envelope is a sinusoidal wave; e.g., wherein the envelope has a monotonically increasing (in time) amplitude (e.g., wherein the envelope has a functional form corresponding to an increasing (in time) exponential)]; e.g., wherein the transformed time-varying wave is the envelope that modulates a carrier wave [e.g., wherein the carrier wave is a periodic wave (e.g., a sinusoidal wave; e.g., a square wave; e.g., a sawtooth wave)(e.g., having a higher frequency than the envelope)]}.

In certain embodiments, a functional form of the waveform output is based on one or more recorded natural sounds (e.g., running water; e.g., ocean waves; e.g., purring; e.g., breathing; e.g., chanting; e.g., gongs; e.g., bells).

In certain embodiments, the device comprises a receiver in communication with the one or more controller boards, wherein the receiver is operable to receive a signal from and/or transmit a signal to a monitoring device (e.g., directly from and/or to the monitoring device; e.g., via one or more intermediate server(s) and/or computing device(s))(e.g., a wearable monitoring device; e.g., a personal computing device; e.g., a fitness tracker; e.g., a heart-rate monitor; e.g., an electrocardiograph (EKG) monitor; e.g., an electroencephalography (EEG) monitor; e.g., an accelerometer; e.g., a blood-pressure monitor; e.g., a galvanic skin response (GSR) monitor) and wherein the one or more controller boards is/are operable to modulate and/or select the waveform output in response to (e.g., based on) the signal from the wearable monitoring device received by the receiver.

In certain embodiments, the device is operable to record usage data (e.g., parameters such as a record of when the device was used, duration of use, etc.) and/or one or more biofeedback signals for a human subject [e.g., wherein the device comprises one or more sensors, each operable to measure and record one or more biofeedback signals (e.g., a galvanic skin response (GSR) sensor; e.g., a heart-rate monitor; e.g., an accelerometer)] [e.g., wherein the device is operable to store the recorded usage data and/or biofeedback signals for further processing and/or transmission to an external computing device, e.g., for computation (e.g., using a machine learning algorithm that receives the one or more biofeedback signals as input, along with, optionally, user reported information) and display of one or more performance metrics (e.g., a stress index) to a subject using the device].

In certain embodiments, the one or more controller boards is/are operable to automatically modulate and/or select the waveform output in response to (e.g., based on) the recorded usage data and/or biofeedback signals (e.g., using a machine learning algorithm that receives the one or more biofeedback signals as input, along with, optionally, user reported information, to optimize the waveform output).

In certain embodiments, a level [e.g., amplitude (e.g., a force; e.g., a displacement)] of at least a portion of the mechanical vibration is based on activation thresholds of one or more target cells and/or proteins (e.g., mechanoreceptors (e.g., C tactile afferents); e.g., nerves; e.g., sensory thresholds corresponding to a level of tactile sensation) [e.g., wherein the one or more controller boards modulate the waveform output based on sub-activation thresholds (e.g., accounting for the response of the mechanical transducers)].

In certain embodiments, an amplitude of the mechanical vibration corresponds to a displacement ranging from 1 micron to 10 millimeters (e.g., approximately 25 microns) (e.g., wherein the amplitude is adjustable over the displacement ranging from 1 micron to 10 millimeters) [e.g., wherein the amplitude corresponds to a force of approximately 0.4N] [e.g., thereby matching the amplitude to activation thresholds of C tactile afferents].

In certain embodiments, the isochronic wave comprises one or more components (e.g., additive noise; e.g., stochastic resonance signals) that, when transduced by the transducer to produce the mechanical wave, correspond to sub-threshold signals that are below an activation threshold of one or more target cells and/or proteins (e.g., below a level of tactile sensation).

In certain embodiments, the isochronic wave comprises one or more components (e.g., additive noise; e.g., stochastic resonance signals) that, when transduced by the transducer to produce the mechanical wave, correspond to supra-threshold signals that are above an activation threshold of one or more target cells and/or proteins (e.g., above a level of tactile sensation).

In another aspect, the invention is directed to a transcutaneous neuromodulation device [e.g., a wearable device; e.g., a non-invasive device (e.g., not comprising any components that penetrate skin)] for treating anxiety and/or an anxiety related disorder in a human subject by promoting nerve stimulation through mechanical vibration, comprising: one or more mechanical transducers, a battery, and one or more controller boards, wherein the one or more mechanical transducers, the battery and the one or more controller boards are in communication (e.g., through one or more connectors; e.g., wirelessly), and wherein the one or more controller boards control waveform output through the one or more mechanical transducers, and the one or more mechanical transducers transcutaneously stimulate one or more nerves of a human subject and wherein the waveform output comprises an isochronic wave.

In another aspect, the invention is directed to a transcutaneous stimulation device [e.g., a wearable device; e.g., a non-invasive device (e.g., not comprising any components that penetrate skin)] for treating anxiety and/or an anxiety related disorder in a human subject by promoting mechanoreceptor stimulation through mechanical vibration, comprising: one or more mechanical transducers, a battery, and one or more controller boards, wherein the one or more mechanical transducers, the battery and the one or more controller boards are in communication (e.g., through one or more connectors; e.g., wirelessly), and wherein the one or more controller boards control waveform output through the transducer, and the one or more mechanical transducers transcutaneously stimulate one or more mechanoreceptors of a human subject and wherein the waveform output comprises an isochronic wave.

In another aspect, the invention is directed to a method of treating anxiety and/or an anxiety related disorder in a subject by providing transcutaneous mechanical stimulation (e.g., non-invasive mechanical stimulation) to the subject via a stimulation device (e.g., a wearable device), the method comprising: generating a mechanical wave by a mechanical transducer of the stimulation device in response to an applied electronic drive signal; controlling a waveform of the electronic drive signal by a controller board (e.g., a controller board of the stimulation device; e.g., a remote controller board), wherein the waveform comprises an isochronic wave; and delivering the mechanical wave to a body location of the subject via the stimulation device, thereby providing the transcutaneous mechanical stimulation to the subject.

In certain embodiments, the mechanical wave promotes stimulation (e.g., wherein the waveform is selected to promote stimulation) of one or more nerves [e.g., a vagus nerve; e.g., a trigeminal nerve; e.g., peripheral nerves; e.g., a greater auricular nerve; e.g., a lesser occipital nerve; e.g., one or more cranial nerves (e.g., cranial nerve VII; e.g., cranial nerve IX; e.g., cranial nerve XI; e.g., cranial nerve XII)]. In certain embodiments, the one or more nerves comprises a vagus nerve and/or a trigeminal nerve. In certain embodiments, the one or more nerves comprises a C-tactile afferent.

In certain embodiments, the mechanical wave promotes stimulation of (e.g., wherein the waveform is selected to promote stimulation of) one or more mechanoreceptors and/or cutaneous sensory receptors in the skin (e.g., to stimulate an afferent sensory pathway and use properties of receptive fields to propagate stimulation through tissue and bone). In certain embodiments, the one or more mechanoreceptors and/or cutaneous sensory receptors comprise Piezo2 protein and/or Merkel cells.

In certain embodiments, the controlling the waveform of the electronic drive signal comprises modulating the waveform to introduce particular signals that include active or inactive pulse durations and frequencies configured to accommodate particular mechanoreceptor recovery periods, adaptation times, inactivation times, sensitization and desensitization times, or latencies.

In certain embodiments, the controlling the waveform of the electronic drive signal comprises modulating the waveform to enhance or inhibit the expression of presynaptic molecules essential for synaptic vesicle release in neurons.

In certain embodiments, the controlling the waveform of the electronic drive signal comprises modulating the waveform to enhance or inhibit the expression of neuroactive substances that can act as fast excitatory neurotransmitters or neuromodulators.

In certain embodiments, the controlling the waveform of the electronic drive signal comprises modulating the waveform to stimulate mechanoreceptor cells associated with Aδ-fibers and C-fibers (e.g., including C tactile fibers) in order to stimulate nociceptive, thermoceptive, interoceptive and/or other pathways modulated by these fibers.

In certain embodiments, the controlling the waveform of the electronic drive signal comprises modulating the waveform using dynamical systems methods to produce a preferred response in neural network dynamics (e.g., via modulation of signal timing).

In certain embodiments, the controlling the waveform of the electronic drive signal comprises modulating the waveform using dynamical systems measures to assess response signals (e.g., electronic) to detect particular network responses correlated with changes in mechanical wave properties (e.g., and modulates the waveform output to target/ optimally enhance particular preferred responses).

In certain embodiments, the delivering the mechanical wave to the body location comprises contacting the mechanical transducer to a surface (e.g., skin) of the subject at the body location.

In certain embodiments, the contacting the mechanical transducer to the surface of the subject at the body location comprises using an adhesive (e.g., a biocompatible adhesive) for adhering at least one of the one or more mechanical transducers (e.g., up to all) to a subject [e.g., skin (e.g., on a neck of; e.g., overlaying at least one mastoid process of; e.g., of an outer or posterior of at least one ear of) a human subject] (e.g., wherein the at least one mechanical transducer is embedded within the adhesive; e.g., wherein the at least one mechanical transducer is surrounded by the adhesive).

In certain embodiments, the contacting the mechanical transducer to the surface of the subject at the body location comprises using one or more ergonomic support components, wherein the one or more transducers are supported by (e.g., housed within; e.g., mounted on) the one or more ergonomic support component(s) (e.g., collectively) and the one or more ergonomic support component(s) is/are formed (e.g., molded) to maintain the transducer in substantial proximity to one or more mastoid regions of a human subject (e.g., by maintaining substantial contact with skin overlaying the one or more mastoid regions).

In certain embodiments, the one or more ergonomic support components comprise(s) a first ergonomic support component, the first ergonomic support component comprising: (a) a first housing comprising a casing (e.g., molded casing) of sufficient size to at least partially house (i) a first transducer set comprising at least a portion (e.g., half; e.g., all) of the one or more mechanical transducers and (ii) a first controller board set comprising at least a portion (e.g., half; e.g., all) of the one or more controller boards, wherein the first transducer set is disposed adjacent to a window in the first housing [e.g., an insulated region of the first housing that contacts skin of the human subject in substantial proximity to a first mastoid region (e.g., on a first (e.g., left; e.g., right) side of head of the subject); e.g., wherein the window comprises fabric, adhesive, etc. placed in between a surface of the transducers of the first transducer set and skin of the subject so as to prevent direct contact with skin]; and (b) a first elastomeric arm comprising a resilient material and formed (e.g., molded) to engage an first ear of the subject and thereby support (e.g., fully) the first housing (e.g., and first transducer set and first controller board set housed therein), wherein the first housing is coupled to a distal end of the first elastomeric arm, wherein the distal end of the first elastomeric arm substantially aligns the window of the first housing with a first body location on the subject in substantial proximity to a first mastoid region (e.g., on a first side of the subject's head; e.g., on a left side; e.g., on a right side), and wherein the resilient material provides a force to hold the first housing against the first body location.

In certain embodiments, the one or more ergonomic support components further comprise(s) a second ergonomic support component, the second ergonomic support component comprising: (a) a second housing comprising a casing (e.g., molded casing) of sufficient size to at least partially house (i) a second transducer set comprising at least a portion (e.g., half; e.g., all) of the one or more mechanical transducers and (ii) a second controller board set comprising at least a portion (e.g., half; e.g., all) of the one or more controller boards, wherein the second transducer set is disposed adjacent to a window in the second housing [e.g., an insulated region of the second housing that contacts skin of the human subject in substantial proximity to a second mastoid region (e.g., on a second (e.g., left; e.g., right) side of head of the subject); e.g., wherein the window comprises fabric, adhesive, etc. placed in between a surface of the transducers of the second transducer set and skin of the subject so as to prevent direct contact with skin]; and (b) a second elastomeric arm comprising a resilient material and formed (e.g., molded) to engage an ear of the subject and thereby support (e.g., fully) the second housing (e.g., and second transducer set and second controller board set housed therein), wherein the second housing is coupled to a distal end of the second elastomeric arm, wherein the distal end of the second elastomeric arm substantially aligns the window of the second housing with a second body location on the subject in substantial proximity to a second mastoid region (e.g., on a second side of the subject's head; e.g., on a right side; e.g., on a left side), and wherein the resilient material provides a force to hold the second housing against the second body location.

In certain embodiments, the first and second ergonomic support components are in wireless communication with each other (e.g., via near-field magnetic induction (NFMI) e.g., so as to avoid/overcome interference from the subject's head) for synchronizing delivery of the mechanical vibration to the first and second mastoid regions of the subject (e.g., for synchronizing delivery of a first mechanical vibration produced by the first transducer set and delivery of a second mechanical vibration produced by the second transducer set).

In certain embodiments, the one or more ergonomic support components comprises: a linkage component formed to engage (e.g., wrap around a top of) a head of the subject; two housings disposed at opposite ends of the linkage component so as to be positioned on opposite sides of the head of the subject, wherein each housing comprising a casing (e.g., a molded casing) of sufficient size to at least partially house a corresponding transducer set comprising at least a portion (e.g., one; e.g., half; e.g., all) of the one or more mechanical transducers, wherein the mechanical transducers are disposed adjacent to a window in each housing; and two elastomeric hinges, each disposed at the opposite ends of the linkage component and mounted to flexibly couple a housings to the linkage component, wherein at least one of the elastomeric hinges is formed and positioned to substantially align the window of each housing with and against opposing mastoid regions on opposite sides of the head of the subject.

In certain embodiments, the linkage component comprises an adjustment mechanism comprising two partially overlaid, interlocking, and sliding curved arms (e.g., curved elastomeric arms), wherein said curved arms are maintained in alignment with each other to form an arc (e.g., approximately matching an average arc of a human head) and slide with respect to each other so as to vary an amount of overlap, thereby varying a size of the arc (e.g., to match different size human heads), and wherein the two elastomeric hinges are disposed on opposing ends of the arc formed by the two sliding arms.

In certain embodiments, the mechanical transducer is a member of a transducer array comprising a plurality of (e.g., two or more) mechanical transducers maintained in a fixed spatial arrangement in relation to each other (e.g., in substantial proximity to each other; e.g., spaced along a straight or curved line segment) and wherein the controller board controls output of the mechanical transducer in relation to other mechanical transducers of the array [e.g., so as to synchronize mechanical vibration produced by each mechanical transducer of the transducer array (e.g., such that each mechanical transducer begins and/or ends producing mechanical vibration at a particular delay with respect to one or more other mechanical transducers of the array; e.g., such that the mechanical transducers are sequentially triggered, one after the other; e.g., wherein the mechanical transducers are spaced along a straight or curved line segment and triggered sequentially along the line segment, such that an apparent source of mechanical vibration moves along the line segment to mimic a stroking motion)] [e.g., wherein a first portion of the mechanical transducers outputs a different frequency mechanical vibration from a second portion of the mechanical transducers of the transducer array (e.g., wherein each mechanical transducer of the transducer array outputs a different frequency mechanical vibration)].

In certain embodiments, the transducer is a linear transducer (e.g., operable to produce mechanical vibration comprising a longitudinal component (e.g., a longitudinal vibration)).

In certain embodiments, the mechanical transducer is incorporated into a headphone (e.g., an in-ear headphone; e.g., an over-the-ear headphone).

In certain embodiments, the controlling the waveform of the electronic drive signal comprises receiving (e.g., by a receiver in communication with the controller board) a signal from a personal computing device (e.g., a smart phone; e.g., a personal computer; e.g., a laptop computer; e.g., a tablet computer; e.g., a smartwatch; e.g., a fitness tracker; e.g., a smart charger)(e.g., to upload new waveforms and/or settings for waveforms).

In certain embodiments, the controlling the waveform of the electronic drive signal comprises modulating and/or selecting the waveform in response to (e.g., based on) the signal received from the personal computing device by the receiver.

In certain embodiments, the delivering the mechanical wave to the body location is performed in a non-invasive fashion (e.g., without penetrating skin of the subject).

In certain embodiments, the method comprising providing, by a secondary stimulation device, one or more external stimulus/stimuli (e.g., visual stimulus; e.g., acoustic stimulus; e.g., limbic priming; e.g., a secondary tactile signal).

In certain embodiments, the isochronic wave comprises a frequency component ranging from 5 to 15 Hz (e.g., ranging from approximately 7 to approximately 13 Hz; e.g., a frequency range matching an alpha brain wave frequency range; e.g., approximately 10 Hz).

In certain embodiments, the isochronic wave comprises a frequency component ranging from 0 to 49 Hz (e.g., from 18 to 48 Hz; e.g., from 15 to 40 Hz; e.g. from 8 to 14 Hz).

In certain embodiments, one or more low-amplitude sub-intervals of the isochronic wave have a duration of greater than or approximately two seconds (e.g., wherein the one or more low-amplitude sub-intervals have a duration of approximately two seconds; e.g., wherein the one or more low-amplitude sub-intervals have a duration ranging from approximately two seconds to approximately 10 seconds; e.g., wherein the one or more low amplitude sub-intervals have a duration ranging from approximately two seconds to approximately 4 seconds).

In certain embodiments, the isochronic wave comprises a carrier wave [e.g., a periodic wave having a substantially constant frequency (e.g., ranging from 5 to 15 Hz; e.g., ranging from approximately 7 to approximately 13 Hz; e.g., a frequency range matching an alpha brain wave frequency range; e.g., approximately 10 Hz)] modulated by an envelope function having one or more low-amplitude sub-intervals [e.g., a periodic envelope function (e.g., a square wave; e.g., a 0.5 Hz square wave); e.g., the one or more low-amplitude sub-intervals having a duration of greater than or approximately equal to two seconds; e.g., the one or more low-amplitude sub-intervals having a duration of approximately two seconds].

In certain embodiments, the isochronic wave is also a transformed time-varying wave. In certain embodiments, the isochronic wave comprises a chirped wave. In certain embodiments, the waveform of the electronic drive signal comprises a transformed time-varying wave having a functional form corresponding to a carrier wave within an envelope {e.g., wherein the transformed-time varying wave is the carrier wave and is further modulated by an envelope [e.g., wherein the envelope is a sinusoidal wave; e.g., wherein the envelope has a monotonically increasing (in time) amplitude (e.g., wherein the envelope has a functional form corresponding to an increasing (in time) exponential)]; e.g., wherein the transformed time-varying wave is the envelope that modulates a carrier wave [e.g., wherein the carrier wave is a periodic wave (e.g., a sinusoidal wave; e.g., a square wave; e.g., a sawtooth wave)(e.g., having a higher frequency than the envelope)]}. In certain embodiments, a functional form of the waveform of the electronic drive signal is based on one or more recorded natural sounds (e.g., running water; e.g., ocean waves; e.g., purring; e.g., breathing; e.g., chanting; e.g., gongs; e.g., bells).

In certain embodiments, the method comprises receiving an electronic response signal from a monitoring device (e.g., directly from and/or to the monitoring device; e.g., via one or more intermediate server(s) and/or computing device(s)) (e.g., a wearable monitoring device; e.g., a personal computing device; e.g., a fitness tracker; e.g., a heart-rate monitor; e.g., an electrocardiograph (EKG) monitor; e.g., an electroencephalography (EEG) monitor; e.g., an accelerometer; e.g., a blood-pressure monitor; e.g., a galvanic skin response (GSR) monitor) and), and wherein the controlling the waveform of the electronic drive signal comprises adjusting and/or selecting the waveform in response to (e.g., based on) the received electronic response signal.

In certain embodiments, the method comprises recording usage data (e.g., parameters such as a record of when the device was used, duration of use, etc.) and/or one or more biofeedback signals for a human subject [e.g., using one or more sensors, each operable to measure and record one or more biofeedback signals (e.g., a galvanic skin response (GSR) sensor; e.g., a heart-rate monitor; e.g., an accelerometer)] [e.g., storing and/or providing the recorded usage data and/or biofeedback signals for further processing and/or transmission to an external computing device, e.g., for computation (e.g., using a machine learning algorithm that receives the one or more biofeedback signals as input, along with, optionally, user reported information) and display of one or more performance metrics (e.g., a stress index) to a subject].

In certain embodiments, the method comprises automatically modulating and/or selecting the waveform of the electronic drive signal in response to (e.g., based on) the recorded usage data and/or biofeedback signals (e.g., using a machine learning algorithm that receives the one or more biofeedback signals as input, along with, optionally, user reported information, to optimize the waveform output).

In certain embodiments, a level [e.g., amplitude (e.g., a force; e.g., a displacement)] of at least a portion of the mechanical wave is (e.g., modulated and/or selected) based on activation thresholds of one or more target cells and/or proteins (e.g., mechanoreceptors (e.g., C tactile afferents); e.g., nerves; e.g., sensory thresholds corresponding to a level of tactile sensation) [e.g., wherein the one or more controller boards modulate the waveform output based on sub-activation thresholds (e.g., accounting for the response of the mechanical transducers)].

In certain embodiments, an amplitude of the mechanical wave corresponds to a displacement ranging from 1 micron to 10 millimeters (e.g., approximately 25 microns)(e.g., wherein the amplitude is adjustable over the displacement ranging from 1 micron to 10 millimeters)[e.g., wherein the amplitude corresponds to a force of approximately 0.4N] [e.g., thereby matching the amplitude to activation thresholds of C tactile afferents].

In another aspect, the invention is directed to a method of treating anxiety and/or an anxiety related disorder in a subject by providing transcutaneous mechanical stimulation (e.g., non-invasive mechanical stimulation) to the subject via a stimulation device (e.g., a wearable device), the method comprising: generating a mechanical wave by a mechanical transducer of the stimulation device in response to an applied electronic drive signal; controlling a waveform of the electronic drive signal by a controller board (e.g., a controller board of the stimulation device; e.g., a remote controller board); and delivering the mechanical wave to a body location of the subject via the stimulation device, wherein the body location is in proximity to a mastoid of the subject (e.g., wherein the mastoid lies directly beneath the body location), thereby providing the transcutaneous mechanical stimulation to the subject.

In another aspect, the invention is directed to a method of treating anxiety and/or an anxiety related disorder in a subject by providing transcutaneous mechanical stimulation (e.g., non-invasive mechanical stimulation) to one or more nerves of the subject via a stimulation device (e.g., a wearable device), the method comprising: generating a mechanical wave by a mechanical transducer of the stimulation device in response to an applied electronic drive signal; controlling a waveform of the electronic drive signal by a controller board (e.g., of the stimulation device; e.g., a remote controller board); and delivering the mechanical wave to a body location of the subject via the wearable stimulation device, thereby stimulating the one or more nerves, wherein the one or more nerves comprise(s) a cranial nerve (e.g., vagus nerve; e.g., trigeminal nerve; e.g., facial nerve) of the subject.

In another aspect, the invention is directed to a method of treating anxiety and/or an anxiety related disorder in a subject by providing transcutaneous mechanical stimulation (e.g., non-invasive mechanical stimulation) to one or more nerves and/or mechanoreceptors of the subject via a stimulation device (e.g., a wearable device), the method comprising: generating a mechanical wave by a mechanical transducer of the stimulation device in response to an applied electronic drive signal; controlling a waveform of the electronic drive signal by a controller board (e.g., a controller board of the wearable stimulation device; e.g., a remote controller board), wherein the waveform comprises a frequency component ranging from approximately 5 Hz to 15 Hz (e.g., approximately 10 Hz; e.g., ranging from approximately 7 Hz to approximately 13 Hz; e.g., a frequency range matching an alpha brain wave frequency); and delivering the mechanical wave to a body location of the subject via the stimulation device, thereby providing the transcutaneous mechanical stimulation of the one or more nerves and/or mechanoreceptors of the subject.

In another aspect, the invention is directed to a method of treating anxiety and/or an anxiety related disorder in a subject by providing transcutaneous mechanical stimulation (e.g., non-invasive mechanical stimulation) to the subject via a stimulation device (e.g., a wearable device), the method comprising: generating a mechanical wave by a mechanical transducer of the stimulation device in response to an applied electronic drive signal; receiving an electronic response signal from a monitoring device (e.g., a wearable monitoring device) operable to monitor one or more physiological signals from the subject and generate, in response to the one or more physiological signals from the subject, the electronic response signal (e.g., wherein the electronic response signal is received directly from the monitoring device; e.g., wherein the electronic response signal is received from the wearable monitoring device via one or more intermediate servers and/or processors); responsive to the receiving the electronic response signal, controlling, via a controller board (e.g., a controller board of the stimulation device; e.g., a remote controller board), a waveform of the electronic drive signal to adjust and/or select the waveform based at least in part on the received electronic response signal; and delivering the mechanical wave to a body location of the subject via the stimulation device, thereby providing the transcutaneous mechanical stimulation to the subject.

In another aspect, the invention is directed to a method of treating anxiety and/or an anxiety related disorder in a subject by providing transcutaneous mechanical stimulation (e.g., non-invasive mechanical stimulation) to the subject via a stimulation device (e.g., a wearable device), the method comprising: (a) generating a mechanical wave by a mechanical transducer of the stimulation device in response to an applied electronic drive signal; (b) accessing and/or receiving [e.g., by a processor of a computing device, of and/or in communication with the stimulation device, e.g., an intermediate server and/or processor (e.g., of a mobile computing device in communication with the stimulation device)] subject response data (e.g., entered by the subjects themselves or biofeedback data recorded via sensors) and/or initialization setting data [e.g., physical characteristics of the subject (e.g., age, height, weight, gender, body-mass index (BMI), and the like); e.g., activity levels (e.g., physical activity levels); e.g., biofeedback data recorded by one or more sensors (e.g., included within the device and/or external to and in communication with the device)(e.g., a heart rate; e.g., a galvanic skin response; e.g., physical movement (e.g., recorded by an accelerometer)); e.g., results of a preliminary survey (e.g., entered by the subject themselves, e.g., via a mobile computing device, an app, and/or online portal; e.g., provided by a therapist/physician treating the subject for a disorder)]; (c) responsive to the accessed and/or received subject response data and/or initialization setting data, controlling, via a controller board (e.g., a controller board of the stimulation device; e.g., a remote controller board), a waveform of the electronic drive signal to adjust and/or select the waveform based at least in part on the subject response data and/or initialization setting data (e.g., using a machine learning algorithm that receives one or more biofeedback signals as input, along with, optionally, user reported information, to optimize the waveform output); and (d) delivering the mechanical wave to a body location of the subject via the stimulation device, thereby providing the transcutaneous mechanical stimulation to the subject.

In certain embodiments, step (b) comprises receiving and/or accessing subject response data [e.g., results of a survey recorded for the subject (e.g., entered by the subject themselves, e.g., via a mobile computing device, an app, and/or online portal; e.g., provided by a therapist/physician treating the subject for a disorder); e.g., biofeedback data recorded by one or more sensors (e.g., included within the device and/or external to and in communication with the device)(e.g., a heart rate; e.g., a galvanic skin response; e.g., physical movement (e.g., recorded by an accelerometer))] provided following their receipt of a round (e.g., a duration) of the transcutaneous mechanical stimulation provided by the stimulation device; and step (c) comprises controlling the waveform of the electronic drive signal based at least in part on the subject feedback, thereby modifying the transcutaneous mechanical stimulation provided to the subject based on subject response data.

In another aspect, the invention is directed to a method of treating anxiety and/or an anxiety related disorder in a subject by providing transcutaneous mechanical stimulation (e.g., non-invasive mechanical stimulation) to the subject via a stimulation device (e.g., a wearable device), the method comprising: generating a first mechanical wave by a first mechanical transducer of the stimulation device in response to a first applied electronic drive signal; controlling a first waveform of the first electronic drive signal by a controller board (e.g., a controller board of the stimulation device; e.g., a remote controller board); delivering the first mechanical wave to a first body location (e.g., on a right side; e.g., a location behind a right ear) of the subject via the stimulation device; generating a second mechanical wave by a second mechanical transducer of the stimulation device in response to a second applied electronic drive signal; controlling a second waveform of the second electronic drive signal by the controller board; and delivering the second mechanical wave to a second body location (e.g., on a left side; e.g., a location behind a left ear) of the subject via the stimulation device, thereby providing the transcutaneous mechanical stimulation to the subject.

In another aspect, the invention is directed to a method of treating anxiety and/or an anxiety related disorder in a subject by providing transcutaneous mechanical stimulation (e.g., non-invasive mechanical stimulation) to the subject via a stimulation device (e.g., a wearable device), the method comprising: generating a first mechanical wave by a first mechanical transducer of the stimulation device in response to an applied electronic drive signal; controlling a waveform of the first electronic drive signal by a controller board (e.g., a controller board of the stimulation device; e.g., a remote controller board); delivering the first mechanical wave to a first body location (e.g., on a right side; e.g., a location behind a right ear) of the subject via the stimulation device; generating a second mechanical wave by a second mechanical transducer of the stimulation device in response to the applied electronic drive signal; delivering the second mechanical wave to a second body location (e.g., on a left side; e.g., a location behind a left ear) of the subject via the stimulation device, thereby providing the transcutaneous mechanical stimulation to the subject.

In another aspect, the invention is directed to a method of treating anxiety and/or an anxiety related disorder in a subject by providing transcutaneous mechanical stimulation (e.g., non-invasive mechanical stimulation) to one or more nerves and/or mechanoreceptors of the subject via a stimulation device (e.g., a wearable device), in combination with one or more rounds of a therapy [e.g., psychotherapy; e.g., exposure therapy (e.g., for treatment of various phobias such as fear of heights, fear of public speaking, social phobia, panic attack, fear of flying, germ phobia, and the like); e.g., cognitive behavioral therapy (CBT); e.g., acceptance and commitment therapy (ACT)] the method comprising: generating a mechanical wave by a mechanical transducer of the stimulation device in response to an applied electronic drive signal;

controlling a waveform of the electronic drive signal by a controller board (e.g., a controller board of the wearable stimulation device; e.g., a remote controller board); and delivering the mechanical wave to a body location of the subject via the stimulation device at one or more times each in proximity to and/or during a round of the therapy received by the subject [e.g., prior to the round of therapy (e.g., such that the subject is in a more relaxed state prior to the round of the therapy; e.g., such that the subject is in a more responsive state prior to the round of the therapy; e.g., such that the subject is more open to an exposure; e.g., such that the subject is in a state of improved receptiveness and/or readiness to change); e.g., during the round of the therapy; e.g., following (e.g., immediately following) the round of the therapy; e.g., in between two or more rounds of therapy], thereby providing the transcutaneous mechanical stimulation of the one or more nerves and/or mechanoreceptors of the subject in combination with one or more rounds of the therapy.

In another aspect, the invention is directed to a method of treating anxiety and/or an anxiety related disorder in a subject by stimulating one or more nerves and/or mechanoreceptors of the subject (e.g., a human subject), the method comprising: using any of the devices described herein, for stimulation of the one or more nerves and/or mechanoreceptors of the subject.

In another aspect, the invention is directed to a method of treating anxiety and/or an anxiety related disorder in a human subject by stimulating one or more nerves of the human subject using a transcutaneous, neuromodulation device [e.g., a wearable device; e.g., a non-invasive device (e.g., not comprising any components that penetrate skin)], the device comprising one or more transducers (e.g., mechanical transducers), a battery, connectors, and one or more controller boards, wherein the one or more controller boards control waveform output through the connectors and the transducers, and wherein the transducers transcutaneously applied stimulates the one or more nerves, the method comprising: contacting the one or more transducers of the device to the human subject, generating the waveform output signal, activating the transducers using the waveform output signal (e.g., by applying the waveform output signal to the transducers to generate a mechanical wave), and stimulating the one or more nerves of the human subject, wherein the waveform output comprises an isochronic wave.

In another aspect, the invention is directed to a method of treating anxiety and/or an anxiety related disorder in a human subject by stimulating one or more mechanoreceptors of the human subject using transcutaneous stimulation device [e.g., a wearable device; e.g., a non-invasive device (e.g., not comprising any components that penetrate skin)], the device comprising one or more mechanical transducers, a battery, connectors, and one or more controller boards, wherein the one or more controller boards control waveform output through the connectors and the one or more mechanical transducers, and wherein the one or more mechanical transducers transcutaneously applied stimulate the one or more mechanoreceptors, the method comprising: contacting the one or more mechanical transducers of the device to the human subject, generating the waveform output signal, activating the mechanical transducers using the waveform output signal (e.g., by applying the waveform output signal to the transducers to generate a mechanical wave), and stimulating the one or more mechanoreceptors of the human subject, wherein the waveform output comprises an isochronic wave.

In another aspect, the invention is directed to a method of adjusting (e.g., controlling) a level of a stress hormone [e.g., cortisol (e.g., reducing a cortisol level); e.g., oxytocin (e.g., increasing an oxytocin level); e.g., serotonin (e.g., increasing a serotonin level)] in a subject, the method comprising transcutaneously delivering mechanical stimulation to the subject using a mechanical wave having a vibrational waveform selected to reduce the level of the stress hormone in the subject upon and/or following the delivering of the mechanical wave to the subject.

In another aspect, the invention is directed to a kit comprising the device of any one of the aspects and embodiments described herein and a label indicating that the device is to be used for reducing stress in a user as measured by a level of a stress hormone [e.g., cortisol (e.g., reducing a cortisol level); e.g., oxytocin (e.g., increasing an oxytocin level); e.g., serotonin (e.g., increasing a serotonin level)] for the subject.

In another aspect, the invention is directed to a transcutaneous neuromodulation device [e.g., a wearable device; e.g., a non-invasive device (e.g., not comprising any components that penetrate skin)] for treating a disorder in a subject (e.g., anxiety and/or an anxiety related disorder) by promoting nerve stimulation through mechanical vibration, comprising: one or more mechanical transducers, a battery, and a controller board, wherein the transducer, battery and controller board are in communication (e.g., through one or more connectors; e.g., wirelessly), and wherein the controller board controls waveform output through the transducer, thereby producing a mechanical vibration, and wherein the disorder is a member selected from the group consisting of: agoraphobia, body focused repetitive behaviors, generalized anxiety disorder, health anxiety, hoarding disorder (HD), obsessive-compulsive disorder, panic disorder, post-traumatic stress disorder (PTSD), separation anxiety, social anxiety disorder, a specific phobia (e.g., fear of heights, fear of public speaking, social phobia, panic attack, fear of flying, germ phobia, and the like), acute stress disorder, adjustment disorder with anxious features, substance-induced anxiety disorder, selective mutism in children, somatic symptom disorder, illness anxiety disorder, attention deficit disorder (ADD), attention deficit hyperactivity disorder, autism.

In another aspect, the invention is directed to a method of treating a disorder in a human subject by promoting nerve stimulation in the human subject through mechanical vibration using a transcutaneous, neuromodulation device [e.g., a wearable device; e.g., a non-invasive device (e.g., not comprising any components that penetrate skin)], the device comprising one or more transducers (e.g., mechanical transducers), a battery, connectors, and a controller board, wherein the controller board controls waveform output through the connectors and the transducers, and wherein the transducers transcutaneously applied stimulates the one or more nerves, the method comprising: contacting the one or more transducers of the device to the human subject, generating the waveform output signal, activating the transducers using the waveform output signal (e.g., by applying the waveform output signal to the transducers to generate a mechanical wave), and promoting stimulation of the one or more nerves of the human subject, wherein the disorder is a member selected from the group consisting of: agoraphobia, body focused repetitive behaviors, generalized anxiety disorder, health anxiety, hoarding disorder (HD), obsessive-compulsive disorder, panic disorder, post-traumatic stress disorder (PTSD), separation anxiety, social anxiety disorder, a specific phobia (e.g., fear of heights, fear of public speaking, social phobia, panic attack, fear of flying, germ phobia, and the like), acute stress disorder, adjustment disorder with anxious features, substance-induced anxiety disorder, selective mutism in children, somatic symptom disorder, illness anxiety disorder, attention deficit disorder (ADD), attention deficit hyperactivity disorder, autism.

In another aspect, the invention is directed to a method of a disorder in a subject by providing transcutaneous mechanical stimulation (e.g., non-invasive mechanical stimulation) to the subject via a stimulation device (e.g., a wearable device), the method comprising: generating a mechanical wave by a mechanical transducer of the stimulation device in response to an applied electronic drive signal; controlling a waveform of the electronic drive signal by a controller board (e.g., a controller board of the stimulation device; e.g., a remote controller board); and delivering the mechanical wave to a body location of the subject via the stimulation device, thereby providing the transcutaneous mechanical stimulation to the subject, wherein the disorder is a member selected from the group consisting of: agoraphobia, body focused repetitive behaviors, generalized anxiety disorder, health anxiety, hoarding disorder (HD), obsessive-compulsive disorder, panic disorder, post-traumatic stress disorder (PTSD), separation anxiety, social anxiety disorder, a specific phobia (e.g., fear of heights, fear of public speaking, social phobia, panic attack, fear of flying, germ phobia, and the like), acute stress disorder, adjustment disorder with anxious features, substance-induced anxiety disorder, selective mutism in children, somatic symptom disorder, illness anxiety disorder, attention deficit disorder (ADD), attention deficit hyperactivity disorder, autism.

In another aspect, the invention is directed to a transcutaneous neuromodulation device [e.g., a wearable device; e.g., a non-invasive device (e.g., not comprising any components that penetrate skin)] for promoting nerve stimulation through mechanical vibration, comprising: one or more mechanical transducers, a battery, and one or more controller boards, wherein the one or more mechanical transducers, the battery and the one or more controller boards are in communication (e.g., through one or more connectors; e.g., wirelessly), and wherein the controller board controls waveform output through the one or more mechanical transducers, thereby producing mechanical vibration, and wherein the waveform output comprises an transformed time-varying wave.

In certain embodiments, the device promotes stimulation (e.g., wherein the waveform is selected to promote stimulation) of one or more nerves [e.g., a vagus nerve; e.g., a trigeminal nerve; e.g., peripheral nerves; e.g., a greater auricular nerve; e.g., a lesser occipital nerve; e.g., one or more cranial nerves (e.g., cranial nerve VII; e.g., cranial nerve IX; e.g., cranial nerve XI; e.g., cranial nerve XII)]. In certain embodiments, the one or more nerves comprises a vagus nerve and/or a trigeminal nerve. In certain embodiments, the one or more nerves comprises a C-tactile afferent.

In certain embodiments, the device promotes stimulation of (e.g., wherein the waveform is selected to promote stimulation of) one or more mechanoreceptors and/or cutaneous sensory receptors in the skin (e.g., to stimulate an afferent sensory pathway and use properties of receptive fields to propagate stimulation through tissue and bone). In certain embodiments, the one or more mechanoreceptors and/or cutaneous sensory receptors comprise Piezo2 protein and/or Merkel cells.

In certain embodiments, the one or more controller boards modulate the waveform output to introduce particular signal that include active or inactive pulse durations and frequencies configured to accommodate particular mechanoreceptor recovery periods, adaptation times, inactivation times, sensitization and desensitization times, or latencies.

In certain embodiments, the one or more controller boards modulate the waveform output to enhance or inhibit the expression of presynaptic molecules essential for synaptic vesicle release in neurons.

In certain embodiments, the one or more controller boards modulate the waveform output to enhance or inhibit the expression of neuroactive substances that can act as fast excitatory neurotransmitters or neuromodulators.

In certain embodiments, the one or more controller boards modulates the waveform output to stimulate mechanoreceptor cells associated with Aδ-fibers and C-fibers (e.g., including C tactile fibers) in order to stimulate nociceptive, thermoceptive, interoceptive and/or other pathways modulated by these fibers.

In certain embodiments, the one or more controller boards modulate the waveform output using dynamical systems methods to produce a preferred response in neural network dynamics (e.g., via modulation of signal timing).

In certain embodiments, the one or more controller boards modulates the waveform output using dynamical systems measures to assess response signals (e.g., electronic) to detect particular network responses correlated with changes in mechanical wave properties (e.g., and modulates the waveform output to target/optimally enhance particular preferred responses).

In certain embodiments, the device comprises an adhesive (e.g., a biocompatible adhesive) for adhering at least one of the one or more mechanical transducers (e.g., up to all) to a subject [e.g., skin (e.g., on a neck of; e.g., overlaying at least one mastoid process of; e.g., of an outer or posterior of at least one ear of) a human subject] (e.g., wherein the at least one mechanical transducer is embedded within the adhesive; e.g., wherein the at least one mechanical transducer is surrounded by the adhesive).

In certain embodiments, the device comprising one or more ergonomic support components, wherein the one or more transducers are supported by (e.g., housed within; e.g., mounted on) the one or more ergonomic support component(s) (e.g., collectively) and the one or more ergonomic support component(s) is/are formed (e.g., molded) to maintain the transducer in substantial proximity to one or more mastoid regions of a human subject (e.g., by maintaining substantial contact with skin overlaying the one or more mastoid regions).

In certain embodiments, the device comprises a first ergonomic support component, the first ergonomic support component comprising: (a) a first housing comprising a casing (e.g., molded casing) of sufficient size to at least partially house (i) a first transducer set comprising at least a portion (e.g., half; e.g., all) of the one or more mechanical transducers and (ii) a first controller board set comprising at least a portion (e.g., half; e.g., all) of the one or more controller boards, wherein the first transducer set is disposed adjacent to a window in the first housing [e.g., an insulated region of the first housing that contacts skin of the human subject in substantial proximity to a first mastoid region (e.g., on a first (e.g., left; e.g., right) side of head of the subject); e.g., wherein the window comprises fabric, adhesive, etc. placed in between a surface of the transducers of the first transducer set and skin of the subject so as to prevent direct contact with skin]; and (b) a first elastomeric arm comprising a resilient material and formed (e.g., molded) to engage an first ear of the subject and thereby support (e.g., fully) the first housing (e.g., and first transducer set and first controller board set housed therein), wherein the first housing is coupled to a distal end of the first elastomeric arm, wherein the distal end of the first elastomeric arm substantially aligns the window of the first housing with a first body location on the subject in substantial proximity to a first mastoid region (e.g., on a first side of the subject's head; e.g., on a left side; e.g., on a right side), and wherein the resilient material provides a force to hold the first housing against the first body location.

In certain embodiments, the device further comprises a second ergonomic support component, the second ergonomic support component comprising: (a) a second housing comprising a casing (e.g., molded casing) of sufficient size to at least partially house (i) a second transducer set comprising at least a portion (e.g., half; e.g., all) of the one or more mechanical transducers and (ii) a second controller board set comprising at least a portion (e.g., half; e.g., all) of the one or more controller boards, wherein the second transducer set is disposed adjacent to a window in the second housing [e.g., an insulated region of the second housing that contacts skin of the human subject in substantial proximity to a second mastoid region (e.g., on a second (e.g., left; e.g., right) side of head of the subject); e.g., wherein the window comprises fabric, adhesive, etc. placed in between a surface of the transducers of the second transducer set and skin of the subject so as to prevent direct contact with skin]; and (b) a second elastomeric arm comprising a resilient material and formed (e.g., molded) to engage an ear of the subject and thereby support (e.g., fully) the second housing (e.g., and second transducer set and second controller board set housed therein), wherein the second housing is coupled to a distal end of the second elastomeric arm, wherein the distal end of the second elastomeric arm substantially aligns the window of the second housing with a second body location on the subject in substantial proximity to a second mastoid region (e.g., on a second side of the subject's head; e.g., on a right side; e.g., on a left side), and wherein the resilient material provides a force to hold the second housing against the second body location.

In certain embodiments, the first and second ergonomic support components are in wireless communication with each other (e.g., via near-field magnetic induction (NFMI) e.g., so as to avoid/overcome interference from the subject's head) for synchronizing delivery of the mechanical vibration to the first and second mastoid regions of the subject (e.g., for synchronizing delivery of a first mechanical vibration produced by the first transducer set and delivery of a second mechanical vibration produced by the second transducer set).

In certain embodiments, the one or more ergonomic support components comprises: a linkage component formed to engage (e.g., wrap around a top of) a head of the subject; two housings disposed at opposite ends of the linkage component so as to be positioned on opposite sides of the head of the subject, wherein each housing comprising a casing (e.g., a molded casing) of sufficient size to at least partially house a corresponding transducer set comprising at least a portion (e.g., one; e.g., half; e.g., all) of the one or more mechanical transducers, wherein the mechanical transducers are disposed adjacent to a window in each housing; two elastomeric hinges, each disposed at the opposite ends of the linkage component and mounted to flexibly couple a housings to the linkage component; wherein at least one of the elastomeric hinges is formed and positioned to substantially align the window of each housing with and against opposing mastoid regions on opposite sides of the head of the subject.

In certain embodiments, the linkage component comprises an adjustment mechanism comprising two partially overlaid, interlocking, and sliding curved arms (e.g., curved elastomeric arms), wherein said curved arms are maintained in alignment with each other to form an arc (e.g., approximately matching an average arc of a human head) and slide with respect to each other so as to vary an amount of overlap, thereby varying a size of the arc (e.g., to match different size human heads), and wherein the two elastomeric hinges are disposed on opposing ends of the arc formed by the two sliding arms.

In certain embodiments, the device comprises at least one transducer array comprising a plurality of (e.g., two or more)

mechanical transducers maintained in a fixed spatial arrangement in relation to each other (e.g., in substantial proximity to each other; e.g., spaced along a straight or curved line segment) and wherein at least a portion of the one or more controller boards (e.g., a single controller board; e.g., two or more controller boards) are in communication with the mechanical transducers of the transducer array to control output of the mechanical transducers of the transducer array in relation to each other [e.g., wherein the at least a portion of the one or more controller boards synchronizes mechanical vibration produced by each mechanical transducer of the transducer array (e.g., such that each mechanical transducer begins and/or ends producing mechanical vibration at a particular delay with respect to one or more other mechanical transducers of the array; e.g., such that the mechanical transducers are sequentially triggered, one after the other; e.g., wherein the mechanical transducers are spaced along a straight or curved line segment and triggered sequentially along the line segment, such that an apparent source of mechanical vibration moves along the line segment to mimic a stroking motion)] [e.g., wherein a first portion of the mechanical transducers outputs a different frequency mechanical vibration from a second portion of the mechanical transducers of the transducer array (e.g., wherein each mechanical transducer of the transducer array outputs a different frequency mechanical vibration)].

In certain embodiments, the transducer is a linear transducer (e.g., operable to produce mechanical vibration comprising a longitudinal component (e.g., a longitudinal vibration)).

In certain embodiments, the device is incorporated into a headphone (e.g., an in-ear headphone; e.g., an over-the-ear headphone).

In certain embodiments, the device comprising a receiver in communication with the one or more controller boards, wherein the receiver is operable to receive a signal from and/or transmit a signal (e.g., wirelessly; e.g., via a wired connection) to a personal computing device (e.g., a smart phone; e.g., a personal computer; e.g., a laptop computer; e.g., a tablet computer; e.g., a smartwatch; e.g., a fitness tracker; e.g., a smart charger)(e.g., to upload new waveforms and/or settings for waveforms).

In certain embodiments, the one or more controller boards is/are operable to modulate and/or select the waveform output in response to (e.g., based on) the signal received from the personal computing device by the receiver.

In certain embodiments, the device is non-invasive (e.g., does not comprise any components for penetrating skin).

In certain embodiments, the device comprises a secondary stimulation device for providing one or more external stimulus/stimuli (e.g., visual stimulus; e.g., acoustic stimulus; e.g., limbic priming; e.g., a secondary tactile signal).

In certain embodiments, the transformed time-varying wave comprises a frequency component ranging from 5 to 15 Hz (e.g., ranging from approximately 7 to approximately 13 Hz; e.g., a frequency range matching an alpha brain wave frequency range; e.g., approximately 10 Hz).

In certain embodiments, the transformed time-varying wave comprises a frequency component ranging from 0 to 49 Hz (e.g., from 18 to 48 Hz; e.g., from 15 to 40 Hz; e.g. from 8 to 14 Hz).

In certain embodiments, the transformed time-varying wave comprises a carrier wave [e.g., a periodic wave having a substantially constant frequency (e.g., ranging from 5 to 15 Hz; e.g., ranging from approximately 7 to approximately 13 Hz; e.g., a frequency range matching an alpha brain wave frequency range; e.g., approximately 10 Hz)] modulated by an envelope function having one or more low-amplitude sub-intervals [e.g., a periodic envelope function (e.g., a square wave; e.g., a 0.5 Hz square wave); e.g., the one or more low-amplitude sub-intervals having a duration of greater than or approximately equal to two seconds; e.g., the one or more low-amplitude sub-intervals having a duration of approximately two seconds].

In certain embodiments, the transformed time varying wave comprises an isochronic wave. In certain embodiments, the transformed time-varying wave comprises a chirped wave. In certain embodiments, a functional form of the waveform output is based on one or more recorded natural sounds (e.g., running water; e.g., ocean waves; e.g., purring; e.g., breathing; e.g., chanting; e.g., gongs; e.g., bells).

In certain embodiments, the device comprises a receiver in communication with the one or more controller boards, wherein the receiver is operable to receive a signal from and/or transmit a signal to a monitoring device (e.g., directly from and/or to the monitoring device; e.g., via one or more intermediate server(s) and/or computing device(s))(e.g., a wearable monitoring device; e.g., a personal computing device; e.g., a fitness tracker; e.g., a heart-rate monitor; e.g., an electrocardiograph (EKG) monitor; e.g., an electroencephalography (EEG) monitor; e.g., an accelerometer; e.g., a blood-pressure monitor; e.g., a galvanic skin response (GSR) monitor) and wherein the one or more controller boards is/are operable to modulate and/or select the waveform output in response to (e.g., based on) the signal from the wearable monitoring device received by the receiver.

In certain embodiments, the device is operable to record usage data (e.g., parameters such as a record of when the device was used, duration of use, etc.) and/or one or more biofeedback signals for a human subject [e.g., wherein the device comprises one or more sensors, each operable to measure and record one or more biofeedback signals (e.g., a galvanic skin response (GSR) sensor; e.g., a heart-rate monitor; e.g., an accelerometer)] [e.g., wherein the device is operable to store the recorded usage data and/or biofeedback signals for further processing and/or transmission to an external computing device, e.g., for computation (e.g., using a machine learning algorithm that receives the one or more biofeedback signals as input, along with, optionally, user reported information) and display of one or more performance metrics (e.g., a stress index) to a subject using the device].

In certain embodiments, the one or more controller boards is/are operable to automatically modulate and/or select the waveform output in response to (e.g., based on) the recorded usage data and/or biofeedback signals (e.g., using a machine learning algorithm that receives the one or more biofeedback signals as input, along with, optionally, user reported information, to optimize the waveform output).

In certain embodiments, a level [e.g., amplitude (e.g., a force; e.g., a displacement)] of at least a portion of the mechanical vibration is based on activation thresholds of one or more target cells and/or proteins (e.g., mechanoreceptors (e.g., C tactile afferents); e.g., nerves; e.g., sensory thresholds corresponding to a level of tactile sensation) [e.g., wherein the one or more controller boards modulate the waveform output based on sub-activation thresholds (e.g., accounting for the response of the mechanical transducers)].

In certain embodiments, an amplitude of the mechanical vibration corresponds to a displacement ranging from 1 micron to 10 millimeters (e.g., approximately 25 microns) (e.g., wherein the amplitude is adjustable over the displacement ranging from 1 micron to 10 millimeters)[e.g., wherein the amplitude corresponds to a force of approximately 0.4N] [e.g., thereby matching the amplitude to activation thresholds of C tactile afferents].

In certain embodiments, the transformed time-varying wave comprises one or more components (e.g., additive noise; e.g., stochastic resonance signals) that, when transduced by the transducer to produce the mechanical wave, correspond to sub-threshold signals that are below an activation threshold of one or more target cells and/or proteins (e.g., below a level of tactile sensation).

In certain embodiments, the transformed time-varying wave comprises one or more components (e.g., additive noise; e.g., stochastic resonance signals) that, when transduced by the transducer to produce the mechanical wave, correspond to supra-threshold signals that are above an activation threshold of one or more target cells and/or proteins (e.g., above a level of tactile sensation).

In another aspect, the invention is directed to a transcutaneous neuromodulation device [e.g., a wearable device; e.g., a non-invasive device (e.g., not comprising any components that penetrate skin)] for promoting nerve stimulation through mechanical vibration, comprising: one or more mechanical transducers, a battery, and one or more controller boards, wherein the one or more mechanical transducers, the battery and the one or more controller boards are in communication (e.g., through one or more connectors; e.g., wirelessly), and wherein the one or more controller boards control waveform output through the one or more mechanical transducers, and the one or more mechanical transducers transcutaneously stimulate one or more nerves of a human subject and wherein the waveform output comprises an transformed time-varying wave.

In another aspect, the invention is directed to a transcutaneous stimulation device [e.g., a wearable device; e.g., a non-invasive device (e.g., not comprising any components that penetrate skin)] for promoting mechanoreceptor stimulation through mechanical vibration, comprising: one or more mechanical transducers, a battery, and one or more controller boards, wherein the one or more mechanical transducers, the battery and the one or more controller boards are in communication (e.g., through one or more connectors; e.g., wirelessly), and wherein the one or more controller boards control waveform output through the transducer, and the one or more mechanical transducers transcutaneously stimulate one or more mechanoreceptors of a human subject and wherein the waveform output comprises an transformed time-varying wave.

In another aspect, the invention is directed to a method of treating a subject by providing transcutaneous mechanical stimulation (e.g., non-invasive mechanical stimulation) to the subject via a stimulation device (e.g., a wearable device), the method comprising: generating a mechanical wave by a mechanical transducer of the stimulation device in response to an applied electronic drive signal; controlling a waveform of the electronic drive signal by a controller board (e.g., a controller board of the stimulation device; e.g., a remote controller board), wherein the waveform comprises an transformed time-varying wave; and delivering the mechanical wave to a body location of the subject via the stimulation device, thereby providing the transcutaneous mechanical stimulation to the subject.

In certain embodiments, the mechanical wave promotes stimulation (e.g., wherein the waveform is selected to promote stimulation) of one or more nerves [e.g., a vagus nerve; e.g., a trigeminal nerve; e.g., peripheral nerves; e.g., a greater auricular nerve; e.g., a lesser occipital nerve; e.g., one or more cranial nerves (e.g., cranial nerve VII; e.g., cranial nerve IX; e.g., cranial nerve XI; e.g., cranial nerve XII)]. In certain embodiments, the one or more nerves comprises a vagus nerve and/or a trigeminal nerve. In certain embodiments, the one or more nerves comprises a C-tactile afferent.

In certain embodiments, the mechanical wave promotes stimulation of (e.g., wherein the waveform is selected to promote stimulation of) one or more mechanoreceptors and/or cutaneous sensory receptors in the skin (e.g., to stimulate an afferent sensory pathway and use properties of receptive fields to propagate stimulation through tissue and bone). In certain embodiments, the one or more mechanoreceptors and/or cutaneous sensory receptors comprise Piezo2 protein and/or Merkel cells. In certain embodiments, the controlling the waveform of the electronic drive signal comprises modulating the waveform to introduce particular signals that include active or inactive pulse durations and frequencies configured to accommodate particular mechanoreceptor recovery periods, adaptation times, inactivation times, sensitization and desensitization times, or latencies.

In certain embodiments, the controlling the waveform of the electronic drive signal comprises modulating the waveform to enhance or inhibit the expression of presynaptic molecules essential for synaptic vesicle release in neurons.

In certain embodiments, the controlling the waveform of the electronic drive signal comprises modulating the waveform to enhance or inhibit the expression of neuroactive substances that can act as fast excitatory neurotransmitters or neuromodulators.

In certain embodiments, the controlling the waveform of the electronic drive signal comprises modulating the waveform to stimulate mechanoreceptor cells associated with Aδ-fibers and C-fibers (e.g., including C tactile fibers) in order to stimulate nociceptive, thermoceptive, interoceptive and/or other pathways modulated by these fibers.

In certain embodiments, the controlling the waveform of the electronic drive signal comprises modulating the waveform using dynamical systems methods to produce a preferred response in neural network dynamics (e.g., via modulation of signal timing).

In certain embodiments, the controlling the waveform of the electronic drive signal comprises modulating the waveform using dynamical systems measures to assess response signals (e.g., electronic) to detect particular network responses correlated with changes in mechanical wave properties (e.g., and modulates the waveform output to target/ optimally enhance particular preferred responses).

In certain embodiments, the delivering the mechanical wave to the body location comprises contacting the mechanical transducer to a surface (e.g., skin) of the subject at the body location.

In certain embodiments, the contacting the mechanical transducer to the surface of the subject at the body location comprises using an adhesive (e.g., a biocompatible adhesive) for adhering at least one of the one or more mechanical transducers (e.g., up to all) to a subject [e.g., skin (e.g., on a neck of; e.g., overlaying at least one mastoid process of; e.g., of an outer or posterior of at least one ear of) a human subject] (e.g., wherein the at least one mechanical transducer is embedded within the adhesive; e.g., wherein the at least one mechanical transducer is surrounded by the adhesive).

In certain embodiments, the contacting the mechanical transducer to the surface of the subject at the body location comprises using one or more ergonomic support components, wherein the one or more transducers are supported by (e.g., housed within; e.g., mounted on) the one or more ergonomic support component(s) (e.g., collectively) and the one or more ergonomic support component(s) is/are formed (e.g., molded) to maintain the transducer in substantial proximity to one or more mastoid regions of a human subject (e.g., by maintaining substantial contact with skin overlaying the one or more mastoid regions).

In certain embodiments, the one or more ergonomic support components comprise(s) a first ergonomic support component, the first ergonomic support component comprising: (a) a first housing comprising a casing (e.g., molded casing) of sufficient size to at least partially house (i) a first transducer set comprising at least a portion (e.g., half; e.g., all) of the one or more mechanical transducers and (ii) a first controller board set comprising at least a portion (e.g., half; e.g., all) of the one or more controller boards, wherein the first transducer set is disposed adjacent to a window in the first housing [e.g., an insulated region of the first housing that contacts skin of the human subject in substantial proximity to a first mastoid region (e.g., on a first (e.g., left; e.g., right) side of head of the subject); e.g., wherein the window comprises fabric, adhesive, etc. placed in between a surface of the transducers of the first transducer set and skin of the subject so as to prevent direct contact with skin]; and (b) a first elastomeric arm comprising a resilient material and formed (e.g., molded) to engage an first ear of the subject and thereby support (e.g., fully) the first housing (e.g., and first transducer set and first controller board set housed therein), wherein the first housing is coupled to a distal end of the first elastomeric arm, wherein the distal end of the first elastomeric arm substantially aligns the window of the first housing with a first body location on the subject in substantial proximity to a first mastoid region (e.g., on a first side of the subject's head; e.g., on a left side; e.g., on a right side), and wherein the resilient material provides a force to hold the first housing against the first body location.

In certain embodiments, the one or more ergonomic support components further comprise(s) a second ergonomic support component, the second ergonomic support component comprising: (a) a second housing comprising a casing (e.g., molded casing) of sufficient size to at least partially house (i) a second transducer set comprising at least a portion (e.g., half; e.g., all) of the one or more mechanical transducers and (ii) a second controller board set comprising at least a portion (e.g., half; e.g., all) of the one or more controller boards, wherein the second transducer set is disposed adjacent to a window in the second housing [e.g., an insulated region of the second housing that contacts skin of the human subject in substantial proximity to a second mastoid region (e.g., on a second (e.g., left; e.g., right) side of head of the subject); e.g., wherein the window comprises fabric, adhesive, etc. placed in between a surface of the transducers of the second transducer set and skin of the subject so as to prevent direct contact with skin]; and (b) a second elastomeric arm comprising a resilient material and formed (e.g., molded) to engage an ear of the subject and thereby support (e.g., fully) the second housing (e.g., and second transducer set and second controller board set housed therein), wherein the second housing is coupled to a distal end of the second elastomeric arm, wherein the distal end of the second elastomeric arm substantially aligns the window of the second housing with a second body location on the subject in substantial proximity to a second mastoid region (e.g., on a second side of the subject's head; e.g., on a right side; e.g., on a left side), and wherein the resilient material provides a force to hold the second housing against the second body location.

In certain embodiments, the first and second ergonomic support components are in wireless communication with each other (e.g., via near-field magnetic induction (NFMI) e.g., so as to avoid/overcome interference from the subject's head) for synchronizing delivery of the mechanical vibration to the first and second mastoid regions of the subject (e.g., for synchronizing delivery of a first mechanical vibration produced by the first transducer set and delivery of a second mechanical vibration produced by the second transducer set).

In certain embodiments, the one or more ergonomic support components comprises: a linkage component formed to engage (e.g., wrap around a top of) a head of the subject two housings disposed at opposite ends of the linkage component so as to be positioned on opposite sides of the head of the subject, wherein each housing comprising a casing (e.g., a molded casing) of sufficient size to at least partially house a corresponding transducer set comprising at least a portion (e.g., one; e.g., half; e.g., all) of the one or more mechanical transducers, wherein the mechanical transducers are disposed adjacent to a window in each housing; two elastomeric hinges, each disposed at the opposite ends of the linkage component and mounted to flexibly couple a housings to the linkage component; wherein at least one of the elastomeric hinges is formed and positioned to substantially align the window of each housing with and against opposing mastoid regions on opposite sides of the head of the subject.

In certain embodiments, the linkage component comprises an adjustment mechanism comprising two partially overlaid, interlocking, and sliding curved arms (e.g., curved elastomeric arms), wherein said curved arms are maintained in alignment with each other to form an arc (e.g., approximately matching an average arc of a human head) and slide with respect to each other so as to vary an amount of overlap, thereby varying a size of the arc (e.g., to match different size human heads), and wherein the two elastomeric hinges are disposed on opposing ends of the arc formed by the two sliding arms.

In certain embodiments, the mechanical transducer is a member of a transducer array comprising a plurality of (e.g., two or more) mechanical transducers maintained in a fixed spatial arrangement in relation to each other (e.g., in substantial proximity to each other; e.g., spaced along a straight or curved line segment) and wherein the controller board controls output of the mechanical transducer in relation to other mechanical transducers of the array [e.g., so as to synchronize mechanical vibration produced by each mechanical transducer of the transducer array (e.g., such that each mechanical transducer begins and/or ends producing mechanical vibration at a particular delay with respect to one or more other mechanical transducers of the array; e.g., such that the mechanical transducers are sequentially triggered, one after the other; e.g., wherein the mechanical transducers are spaced along a straight or curved line segment and triggered sequentially along the line segment, such that an apparent source of mechanical vibration moves along the line segment to mimic a stroking motion)] [e.g., wherein a first portion of the mechanical transducers outputs a different frequency mechanical vibration from a second portion of the mechanical transducers of the transducer array (e.g., wherein each mechanical transducer of the transducer array outputs a different frequency mechanical vibration)].

In certain embodiments, the transducer is a linear transducer (e.g., operable to produce mechanical vibration comprising a longitudinal component (e.g., a longitudinal vibration)).

In certain embodiments, the mechanical transducer is incorporated into a headphone (e.g., an in-ear headphone; e.g., an over-the-ear headphone).

In certain embodiments, the controlling the waveform of the electronic drive signal comprises receiving (e.g., by a receiver in communication with the controller board) a signal from a personal computing device (e.g., a smart phone; e.g., a personal computer; e.g., a laptop computer; e.g., a tablet computer; e.g., a smartwatch; e.g., a fitness tracker; e.g., a smart charger)(e.g., to upload new waveforms and/or settings for waveforms).

In certain embodiments, the controlling the waveform of the electronic drive signal comprises modulating and/or selecting the waveform in response to (e.g., based on) the signal received from the personal computing device by the receiver.

In certain embodiments, the delivering the mechanical wave to the body location is performed in a non-invasive fashion (e.g., without penetrating skin of the subject).

In certain embodiments, the method comprising providing, by a secondary stimulation device, one or more external stimulus/stimuli (e.g., visual stimulus; e.g., acoustic stimulus; e.g., limbic priming; e.g., a secondary tactile signal).

In certain embodiments, the transformed time-varying wave comprises a frequency component ranging from 5 to 15 Hz (e.g., ranging from approximately 7 to approximately 13 Hz; e.g., a frequency range matching an alpha brain wave frequency range; e.g., approximately 10 Hz).

In certain embodiments, the transformed time-varying wave comprises a frequency component ranging from 0 to 49 Hz (e.g., from 18 to 48 Hz; e.g., from 15 to 40 Hz; e.g. from 8 to 14 Hz).

In certain embodiments, the transformed time-varying wave comprises a carrier wave [e.g., a periodic wave having a substantially constant frequency (e.g., ranging from 5 to 15 Hz; e.g., ranging from approximately 7 to approximately 13 Hz; e.g., a frequency range matching an alpha brain wave frequency range; e.g., approximately 10 Hz)] modulated by an envelope function having one or more low-amplitude sub-intervals [e.g., a periodic envelope function (e.g., a square wave; e.g., a 0.5 Hz square wave); e.g., the one or more low-amplitude sub-intervals having a duration of greater than or approximately equal to two seconds; e.g., the one or more low-amplitude sub-intervals having a duration of approximately two seconds].

In certain embodiments, the transformed time varying wave comprises an isochronic wave. In certain embodiments, the transformed time-varying wave comprises a chirped wave. In certain embodiments, the waveform of the electronic drive signal comprises a transformed time-varying wave having a functional form corresponding to a carrier wave within an envelope {e.g., wherein the transformed-time varying wave is the carrier wave and is further modulated by an envelope [e.g., wherein the envelope is a sinusoidal wave; e.g., wherein the envelope has a monotonically increasing (in time) amplitude (e.g., wherein the envelope has a functional form corresponding to an increasing (in time) exponential)]; e.g., wherein the transformed time-varying wave is the envelope that modulates a carrier wave [e.g., wherein the carrier wave is a periodic wave (e.g., a sinusoidal wave; e.g., a square wave; e.g., a sawtooth wave)(e.g., having a higher frequency than the envelope)]}.

In certain embodiments, a functional form of the waveform of the electronic drive signal is based on one or more recorded natural sounds (e.g., running water; e.g., ocean waves; e.g., purring; e.g., breathing; e.g., chanting; e.g., gongs; e.g., bells).

In certain embodiments, the method comprises receiving an electronic response signal from a monitoring device (e.g., directly from and/or to the monitoring device; e.g., via one or more intermediate server(s) and/or computing device(s)) (e.g., a wearable monitoring device; e.g., a personal computing device; e.g., a fitness tracker; e.g., a heart-rate monitor; e.g., an electrocardiograph (EKG) monitor; e.g., an electroencephalography (EEG) monitor; e.g., an accelerometer; e.g., a blood-pressure monitor; e.g., a galvanic skin response (GSR) monitor), and wherein the controlling the waveform of the electronic drive signal comprises adjusting and/or selecting the waveform in response to (e.g., based on) the received electronic response signal.

In certain embodiments, the method comprises recording usage data (e.g., parameters such as a record of when the device was used, duration of use, etc.) and/or one or more biofeedback signals for a human subject [e.g., using one or more sensors, each operable to measure and record one or more biofeedback signals (e.g., a galvanic skin response (GSR) sensor; e.g., a heart-rate monitor; e.g., an accelerometer)] [e.g., storing and/or providing the recorded usage data and/or biofeedback signals for further processing and/or transmission to an external computing device, e.g., for computation (e.g., using a machine learning algorithm that receives the one or more biofeedback signals as input, along with, optionally, user reported information) and display of one or more performance metrics (e.g., a stress index) to a subject].

In certain embodiments, the method comprises automatically modulating and/or selecting the waveform of the electronic drive signal in response to (e.g., based on) the recorded usage data and/or biofeedback signals (e.g., using a machine learning algorithm that receives the one or more biofeedback signals as input, along with, optionally, user reported information, to optimize the waveform output).

In certain embodiments, a level [e.g., amplitude (e.g., a force; e.g., a displacement)] of at least a portion of the mechanical wave is (e.g., modulated and/or selected) based on activation thresholds of one or more target cells and/or proteins (e.g., mechanoreceptors (e.g., C tactile afferents); e.g., nerves; e.g., sensory thresholds corresponding to a level of tactile sensation) [e.g., wherein the one or more controller boards modulate the waveform output based on sub-activation thresholds (e.g., accounting for the response of the mechanical transducers)].

In certain embodiments, an amplitude of the mechanical wave corresponds to a displacement ranging from 1 micron to 10 millimeters (e.g., approximately 25 microns)(e.g., wherein the amplitude is adjustable over the displacement ranging from 1 micron to 10 millimeters)[e.g., wherein the amplitude corresponds to a force of approximately 0.4N] [e.g., thereby matching the amplitude to activation thresholds of C tactile afferents].

In another aspect, the invention is directed to a method of stimulating one or more nerves and/or mechanoreceptors of a subject (e.g., a human subject), the method comprising: using any of the devices describd herein, for stimulation of the one or more nerves and/or mechanoreceptors of the subject.

In another aspect, the invention is directed to a method of stimulating one or more nerves of a human subject using a transcutaneous, neuromodulation device [e.g., a wearable device; e.g., a non-invasive device (e.g., not comprising any components that penetrate skin)], the device comprising one or more transducers (e.g., mechanical transducers), a battery, connectors, and one or more controller boards, wherein the one or more controller boards control waveform output through the connectors and the one or more transducers, and wherein the transducers transcutaneously applied stimulate the one or more nerves, the method comprising: contacting the one or more transducers of the device to the human subject, generating the waveform output signal, activating the transducers using the waveform output signal (e.g., by applying the waveform output signal to the transducers to generate a mechanical wave), and stimulating the one or more nerves of the human subject, wherein the waveform output comprises an transformed time-varying wave.

In another aspect, the invention is directed to a method of stimulating one or more mechanoreceptors of a human subject using transcutaneous stimulation device [e.g., a wearable device; e.g., a non-invasive device (e.g., not comprising any components that penetrate skin)], the device comprising one or more mechanical transducers, a battery, connectors, and one or more controller boards, wherein the one or more controller boards control waveform output through the connectors and the one or more mechanical transducers, and wherein the one or more mechanical transducers transcutaneously applied stimulate the one or more mechanoreceptors, the method comprising: contacting the one or more mechanical transducers of the device to the human subject, generating the waveform output signal, activating the mechanical transducers using the waveform output signal (e.g., by applying the waveform output signal to the transducers to generate a mechanical wave), and stimulating the one or more mechanoreceptors of the human subject, wherein the waveform output comprises an transformed time-varying wave.

Elements of embodiments involving one aspect of the invention (e.g., compositions, e.g., systems, e.g., methods) can be applied in embodiments involving other aspects of the invention, and vice versa.

BRIEF DESCRIPTION OF THE DRAWINGS

The foregoing and other objects, aspects, features, and advantages of the present disclosure will become more apparent and better understood by referring to the following description taken in conjunction with the accompanying drawings, in which:

FIG. 3 is a table showing biological targets of the devices and methods, in certain embodiments.

FIG. 5 is a schematic of a stimulation device, according to an illustrative embodiment;

FIG. 8C is a block flow diagram of a process for treating a subject via mechanical stimulation by stimulating a cranial nerve of the subject, according to an illustrative embodiment;

FIG. 15D is a graph of an example waveform comprising a transformed time-varying wave (TTVW), according to an illustrative embodiment;

FIG. 27 is a set of two images and a schematic illustrating collection of electroencephalogram (EEG) data, according to an illustrative embodiment.

FIG. 33A is a schematic perspective view of an alternative transcutaneous neuromodulation device in accordance with one or more embodiments of the invention.

FIG. 33C is a schematic showing a view of a portion of the transcutaneous neuromodulation device of FIG. 33A showing an interior of an adjustment mechanism, according to an illustrative embodiment.

FIG. 33D is a 3D rendered version of the view shown in FIG. 33C.

FIG. 35 is a block diagram of an exemplary cloud computing environment, used in certain embodiments.

FIG. 43C is a set of graphs showing individual results from a third participant in a pilot study assessing efficacy of embodiments of the devices and methods described herein for treatment of anxiety.

FIG. 43D is a set of graphs showing individual results from a fourth participant in a pilot study assessing efficacy of embodiments of the devices and methods described herein for treatment of anxiety.

FIG. 44A is a histogram showing GAD-7 scores at enrollment, interim, and exit for participants in a pilot study assessing efficacy of embodiments of the devices and methods described herein for treatment of anxiety.

FIG. 44B is a histogram showing VAS scores at enrollment, interim, and exit for participants in a pilot study assessing efficacy of embodiments of the devices and methods described herein for treatment of anxiety.

FIG. 44C is a histogram showing STAI-STATE scores at enrollment, interim, and exit for participants in a pilot study assessing efficacy of embodiments of the devices and methods described herein for treatment of anxiety.

FIG. 44D is a histogram showing STAI-TRAIT scores at enrollment, interim, and exit for participants in a pilot study assessing efficacy of embodiments of the devices and methods described herein for treatment of anxiety.

Figure 1A:
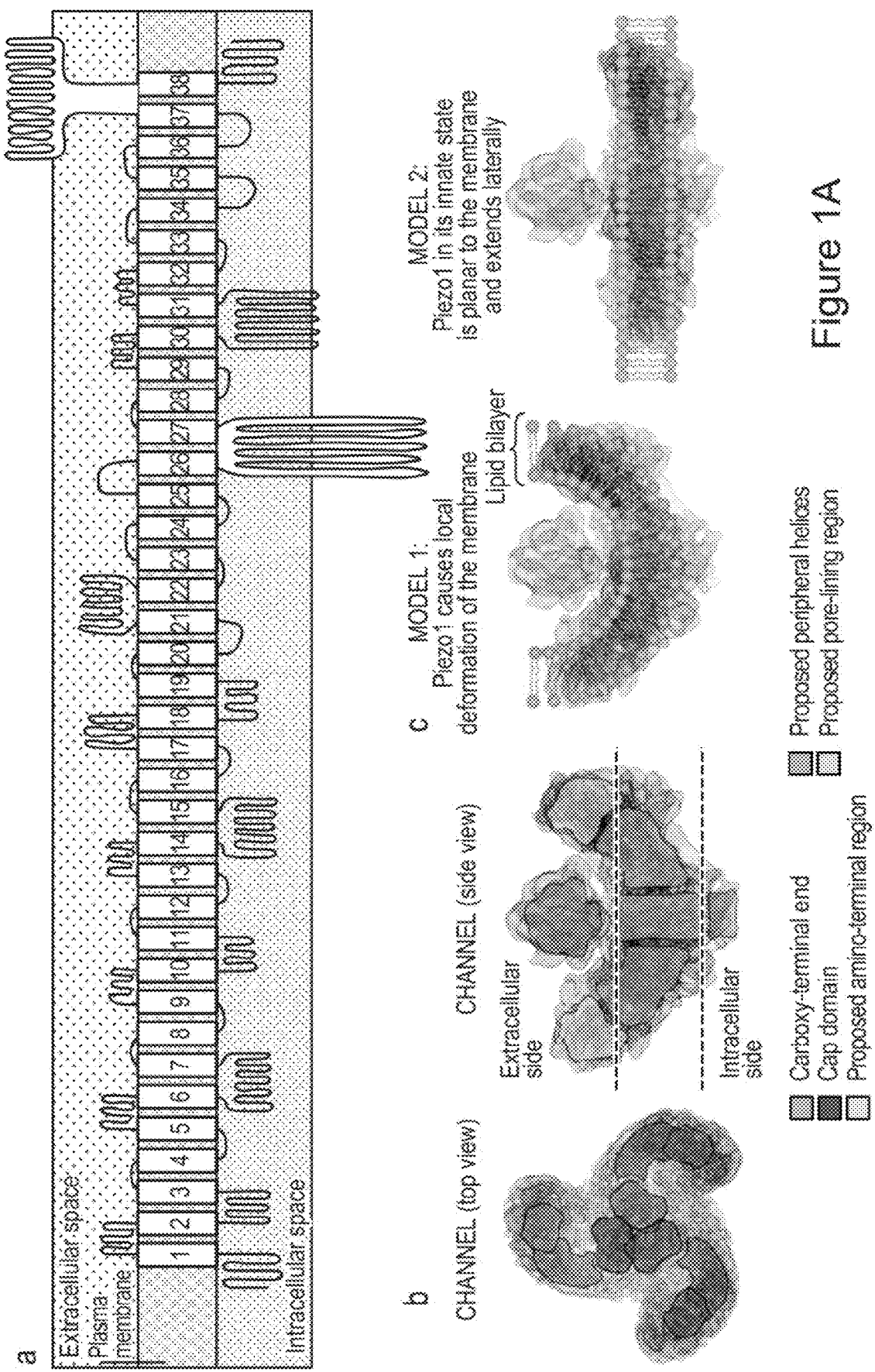
FIG. 1A is a schematic showing Piezo1 mechanical triggered cell surface protein channels, which modulate nerves, vascular endothelial, and other cell types; (from Murthy, 2017)

The features and advantages of the present disclosure will become more apparent from the detailed description set forth below when taken in conjunction with the drawings, in which like reference characters identify corresponding elements throughout. In the drawings, like reference numbers generally indicate identical, functionally similar, and/or structurally similar elements.

Definitions

Nerve stimulation: As used herein, the terms "stimulate" and "stimulating", when used in reference to nerves, such as in "stimulating one or more nerves" refer to any action that causes a change in the behavior of one or more nerves including, but not limited to, causing of firing one or more action potentials along the nerve. For example, changes in nerve behavior resulting from nerve stimulation may include, without limitation, changes in firing threshold, response to network activity, action potential amplitude, and timing of firing.

Nerves may be stimulated through a variety of mechanisms. For example, nerves may be stimulated by a signal, such as a mechanical vibration, through the interaction of a variety of proteins and cells. In particular, sensory proteins and cells may form a mechanosensory network through which a mechanical signal initiates a process, or modifies an ongoing process, resulting in a series of biological signals (e.g., chemical signals) within the network, ultimately causing stimulation of a nerve. Nerves may also be stimulated directly, without necessarily involving additional biomolecules, cells, and the like. For example, when free ends of nerves are subjected to mechanical force (e.g., as delivered via a mechanical vibration), a change in behavior may be generated within the nerve, such that the nerve is stimulated.

Isochronic wave: As used herein, the term "isochronic wave" refers to a time-varying signal (e.g., an electronic signal) comprising one or more low-amplitude sub-intervals within which an amplitude of the signal is substantially reduced in comparison with its amplitude at other sub-intervals.

In certain embodiments, the amplitude of the isochronic wave within the one or more low-amplitude sub intervals is approximately zero.

In certain embodiments, a duration of the one or more low-amplitude sub-intervals corresponds to (e.g., is approximately equal to; e.g., is greater than or approximately equal to) a refractory period of a mechanoreceptor and/or nerve target, such as a Piezo2 protein, a Merkel Cell, a Vagus nerve, a C-tactile afferent, and the like. In certain embodiments, a duration of the one or more low-amplitude sub-intervals corresponds to a refractory period of a Piezo2 protein (e.g., approximately two seconds; e.g., greater than or approximately equal to two seconds).

In certain embodiments, a functional form of the isochronic wave corresponds to a carrier wave modulated by an envelope function, the envelope function comprising one or more low-amplitude sub-intervals within which its amplitude is substantially reduced in comparison with its amplitude at other times. The one or more low-amplitude sub-intervals of such an isochronic wave thus correspond to those of the envelope function.

As used herein, the term "modulated" refers to the functional form of the isochronic wave, and is not intended to limit the manner in which the isochronic wave is produced.

In certain embodiments, the carrier wave is a periodic wave. In certain embodiments, a frequency of the periodic carrier wave is selected for stimulation of a particular nerve and/or mechanoreceptor target, such as a Piezo2 protein (e.g., less than or approximately equal to 100 Hz), a Merkel Cell (e.g., ranging from approximately 5 to 15 Hz), a vagus nerve (e.g., ranging from approximately 20 to 200 Hz; e.g., 50 to 200 Hz; e.g., 100 to 200 Hz; e.g., 130 to 180 Hz), e.g., a C-Tactile Afferent (e.g., less than or approximately equal to 50 Hz). In certain embodiments, a frequency of the carrier wave corresponds to a frequency of a particular type of brain wave (e.g., for entrainment of brain waves). For example, theta, alpha, beta, gamma brain waves have frequencies ranging from 4-8 Hz, 8-16 Hz, 16-30 Hz, and 30-60 Hz, respectively.

In certain embodiments, the envelope function is periodic, such that the one or more low-amplitude sub intervals repeat, in periodic fashion. In certain embodiments, the envelope function is a square wave. In certain embodiments, a frequency of the periodic envelope function corresponds to a breathing rate of a subject (e.g., corresponding to 6 to 10 breaths per minute; e.g., approximately 0.1 Hz)

In certain embodiments, an isochronic wave is also a transformed time-varying wave.

Transformed time-varying wave: As used herein, the term "transformed time varying wave" refers to a signal (e.g., an electronic signal) whose functional form is a modified base time-varying wave, such that variation in the amplitude of the base time-varying wave is transformed over one or more sub-intervals of the base time-varying wave. In certain embodiments one or more of the sub-intervals each span a peak of the base-time varying wave.

As used herein, the terms "transformed" and "modified" refer to the functional form of the transformed periodic wave, and are not intended to limit the manner in which the transformed time-varying wave is produced.

In certain embodiments, the amplitude of transformed time-varying wave is substantially flat within one or more of the one or more sub-intervals. In certain embodiments, the amplitude of the transformed time-varying wave varies as a linear or near-linear ramp within one or more of the one or more sub-intervals. The linear ramp may have a positive or negative slope with respect to time. In certain embodiments, the amplitude of the transformed time-varying wave has a sinusoidal functional form within one or more of the one or more sub-intervals. In certain embodiments, a functional form of the transformed time-varying wave is the same for each sub-interval. In certain embodiments, the transformed time-varying wave has a first functional form within a first sub-interval and a second functional form within a second sub-interval.

In certain embodiments, the base time-varying wave is a periodic wave (a base periodic wave). In certain embodiments, the base periodic wave is a sinusoidal wave. In certain embodiments, the base periodic wave is a square wave. In certain embodiments, the base periodic wave is a periodic pulse train. The base periodic wave may have a substantially constant frequency. For example, the base periodic wave may have a frequency ranging from approximately 18 and 48 Hz. In certain embodiments, the base periodic wave has a time-varying frequency. In certain embodiments, the base periodic wave is chirped. In certain embodiments, the base time-varying wave is aperiodic. In certain embodiments, the base time-varying wave is a random signal.

In certain embodiments, a transformed time-varying wave has a mathematical form described as follows. If the total duration of a signal is T, and if the time interval [0; T] is divided in N subintervals $[t_i, t_{i+1}] 0 <= i <= N-1$, where $t_0=0$ and $t_N=T$, a transformed time-varying wave refers to a signal which is defined on each subinterval $[t_i, t_{i+1}]$ as either a portion of a base-time varying wave as defined above, or a curved or linear segment with a net negative, positive or null derivative over each subinterval $[t_i, t_{i+1}]$.

A particular example of a transformed time-varying wave is a polygonal pulse train wherein the signal on each subinterval $[t_i, t_{i+1}] 0 <= i <= N-1$ is a linear segment.

Polygonal pulse train: As used herein, the term "polygonal pulse train" refers to a signal that is composed of a succession of polygonal pulse shapes. A polygonal pulse shape has a functional form P(t) where t is the time variable on an interval [0; T] such that and $P(t+T(t))=P(t)$ where $T(t)=1/f(t)$ is the period of the pulse shape and f(t) is a constant or time-varying waveform frequency. The time interval [0; T] may be divided into subintervals $[t_i: t_{i+1}]$, such that for any time t such that $t_i < t < t_{i+1}$, the signal amplitude P(t) is equal to $a_i t + b_i$, where $a_i$ and $b_i$ are constants determining the slope and height of the linear polygon edge on the time interval $[t_i: t_{i+1}]$. The resulting series of linear ramps are concatenated into a polygonal pulse of duration T, such that the time index $t_i$ takes values between 0 and T. Accordingly, P(t) is composed of between 1 and less than or equal to T*Fs-1 (where Fs is the signal sampling rate) linear ramps defining the polygonal pulse shape repeating with period T(t). The polygonal pulse train may be composed of a single polygonal pulse shape or a concatenation of 2 or more polygonal pulse shapes.

Aperiodic time-varying wave: As used herein, the term "aperiodic time-varying wave" refers to a signal, A(t), such as there is no possible value T where $A(t+T)=A(t)$ for each time t in the time interval on which A is defined. An example of an aperiodic time-varying wave is a signal having a functional form corresponding to a sum of two sine waveforms of respective frequencies f and f', wherein f divided by f' is an irrational number.

Contact, contacting: As used herein, the terms "contact" and "contacting" as used in reference to a transducer refer to placing the transducer in sufficient proximity to a body (e.g., a surface of a subject) so as to deliver a mechanical wave generated by the mechanical transducer to the body (e.g., to a tissue of interest at and/or beneath a surface of the subject). In certain embodiments, a surface of the mechanical transducer is placed in physical contact (e.g., touching) a surface of the body. In certain embodiments, there may be a small gap between the surface of the mechanical transducer and the surface of the body. In certain embodiments, the gap is an air gap, filled with air. In certain embodiments, another material, such as an adhesive, insulating material, etc., is in between the surface of the mechanical transducer and the surface of the body.

Dynamical system, dynamical systems methods, dynamical systems measures: As used herein, the term "dynamical system", refers to a state space S, a set of times T and a rule R for evolution, R: S×T→S that gives the consequent(s) to a state s∈S. A dynamical system can be considered to be a model describing the temporal evolution of a system. The state space S may be a discrete or continuous collection of coordinates that describe the state of the system. The state space S and/or set of times T may also be discrete or continuous. In certain embodiments, the state space S and/or set of times T may be represented by a topological group. Given the current state of the system, the evolution rule R predicts the next state or states. The evolution rule R provides a prediction of a next state and/or states that follow from the current state space value.

As used herein, the term "dynamical systems methods" refers to formal or mathematical descriptions of dynamical systems. As used herein, the term "dynamical systems measures" refers to techniques used to evaluate and identify particular dynamical systems states S and rules for evolution R.

Tissue: As used herein, the term "tissue" refers to bone (osseous tissue) as well as soft-tissue.

DETAILED DESCRIPTION OF THE INVENTION

It is contemplated that systems, devices, methods, and processes of the claimed invention encompass variations and adaptations developed using information from the embodiments described herein. Adaptation and/or modification of the systems, architectures, devices, methods, and processes described herein may be performed, as contemplated by this description.

Throughout the description, where articles, devices, and systems are described as having, including, or comprising specific components, or where processes and methods are described as having, including, or comprising specific steps, it is contemplated that, additionally, there are articles, devices, and systems of the present invention that consist essentially of, or consist of, the recited components, and that there are processes and methods according to the present invention that consist essentially of, or consist of, the recited processing steps.

It should be understood that the order of steps or order for performing certain action is immaterial so long as the invention remains operable. Moreover, two or more steps or actions may be conducted simultaneously.

The mention herein of any publication, for example, in the Background section, is not an admission that the publication serves as prior art with respect to any of the claims presented herein. The Background section is presented for purposes of clarity and is not meant as a description of prior art with respect to any claim.

Documents are incorporated herein by reference as noted. Where there is any discrepancy in the meaning of a particular term, the meaning provided in the Definition section above is controlling.

Headers are provided for the convenience of the reader—the presence and/or placement of a header is not intended to limit the scope of the subject matter described herein.

A. NERVE STIMULATION AND HEALTH BENEFITS

Since the Egyptians, Greeks, and Romans first used electric eels to treat disease and injury, treatment stimulation of nerves has primarily involved electrical stimulation of the nerve and connected tissues. The modern era of electrical neurostimulation began in 1780 when Luigi Galvani showed that a leg of a dead frog could be moved by applying a voltage to nerves and tissues.

However, while nerves conduct instructions between the brain and tissues and organs via electrical current, the application of electric currents is almost never the manner by which sensory nerves are stimulated in nature. For example, somatosensory nerves have evolved specific responses to a wide variety of stimuli: skin receptors (exteroceptors) close to the skin surface detect touch, pressure, vibration, temperature, pain; muscle and joint receptors (proprioceptors) in tendons, muscles and joints detect body position and movement; and visceral receptors (interoceptors) through the body monitor internal organ states and detect critical parameters such as heart rate and blood pressure. Different types of sensory nerves in the skin are triggered by specific types of inputs to afferent neurons: mechanoreceptors triggered by touch, stretch, pressure, hair vibrations; mechanoreceptors triggered by low frequency acoustic stimuli; tactile corpuscles that respond to touch and low frequency vibrations around 50 Hz; lamellar corpuscles that detect rapid vibrations in the range of 200-300 Hz; Ruffini endings that detect tension in the skin and fascia; Merkel endings that detect sustained pressure and inflammation; baroreceptors that are excited through stretching blood vessels; hair follicles that transmit vibrations and acoustic stimuli all over the body, including hearing in the cochlea by transducing sound; ligaments composed of multiple types of mechanoreceptors to help proprioception and balance; nociceptors triggered by trauma results in pain signals to local tissues and the brain; and thermoreceptors are portions of sensory neurons that sense temperature and heat.

Mechanoreceptors in the skin allow for the detection of diverse stimuli, conveying sensory information for pain, temperature, itch, and a broad spectrum of touch information to the central nervous system. In mammals, cutaneous low-threshold mechanoreceptors (LTMRs) constitute a diverse group of primary somatosensory neurons that function to sense external mechanical force (Olson, 2016). LTMRs are a subpopulation of dorsal root ganglion (DRG) and trigeminal ganglion (TG) neurons that elaborate a single axonal process that bifurcates into a peripheral branch innervating the skin/hair and a central branch innervating the spinal cord or brainstem (Olson, 2016). Innocuous (non-painful) touch sensations are conveyed from LTMRs innervating a wide variety of combinations of mechanosensory end organs adapted for the detection of diverse stimuli (Zimmerman, 2014). LTMRs occur in a variety of subtypes capable of mediating unique functional responses or aspects of touch through different structures and functions, diverse peripheral innervation patterns, and physiological responses to stimulation. The different types of mammalian LTMRS are traditionally categorized according to their action potential conduction velocity and cell morphology, and include Aβ-LTMRs (rapid-conducting), Aδ-LTMRs (medium conduction velocity), and C-LTMRs (slow-conducting), which exhibit great diversity in their physiological, molecular, anatomical, and functional properties (Olson, 2016). These can be further classified by the type of response to sustained mechanical stimuli, including rapidly adapting (RA—burst firing at stimulus onset/offset), slowly adapting (SA—sustained firing throughout the stimulus), and intermediate adapting (IA—burst at stimulus onset followed by sustained firing throughout stimulus at a rate lower than SA-LTMRs) (Olson, 2016). Aβ-LTMRs are the principal type of primary sensory neurons that mediate discriminative touch and tactile perception in mammals, and particular types of LTMRs innervate the different types of mechanoreceptors complexes, including: Aβ SA1-LTMRs, which innervate Merkel cells in the basal epidermis and convey information on sustained touch stimuli; Aβ SA2-LTMRs, hypothesized to terminate in Ruffini corpuscles in the dermis and exhibit high sensitivity to skin stretch; Aβ RA1-LTMRs, which innervate Meissner's corpuscles in dermal papillae, and respond to movement across the skin; and Aβ RA2-LTMRs, which terminate in Pacinian corpuscles in the deep dermis and exhibit sensitivity to high-frequency vibration (Zimmerman, 2014).

At the molecular level, the processes underlying translation of mechanical forces into biological signals involve the activation of ion channels in the cell membrane. Mechanosensitive ion channels are relevant for a wide range of physiological processes, and have been shown to mediate touch, pain, proprioception, hearing, regulation of vascular tone and muscle and tendon stretch. For example, Merkel cells, excitatory cells capable of firing $Ca^{+2}$ action potentials, have been identified as the primary sites of tactile transduction (Ma, 2014). Each of these Merkel-neurite complexes, known as a 'touch spot' in glabrous skin and a 'touch dome' in hairy skin, consists of an Aβ neuronal fiber forming a receptor network with a cluster of approximately 5-150 Merkel cells (Olson, 2016). The LTMRs that innervate touch domes exhibit exquisite sensitivity to gentle touch stimulation.

Merkel cells are unique among epithelial cells; they are the only known neuron-like cells in vertebrate skin, forming close synaptic-like contacts with Aβ SA1-LTMRs at the epidermal-dermal junction (Maksimovic, 2013), and clustered complexes composed of Merkel cells and afferent Aβ nerve fibers directly transduce tactile information into afferent Aβ signaling. In a manner similar to that of the gustatory system and hair cells of the auditory system, where non-neuronal cells participate in stimulus-specific transduction, in Merkel-Aβ SA1-LTMR complexes, non-neuronal components of cutaneous touch complexes detect stimuli and potentiate LTMR responses: both Merkel cells themselves and Aβ SA1-LTMRs respond directly to cutaneous mechanical stimulation, and Merkel cells signal to Aβ SA1-LTMRs to achieve optimal activation of the LTMR (Zimmerman, 2015). Thus, both Merkel cells and Aβ SA1-LTMRs function as mechanoreceptors, with Merkel cells in touch dome complexes mediating sustained firing to static touch. Moreover, Merkel cells express numerous types of presynaptic molecules involved in synaptic vesicle release in neurons, and also produce a large number of neuroactive substances, including classical neurotransmitters and neuropeptides that can act as fast excitatory neurotransmitters or neuromodulators (Maksimovic et al., 2013). These multiple spike encoders may send reciprocal messages such that a spike generated at any spike encoder antidromically propagates to all other spike encoders, initiating absolute refractory periods and restarting the process of spike initiation, a mechanism to maintain a stable overall response to sustained stimulus observed in Merkel cell complexes (Lesniak, 2015).

Figure 1B:
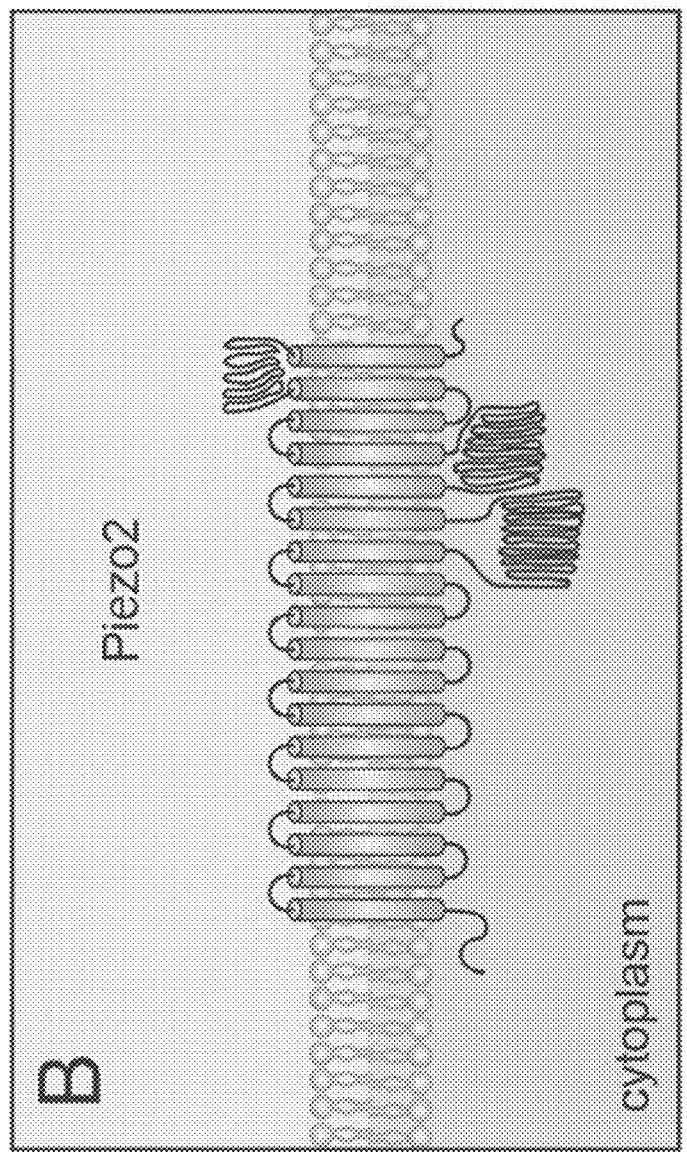
FIG. 1B is a schematic showing a Piezo2 mechanically triggered cell surface protein, which modulate nerves, vascular endothelial, and other cell types; (from Qiu, 2018)

Piezo proteins are a class of mechanically activated ion channels that are believed to play roles in a variety of sensory modalities (Xu, 2016). Piezo proteins, including Piezo1 and Piezo2, convert mechanical forces into biological signals via ion channel activation, and can induce mechanically activated cationic currents in numerous eukaryotic cell types. Piezo proteins are relevant to touch perception, proprioception, pulmonary respiration, red blood cell volume regulation, vascular physiology, and various human genetic disorders (Murthy, 2017). FIGS. 1A and 1B show schematics of piezo proteins Piezo1 and Piezo2, respectively.

In particular, Piezo2, as found in primary sensory neurons and specialized touch receptors located in the skin, mediates gentle touch sensation and proprioception (Xu, 2016), and is found in sensory tissues such as the dorsal root ganglia sensory neurons and Merkel cells that respond to touch (Wu, 2017). In Merkel cells, the Piezo2 mechanosensitive ion channel has recently been shown to be involved in driving direct mechano-afferent coupling Aβ nerve fibers (Ma, 2014; Woo, 2014). Piezo2 channels exhibit extremely short response latency (0.2 ms), producing signals in afferent Aβ-fibers capable of one-on-one responses to high-frequency stimuli (up to 1,200-1,500 Hz) for long periods of time (Gottschaldt and VahleHinz, 1981). These two features may offer a direct mechanosensitive pathway between Piezo2 ion channel activity and afferent Aβ-afferent nerve sites (Ma, 2014). Further, in addition to tactile Aβ-fibers, Merkel cell complexes in the dermis are also innervated by a minority of noci- and thermoceptive Aδ-fibers, and nociceptive C-fibers. Piezo2-driven complexes of dermal Merkel cells may play in these other sensory pathways.

Neural Signaling Dynamics

The nervous system is a complex nonlinear network composed of elements (neurons) which themselves exhibit nonlinear behaviors (Rulkov, 2002). As a result, the output of the nonlinear dynamical nervous system, is not a linear weight average of the input it receives, but rather, neural signaling arises from the interplay of dynamic processes across multiple scales of interaction within the network (Nanni, 2017). These dynamic interactions give rise to emergent properties that are not deducible from the properties of individual neurons in isolation. The dynamic interactions result from the dynamic relationships and dependencies formed when these are linked together in a network. For example, the transposition from microscopic pulse frequencies at the receptor level (sensory microscopic signal) to mesoscopic pulse and wave densities at the microcircuit and network level (perceptual mesoscopic signal) results from multiple interactions between large numbers of otherwise autonomously active nonlinear neurons, producing mesoscopic dynamics that cannot be predicted from the behavior of individual neurons only (Freeman, 2009).

Dynamical systems formalisms describe the processes by which the interactions of large numbers of network components give rise to the emergence of dynamic mesoscopic processes such as these. Models for describing nonlinear dynamical processes have applied methods from a wide range of mathematical techniques, including time series analyses, chaoticity, entropy, nonlinearity, fractality analysis (Nanni, 2017), phase space reconstruction, recurrence quantification analysis, fractal and multifractal analysis, detrended fluctuation analysis, power spectral density analysis, wavelet analysis (Ivanov, 1996), complexity matching (West, 2008), autocorrelation analysis (Sokunbi, 2014), independent component analysis, and artificial intelligence modeling.

Dynamical systems methods predict the emergence of mesoscopic masses, ensembles, and populations observed in biology including changes in state (Freeman, 2009), bifurcations (Cessac, 2009), intermittency (Kwok, 2005), bursting (Cessac, 2009), bistability, multistability, phase transitions, hysteresis, nonlinear oscillations, limit cycles, phase-resetting, entrainment, pacemaker annihilation, scale-invariance, fractal and multifractal scaling, long-range correlations, soft assembly (Wiltshire, 2017), power-law scaling, self-similarity, and self-organized criticality (Werner, 2010), self-organized criticality, diffusion limited aggregation, cardiac alternans phenomena, nonlinear waves (e.g., spirals, scrolls, solitons), complex periodic cycles and quasiperiodicities, stochastic resonance and related noise-modulated mechanisms (Levin, 1996; Gammaitoni, 1998; Allegrini, 2009; Rigoli, 2014), time irreversibility, complex responses, and chaos.

Biological signals such as EEG, MEG, or heart rate variability (HRV) contain information about dynamical changes in the activity of different parts of the nervous system (Di Leva, 2015). Dynamical systems methods may be applied to a wide range of electrophysiological recordings, including microelectrode (ME) recordings, electroencephalograms (EEG), magnetoencephalograms (MEG), electrocardiograms (ECG), functional magnetic resonance imaging (fMRI) data, electromyograms (EMG), electrocorticograms (ECoG), electro-oculograms (EOG), galvanic skin response (GSR), and pupillary response (PR) (Nanni 2017). For example, following from seminal work in the study of complexity in neural signaling (Linkenkaer-Hansen et al., 2001), a number of EEG studies (Linkenkaer-Hansen et al., 2004) and work in other neurophysiological modalities have now linked either fractal scaling relations or the correlation dimension to various functional states or clinical disorders (Hardstone et al., 2012). Further, nonlinear dynamical measures of EEG and fMRI complexity exhibit specific features in health, disease, different states of consciousness, self-esteem (Delignieres, 2004), and a variety of neurologic and neuropsychiatric conditions (Yang, 2013), including sleep disorders (Bianchi, 2013), mood disorders, anxiety (Srinivasan, 2002), depression (Mendez, 2012), post-traumatic stress disorder (Chae, 2004), attention-deficit/hyperactivity disorder (Fernandez, 2009), obsessive/compulsive disorder (Fernandez, 2010), autism spectrum disorder (Ahmadlou, 2010), attention deficit hyperactivity disorder (Li, 2007), dyslexia (Sandu, 2008), epilepsy (Onias, 2014; Weng, 2015), stroke (Yperzeele, 2015), Alzheimer's disease (Mizuno, 2010), multiple sclerosis (Esteban, 2009), schizophrenia (Fernandez, 2014), and Creutzfeldt-Jakob Disease (Morabito, 2017). Nonlinear dynamical measures derived using dynamical systems methods applied to biological signaling, including measures of psychophysiological time series, such as respiration, galvanic skin response, blood volume pulse, ECG and EEG, have been shown to be predictive of affective states such as relaxation, engagement, stress, and anger (Onorati, 2013). Further, analysis of ECG signals provides information about autonomic nervous system activity relevant diagnostics of atrial fibrillation and many disease conditions which are not easily detectable using other diagnostic methods (Pierzchalski, 2011).

Relatedly, measures of scaling relationships and fractality in biological systems are often interpreted as an indicator of healthy and efficient functioning (Goldberger, 1987), in organ systems (Bassingthwaighte, 1994), cardiac risk and forecasting sudden cardiac death (Pen, 1995), overall health and well-being (Van Orden, 2007), and both task-oriented and resting-state fMRI time series data (Ciuciu, 2012). Further, recent studies on heart rate variability (HRV) have confirmed the presence of state-specific nonlinear dynamical structures in these time series, with demonstrated ability to separate normal subjects from patients suffering from cardiovascular diseases (Cerutti, 2012) and accurately characterize affective haptic perception (Valenza, 2016; Triscoli 2017). Compared to conventional linear measures, nonlinear dynamical HRV indices explain a greater percentage of the variance in attention, memory, reaction times and mood (Young, 2015). Dynamical systems methods can be used to produce appropriate measures such as these for the detection of changes in health, wellbeing, cognitive function and disease states (Cheng, 2013).

For example, measures of complexity and fractal dimension (FD) allow for the assessment of the variability or roughness of a quantity or object across an interval of time, over a region of space, or with respect to other mathematical measures or data. A variety of techniques for assessing complexity and FD have been employed, including Katz's method, Higuchi's method, rescaled range method, Hausdorff-Besicovitch dimension, Hurst exponent (Balocchi, 2011), Feigenbaum number (Gisiger, 2001), correlation dimension (Güçlü, 2011), temporal structure function analysis (Nanni, 2017) phase portrait analysis, Poincaré section analysis, correlation dimension analysis, Lyapunov exponent, and Kolmogorov entropy (Voss, 2009). A wide variety of neurological time series signals neurosciences have been shown to possess fractal structure (DiLeva, 2013, 2015), and fractal analyses have been used to objectively quantify complex patterns found in neuroscience and neurology and make predictions about clinical outcomes, categorize pathological states, and generate diagnoses (John, 2015). For example, fractals in heart beat dynamics have been a useful differentiator between physiological states such as sleep and wakefulness, as well as different states of pathology and aging (Ivanov et al., 1996, 1999a,b; Amaral et al., 1998), and fractal analysis of EEG signals using Higuchi's method has shown predictive power for medical issues such as monitoring the depth of anesthesia and sedation, sleep staging, bright light therapy and seasonal affective disorder, analysis of posturography signals, and evoked EEG (Klonowski, 2007, 2016). Improved signals of the devices and methods described herein, e.g., to encourage a suboptimal or pathological system towards a more optimal or healthy dynamic may be based upon dynamical systems measures such as complexity and FD.

Vagus Nerve Stimulation

Figure 2A:
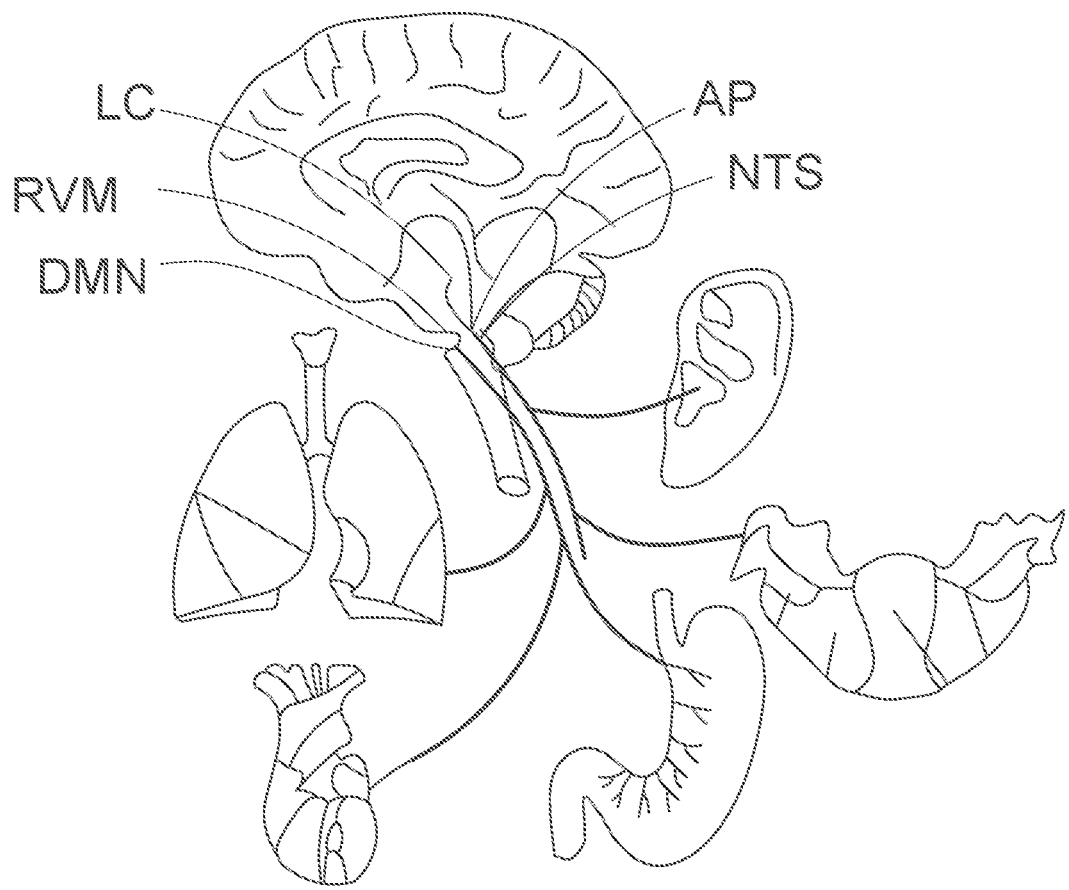
FIG. 2A is a schematic showing the vagal pathway; from (He, 2012)
Figure 2B:
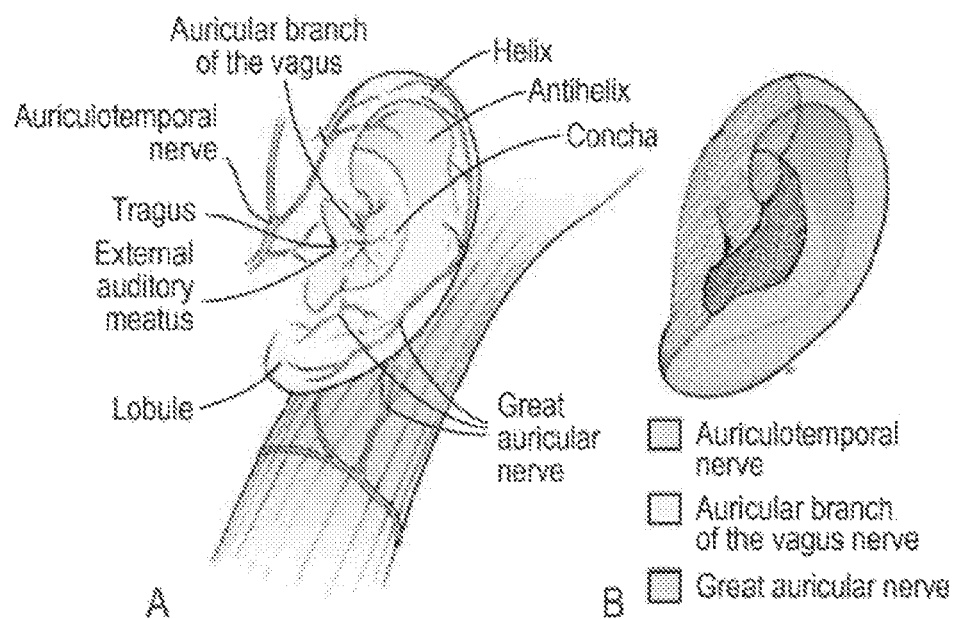
FIG. 2B is a schematic showing vagal innervation and sensory distribution of the ear; from (Riviello, 2016)

The vagus nerve, also known as cranial nerve X, is an interwebbing nerve bundle connecting almost every organ's sensory receptors to the brain. The vagus nerve interacts and regulates the parasympathetic nervous system or "rest and digest" control. The vagus nerve complex forms a bi-directional neural connection between the immune and nervous systems (Tracey, 2002; 2007) which acts to regulate inflammation and innate immune responses during tissue injury and pathogen invasion (FIG. 2A). As shown in FIG. 2A, the vagal pathway includes the heart, lungs, stomach, cervix, and many other organs and/or regions of the body (e.g., not pictured in FIG. 2A). Various organs and/or regions of the body in the vagal pathway can be accessed through the ear and project to the solitary nucleus (NTS), dorsal motor nucleus (DMN), area postrema (AP), rostral ventrolateral medulla (RVM), and the locus coeruleus (LC). FIG. 2B shows further detail regarding vagal innervation and sensory distribution of the ear.

Efferent vagal signaling plays roles in cardiac control (Thayer, 2006) and can inhibit cytokine production via acetylcholine receptor signaling in the spleen (Tracey, 2007). The interrelatedness of afferent and efferent signaling is highlighted in the manner by which afferent signals carried in the vagus nerve can activate an efferent response that inhibits cytokine release, or "cholinergic inflammatory reflex" (Tracey, 2007). Depressed vagus nerve activity is associated with increased morbidity and mortality in sepsis, rheumatoid arthritis, lupus, sarcoidosis, inflammatory bowel diseases, trauma (Tracey, 2007), depression, and stress (Porges, 1995). Enhanced vagal tone is associated with a variety of benefits, including increased social and psychological well-being (Kok, 2010; Oke, 2009) and yoga (Field, 2011).

Vagus nerve stimulation (VNS) using implantable devices has received FDA approvals for epilepsy, depression, and obesity, and the first approval for a noninvasive transcutaneous treatment was granted to the Gammacore device (Electrocore, USA) in 2017. Transcutaneous VNS methods are currently being investigated (and found to be effective and safe) for a variety of conditions, including atrial fibrillation (Stavrakis, 2015; Yu, 2013), depression (Hein, 2013; Aaronson, 2013), diabetes (Huan, 2014), endotoxemia (Huston, 2007), memory (Jacobs, 2015), myocardial infarction (Wang, 2016), tinnitus (Kreuzer, 2014), and stroke (Cai, 2014).

Transcutaneous access is found through the auricular branch of the vagus nerve (ABVN). The ABVN, which is the only peripheral branch of the vagus nerve, mainly supplies the auricular concha and most of the area around the auditory meatus. Vagal nerve stimulation has been investigated using electrical stimulation (Hei, 2013; Yakunina, 2017), acupuncture (He, 2012) and magnetic resonance imaging (Frangos, 2015).

Vagal Tone and Wellbeing

Enhanced vagal tone (VT) is associated with numerous indices of psychological well-being, including trait positive emotionality, pro-social behaviour, sympathy and decreased maladaptive coping, including working memory, directed attention, fewer negative responses to environmental stressors, greater self-regulatory capacity, and better ability to regulate negative facial expressions. Individuals higher in VT appear to be more cheerful and kind and deal better with stress (Kok, 2010). Enhanced VT is also associated with the benefits of many of mind-body therapies (MBTs) and yoga (Kok, 2010; Oke, 2009; Field, 2011; Muehsam, 2016).

Enhanced VT could also be used to improve symptoms of common stress-related disorders such as insomnia and reduced libido or sexual function. In both men and women, sexual arousal and orgasm are mediated by afferent vagal signaling to specific brain centers (Stoléru, 2012): observations that women with complete spinal cord injury were able to perceive genital stimulation and respond, including to orgasm, showed that vagus nerves provide a direct sensory pathway between the vagina, cervix, uterus, and the brain (Whipple, 2002). Accordingly, as described herein, present device and method may be used for priming of sexual arousal or desire, priming of the limbic system, enhanced pleasure, climax and orgasm.

Enhanced VT may play a role in our ability to cope with stressors through increased ability to resolve stress-related signaling in the vagally mediated hypothalamic-pituitary-adrenal (HPA) axis (Kok, 2010; Muehsam, 2016). VT modulates the ability of the HPA axis to resolve stress responses that mediate the production of cortisol. For example, chronic cortisol elevations due to physical, psychological and psychosocial stress contribute to inflammation and can cause the immune system to become less sensitive to cortisol, resulting in compromised immune responses. Conversely, interventions such as VNS can improve health outcomes and wellbeing by lessening allostatic load and the associated neuroendocrine signaling that results in downstream immunologic and nervous system consequences (Muehsam, 2016). More plainly put, VNS can produce benefits by removing or ameliorating the harmful effects of chronic stressors, thus allowing the body's innate healing responses to be more fully expressed.

Interoception

Interoceptive signaling is a process that sends neural information from the body to the brain. Early views on interoception described it as "the sense of the physiological condition of the entire body," beginning with the senses of temperature, pain, and itching (Craig, 2002). Interoception is believed to regulate many life processes at the most basic levels, and plays roles in modulating emotional experience and subjective awareness at "the most complex levels" (Duquette, 2017). Interoception is how we perceive the inner landscape of our bodies, thoughts and feelings. In a sense, interoception is how we perceive ourselves.

Interoceptive stimuli send direct messages to the brain, providing information about many vital activities, including thirst, itch, dyspnea, 'air hunger', the Valsalva maneuver, sensual touch, penile stimulation, sexual arousal, coolness, warmth, exercise, heartbeat, wine-tasting (in sommeliers), and distension of the bladder, stomach, rectum or esophagus (Craig, 2009).

Interoception emerges when afferent information is processed, such as from C-tactile nerves or the vagus nerve and its branches, including the auricular branch of the vagus nerve. There are specialized areas of the CNS, for example, the nucleus tractus solitarii, that receive afferent signals from the periphery and/or the insula and/or the anterior cingulate cortex and/or related regions that have specialize structures where information from afferent nerve projections is processed. In addition to generating conscious feelings of the visceral state, further specialization in these structures in social mammals (humans, higher apes, elephants, and cetaceans at least) where specialized neurons may be associated with empathy or the visceral apprehension of another's emotional state. The ability in these social mammals to sense the interoceptive state of other members may serve to enhance social cohesion and reduce negative interactions.

Interoceptive signaling can be tested in a variety of ways, the most common of which is heartbeat detection: studies have found that higher scores on heartbeat detection predict superior performance on some laboratory gambling tasks, for stock market traders as compared to non-traders, and that heartbeat detection scores were predictive of the traders' profit and loss statements (Kandasamy, 2016).

Enhanced interoception through nerve stimulation may provide for improving resilience and symptoms of common stress-related disorders such as insomnia, reduced anxieties including, performance anxiety, social anxiety, fear, PTSD, and ADHD. Other benefits of the present device and method include enhanced attention and engagement, lower blood pressure, and reduced blood cortisol levels. Enhanced interoception also offers a means for ameliorating reduced libido or sexual function. In both men and women, sexual arousal and orgasm are mediated by afferent vagal signaling to specific brain centers (Stoléru, 2012): observations that women with complete spinal cord injury were able to perceive genital stimulation and respond, including to orgasm, showed that vagus nerve fibers provide a direct sensory pathway from the vagina, cervix, and uterus to the brain (Whipple, 2002). Benefits of present device and method thus also include priming of sexual arousal or desire, priming of the limbic system, enhanced pleasure, climax and orgasm.

While electrical stimulation has been utilized for nerve stimulation, mechanical stimulation approaches are relatively uncommon. Ultrasound (>20 KHz) has been shown to activate peripheral nerves (Legon 2012, Gavrilov 1976) and low frequency acoustic vibrations (<20 KHz) targeted at activating somatosensory mechanoreceptors have demonstrated success in enhancing proprioception (Harry 2012, U.S. Pat. No. 8,308,665). While mechanical stimulation has demonstrated ability to activate nerves, the mechanisms have not yet been fully elucidated, nor has the gamut of potential downstream effects been fully explored, such as the ability to modulate psychophysiological arousal, produce benefits through neural plasticity, or develop treatments for disease conditions and symptoms.

Mechanical stimulation approaches, however, offer a number of advantages in comparison with electrical stimulation. Notably, mechanical stimulation offers a substantially more robust safety profile than electrical stimulation. Notably, electrical stimulation side effects include: 1) skin irritation resulting from the gels needed for good skin contact, 2) the possibility of burns or rashes, and 3) pain or irritation at the stimulation site. In contrast, mechanical stimulation results in soft buzzing and/or gentle warming sensation on the skin underneath the device, does not require as precise placement, and does not require skin-irritating gels or pose the same risk of burns or rashes.

Development of appropriate mechanical stimulation approaches and devices is non-trivial. Mechanical and electrical stimulation rely on different mechanisms of action to activate nerves. Accordingly, because the approaches for delivering electricity are inherently different than those used for delivering mechanical stimulation, it is effective parameters used in transcutaneous electric stimulation are not directly applicable to mechanical stimulation approaches.

In certain embodiments, mechanical stimulation uses displacement of mechanoreceptors and cutaneous sensory receptors in the skin to stimulate the afferent sensory pathway and uses the properties of receptive fields to propagate stimulation through tissues and bone. Mechanical stimulation by mechanical transducers can stimulate peripheral nerves to benefit sensation, peripheral neuropathy, balance, and proprioception.

The approaches described herein include mechanical stimulation of nerves beyond peripheral nerves, such as cranial nerves and other nerve types. Stimulation of nerves other than peripheral nerves can produce changes in both well-accepted biometric measures—such as heart rate, heart rate variability, blood pressure, electroencephalography, and blood levels of neurotransmitters and proteins—and clinically-validated subjective assessments of mood and cognitive state.

Moreover, in certain embodiments, the systems, methods, and devices described herein are directed to a new family of waveforms and treatment protocols delivered by vibratory devices for non-invasively stimulating nerves, tissues and vasculature, resulting in different and unique modulation of these peripheral nerves and tissues, along with the sensory and motor nerve processes they govern. As described herein, in certain embodiments, the waveforms differ from traditional sinusoidal and square waves through the introduction of particular transformed time-varying waves, modulation frequencies, waveshapes, aperiodic waveforms, polygonal pulse trains, or transformed periodic signals, including sinusoids, square waves, triangle waves, or sawtooth waves and other configurations. Because these waveforms result in biometric and mood responses that are different than those achieved using traditional neurostimulation waveforms, a health professional or patient can stimulate a particular response or produce an enhanced effect using a single device.

These new non-invasive neurostimulation protocols with resulting unique and improved physiological responses provide major advantages over using multiple different devices, different body placement designs, and/or surgical implantation to achieve different neuromodulation goals. Different neuromodulation goals include: increasing or decreasing alertness versus fatigue and sleepiness; decreasing tension and stress more quickly and to a greater degree; enhancing resilience and recovery from stress events; vibrating tissues and interrelated nerve systems in a particular body location; affecting emotional states such as arousal, enjoyment, hunger, anger, mood, depression, and alertness; and resulting body states of fight/flight versus calm/rest/digest.

B. STIMULATION TARGETS

The devices and methods described herein may be used for providing mechanical stimulation that elicits a response from a variety of nerve, mechanoreceptor, and protein targets, as well as for entrainment of brain waves. In particular, characteristics of mechanical waves produced via the devices and methods described herein can be tailored to target particular components (e.g, nerves, mechanoreceptors, proteins) of biological pathways, or brain waves types. For example, FIG. 3 shows a table of various protein, cell, and nerve targets, and associated frequency ranges to which they respond. Also shown in the table of FIG. 3 are frequencies associated with different types (theta, alpha, beta, and gamma) of brain waves. Mechanical stimulation having frequencies corresponding to these different types of brain waves can be used to entrain brain waves of a subject.

i. Nerve Stimulation

In certain embodiments the systems, methods, and devices described herein provide for mechanical stimulation of one or more specific nerves. In certain embodiments, the one or more nerves include a C-tactile afferent nerve, a vagus nerve and/or a trigeminal nerve. The one or more nerves may include one or more of: a peripheral nerve, a vestibular nerve, baroreceptors, a greater auricular nerve, a lesser occipital nerve, cranial nerve VII, cranial nerve IX, cranial nerve XI, and cranial nerve XII.

Nerves may be stimulated via mechanical waves generated by the systems, methods, and devices described herein in a variety of manners. For example, in certain cases, mechanical waves applied to a subject's skin stimulate mechanoreceptors, which, as described herein, in turn lead to stimulation of one or more nerves. Nerves may also be stimulated directly via mechanical waves without necessarily involving mechanoreceptors. In particular, subjecting free ends of nerves to mechanical stress can stimulate nerves directly.

In certain embodiments, the mechanical waves produced by the systems, methods, and devices described herein are tailored depending on the particular nerves to be stimulated. For example, certain mechanical wave signals may be well suited to, and, accordingly, used for the stimulation of certain nerves, such as a vagus nerve, and different signals may be used for stimulation of other nerves. In certain embodiments, the mechanical wave used for nerve stimulation may also be controlled and tailored based on a particular mechanisms of nerve stimulation. For example, one type of mechanical wave may be used for stimulation of nerves using mechanoreceptors, while another type may selectively target and/or be optimized for direct stimulation of nerve free ends.

In certain embodiments, as shown in the table of FIG. 3, different nerves may respond to different frequency ranges. For example, the Vagus nerve may be targeted via stimulation having a frequency ranging from approximately 20 to 200 Hz (e.g., 50 to 200 Hz; e.g., 100 to 200 Hz; e.g., 130 to 180 Hz), while a C-tactile afferent may be targeted via stimulation having a frequency less than or approximately equal to 50 Hz.

ii. Mechanoreceptor Stimulation

In certain embodiments, the systems, methods, and devices described herein provide for stimulation of non-nerve targets such as mechanoreceptors (e.g., Merkel cells; e.g., baroreceptors), tissue regions, and vascular targets (e.g., a carotid artery). Stimulation of mechanoreceptors, tissue regions, and vascular targets may provide health benefits without necessarily requiring nerve stimulation (although nerves may still be stimulated). In certain embodiments, as with various different nerves, the systems, methods, and devices described herein utilize mechanical waves that are selectively tailored depending on the particular non-nerve target to be stimulated.

For example, as shown in the table of FIG. 3, Merkel cells respond to frequencies ranging from 5 to 15 Hz. Accordingly, in certain embodiments, mechanical stimulation having a frequency ranging from 5 to 15 Hz may be used for stimulation of Merkel cells.

iii. Piezo ProteinStimulation

In certain embodiments, the systems, methods, and devices described herein provide for stimulation of piezo proteins. Specific mechanical waves may be produced by the systems, methods, and devices described herein to target/optimally stimulate various piezo proteins (e.g., Piezo1; e.g., Piezo2).

For example, constant stimulus of sensory receptors can produce desensitization, and Piezo1 and Piezo2 desensitize, ceasing to promote cation current, with different voltage-dependent time constants (Wu, 2017). Following complete desensitization, an inactivation mechanism operates such that the ion channel cannot be efficiently opened without first returning the initial stimulus to baseline for a recovery period (Gottlieb, 2012). For both Piezo1 and Piezo2, the recovery period required before fully responding to a new stimulus is on the order of hundreds of milliseconds to seconds (Coste, 2012). Accordingly, in certain embodiments, the devices, systems, and methods described herein may generate and deliver mechanical waves that are tailored (e.g., having particular frequency components) to couple with these sensitization and inactivation time constants, thereby producing preferred modes of stimulation.

Figure 4:
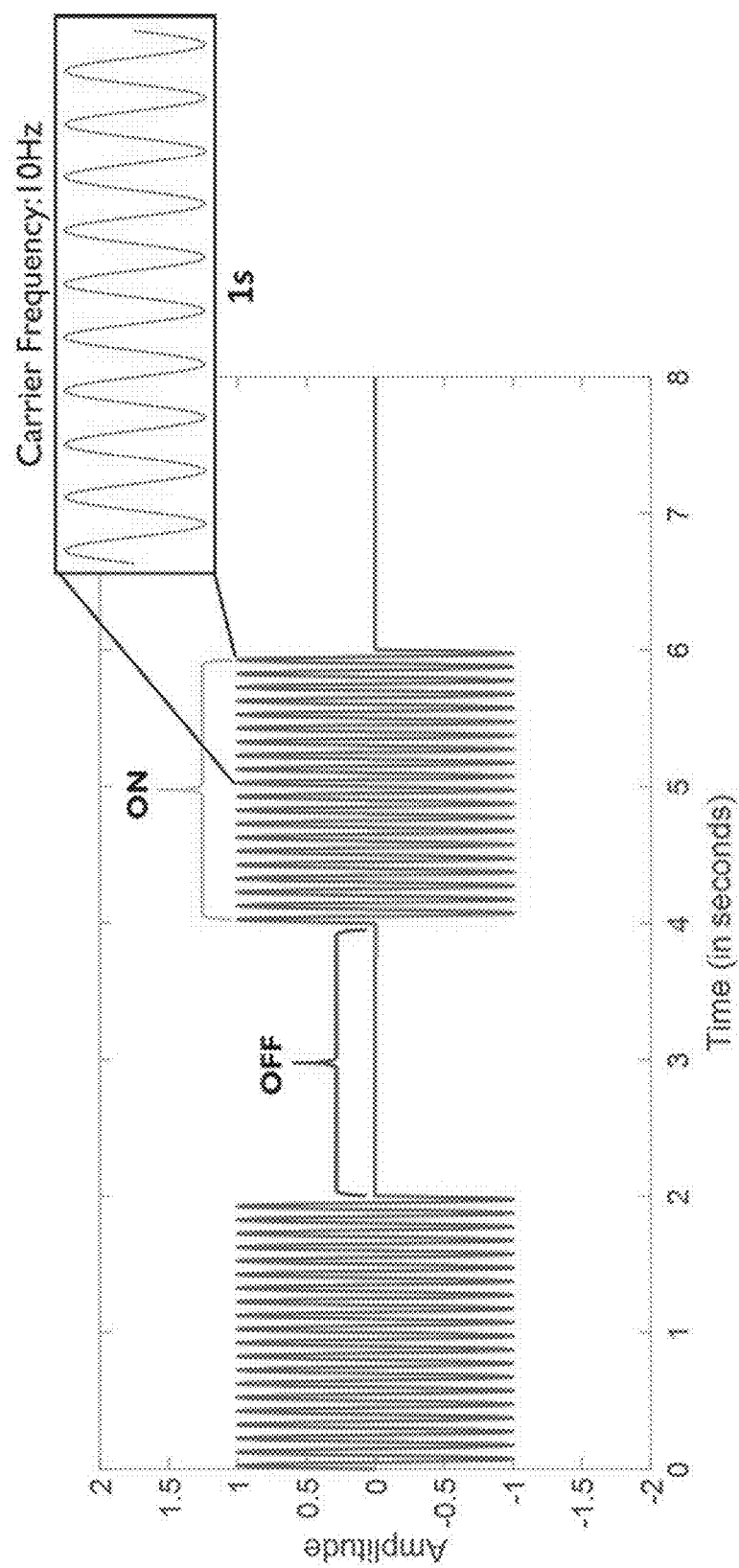
FIG. 4 is a graph showing an example isochronic wave, according to an illustrative embodiment.

For example, as shown in the table of FIG. 3, Piezo2 proteins respond to frequencies below 100 Hz and have a refractory range of approximately 2 seconds. Accordingly, mechanical waves having frequency components below 100 Hz may be used for stimulation of Piezo2 proteins. Mechanical waves, such as isochronic signals as described herein, may also be tailored to accommodate the refractory range (e.g., recovery period) of Piezo2 proteins. In particular, isochronic signals have one or more low-amplitude sub-intervals, the duration of which can be selected to accommodate the recovery period Piezo2 proteins. For example, the isochronic signal shown in FIG. 4 is a periodic signal having low-amplitude sub-intervals lasting 2 seconds, during which the signal has substantially zero amplitude (e.g., it is effectively 'turned off'). Accordingly, such a signal allows for recovery of the Piezo2 proteins before amplitude of the signal is increased (e.g., 'turned on') and stimulus is again applied. Other isochronic signals incorporating low-amplitude sub-intervals that accommodate recovery periods of Piezo2 proteins may also be used. Low-amplitude sub-intervals of isochronic signals may be analogously tailored for recovery periods of other biological targets, such as Piezo1 proteins and other biological targets.

iv. Dynamical Systems Approaches

In certain embodiments, the mechanical waves produced by the systems, methods, and devices described herein are controlled using dynamical systems methods. Dynamical systems measures may be used to assess electronic response signals (e.g., electronic) to detect particular network responses correlated with changes in mechanical wave properties. Particular waveforms of the electronic drive signal are controlled based on the dynamical properties of the electronic response signal such that the mechanical waves delivered to the body location of the subject are modulated to target/optimally enhance particular preferred responses. A block flow diagram of an example process for using a dynamical systems method for tailoring mechanical waves generated and delivered by the approaches described herein is shown in FIG. 14C.

v. Brain Wave Entrainment

In certain embodiments, the mechanical waves produced by the systems, methods, and devices described herein are tailored for entrainment of brain waves. The table in FIG. 3 lists four types of brain waves and their corresponding frequencies. As shown in the table of FIG. 3, theta waves are associated with frequencies ranging from approximately 4 to 8 Hz, alpha waves are associated with frequencies ranging from approximately 8 to 16 Hz, beta waves are associated with frequencies ranging from approximately 16 to 30 Hz, and gamma waves are associated with frequencies ranging from approximately 30 to 60 Hz. Frequencies of the mechanical stimulation provided by the devices, systems, and methods described herein can be selected to fall within a range associated with a particular type of brain wave. In certain embodiments, by providing mechanical stimulation corresponding to a particular brainwave type in this manner, the particular brainwave type corresponding to the provided mechanical stimulation is induced in the subject.

C. STIMULATION DEVICE

As described herein, a stimulation (e.g., a neurostimulation) device may be used to generate a mechanical wave and deliver it to a subject in order to stimulate nerves and/or targets such as mechanoreceptors, mechanosensitive proteins, tissue regions, and vascular targets. FIG. 5 shows a schematic of an example stimulation device 500. The stimulation device comprises one or more mechanical transducers 504, one or more controller boards 502, and a battery 506. The controller board(s) 502, mechanical transducer(s) 504, and battery 506 are in communication (e.g., through one or more connectors; e.g., wirelessly). The controller board(s) 502 control(s) a waveform output that is applied to the transducer(s) 504 in order to generate a mechanical wave. The waveform output is an electronic signal that drives the transducer(s), which, in response, generate a mechanical wave. The mechanical wave can then be delivered to the subject, for example by placing the transducers in contact with the subject's skin at various body locations, in order to stimulate various nerves and/or other targets via mechanical vibration. In certain embodiments, the stimulation device is a wearable stimulation device. As shown in FIGS. 6A-6D, in various embodiments of the neuromodulation devices described herein, multiple mechanical transducers may be used and controlled via one or more controller boards. Approaches and device designs utilizing multiple mechanical transducers are described in further detail below (in section C.iii).

In certain embodiments, the controller board(s) is/are in communication with an external computing device, such as a personal computing device (e.g., a personal computer; e.g.; a smartphone; e.g., a laptop computer; e.g., a tablet computer; e.g., a smartwatch; e.g., a fitness tracker), such that the waveform output may be controlled via the external device. For example, a user may use a smartphone to control the waveform output by sending a wireless signal from the smartphone to the controller board(s) of the stimulation device. In certain embodiments, the device comprises various buttons, dials, and the like that are connected to and/or in communication with the controller board(s) and which may be adjusted to control the waveform output.

Figure 7:
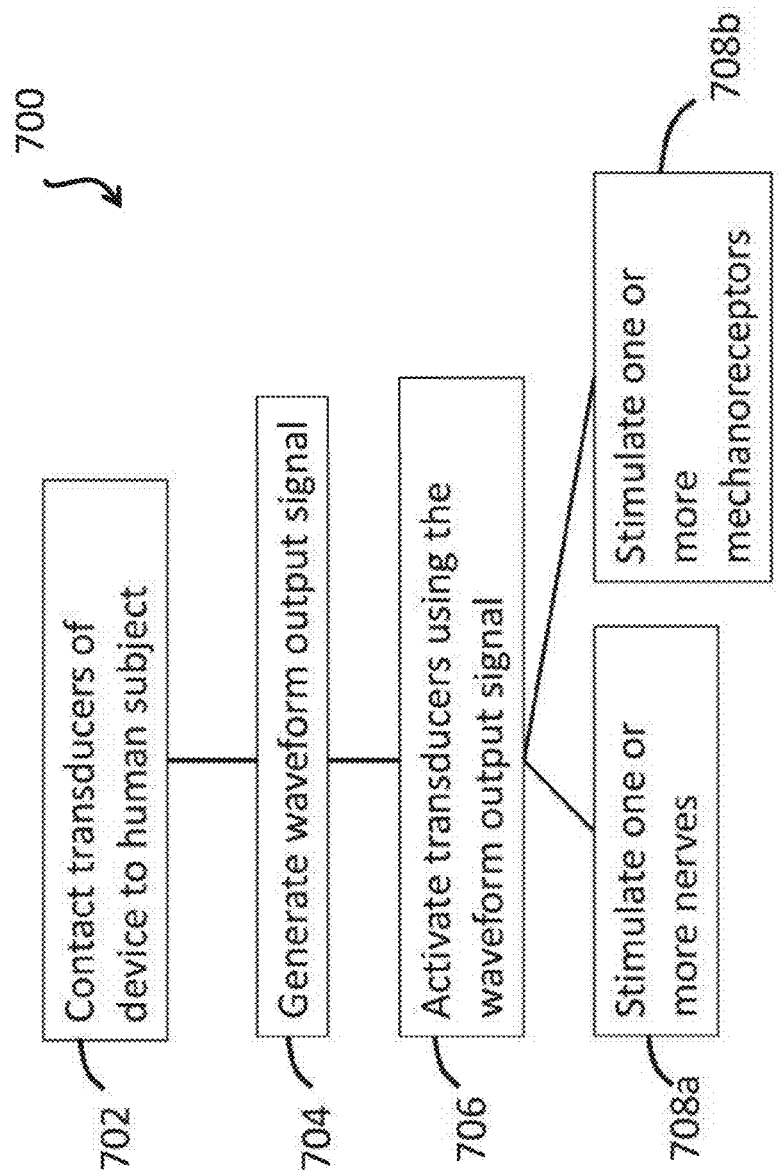
FIG. 7 is a block flow diagram of a process for stimulating one or more nerves and/or one or more mechanoreceptors, according to an illustrative embodiment.

FIG. 7 shows an example process 700 for providing mechanical stimulation to a subject (e.g., for treatment) using the devices described herein. In process 700, transducers of the device are contacted to the subject 702, a waveform output signal is generated 704 and used to activate the transducers 706 in order to deliver mechanical stimulation to the subject. The delivered mechanical stimulation may stimulate one or more nerves 708a and/or one or more mechanoreceptors 708b of the subject.

Figure 8A:
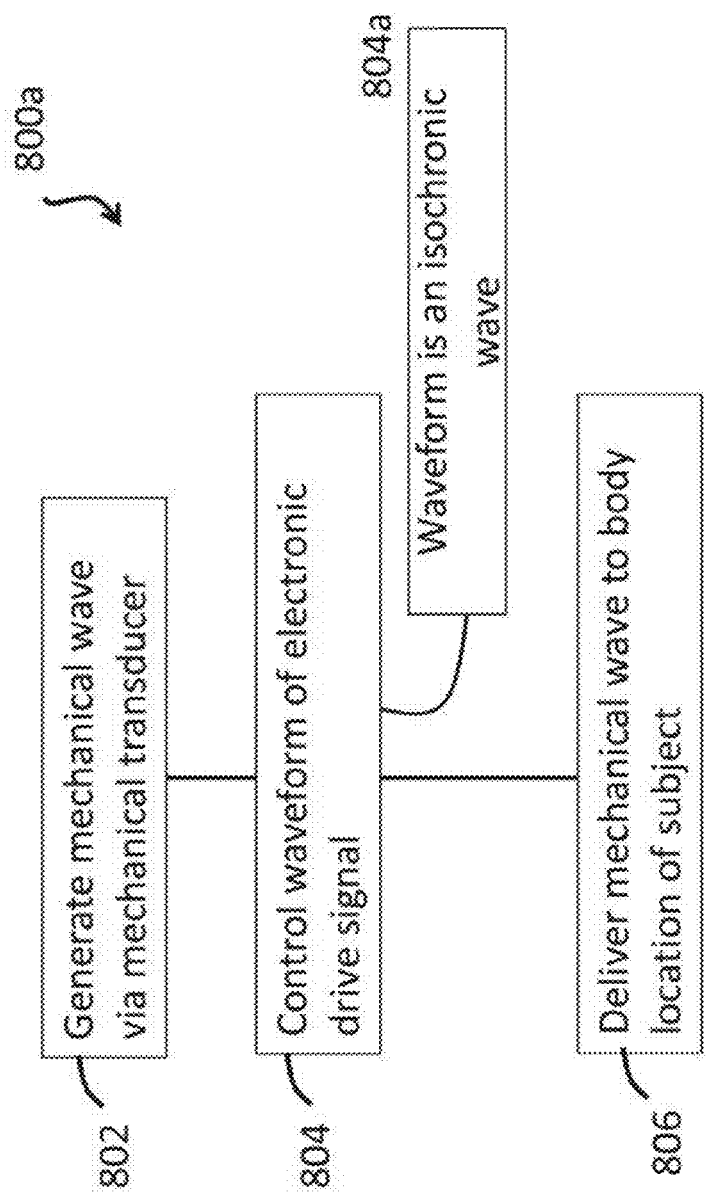
FIG. 8A is a block flow diagram of a process for treating a subject via mechanical stimulation using a transformed time varying wave, according to an illustrative embodiment.
Figure 8B:
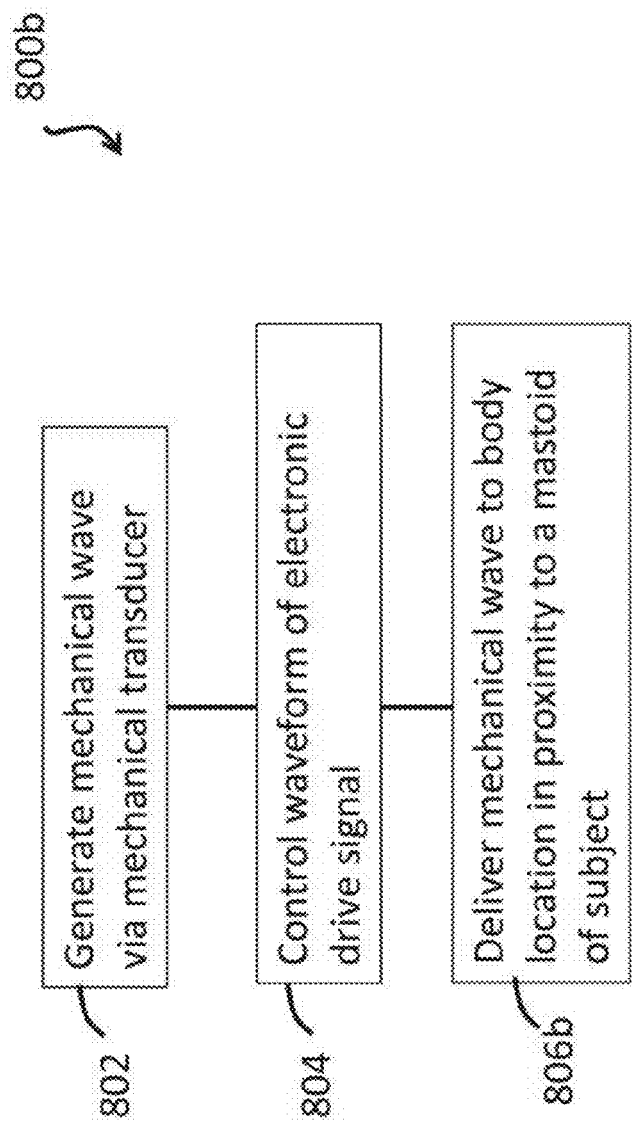
FIG. 8B is a block flow diagram of a process for treating a subject by delivering mechanical stimulation to a mastoid location, according to an illustrative embodiment.
Figure 8D:
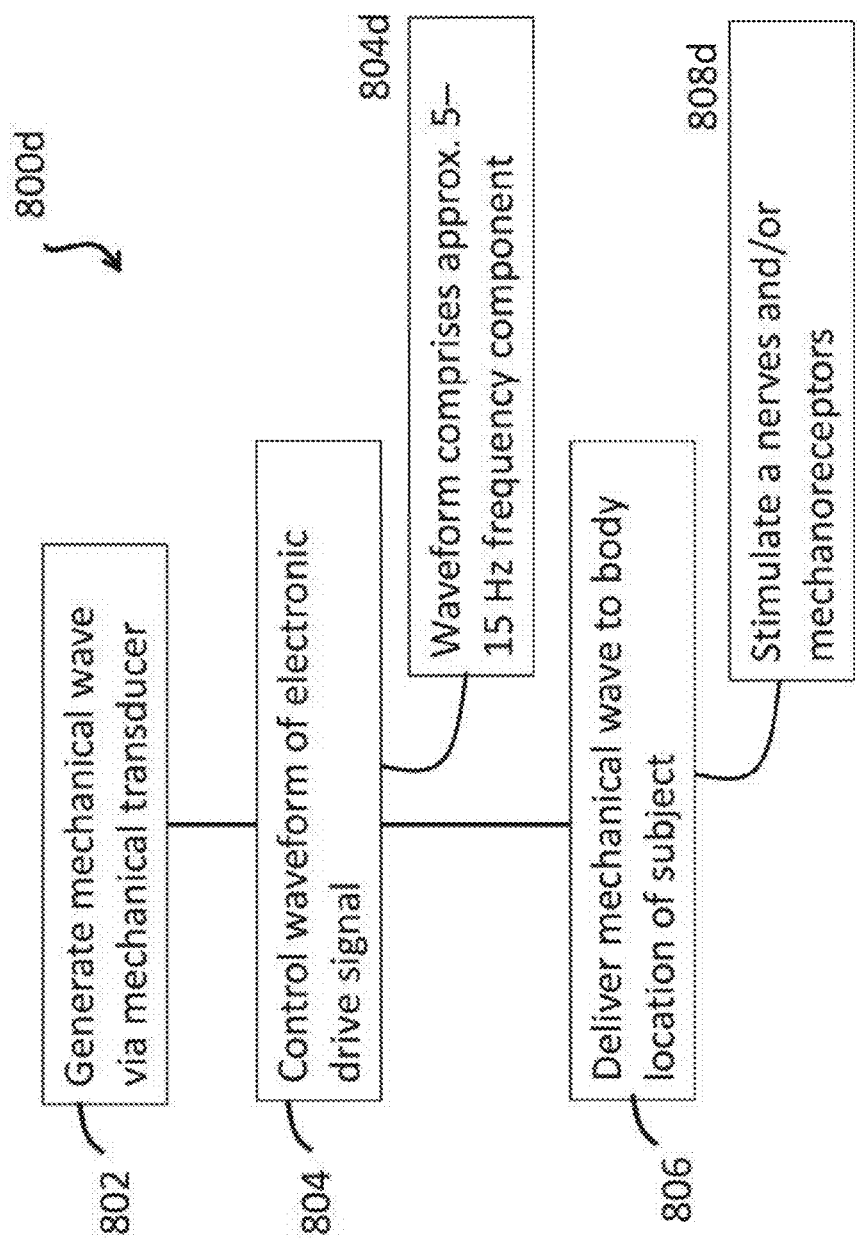
FIG. 8D is a block flow diagram of a process for treating a subject via mechanical stimulation of one or more nerves and/or mechanoreceptors, wherein the mechanical stimulation is generated using a waveform comprising a frequency component ranging from approximately 5 to 15 Hz, according to an illustrative embodiment.
Figure 9:
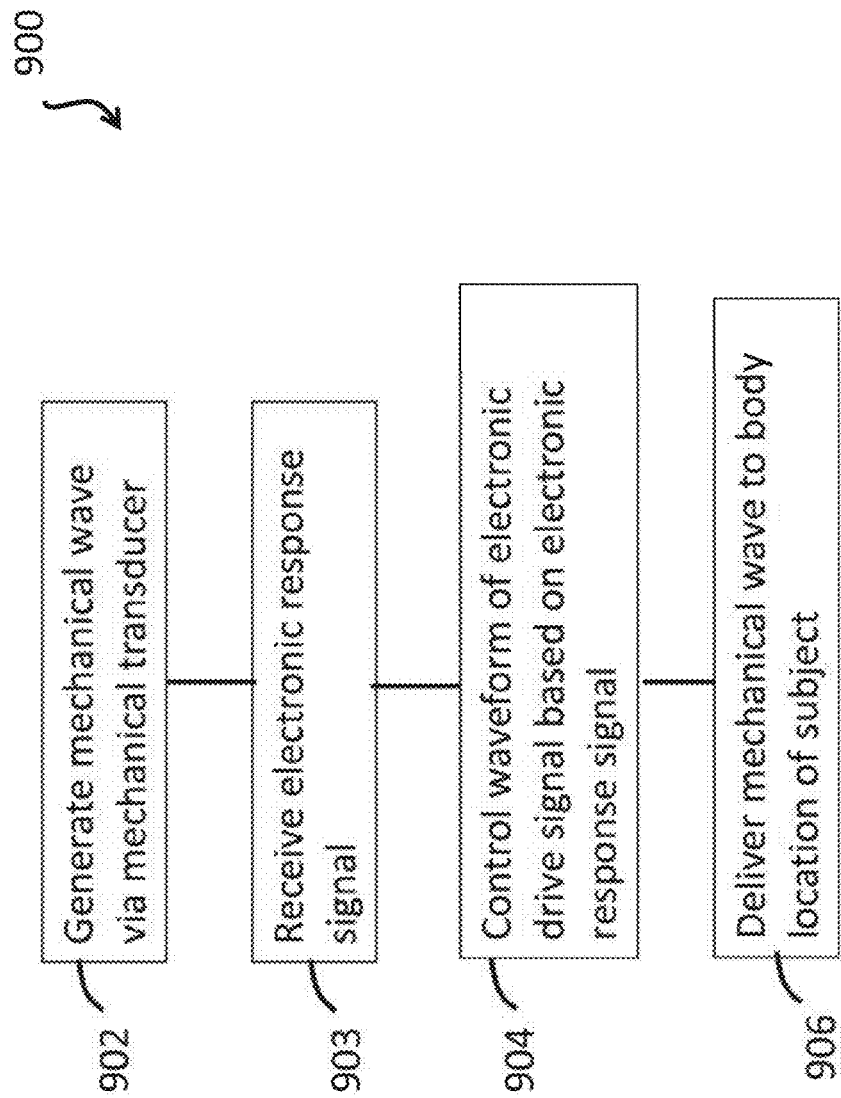
FIG. 9 is a block flow diagram of a process for treating a subject via mechanical stimulation generated and/or modulated in response to feedback from a monitoring device, according to an illustrative embodiment.
Figure 10:
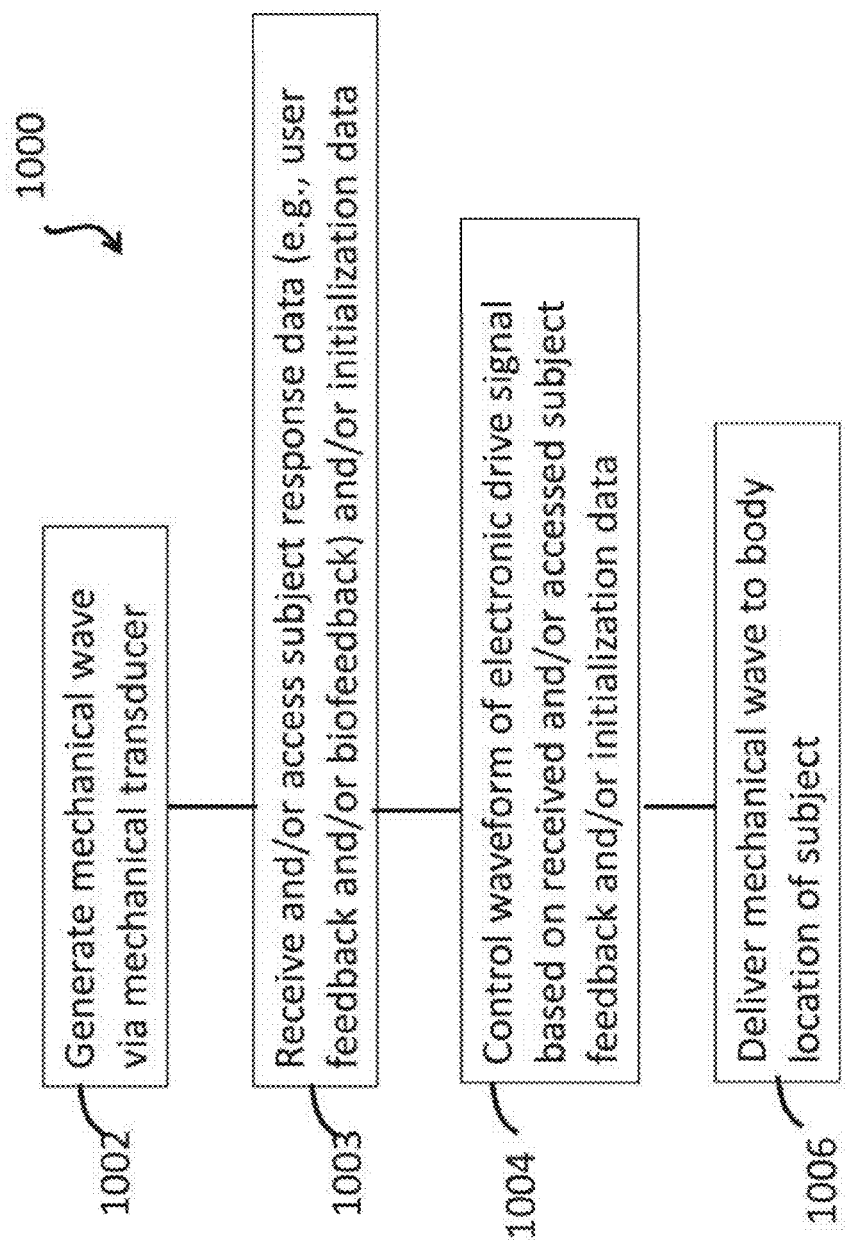
FIG. 10 is a block flow diagram of a process for treating a subject via mechanical stimulation generated and/or modulated based on subject feedback and/or initialization setting data, according to an illustrative embodiment.
Figure 11:
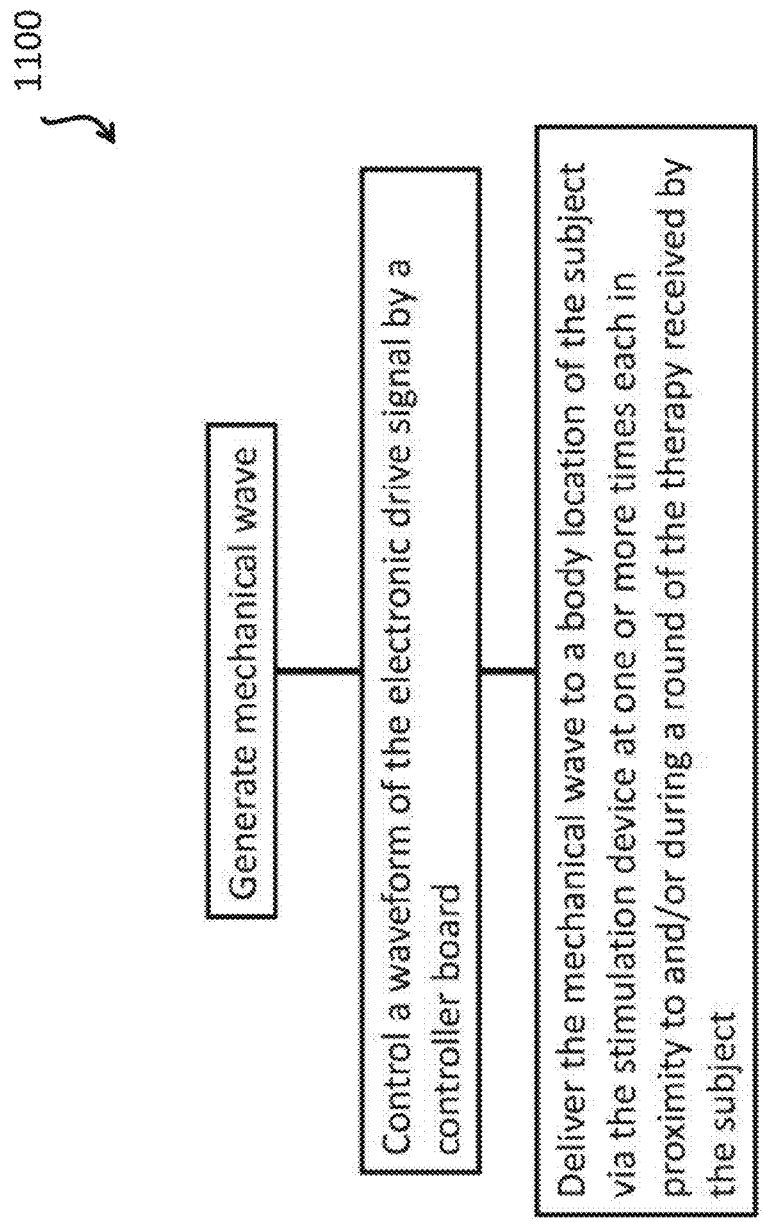
FIG. 11 is a block flow diagram showing a processes for treating anxiety and/or an anxiety related disorder by providing transcutaneous mechanical stimulation in combination with one or more rounds of therapy, according to an illustrative embodiment.
Figure 12:
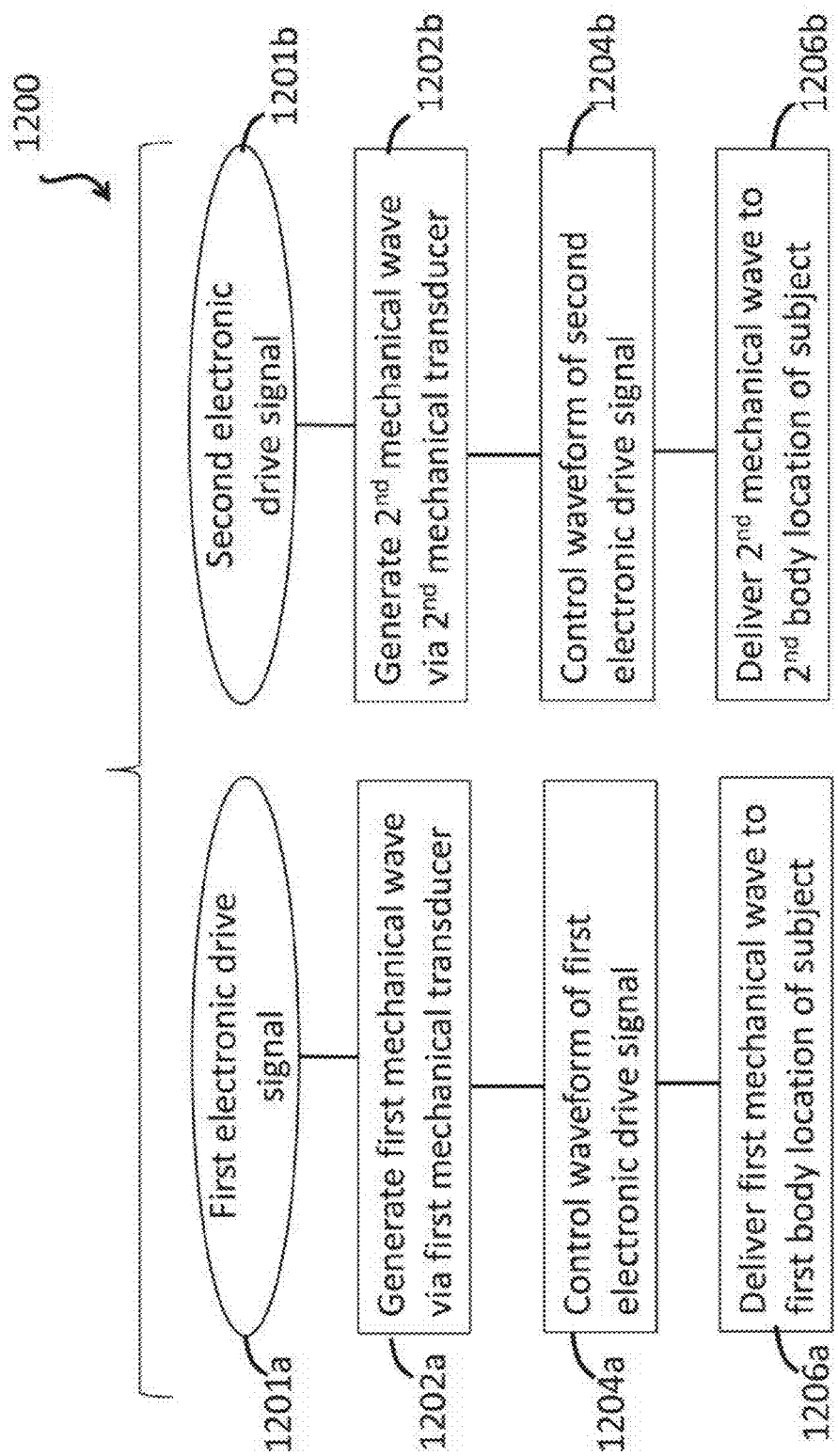
FIG. 12 is a block flow diagram of a process for treating a subject via mechanical stimulation delivered to the subject in a binaural fashion, according to an illustrative embodiment.
Figure 13:
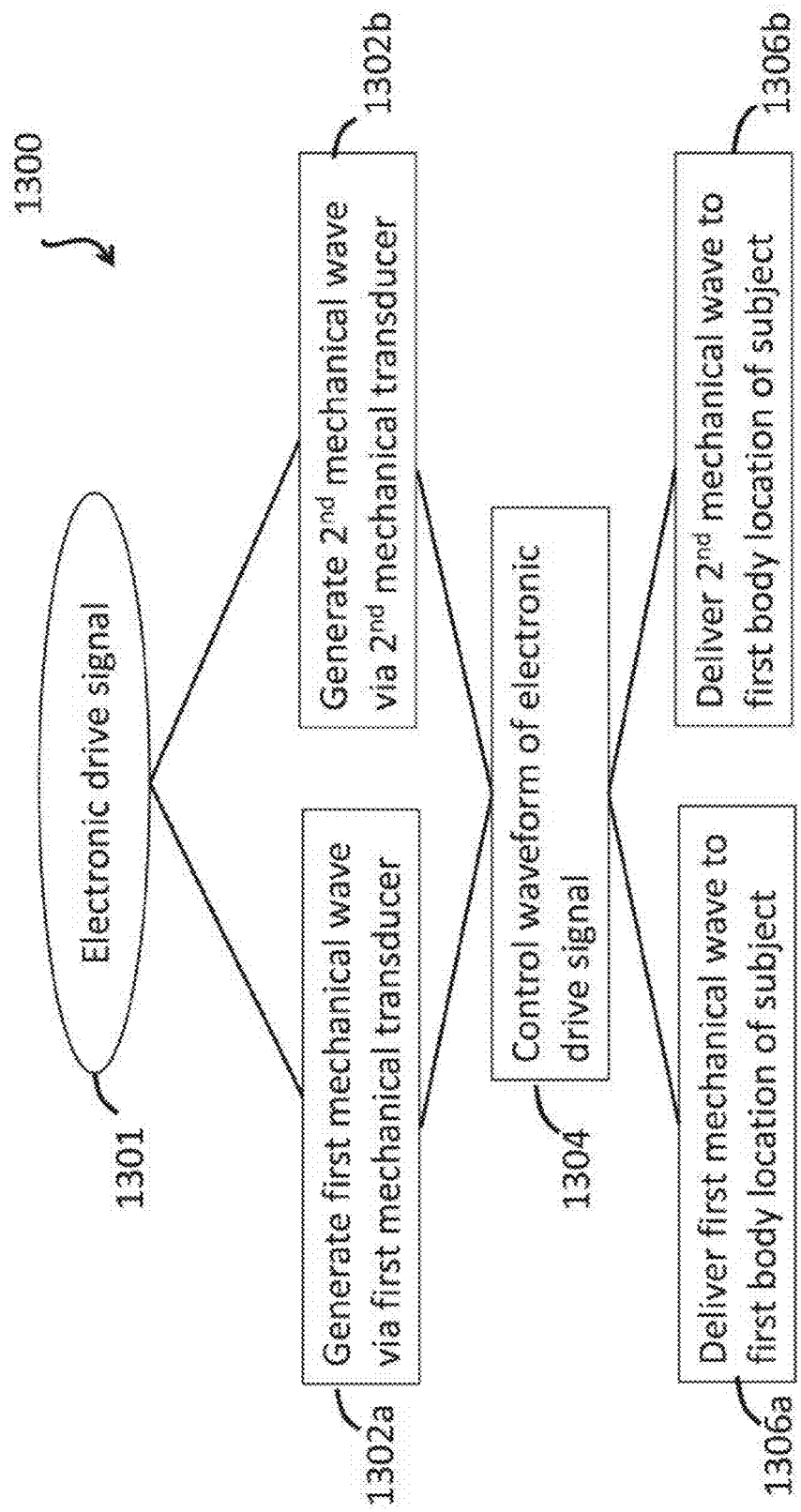
FIG. 13 is a block flow diagram of a process for treating a subject via mechanical stimulation delivered to the subject in a monaural fashion, according to an illustrative embodiment.
Figure 14A:
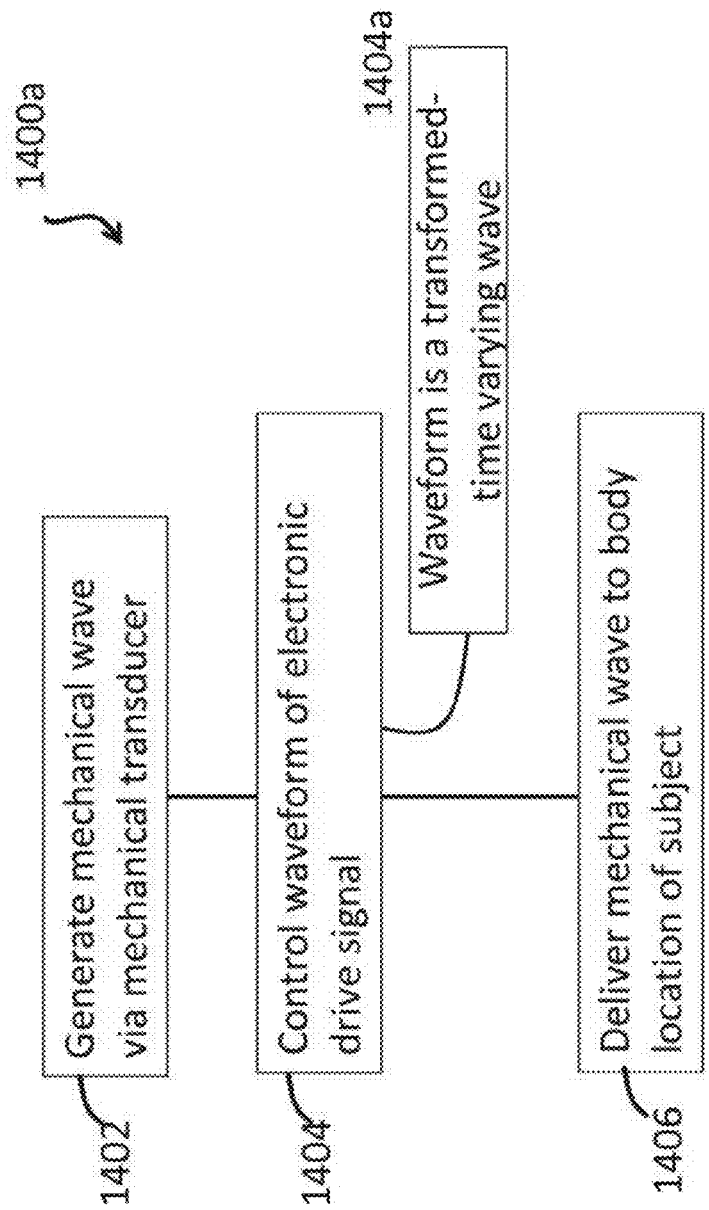
FIG. 14A is a block flow diagram of a process for treating a subject via mechanical stimulation using a transformed time varying wave, according to an illustrative embodiment.
Figure 14B:
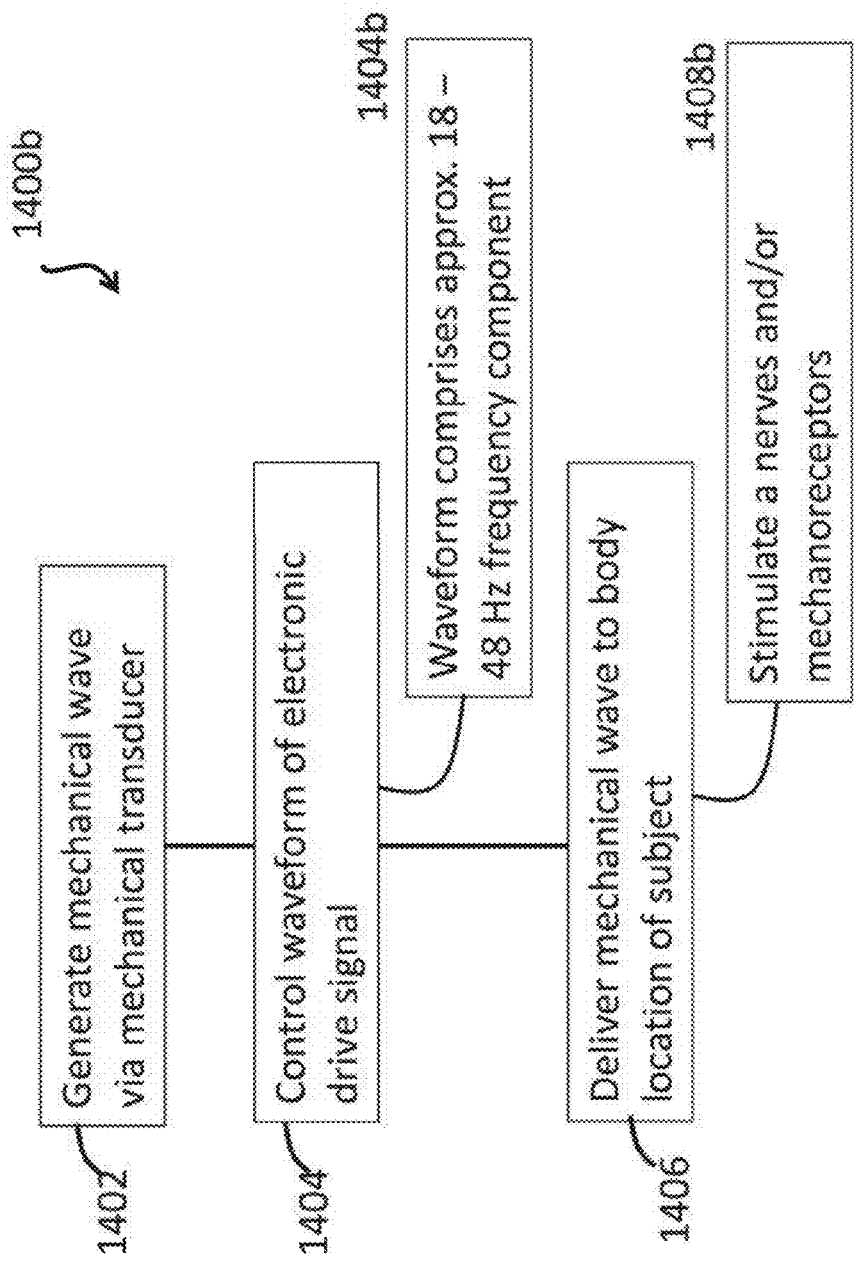
FIG. 14B is a block flow diagram of a process for treating a subject via mechanical stimulation of one or more nerves and/or mechanoreceptors, wherein the mechanical stimulation is generated using a waveform comprising a frequency component ranging from approximately 8 to 48 Hz, according to an illustrative embodiment.
Figure 14C:
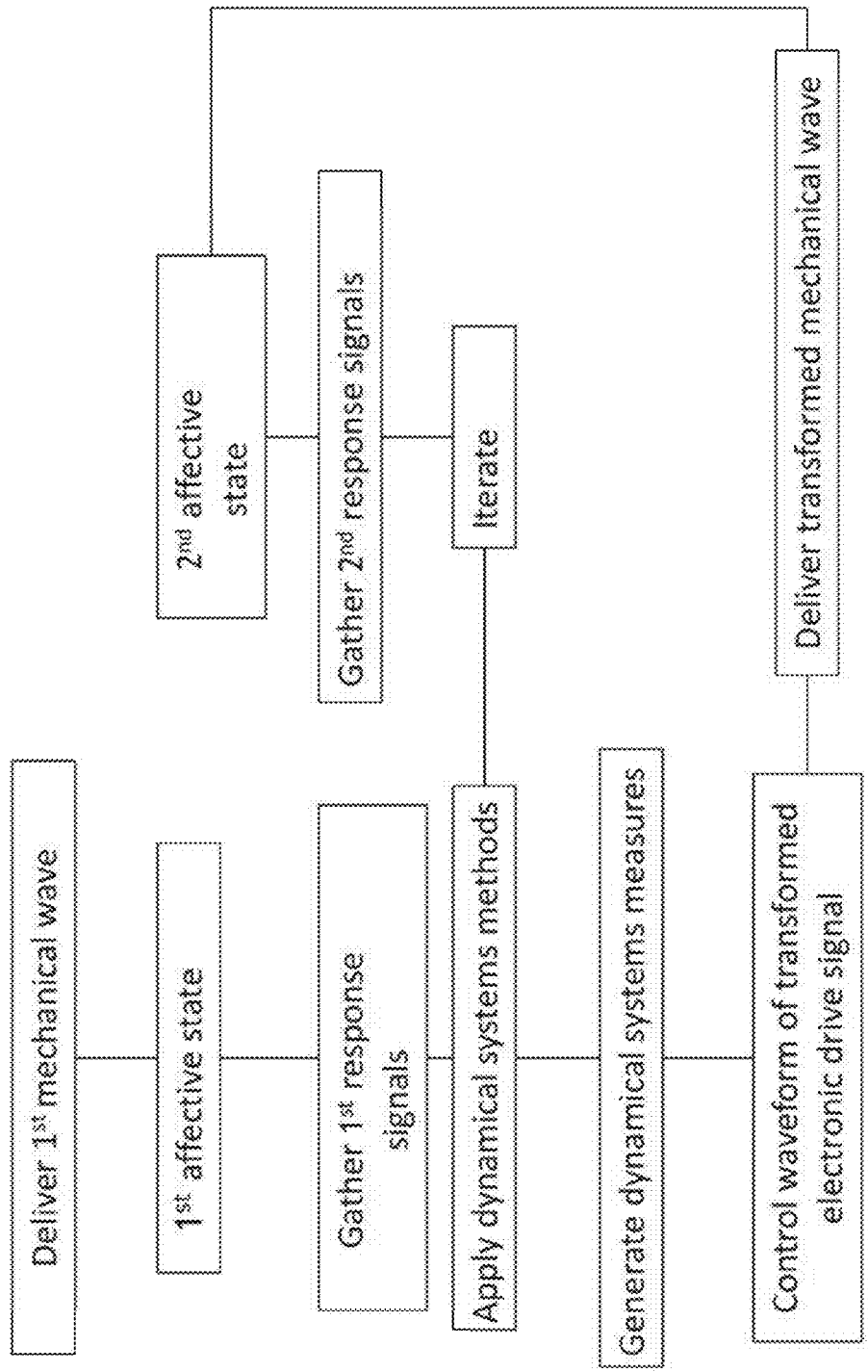
FIG. 14C is a block flow diagram of a process for controlling a waveform using dynamical systems methods, according to an illustrative embodiment.

FIGS. 8A-8D, 9-13 and 14A-14C also show example processes for providing mechanical stimulation to a subject (e.g., for treatment) based on various waveform types, target regions of a subject's body, stimulation protocols, and the like. For example, FIG. 8A shows an example process 800a for providing mechanical stimulation to a subject using an isochronic waveform. FIG. 8B shows an example process for providing mechanical stimulation to a body location of a subject in proximity to a mastoid region. FIG. 8C shows an example process for delivering mechanical stimulation to stimulate a cranial nerve of a subject. FIG. 8D shows an example process 800d for stimulating one or more nerves and/or mechanoreceptors of a subject using a waveform comprising a frequency component ranging from approximately 5 to 15 Hz. FIGS. 9 and 10 show an example processes 900 and 1000, respectively, for controlling a waveform of an electronic drive signal used to drive a mechanical transducer in an interactive fashion (e.g., based on a response signal providing biofeedback data for a subject, initialization data, user feedback, and the like). FIG. 11 shows an example process 1100 for providing mechanical stimulation in via the devices and methods described herein in combination with therapy. FIGS. 12 and 13 show example processes, 1200 and 1300, respectively, for providing mechanical stimulation in the form of binaural and monaural beats. FIG. 14A shows an example process 1400a for providing mechanical stimulation using a transformed time varying wave. FIG. 14B shows an example process for providing mechanical stimulation via a waveform comprising a frequency component ranging from approximately 18 Hz to approximately 48 Hz. Further details of these example processes are described herein. FIG. 14C shows an example process using dynamical systems approaches. Elements and features of any of the processes shown these Figures, or others, and described herein can be combined with other processes shown in the Figures and/or described herein, as well as other approaches.

As described herein (e.g., above), the mechanical vibration delivered to the subject can be tailored depending on the particular target. In certain embodiments, the controller board controls the waveform output in order to adjust the waveform output and, in turn the generated mechanical wave accordingly. The manner in which the waveform output is adjusted may account for a particular response function of the transducers such that the mechanical wave has a desired form.

i. Mechanical Transducers

Various transducers can be used to generate a mechanical wave in response to an electronic drive signal, and deliver it to a subject. Examples of such mechanical transducers include, without limitation, piezoelectric, magnetic, and mechanoelectric transducers. Transducer size may be varied, along with amplitude of the mechanical wave, as well as the direction of the mechanical force of the wave. For example, longitudinal (e.g., compression) waves may be generated or transverse (e.g., shear) waves may be generated.

Various other transducers may also be used. Different transducers have different characteristics, such as operational principle, frequency range, voltage, and area. A particular transducer may be advantageous for a particular treatment application based on its particular characteristics, and accordingly be selected for use in a device for that particular treatment application. For example, a linear transducer (e.g., a linear resonance transducer) that operates over a wide frequency range may be used. Movement of a vibrating element used to produce a mechanical wave in a linear transducer, and, accordingly, produces a longitudinal (e.g., compression) wave when placed in contact with a body location on the subject. It has been discovered that such linear motion is advantageous for stimulating certain mechanoreceptors, such as Merkel cells.

The transducers can include adhesives for contacting to the skin. The adhesives may be biocompatible adhesives. The transducers may be embedded within an adhesive or surrounded by the adhesive.

The device may also include ergonomic support components within which and/or on which the transducers are housed and/or mounted, respectively.

Such adhesives and/or ergonomic support components allow the transducers to be placed in contact with a variety of body locations on the subject, such that mechanical waves can be delivered to desired locations accordingly.

For example, in certain embodiments, the transducers are placed in proximity to a mastoid region. Transcutaneous mechanostimulation in the mastoid region presents three primary nervous system targets: the great auricular nerve, composed of branches of spinal nerves C2 and C3, the trigeminal nerve, and the auricular branch of the vagus nerve. The innervation of the mastoid region is closely linked with that of the outer ear, which offers another region for stimulation. The innervation of the auricle is characterized by a great deal of overlap between multiple cranial and spinal nerves. Innervations of at least four nerves supply the anterior auricle: the auriculotemporal nerve, the ABVN, the lesser occipital nerve, and the greater auricular nerve (He, 2012). All of these nerves and their associated networks can be affected by auricular mechanostimulation. Thus, due to the physical properties of mechanical vibration, stimulation is able to propagate beyond the target location the ABVN and trigeminal nerve but potentially the greater auricular nerve as well as cranial nerves VII, IX, XI, and XII, and the lesser occipital nerve.

For example, FIG. 8B shows an example process 800b for providing mechanical stimulation by placing transducers in proximity to a mastoid of a subject. As shown, an electronic drive signal may be applied to a mechanical transducer to generate a mechanical wave 802. As described herein, a waveform of the electronic drive signal may be controlled, for example to produce a desired response, and based on the particular location target (e.g., the mastoid) 804. The mechanical wave is delivered to a body location of a subject that is in proximity to (e.g., directly above) a mastoid of the subject 806b, thereby providing mechanical stimulation to the subject.

FIG. 8C shows an example process 800c for stimulating cranial nerves of a subject 808c. Cranial nerves of a subject may be stimulated by delivering a mechanical wave to a body location of the subject in proximity to a mastoid, as in process 800b. Cranial nerves of a subject may also be stimulated by delivering a mechanical wave to other body locations of the subject.

ii. Coordinating Multiple Transducers in Transducer Arrays

In certain embodiments, the devices and methods described herein may utilize multiple mechanical transducers, arranged in one or more transducer arrays. Combining multiple transducers in a transducer array, and controlling their output in a synchronized fashion provides an additional mechanism for tailoring delivery of mechanical stimulation to a subject in order to produce a desired response. In certain embodiments, various tactile sensations can be mimicked by combining multiple transducers in transducer arrays. For example in order to mimic a stroking motion, transducers can be spaced along a straight or curved line segment and triggered in a sequential fashion. Producing mechanical vibration that mimics a stroking motion can be particularly useful for simulating affective touch and producing a relaxed feeling in a subject and/or managing anxiety and related disorders.

The transducers in a transducer array may be triggered in a synchronized fashion such that each mechanical transducer begins and/or ends producing mechanical vibration at a particular delay with respect to each other. The transducers in a transducer array may also be controlled so as to deliver different frequencies of mechanical vibration (e.g., by controlling electric drive signal waveforms used to drive each transducer).

Multiple transducers in a transducer array can be connected and controlled via one or more controller boards in a number of different manners, several embodiments of which are shown in FIGS. 6A-6D.

Figure 6A:
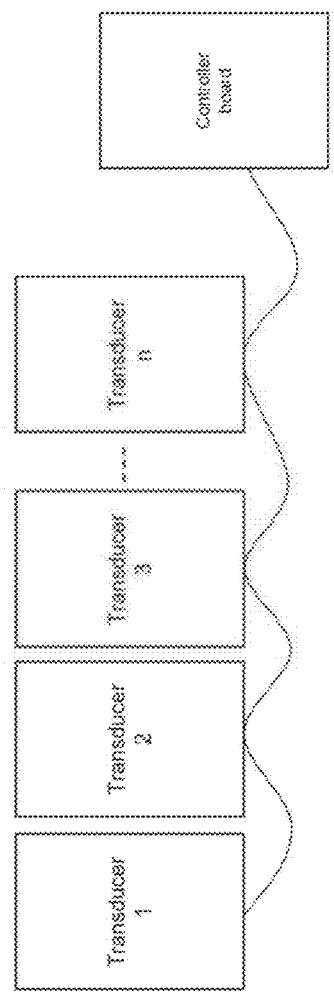
FIG. 6A is a schematic showing multiple transducers connected to a controller board in series, according to an illustrative embodiment.
Figure 6B:
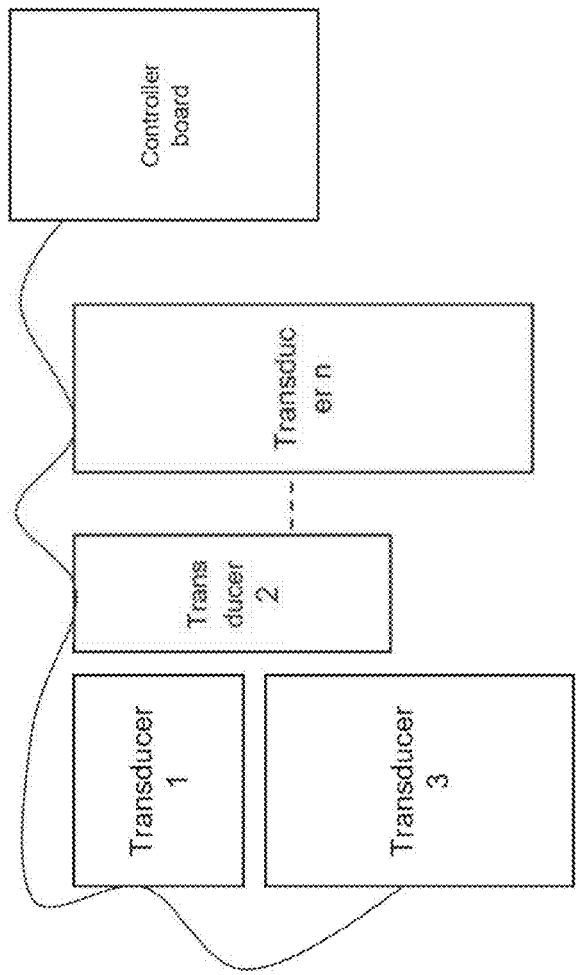
FIG. 6B is a schematic showing multiple transducers of differing sizes connected to a controller board in series, according to an illustrative embodiment.

For example, if the waveform and frequency used to drive each transducer in the transducer array is the same, then the transducers can be connected in series and the waveform sent to them at the same time by a single controller board. FIG. 6A illustrates such an embodiment, wherein an array of multiple transducers is connected to a single controller board. The particular arrangement and connection path may be varied and optimized to reduce/minimize noise, particularly when transducers of different sizes are used in a single transducer array, as shown in FIG. 6B. If the waveform and frequency of the electronic signal used to drive each transducer is the same, transducers of an array may be connected in series.

Figure 6C:
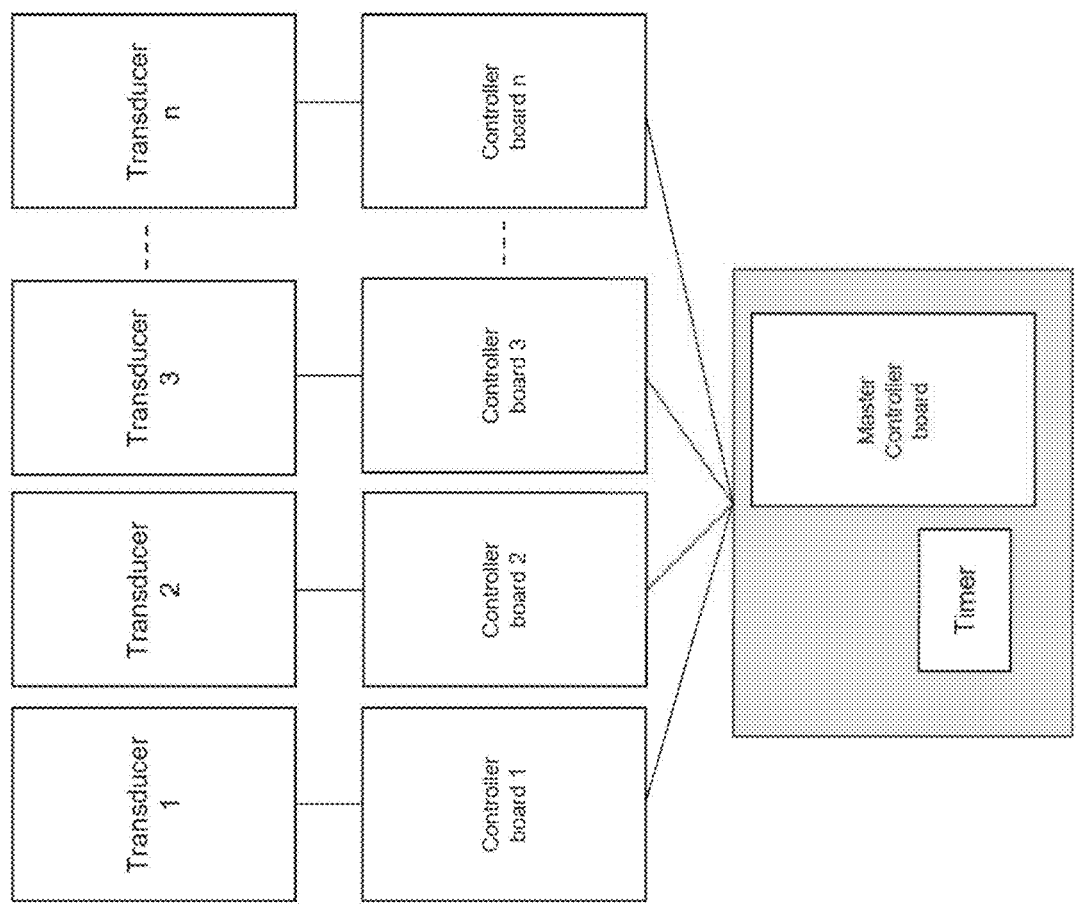
FIG. 6C is a schematic showing multiple transducers, each connected to a dedicated controller board, along with a master controller board, according to an illustrative embodiment.

In embodiments wherein different transducers are driven by different waveforms and/or frequencies, multiple controller boards may be used (e.g., a particular controller board for each waveform/frequency, the particular controller board connected to one or more transducers), for example as shown in FIG. 6C. The controller boards can be connected to a master controller board that manages synchronization of the timing at which the various different waveforms are delivered to the mechanical transducers of the transducer array. For example, the master controller board may comprise a timer to ensure that waveforms are sent at an appropriate time. The timer can be built in or external.

Figure 6D:
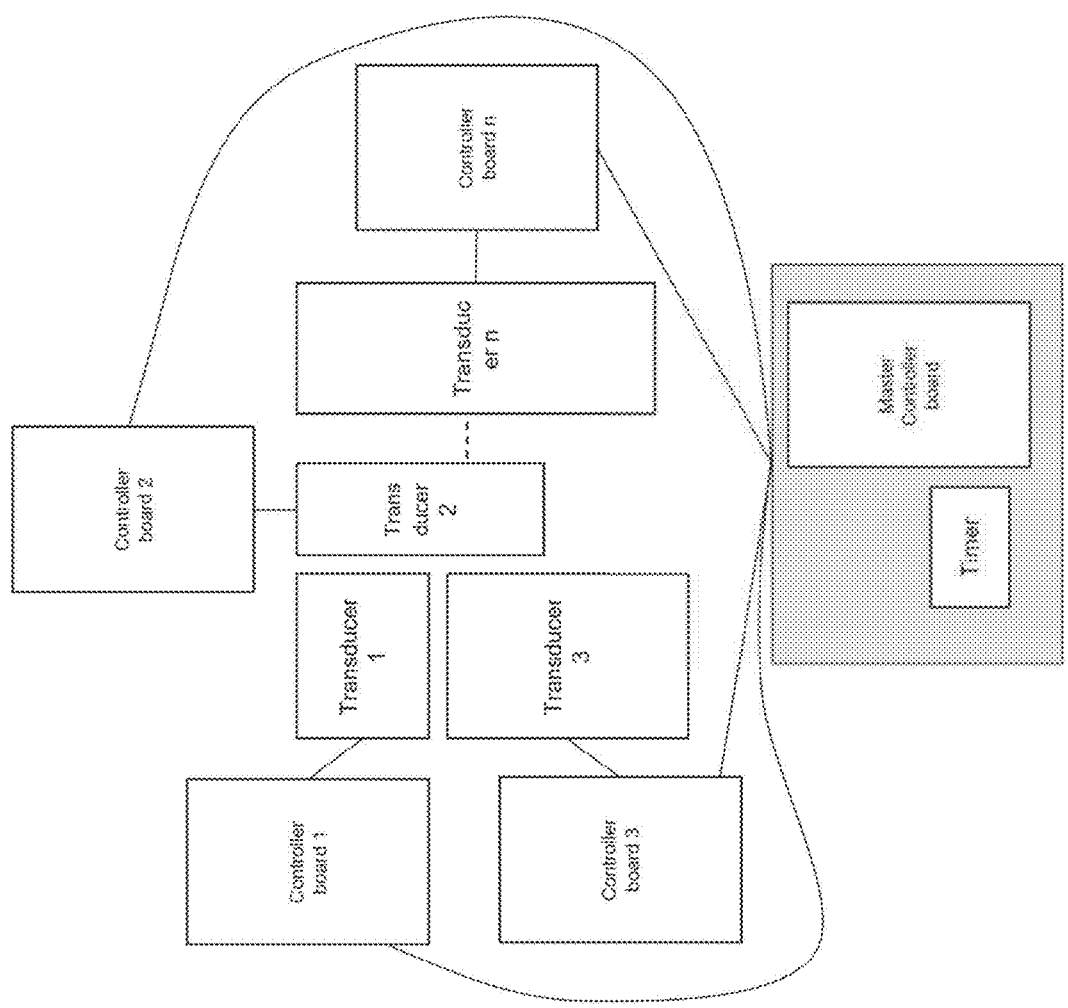
FIG. 6D is a schematic showing multiple transducers of differing sizes, each connected to a dedicated controller board, along with a master controller board, according to an illustrative embodiment.

In certain embodiments, just as the connection path for transducers of different sizes driven by a single waveform/frequency can be optimized to reduce/minimize noise (e.g., as described above with regard to FIG. 6B), the connection path used to connect multiple controller boards to a master controller can also be optimized to reduce/minimize signal noise when driving different transducers with different waveforms and/or frequencies (see FIG. 6D).

iii. Additional Components

The device can be stand-alone, combined with a mobile device or computer app, employ headphones (e.g., over-the-ear headphones; e.g., in-ear headphones) or a device which can modulate the pressure of the transducer contact on the skin surface, thus allowing for control of the transmission of the mechanical stimulation into the body.

The device may coordinate with an external signal (e.g., from a wearable fitness or biometric monitor etc.).

The device may coordinate with external stimuli, and or coaching (e.g., via an app) without the use of a control signal. In this case, for example, a pre-set stimulation routine may deliver stimulation in synchronization with external stimuli and/or coaching. For example, a breath coaching app may be used so that the user controls their breathing to breath at a specific cadence, and the device may deliver synchronized mechanical stimulation.

D. WAVEFORMS FOR MECHANICAL STIMULATION

A variety of waveforms may be used to generate the mechanical stimulation used in the approaches and in the devices described herein. In certain embodiments, various waveforms may be tailored to produce a particular desired response in a subject. For example, as described above, and in further detail below, an isochronic waveform, such as the waveform shown in FIG. 4, may be used to reduce stress and/or treat anxiety and related disorders in a subject. Examples of various waveforms are also shown in FIGS. 15A-15E, FIGS. 16A and 16B, FIGS. 17A and 17B, and FIGS. 18A-18H.

Figure 15A:
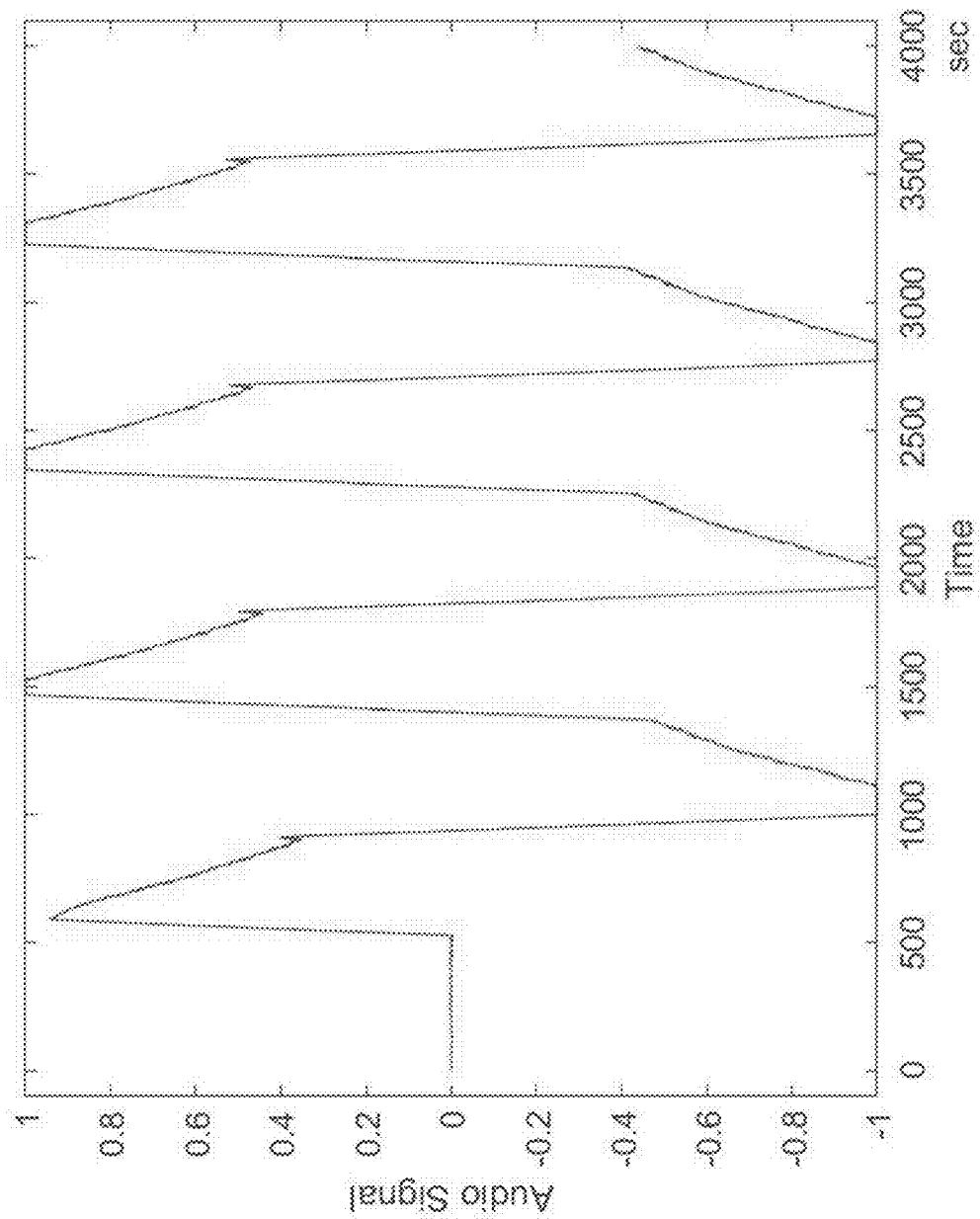
FIG. 15A is a graph of an example waveform comprising a transformed time-varying wave (TTVW), according to an illustrative embodiment.
Figure 15B:
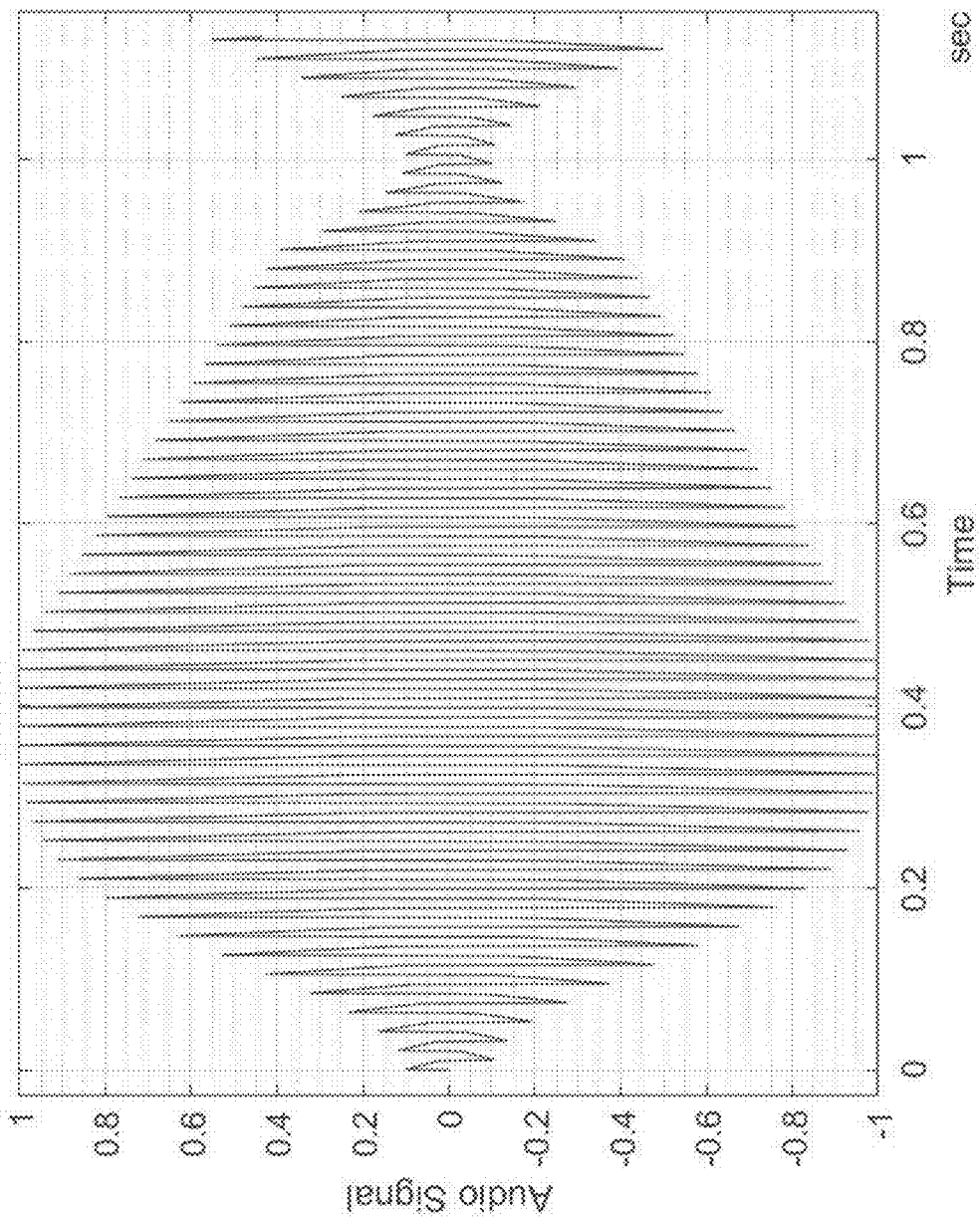
FIG. 15B is a graph of an example waveform comprising a transformed time-varying wave (TTVW), according to an illustrative embodiment.
Figure 15C:
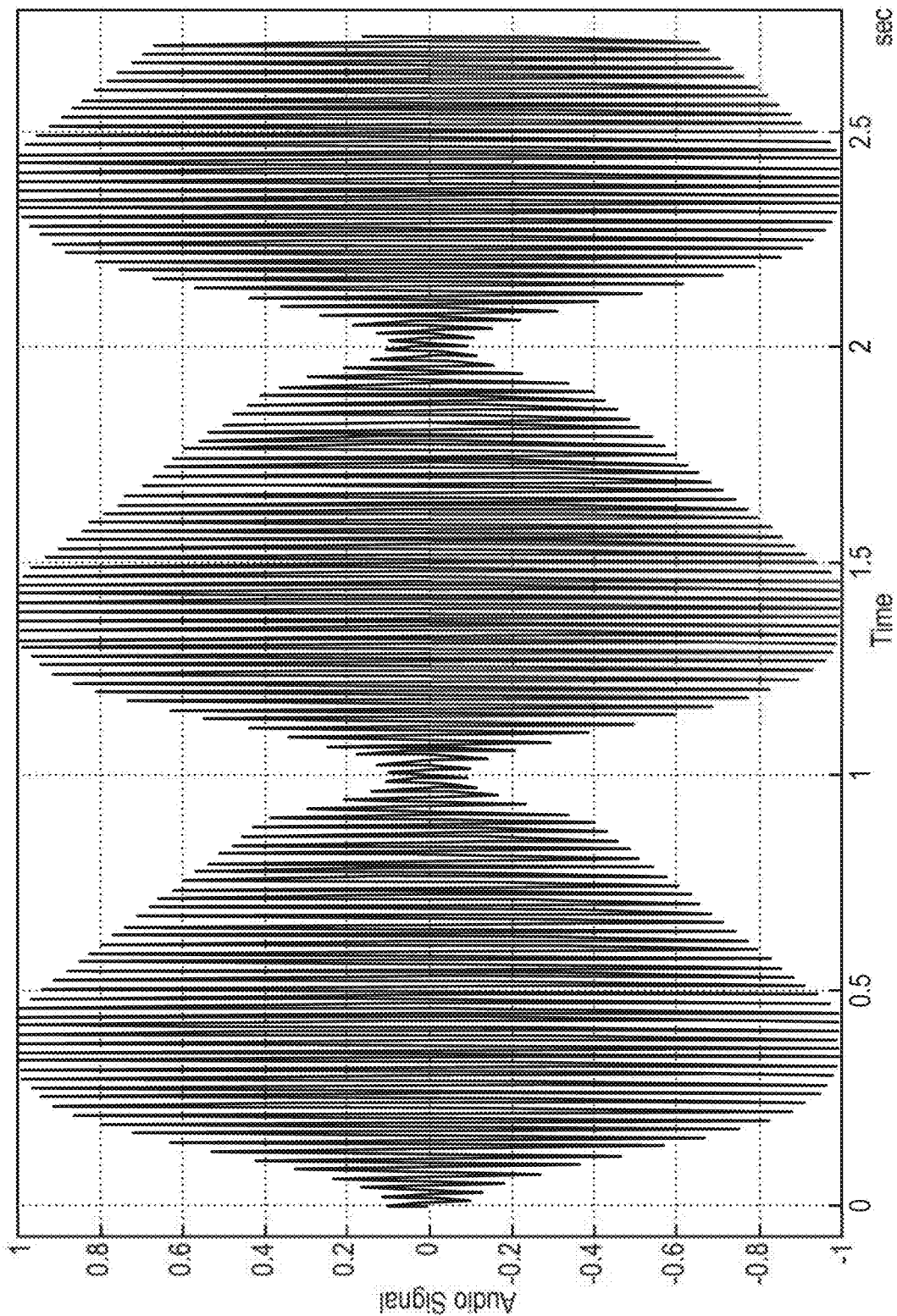
FIG. 15C is a graph of an example waveform comprising a transformed time-varying wave (TTVW), according to an illustrative embodiment.
Figure 15E:
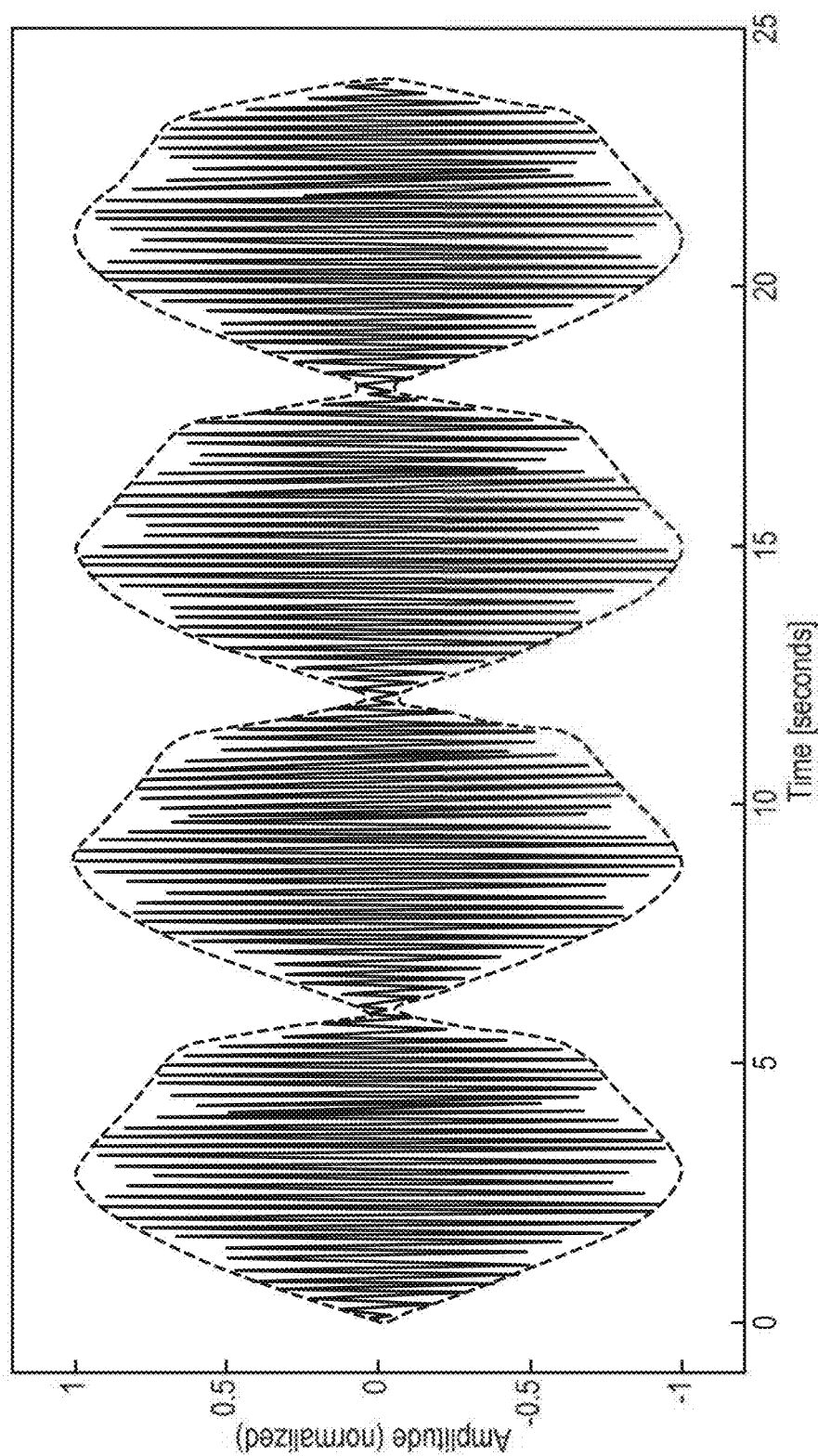
FIG. 15E is a graph of an example waveform comprising a transformed time-varying wave (TTVW), according to an illustrative embodiment.
Figure 16B:
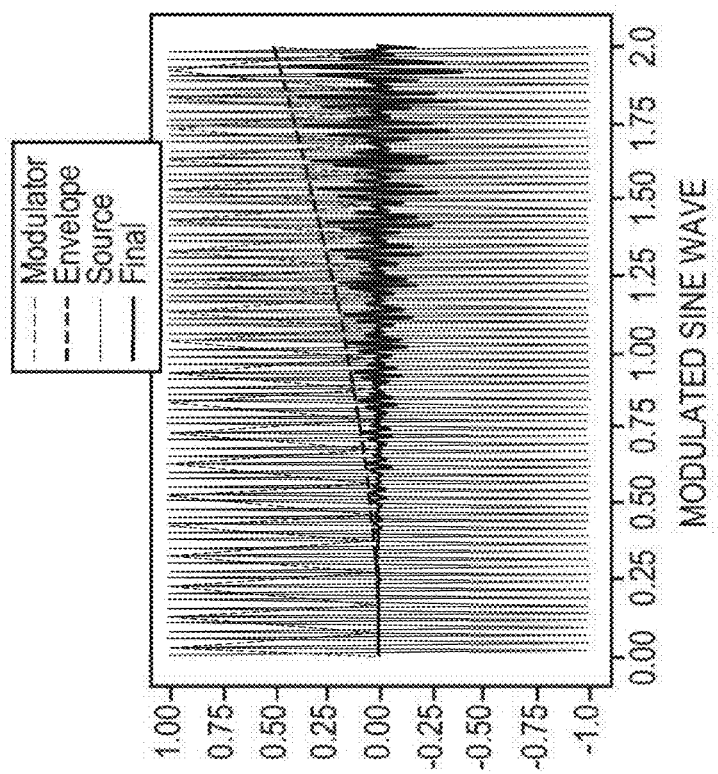
FIG. 16B is a graph of an example waveform comprising a modulated sine wave, according to an illustrative embodiment.
Figure 16A:
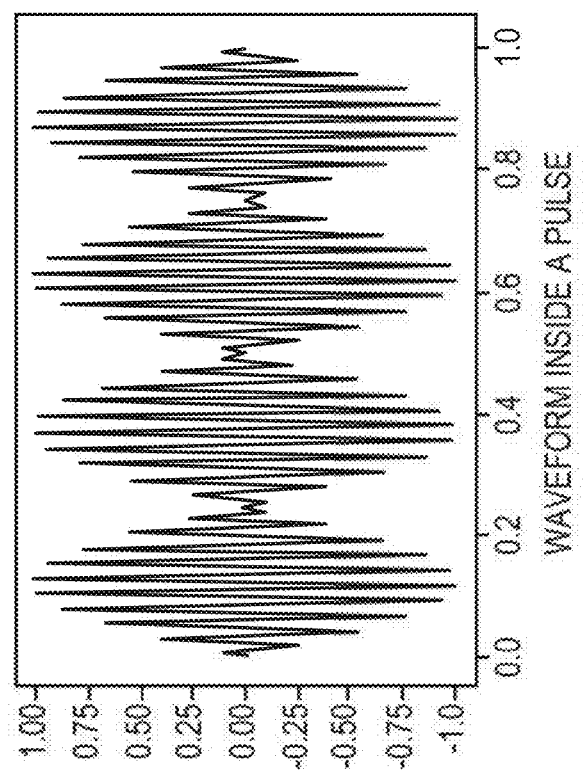
FIG. 16A is a graph of an example waveform comprising a sine wave inside a pulse, according to an illustrative embodiment.
Figure 17B:
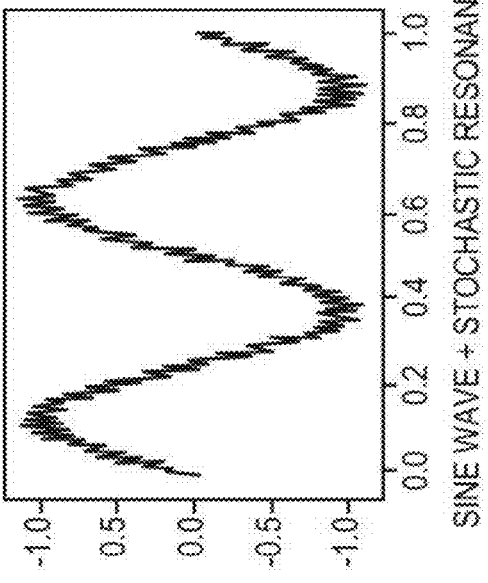
FIG. 17B is a graph showing a waveform comprising a sine wave with added stochastic resonance noise, according to an illustrative embodiment.
Figure 17A:
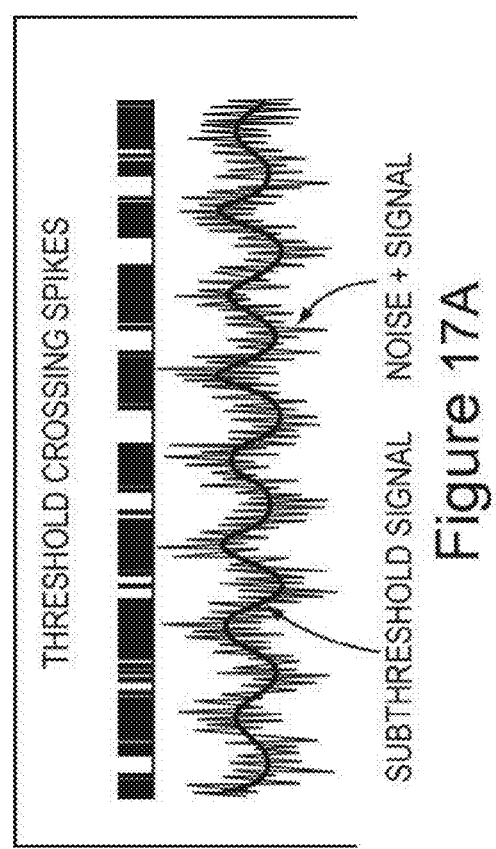
FIG. 17A is a schematic illustrating a waveform comprising additive subthreshold noise; modified from (Moss, 2004)
Figure 18A:
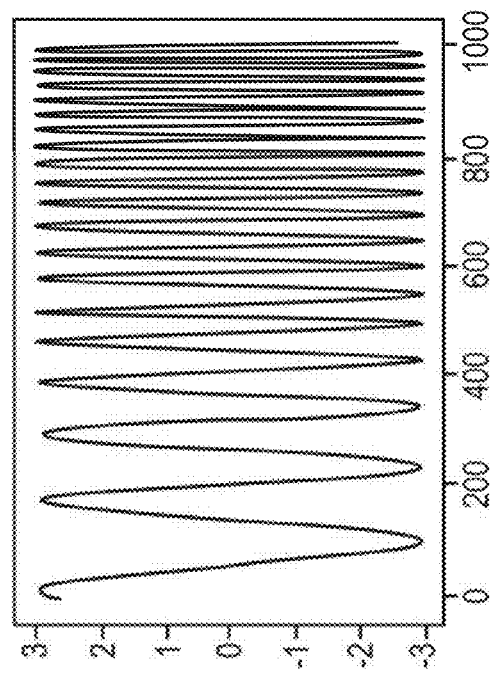
FIG. 18A is a graph showing a waveform comprising a chirped wave, according to an illustrative embodiment.
Figure 18B:
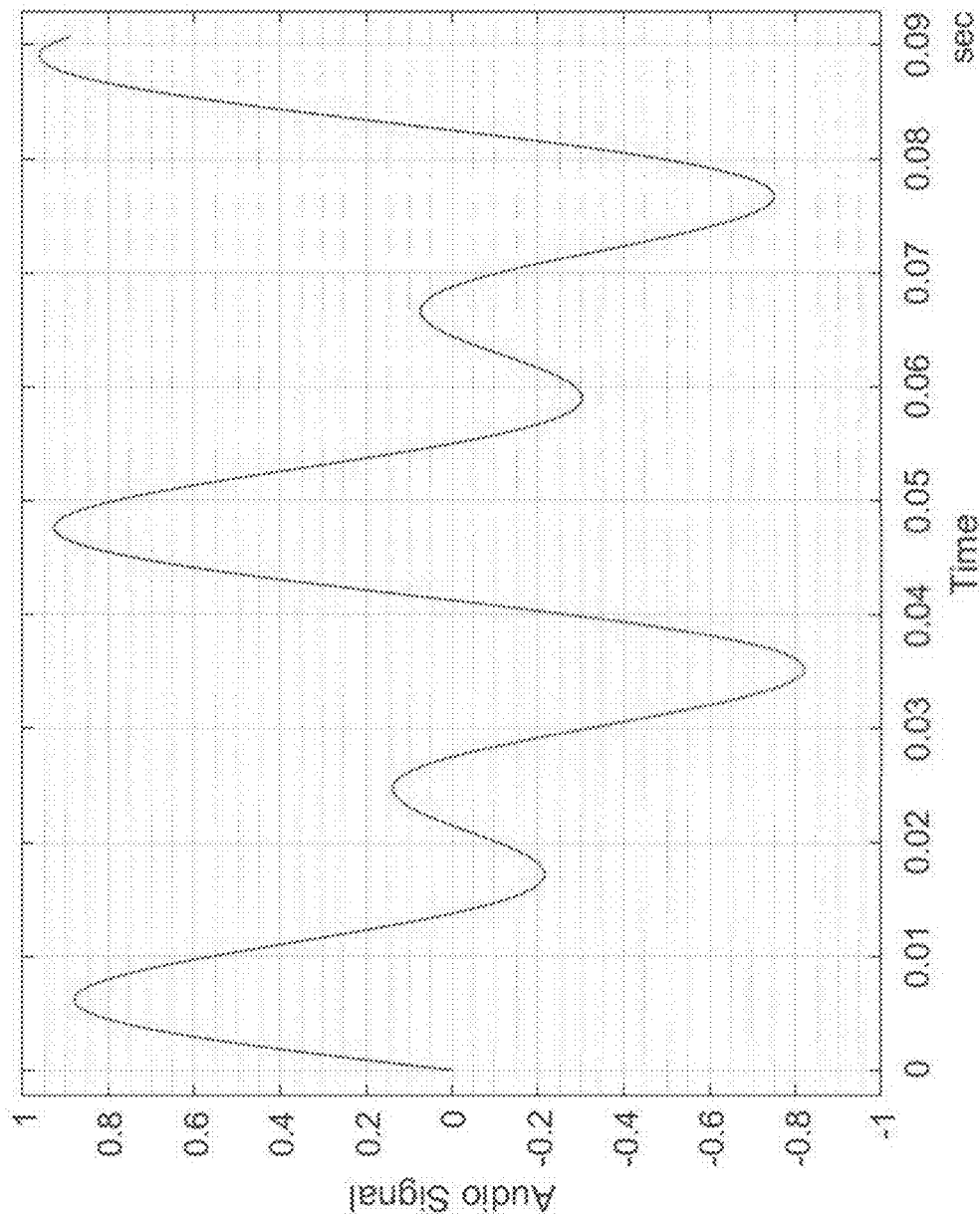
FIG. 18B is a graph of an example aperiodic waveform, according to an illustrative embodiment.
Figure 18C:
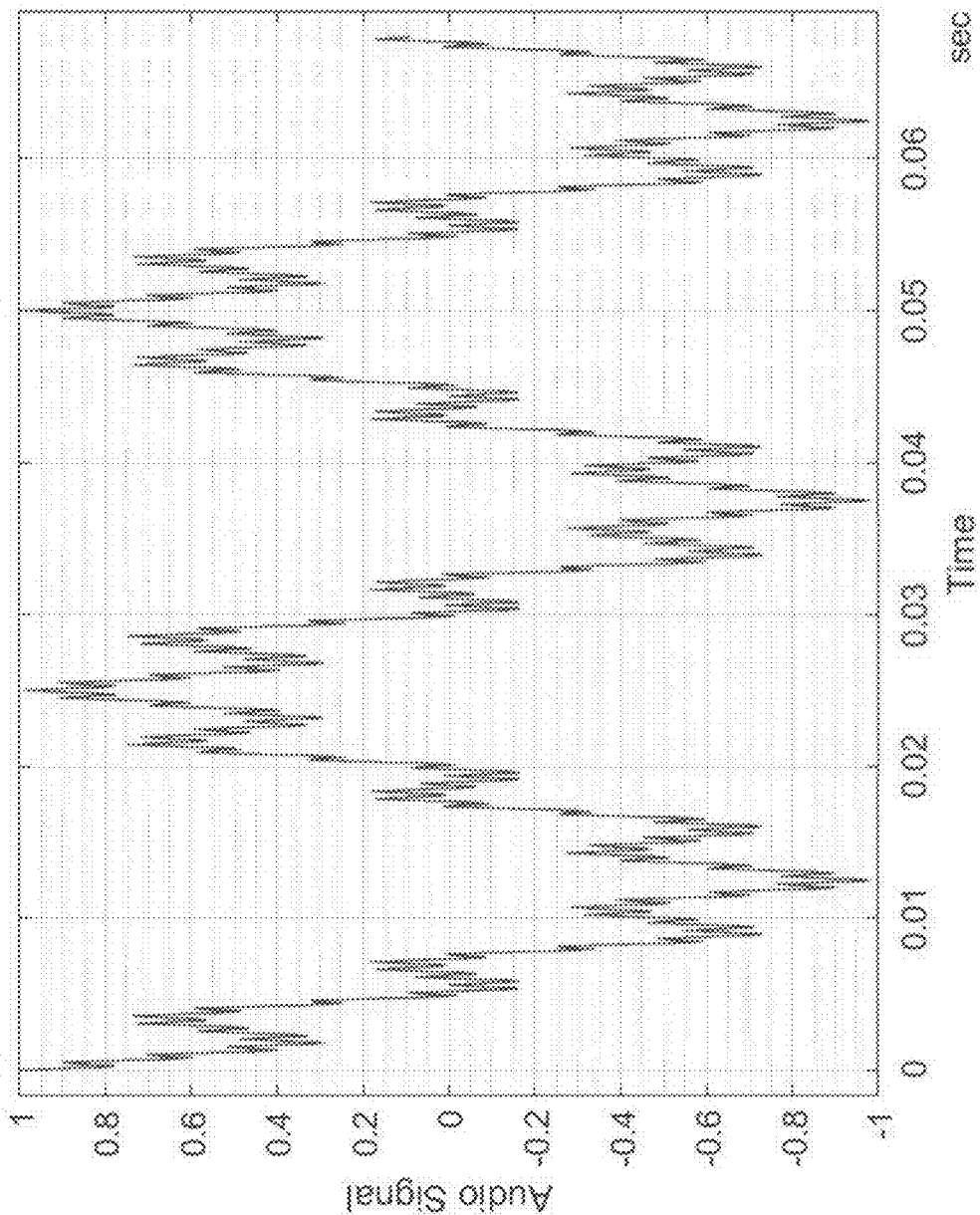
FIG. 18C is a graph of an example waveform, according to an illustrative embodiment.
Figure 18D:
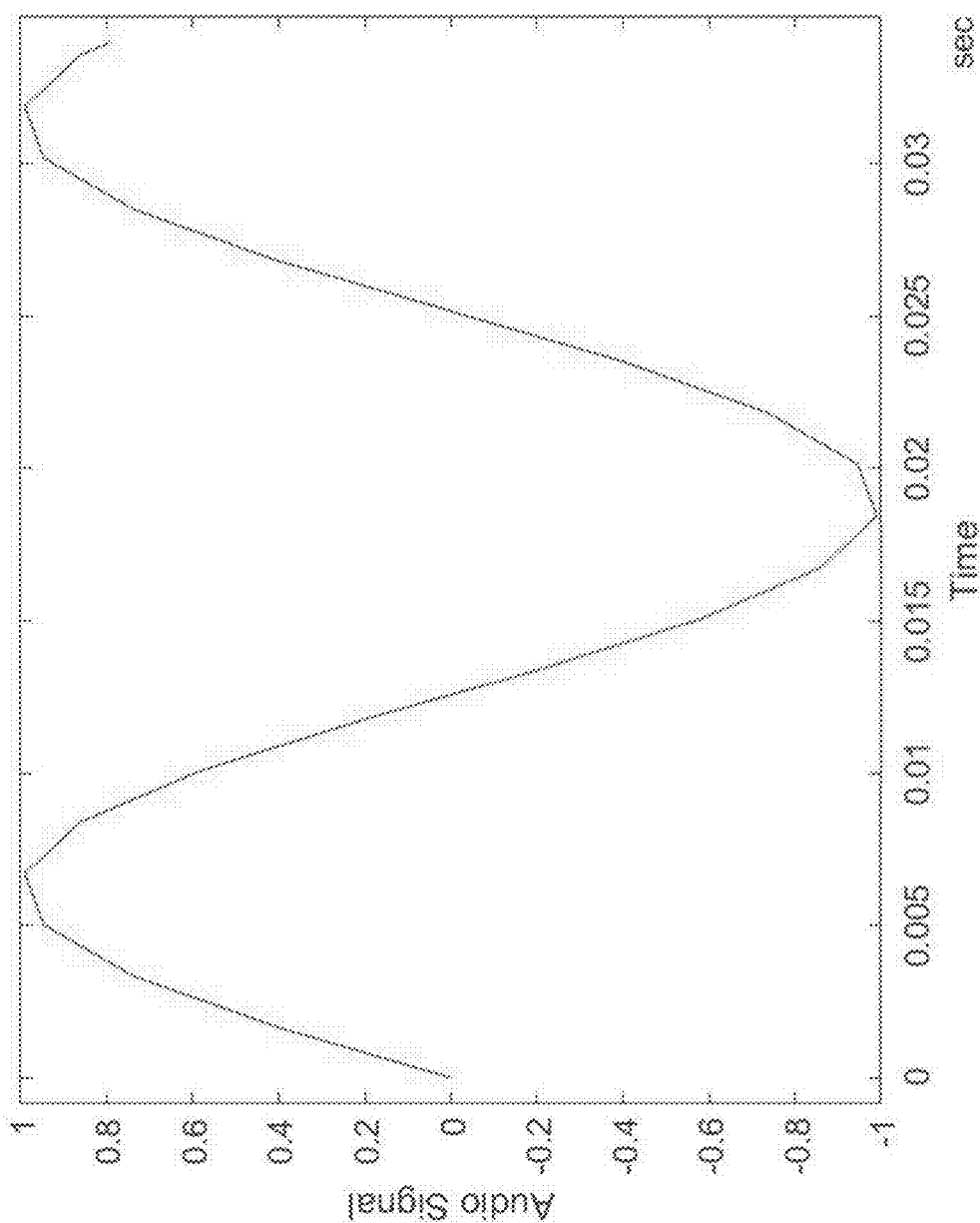
FIG. 18D is a graph of an example waveform, according to an illustrative embodiment.
Figure 18E:
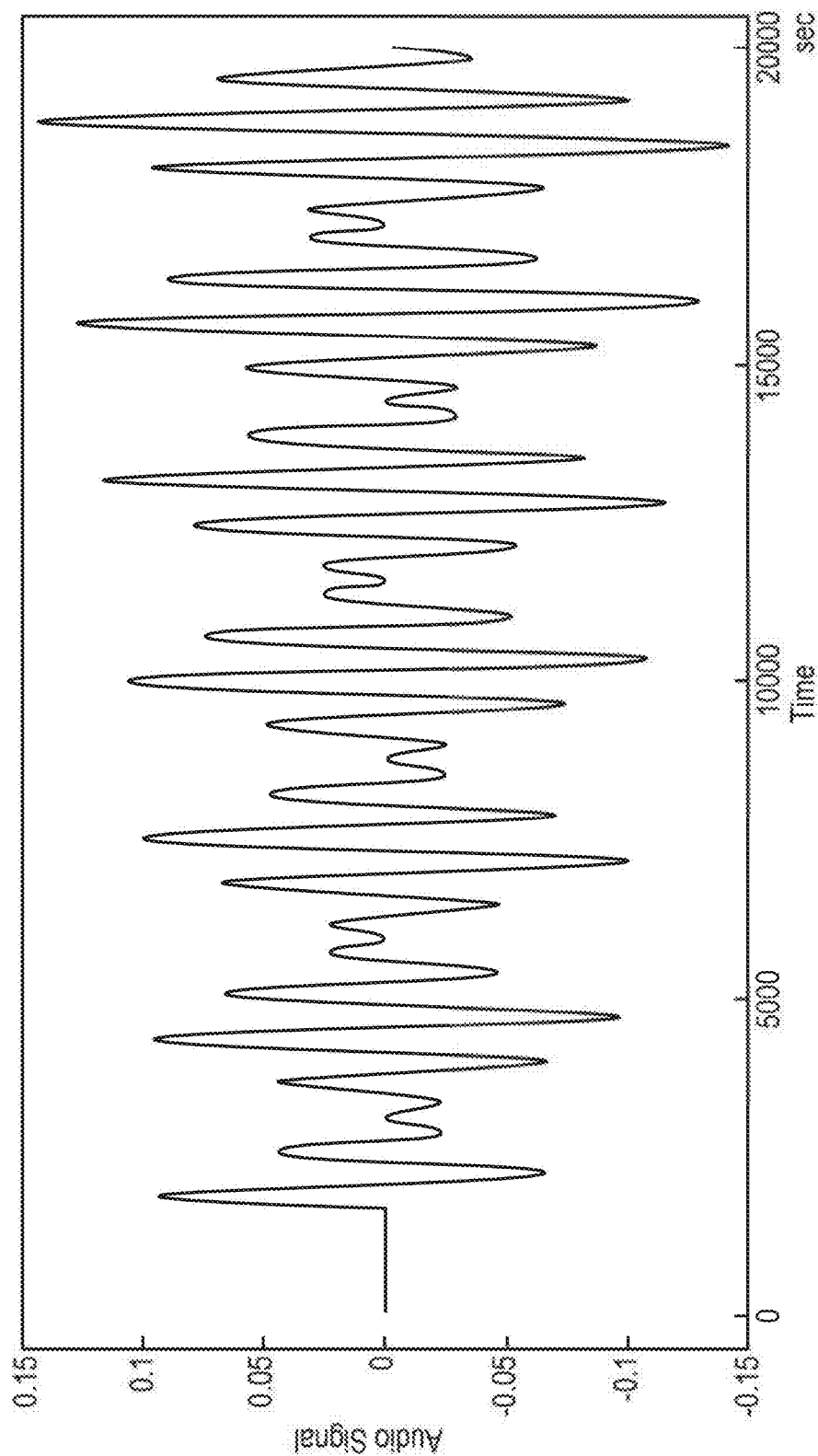
FIG. 18E is a graph of an example waveform, according to an illustrative embodiment.
Figure 18F:
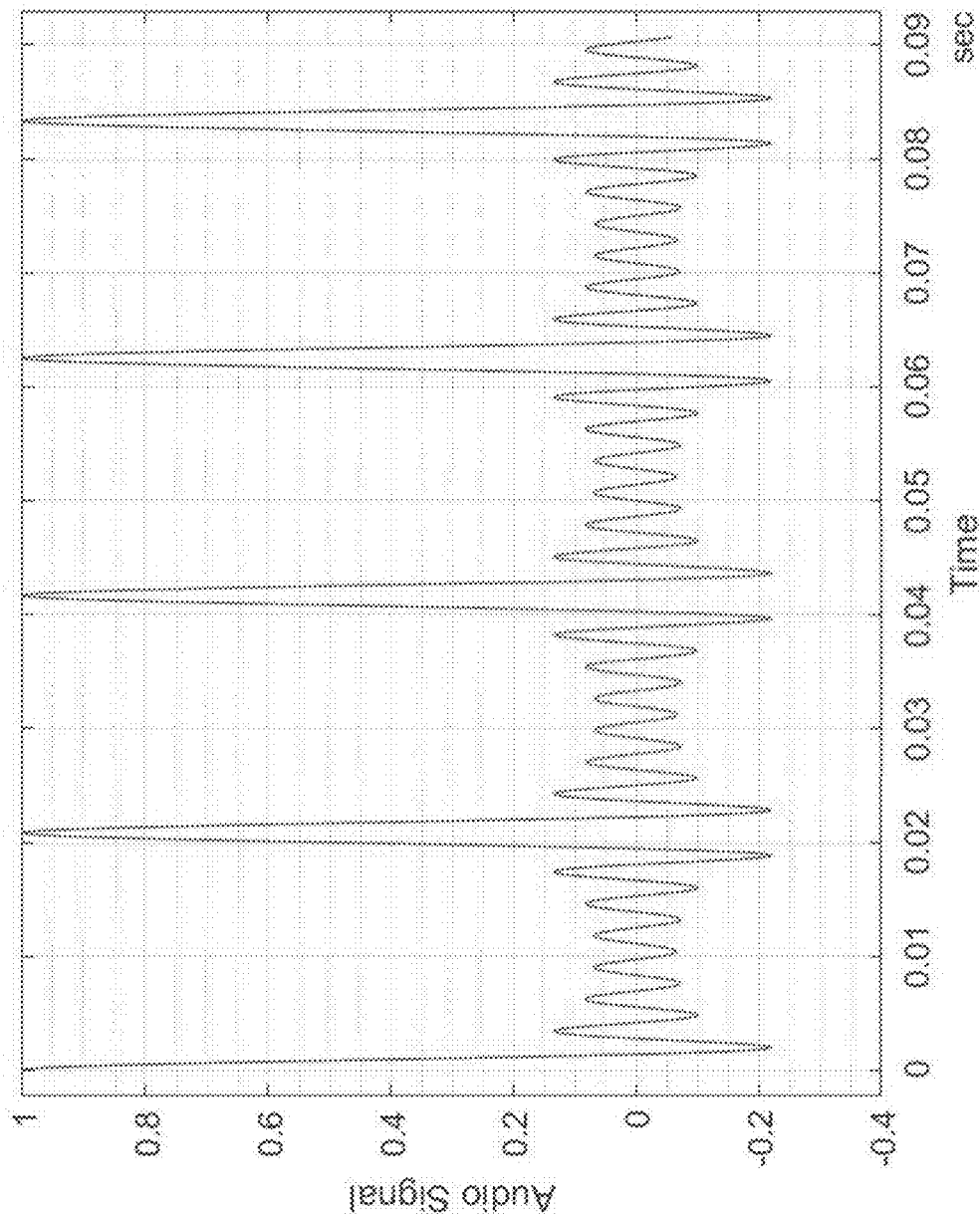
FIG. 18F is a graph of an example waveform, according to an illustrative embodiment.
Figure 18G:
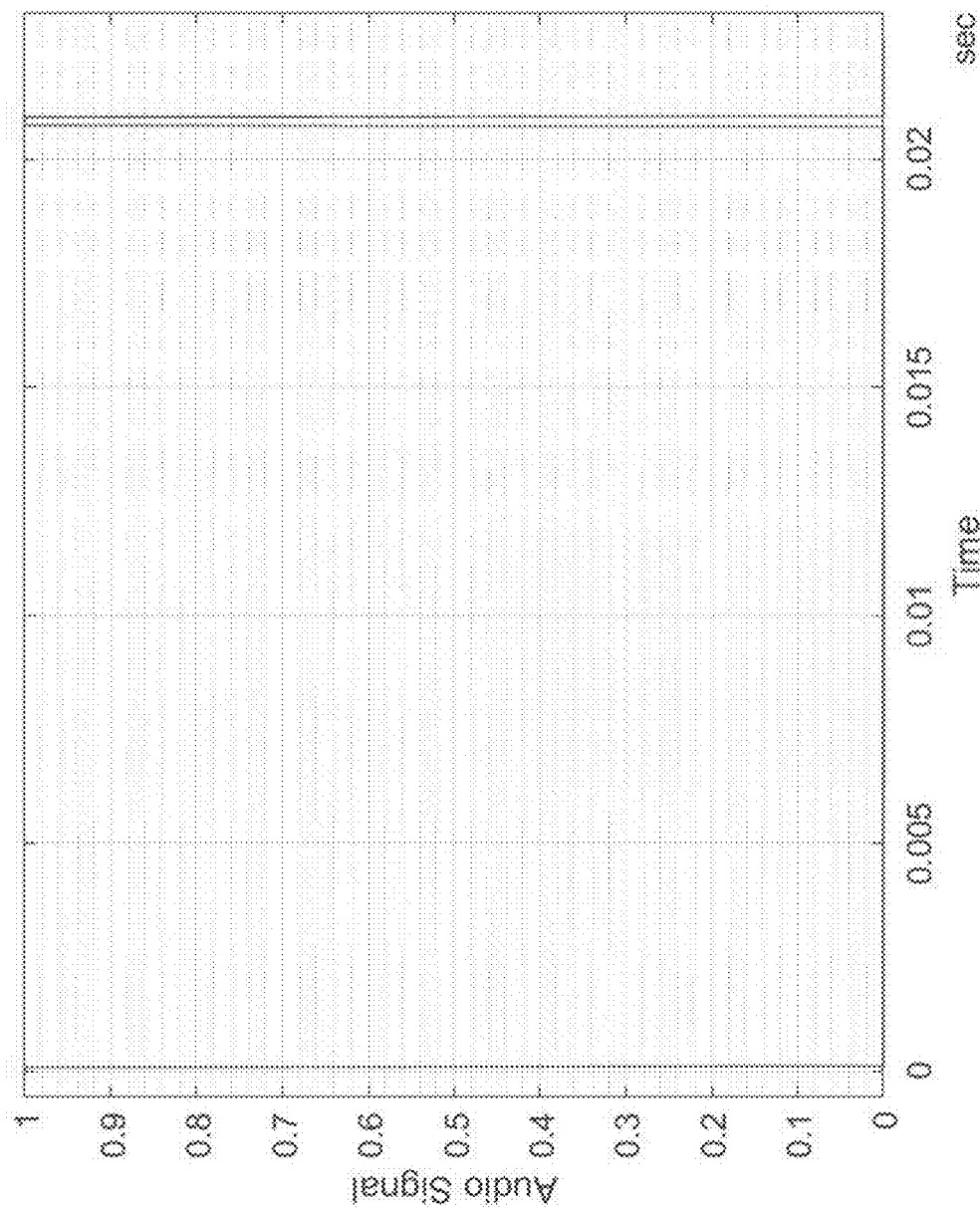
FIG. 18G is a graph of an example waveform, according to an illustrative embodiment.
Figure 18H:
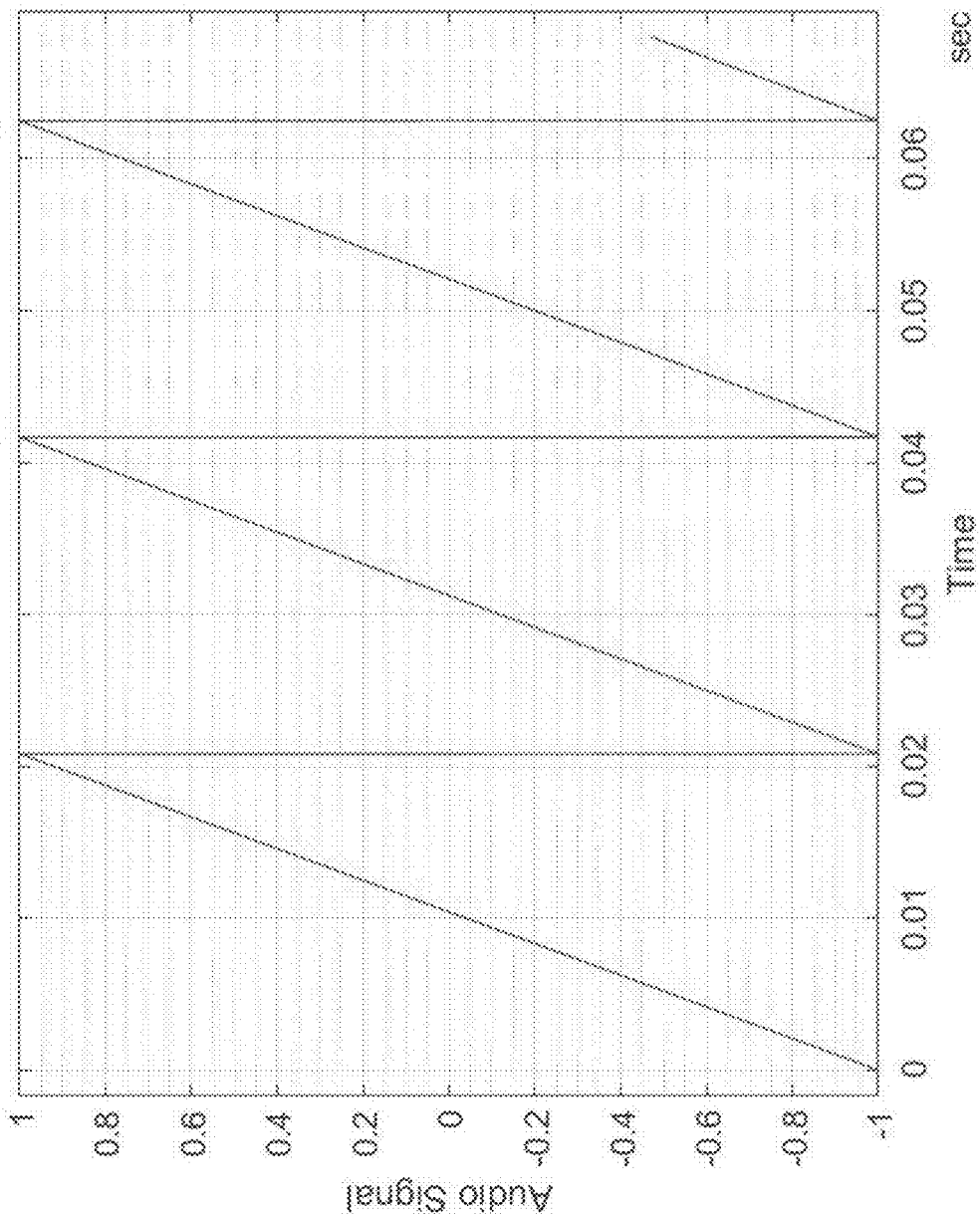
FIG. 18H is a graph of an example sawtooth waveform, according to an illustrative embodiment.

FIGS. 15A-15E show examples of transformed time-varying waves (TTVWs), including examples of carrier and envelope waveforms, wherein a TTVW may be used as a carrier and/or an envelope, described further herein. FIGS. 16A and 16B show examples of sine waves modulated by an envelope function. FIGS. 17A and 17B show examples of stochastic resonance signals. Various additional examples of waveforms are shown in FIGS. 18A-18H.

Figure 19:
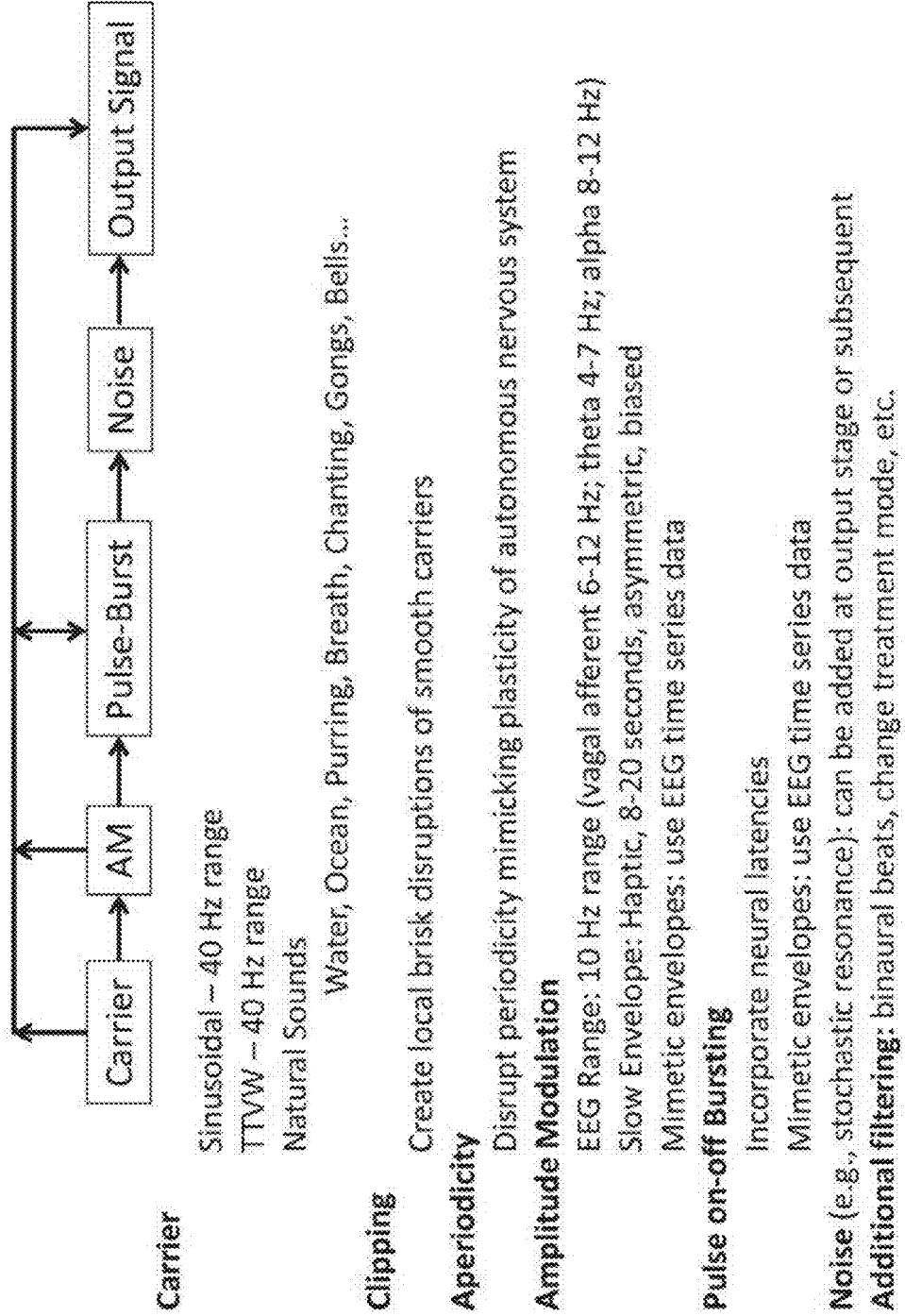
FIG. 19 is a chart showing approaches for producing various waveforms according to illustrative embodiments used with the systems, methods, and devices described herein.

FIG. 19 shows a block flow diagram illustrating a general approach for building different waveforms, and how various characteristics of waveforms can be mixed and/or combined.

i. Isochronic Signals

In certain embodiments, an isochronic wave is used for mechanical stimulation of a subject. As described herein, isochronic waves include one or more low-amplitude sub-intervals, over which an amplitude of the isochronic wave is substantially less than its amplitude at other times. The low-amplitude sub-intervals can be used to accommodate recovery periods of particular biological targets, for example as described herein with regard to Piezo2 proteins. FIG. 4 shows an example isochronic wave used for targeting Piezo2 proteins and Merkel Cells. The example isochronic wave shown in FIG. 4 corresponds to a periodic carrier wave that is modulated by a square wave envelope. The periodic carrier wave is a sine wave, having a frequency of 10 Hz. The 10 Hz frequency is selected to fall within the 5-15 Hz range to which Merkel cells respond, as shown in FIG. 3. The square wave envelope has a 0.5 Hz frequency, which produces periodic low-amplitude sub-intervals lasting two seconds, which correspond to a recovery period of Piezo2 proteins. Such an isochronic wave can be used as an electronic drive signal that, when applied to a mechanical transducer, generates a substantially similar mechanical wave that includes frequency components tailored to the response frequencies of Merkel cells, as well low-amplitude sub-intervals—periods where little to no stimulation is applied that accommodate recovery periods of Piezo2 proteins. In this manner, stimulation can be designed to account for various biological targets that are part of a particular stimulation pathway.

Other isochronic signals may also be used. For example, other types of periodic and non-periodic carrier waves and envelopes described herein may be used. In certain embodiments, an isochronic signal also comprising a TTVW is used. The TTVW may be the carrier wave and/or the envelope.

FIG. 8A shows an example process 800a for providing mechanical stimulation using an isochronic wave. As shown in FIG. 8A, a waveform of an electronic drive signal is controlled 804, such that the electronic drive signal's waveform is an isochronic wave 804a. The mechanical wave generated by applying the electronic drive signal is delivered to a body location (not necessarily a mastoid) of the subject 806, thereby providing mechanical stimulation.

FIG. 8D shows an example process 800d for providing mechanical stimulation using electronic drive signals having waveforms comprising frequency components ranging from 5 to 15 Hz (804d) in accordance with the frequency range to which Piezo proteins are believed to respond, as described herein. In certain embodiments, frequency ranges within this interval, such as frequencies between 7 and 13 Hz, may be used so provide mechanical stimulation having a frequency matching that of alpha brain waves. Mechanical waves produced in this manner and delivered to a body location of a subject can be used to stimulate nerves and/or mechanoreceptors of the subject 808d.

ii. Interactive Stimulation

As described herein, in certain embodiments, waveforms may be varied and controlled in an interactive fashion, for example by a user (e.g., through an app in communication with the devices described herein) or in response to received feedback and physiological signals from the user.

FIG. 9 shows an example process 900 for providing interactive mechanical stimulation to a subject in response to received feedback in the form of an electronic response signal. In process 900, a mechanical wave is generated by a mechanical transducer using an electronic drive signal 902. An electronic response signal from a monitoring device (e.g., a wearable monitoring device; e.g., a personal computing device; e.g., a fitness tracker; e.g., a heart-rate monitor; e.g., an electrocardiograph (EKG) monitor; e.g., an electroencephalography (EEG) monitor) operable to monitor one or more physiological signals from the subject is received (e.g., directly from and/or to the monitoring device; e.g., via one or more intermediate server(s) and/or computing device(s)) 903. A waveform of the electronic drive signal is controlled based on the electronic response signal 904 such that the mechanical wave delivered to the body location of the subject 906 is modulated accordingly, reflecting the received feedback. Accordingly, the systems, methods, and devices described herein provide for adjustment and/or selection of a particular waveform, tailored to a particular subject, based on received feedback corresponding to subject biometrics such as blood-pressure (BP), heart rate variability (HRV), galvanic skin response (GSR), EEG signal, and the like.

Figure 20:
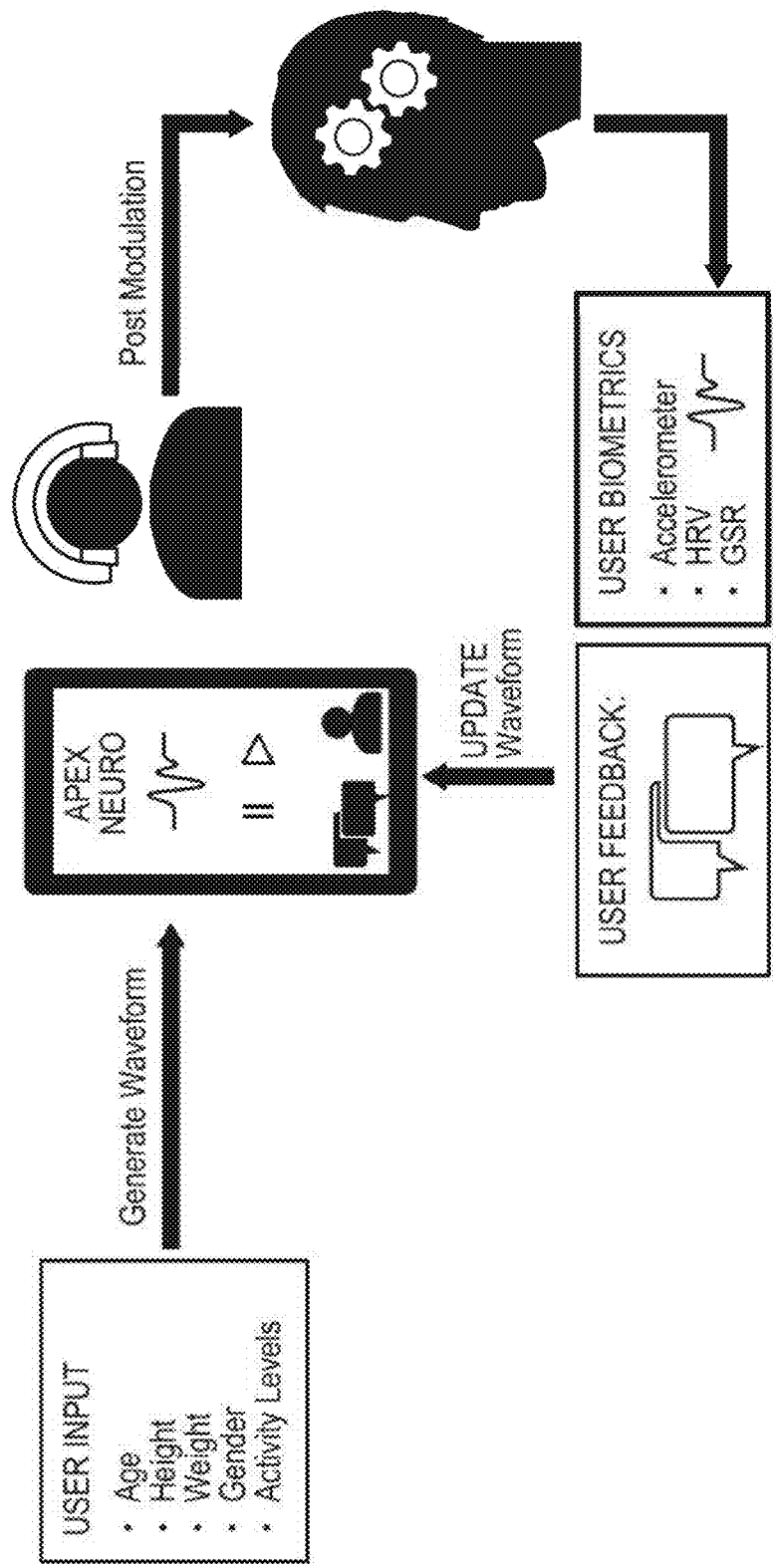
FIG. 20 is a schematic illustrating an approach for generating and updating a personalized waveform tailored to an individual user, according to an illustrative embodiment.

FIG. 20 shows flow diagram for personalization of a waveform. As shown in FIG. 20, physiological signals (e.g., subject biometrics) such as accelerometer data (e.g., to measure activity levels), HRV, and GSR can be used to adjust and/or select a particular waveform, tailoring to a user. As shown in the Figure, such physiological signals can be measured during and/or after providing mechanical stimulation to a subject, for example to evaluate the subject's response to the mechanical stimulation. Based on the measured physiological signals, the waveform can be adjusted (e.g. to improve efficacy and/or produce a particular response in the subject). Other physiological signals may be recorded via sensors such as a blood pressure (BP) monitor and EEG monitor.

Figures 21, 22:
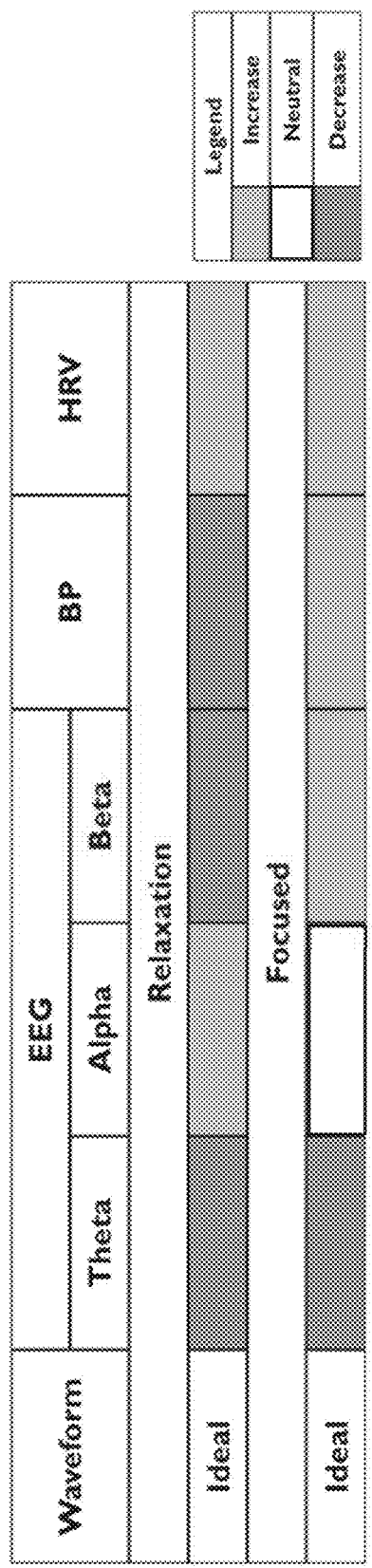
FIG. 21 is a graph showing characteristics of various physiological signals associated with relaxation and focused states of a subject, according to an illustrative embodiment.
FIG. 22 is a schematic illustrating a label to be included in a kit comprising the devices described herein, according to an illustrative embodiment.

For example, FIG. 21 shows characteristics of various physiological signals associated with relaxation and focused states of a subject. As shown in FIG. 21, in a state of relaxation EEG measurements indicate decreased theta and beta waves and increased alpha waves in a subject. BP and HRV measurements show decreases in BP and increases in HRV, respectively. Accordingly, to produce a relaxation state in a subject undergoing mechanical stimulation, physiological signals, such as various brain waves (e.g., as measured via EEG), BP, and HRV, can be monitored for the subject, and waveform characteristics can be modified to produce brain wave, BP, and HRV characteristics that are associated with the relaxation state, such as those shown in FIG. 21.

Other states in a subject can be produced by modifying a waveform to produce that state. For example, as shown in FIG. 21, a focused state is associated with decreased theta waves, neutral alpha waves, increased beta waves, increased BP, and increased HRV.

One or more of the characteristics, such as those shown in FIG. 21, can be targeted in this manner, via monitoring of one or more corresponding physiological signals, to produce a desired state in a subject.

Feedback regarding the effects of mechanical stimulation may also be obtained, and used for modification and tailoring of waveforms, via other approaches. For example, as illustrated in FIG. 20, subject feedback in a form of written or entered data may be obtained and used to update a waveform used for providing mechanical stimulation. For example, following receipt of a round of mechanical stimulation, a subject may take a survey to assess their response to the round of mechanical stimulation. The subject may enter their survey responses themselves, for example via a mobile computing device, an app, an online portal, and the like. Subject feedback data may also be provided by a therapist/physician treating the subject. Such feedback may then be evaluated, for example processed via a mobile computing device or intermediate server in communication with the stimulation device, and used to update waveform characteristics. This approach, of subjecting a subject to a round of stimulation, receiving and assessing feedback, and updating a waveform accordingly, may be repeated for multiple rounds of treatment using the stimulation.

Waveform characteristics may also be tailored prior to providing stimulation to a subject, using initialization setting data. For example, a subject may provide data relating to their age, height, weight, gender, body-mass index (BMI), and the like, activity levels, such as physical activity levels, or results of a preliminary survey (e.g., entered by the subject themselves, e.g., via a mobile computing device, an app, and/or online portal; e.g., provided by a therapist/physician treating the subject for a disorder). Based on such initialization settings data, an initial waveform may be selected and/or tailored for the subject.

FIG. 10 shows an example process 1000 for treating a subject using feedback and/or initialization settings data. In the example process 1000, a mechanical wave is generated via a mechanical transducer 1002, subject feedback and/or initialization data is received and/or accessed 1003, and a waveform of an electronic drive signal used to drive the mechanical transducer and generate the mechanical waves is controlled based on the received and/or accessed subject feedback and/or initialization data 1004. The generated mechanical wave is delivered to a body location of the subject to provide transcutaneous mechanical stimulation 1006.

iii. Transformed Time-Varying Waveforms (TTVWs)

In certain embodiments, a transformed time-varying waveform (TTVW) is used. FIG. 15A shows an example of a TTVW. The example TTVW shown in FIG. 15A is a modified version of a sine wave (e.g., the base time-varying wave is a sine wave), wherein the peaks of the sine wave are 'clipped' via a linear ramp. Various other embodiments of TTVWs, as described herein, can be used.

FIG. 14A shows an example process 1400a for providing mechanical stimulation using a transformed time varying wave. As shown in FIG. 14A, a waveform of an electronic drive signal is controlled 1404, such that the electronic drive signal's waveform is a transformed time varying wave 1404a. The mechanical wave generated by applying the electronic drive signal is delivered to a body location (not necessarily a mastoid) of the subject 1406, thereby providing mechanical stimulation.

iv. Frequency Ranges from 18-48 Hz

In certain embodiments, the waveforms used herein comprise a frequency component in another frequency range (e.g., not necessarily the 5-15 Hz range described above for stimulating affective touch sensations). For example, a frequency component ranging from 18-48 Hz. Frequency components in this range are also desirable for stimulation. Notably, brain waves such as beta waves include components in this frequency range and, accordingly, waveforms with such frequency components serve as biomimetic signals. Such frequency components may be used for stimulating other sensations, either instead of or in addition to the affective touch sensations described herein.

FIG. 14B shows an example process 1400b for providing mechanical stimulation using electronic drive signals having waveforms comprising frequency components ranging from 18 to 48 Hz (1404b). Mechanical waves produced in this manner and delivered to a body location of a subject can be used to stimulate nerves and/or mechanoreceptors of the subject 1408b.

v. Carrier and Envelope Waveforms

In certain embodiments, the waveforms used herein have forms of a carrier wave modulated by an envelope. FIGS. 16A and 16B show two examples of such waveforms ("Waveform inside a Pulse", FIG. 16A, and "Modulated Sine Wave", FIG. 16B). Notably, a waveform may include a TTVW (e.g., such as the modified sine wave of FIG. 15A) that is a carrier signal, which is modulated by an envelope (e.g., a more slowly varying signal) and/or may comprise a TTVW that is an envelope that modules a more rapidly varying signal. FIG. 15B and FIG. 15C show examples of a TTVW that is a carrier signal modulated by an envelope. In particular, FIG. 15B shows an expanded view of a portion of the waveform such that the linear ramp portions of the TTVW are visible, and FIG. 15C shows a graph of the same waveform over a greater time range illustrating the periodic nature of the example signal. FIG. 15D and FIG. 15E are example waveforms wherein a TTVW is an envelope that modulates a more rapidly varying signal.

In certain embodiments, a frequency of the envelope corresponds to a breathing rate of a subject (e.g., corresponding to 6 to 10 breaths per minute; e.g., approximately 0.1 Hz).

vi. Sub-Threshold and Supra-Threshold Stimulation

In certain embodiments, the approaches described herein may utilize activation thresholds of target cells and/or proteins, such as mechanoreceptors and/or nerves to set stimulation levels (e.g., amplitudes). In particular, stimuli that are of insufficient magnitude to activate a particular target cell and/or protein and initiate signaling are referred to as subthreshold, while stimuli that are above such an activation threshold and, accordingly, are of sufficient magnitude to activate a particular cell and/or protein and initiate signaling are referred to as suprathreshold. In certain embodiments, such activation thresholds correspond to sensory thresholds, such that suprathreshold stimuli cause a tactile sensation in the subject, while subthreshold stimuli do not.

In certain embodiments, subthreshold and suprathreshold signals can provide a source of acoustic frequency-range white noise, pink noise, or noise spectra mimetic of biological noise sources such as 1/f or shot noise. In certain embodiments, subthreshold stimuli can be used to elicit stochastic resonance effects in particular cells and signaling pathways that comprise them.

FIGS. 17A and 17B show examples of stochastic resonance signals. Stochastic noise is the counter-intuitive fact that adding noise into a modulating system, such as a biological system does not necessarily mask endoengous signals, but can enhance the signal so it may be better detected at some threshold (Hanggi 2002). FIG. 17A illustrates addition of stochastic resonance noise, which can increase signal detection above sensory thresholds and action potential firing. FIG. 17B shows a sine wave with stochastic resonance noise added. In certain embodiments, such waveforms incorporating stochastic resonance signals are used to for providing mechanical stimulation to a subject.

vii. Multiple Signals-Binaural and Monaural Beats

Mechanical stimulation may be provided in a variety of manners, including in a binaural and/or a monaural fashion. For example, FIG. 12 shows an example process 1200 for providing mechanical stimulation in a binaural manner. As shown in FIG. 12, a first and second electronic drive signal 1201a and 1201b are used to generate a first 1202a and second 1202b mechanical wave, respectively. The first mechanical wave is delivered to a first body location 1206a and the second mechanical wave is delivered to a second body location 1206b. Waveforms of the first and second electronic drive signals may be controlled (e.g., separately) (1204a and 1204b) to produce a desired response. The second electronic drive signal may be a delayed version of the first electronic drive signal, or may be a different signal.

FIG. 13 shows an example process 1300 for providing mechanical stimulation in a monaural fashion. As shown in FIG. 13, in process 1300 the same electronic drive signal 1301 is used to generate two mechanical waves—a first mechanical wave 1302a and a second mechanical wave 1302b. The first and second mechanical waves are delivered to first and second body locations (1306a and 1306b). The electronic drive signal is controlled 1304 to produce desired first and second mechanical waves and, accordingly, a desired response.

E. INDICATIONS

The systems, methods, and devices described herein may be used for a variety of indications. In certain embodiments, the device is included in a kit, along with a label describing the indication for which the device is to be used. FIG. 22 shows an example of a label. Other labels indicating that the device is to be used for other indications, including, without limitation, any of the indications described herein, may be including in a kit as appropriate.

i. Improved Interoception

In certain embodiments, the device, systems, and methods described herein can be used for enhancement of interoception. As described herein, enhanced interoception can improve a number of conditions that are related to dysregulated or otherwise impaired interoception. For example, many contemporary health problems involve dysregulated interoceptive processes, including affective disorders, addiction, eating disorders, chronic pain, dissociative disorders, post-traumatic stress disorder, and somatoform disorders (Farb, 2015). Accordingly, in certain embodiments, nerve stimulation using the present device and method provides for improving resilience to and symptoms of common stress-related disorders such as insomnia, reduced anxieties including, performance anxiety, social anxiety and blushing, vertigo, stress-induced infertility, fear, PTSD, and ADHD. Other benefits may include enhanced attention and engagement, lower blood pressure, and reduced blood cortisol levels. Interventions aimed at enhancing beneficial interoceptive signaling may provide enhanced quality of life and benefit for a variety of common stress-induced ailments, and psychiatric conditions such as panic disorder, depression, withdrawal symptoms of addiction, somatic symptom disorders, anorexia nervosa, and bulimia nervosa (Khalsa, 2016).

For example, in certain embodiments, the approaches describe herein may be used to generate a mechanical wave having a vibrational waveform selected to improve interoception in a subject. Such a mechanical wave may be generated by applying an electronic drive signal to a mechanical transducer, wherein a waveform of the electronic drive signal comprises (i) an isochronic signal and/or a TTVW with at least one component designed to enhance one or more EEG frequency(ies), brain-wave frequencies, and the like, (ii) a frequency component in the 5 to 15 Hz band, 10-48 Hz band, and/or other modulation components. The mechanical wave may be delivered to the subject by placing the transducer in proximity to afferent nerve complexes on the head ear or neck. Stimulation of these complexes and associated pathways and networks can bring individuals enhanced control over their subjective responses to internal bodily changes before those changes manifest behaviorally (panic, depression, rage, etc.).

In certain embodiments, enhanced interoception can generate enhanced empathy and sensitivity to others, through neural pathways directly associated with interoception and found only in higher social mammals. In another example, improving interoception may enhance sexual responsiveness in women who engaged in interoceptive training. Interoceptive sensitizing and training can be assessed by the concordance between quiet unaided heart-beat counting and actual heart best over a period. Higher scoring means improving interoception.

ii. Promotion of Relaxation and Stress Management

In certain embodiments, the approaches described herein may be used to promote relaxation and/or to manage stress. For example, in certain embodiments, the approaches described herein may be used to generate a mechanical wave having a vibrational waveform selected to promote relaxation and/or reduce stress in a subject. Such a mechanical wave may be generated by applying an electronic drive signal to a mechanical transducer, wherein a waveform of the electronic drive signal comprises (i) an isochronic signal and/or a TTVW with at least one component designed to enhance one or more EEG frequency(ies), brain-wave frequencies, and the like, (ii) a frequency component in the 5 to 15 Hz band, 10 to 48 Hz band, and/or other modulation components. The mechanical wave may be delivered to the subject by placing the transducer in proximity to afferent nerve complexes on the head ear or neck. Stimulation of these complexes and associated pathways and networks can improve the ability to sense somatic stress and remediate it to create a more calm and/or focused feeling. In certain embodiments, the stimulation may include components that generate a soothing acoustic experience. In certain embodiments, such approaches can improve and hasten the onset of meditative and/or mindfulness states and enhance those practices. These effects can be assessed, for example, via EEG, EKG, pupillometry, blood pressure, heart rate variability, and other metrics.

iii. Improvement of Mental Acuity and/or Concentration

In certain embodiments, the approaches described herein may be used to improve mental acuity and/or concentration. For example, in certain embodiments, the approaches describe herein may be used to generate a mechanical wave having a vibrational waveform selected to improve mental acuity and/or concentration in a subject. Such a mechanical wave may be generated by applying an electronic drive signal to a mechanical transducer, wherein a waveform of the electronic drive signal comprises (i) an isochronic signal and/or a TTVW with at least one component designed to enhance one or more EEG frequency(ies), brain-wave frequencies, and the like, (ii) a frequency component in the 5 to 15 Hz band, 10 to 48 Hz band, and/or other modulation components. The mechanical wave may be delivered to the subject by placing the transducer in proximity to afferent nerve complexes on the head ear or neck of the subject. Stimulation these complexes and associated pathways and networks may improve focus, concentration or mental acuity directly or coupled with the appropriate cognitive, mental or emotional task or additional stimuli. In certain embodiments, the mechanical wave stimulation provided by the approaches described herein facilitates neuroplasticity, which, in the context of training, can accelerate performance in the targeted domain. In EEG biometrics as well as objective performance on tasks within the domain of interest (e.g. concentration, memory, memory consolidation, working memory) can be used to assess effects.

iv. Enhanced Learning Capacity and Memory

In certain embodiments, the approaches described herein can be used to enhance learning capacity and/or memory in a subject. For example, in certain embodiments, the approaches describe herein may be used to generate a mechanical wave having a vibrational waveform selected to improve enhance learning capacity and/or memory in the subject. Such a mechanical wave may be generated by applying an electronic drive signal to a mechanical transducer, wherein a waveform of the electronic drive signal comprises (i) an isochronic signal and/or a TTVW with at least one component designed to enhance one or more EEG frequency(ies), brain-wave frequencies, and the like, (ii) a frequency component in the 5 to 15 Hz band, 10 to 48 Hz band, and/or other modulation components. The mechanical wave may be delivered to the subject by placing the transducer in proximity to afferent nerve complexes on the head ear or neck. Stimulation of these complexes and associated pathways and networks can improve rate and depth of learning, either with the use of the mechanical stimulation alone or in the context of one or more of (i) specific types of training (e.g. stimulation while learning a new language, learning a new surgical technique, learning to assess financial data and markets in real time), (ii) didactic learning (e.g. in traditional teacher led classrooms or virtual analogs), (iii) in real-time assessment, situational awareness, and (iv) a particular environment (e.g. physical, virtual, etc.). EEG biometrics as well as objective performance on tasks within a domain of interest (e.g. proficiency at robotic surgery) can be used to assess effects.

v. Additional Indications

In certain embodiments, the approaches described herein may be used to improve a subject's quality of life when the subject has a particular conditions. Specific conditions for which the device may provide for improvements in quality of life through its use include, without limitation, high blood pressure, tinnitus, and anxiety.

In certain embodiments, the approaches described herein may be used to address a variety of other indications, including, without limitation, one or more of the following: management of a social phobia (e.g., reducing negative effects of the social phobia; e.g., provide relief from the social phobia); reducing performance anxiety; reducing (e.g., frequency of; e.g., intensity of) stress-induced headaches; reducing stress-induced infertility; managing stress-induced high blood pressure; improving peripheral nerve sensitivity; improving peripheral nerve sensitivity; improving and/or supporting immune system function; managing stress-induced anger and/or mood problems; managing stress-induced sleep problems; reducing stress-induced menstrual cramping; improving appetite and/or salivation; improving balance; improving alpha brain waves; enhancing heart rate variability; improving vagal tone; promoting sleep management; reducing stress induced ringing in the ears; enhancing sexual function; and enhancing libido, sexual arousal, and/or orgasm.

As used herein, stress induced ringing in the ears refers to a specific sensation of ringing in ears of a subject, which may or may not physiologically originate (e.g., be produced) in the subjects ears (e.g., it may originate from a neurological condition not including nerves in the subject's ears).

F. TREATMENT OF ANXIETY VIA MECHANICAL STIMULATION

In certain embodiments, the devices, systems, and methods described herein are used for treatment of anxiety in a subject. As described herein, treatment of anxiety related clinical indications in a subject may be achieved by tailoring mechanical stimulation to stimulate particular biological targets in order to produce a particular state in the subject. Treatment efficacy for various mechanical stimulation types (e.g., different waveforms) can be validated via EEG and HRV analysis, as well as via measurement of stress hormone levels in a subject. In certain embodiments, as described herein, treatment via mechanical stimulation may be combined with other therapy, such as psychotherapy, exposure therapy [e.g., for treatment of various phobias (e.g., fear of heights, fear of public speaking, social phobia, panic attack, fear of flying, germ phobia, and the like)], cognitive behavioral therapy (CBT), and acceptance and commitment therapy (ACT).

i. Signal Design

Figure 23:
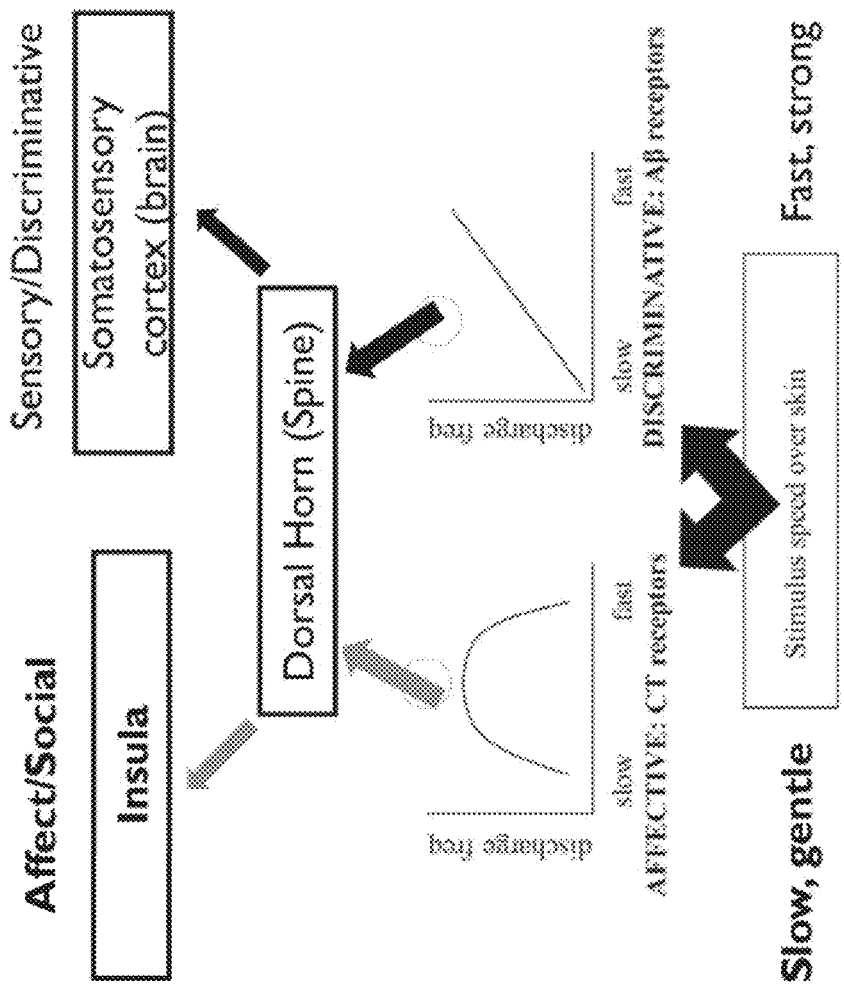
FIG. 23 is a schematic illustrating how, in certain embodiments, different stimuli types can elicit different responses in a subject.

Turning to FIG. 23, different types of feelings and states in a subject may be produced via different types of stimulation. In particular, stimulus type applied to a body location of a subject (e.g., at their skin) determines response in the brain. For example, from the cell membrane through mechanoreceptors, to associated nerves (e.g., C-tactile afferents), to the brain, there are endogenous preferences for signals. In certain embodiments, signals that are most effective at generating relaxation, positive feelings, and enhancing social interactions are slow and gentle. For example, a preferred speed of affective touch is approximately 3 centimeters per second (cm/s). For example, a frequency associated with enhanced social interaction may correspond to a breathing rate of a subject (e.g., corresponding to 6 to 10 breaths per minute; e.g., approximately 0.1 Hz)

Figure 24:
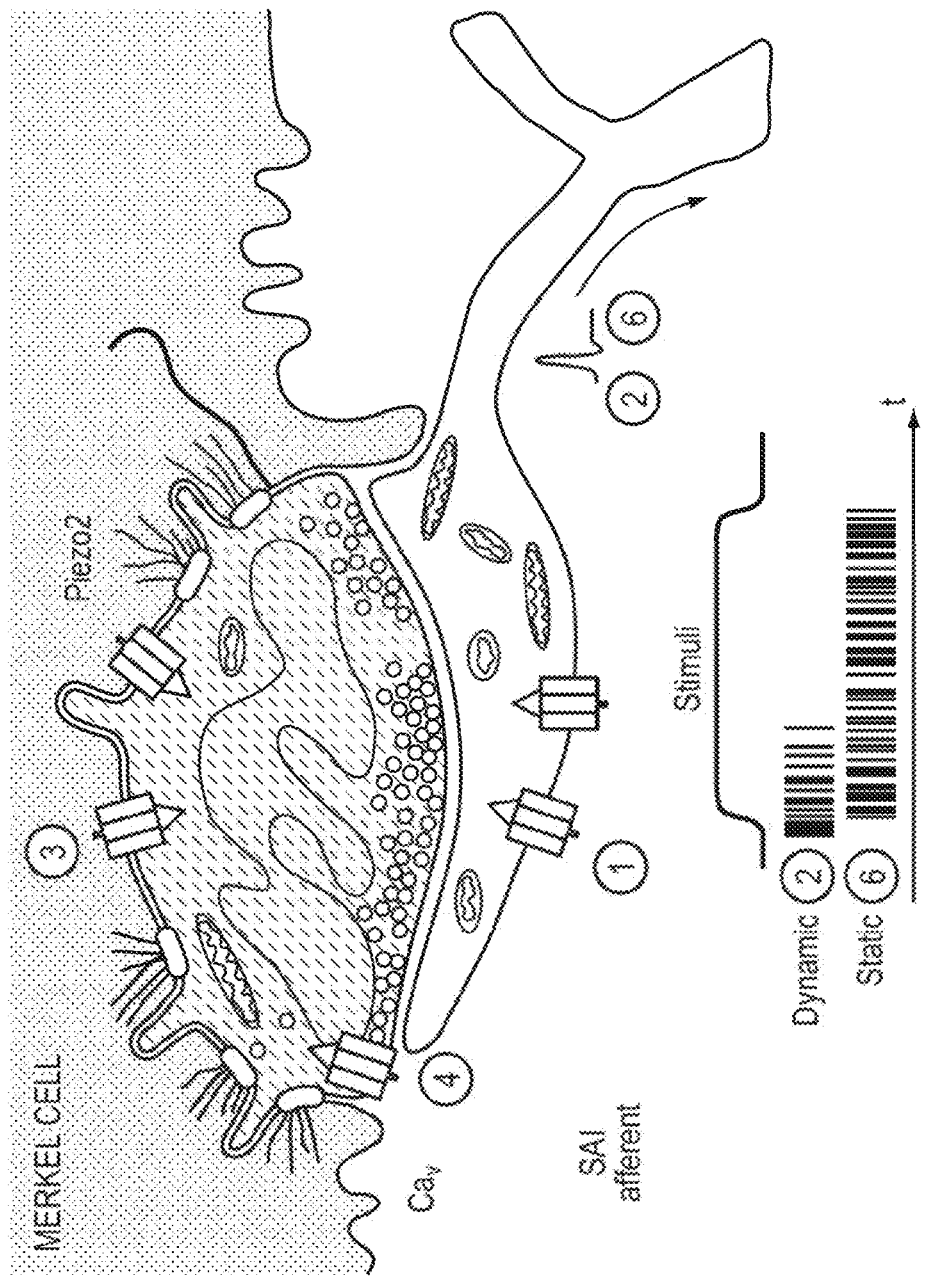
FIG. 24 is a schematic of an example mechanotransduction pathway for stimulating afferent nerves.

Turning to FIG. 24, mechanotransduction, as used herein, refers to any of various mechanisms by which cells convert mechanical stimulus into electrochemical activity. Without wishing to be bound to any particular theory, it is believed that this form of sensory transduction is responsible for a number of senses and physiological processes in the body, including proprioception, touch, balance, and hearing.

FIG. 24 shows an example mechanotransduction pathway for stimulating an insula region of a brain of a subject. As shown in FIG. 24, specialized ion channels—Piezo2 proteins respond to mechanical stimulation and cause firing of specialized Merkel cells that stimulate nerves leading up to the insula.

Figure 25:
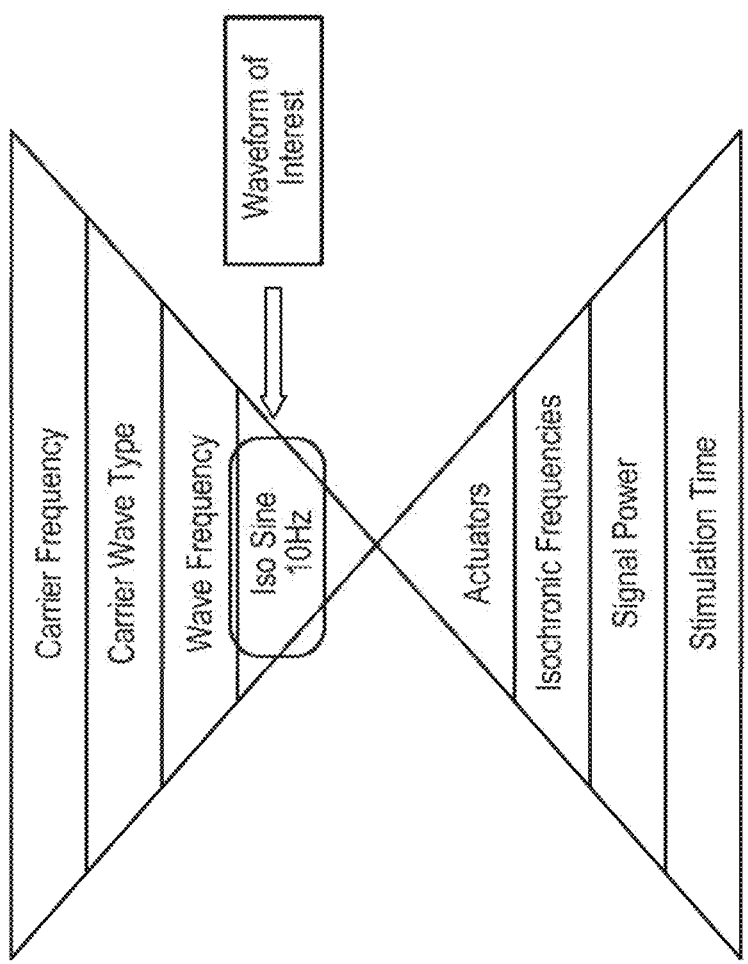
FIG. 25 is a diagram illustrating example characteristics of mechanical stimulation that can be tailored to elicit a particular response in a subject, according to an illustrative embodiment.

In certain embodiments, mechanical stimulation can be tailored to stimulate a particular pathway, such as that shown in FIG. 24, in order to produce a particular response (e.g., state) in a subject. FIG. 25 illustrates several stimulation characteristics that can be tailored according to an understanding of a particular pathway and mechanism of action for producing a desired response in a subject. In particular, as described herein, an isochronic wave having a particular carrier frequency and duration of low-amplitude sub-intervals was designed to target specific biological targets that are part of the pathway described in FIG. 24, and produce a relaxation response and treat anxiety related clinical indications in a subject.

In particular, as described herein, for example in section D.i, an isochronic signal having frequency components falling within a range of those to which Merkel cells respond, along with low-amplitude sub-intervals that allow for recovery of Piezo2 proteins was discovered to be effective at producing a relaxation state in a subject, and, accordingly, for use in treatment of anxiety. FIG. 4 shows an example of such an isochronic signal.

Figure 26:
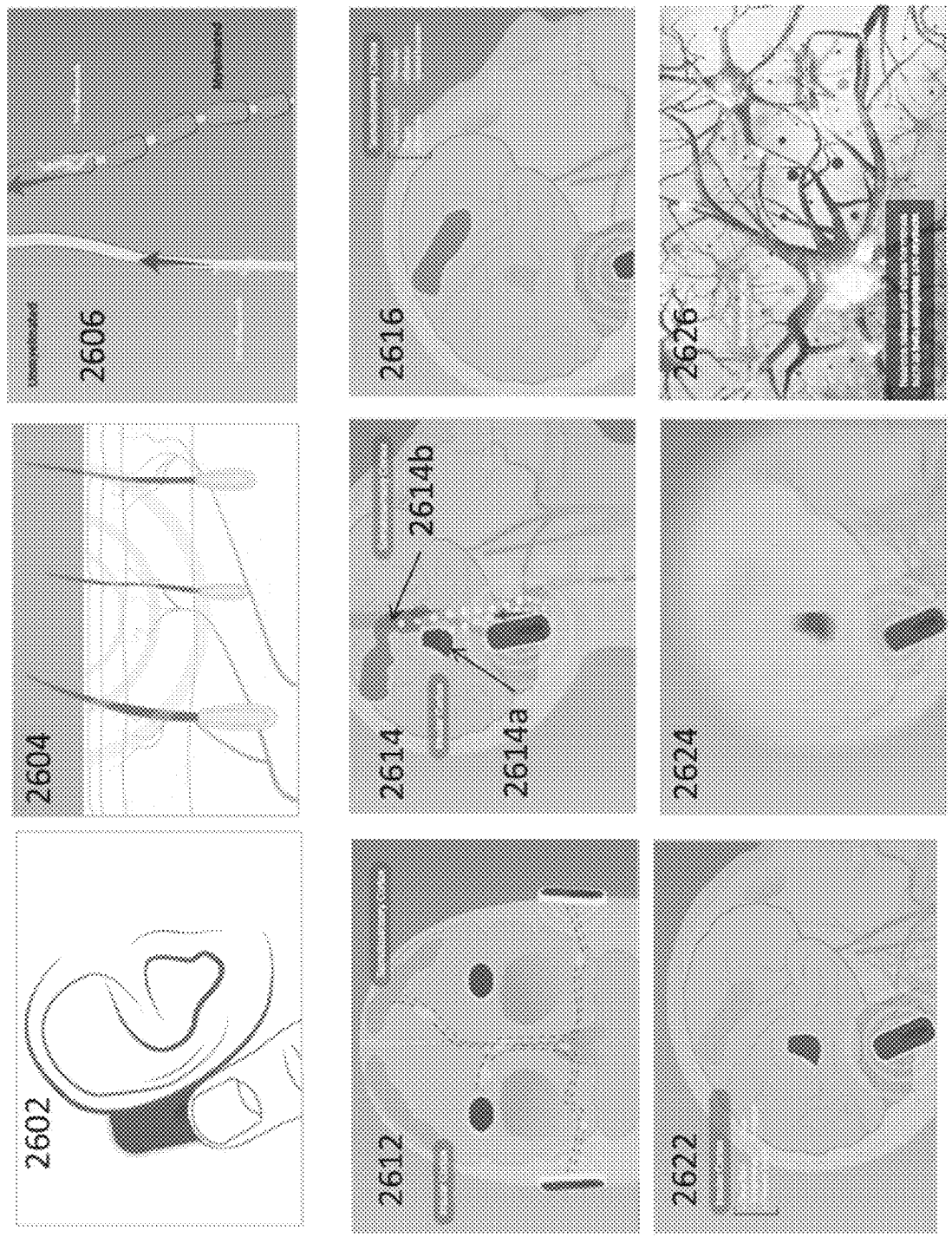
FIG. 26 is a series of schematics illustrating a proposed use of the devices and methods described herein for treating a subject, according to an illustrative embodiment.

FIG. 26 summarizes an embodiment of use of a device for treatment of anxiety and increasing feelings of calm in a subject. Transducers of the device are placed in proximity to a mastoid region, for example, behind an ear of the subject (2602). Mechanical vibration produced by the transducers of the device stimulates various receptors (e.g., mechanoreceptors) in the skin (in particular, in glabrous, hairy skin), as described herein (2604). While certain mechanoreceptors are not impacted, waveform and frequency of the mechanical stimulation produced by the transducers is designed to target receptors involved in afferent pathways, in particular mechanoreceptors and C-tactile afferents. Signal may be propagated down unmyelinated and myelinated nerves (2606). Myelinated signals travel to the somatosensory cortex, while unmyelinated signals travel to the insular cortex. Slower nerve fibers (e.g., unmyelinated) stimulate the insula longer than the myelinated nerves stimulate the somatosensory cortex (2612). The insular cortex 2614a and somatosensory cortex 2614b are shown in a side view of the subject's head 2614. Sensations such as fast touch, pokes, pinpricks, pressure, vibration, and spatial location are picked up (e.g., stimulate) by the somatosensory cortex (2616), while the insular cortex is involved in sensations such as deep pain, temperature, pleasant touch, taste, and emotion (2622). Moreover, research findings have implicated the insula in an overwhelming variety of functions ranging from sensory processing to representing feelings of motion, autonomical and motor control, risk prediction and decision-making, bodily and self-awareness, and complex social functions like empathy. Accordingly, by supplying mechanical vibration that targets pathways that stimulate the insula, the devices and methods described herein can, in certain embodiments, provide treatment of anxiety and related disorders (2624). In certain embodiments, mechanical stimulation provided by devices and methods as described herein can result in changes in levels of particular stress-related hormones. For example, by increasing release of hormones such as oxytocin and serotonin and/or reducing levels of cortisol, mechanical stimulation can mitigate anxiety in a subject (2626).

ii. Validation Results

Figure 28A:
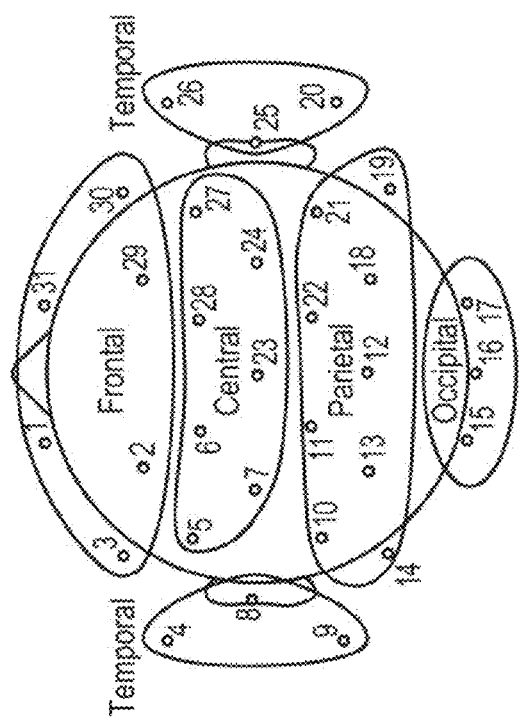
FIG. 28A is a schematic showing different brain regions from which EEG sensors collect signal, according to an illustrative embodiment.
Figure 28B:
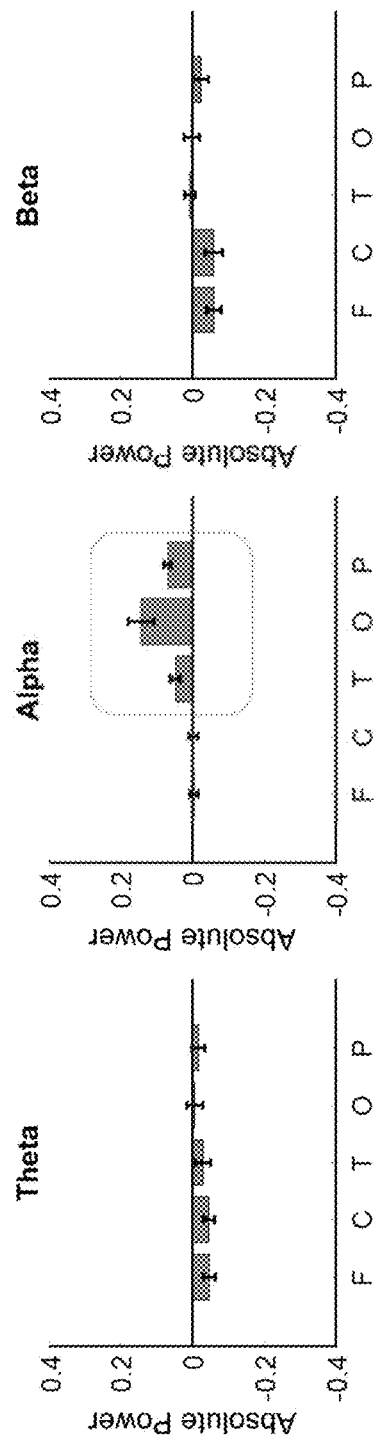
FIG. 28B is a set of three graphs showing changes in absolute power measured by EEG sensors in different brain regions.

Efficacy of mechanical stimulation treatment of anxiety was evaluated using EEG and HRV measurements and analysis. Turning to FIG. 27, EEG captures fluctuations of electrical voltage in a cortex of a subject through electrodes placed on scalp. Power spectral analysis of EEG data can show changes in EEG frequencies that may be relevant to physiological activities of the brain. FIG. 28A shows an example of different regions of a brain, identifying different collections of electrodes associated with each region. As shown in FIG. 28A, different collections of electrodes are used to measures signals from a Temporal region of the brain (T—red contours), a Frontal region (F—green contour), a Central region (C—cyan contour), a Parietal region (P—purple contour), and an Occipital region (O—orange contour). FIG. 28B is a set of three graphs showing changes in absolute power in three different frequency bands associated with three different types of brain waves following mechanical stimulation using the isochronic wave shown in FIG. 4. Each graph corresponds to a particular brain wave type and shows changes in absolute power measured in each of the five aforementioned regions of the brain (T, F, C, P, and O). The left graph shows changes in absolute power of frequencies associated with theta brain waves, the middle graph shows changes in absolute power of frequencies associated with alpha brain waves, and the right graph shows changes in absolute power of frequencies associated with beta brain waves. The measurements show that alpha waves were increased in the temporal, occipital, and parietal regions. As shown in FIG. 21, an increase in alpha waves is associated with relaxation.

Figure 29:
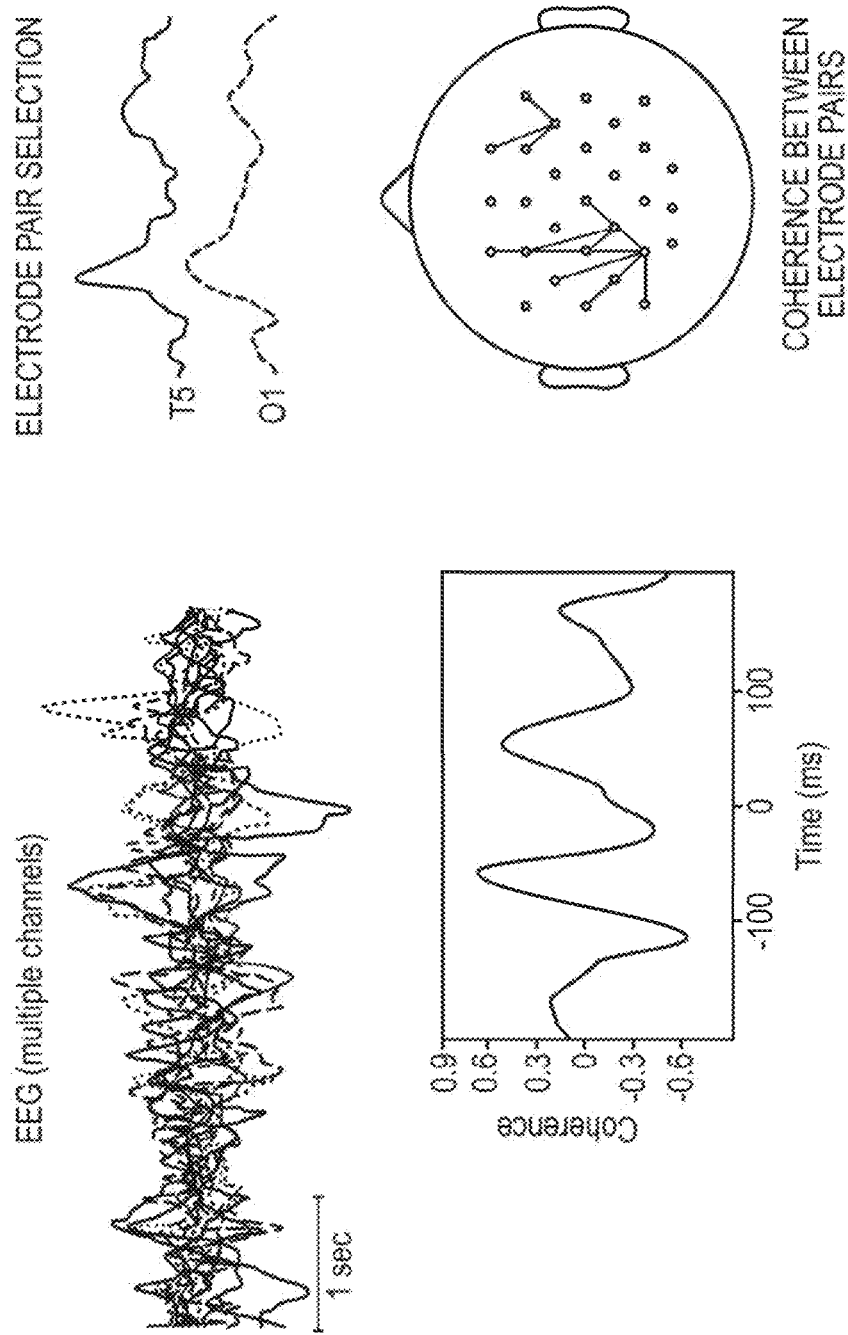
FIG. 29 is a set of graphs illustrating coherence analysis in EEG measurements, according to an illustrative embodiment.
Figure 30:
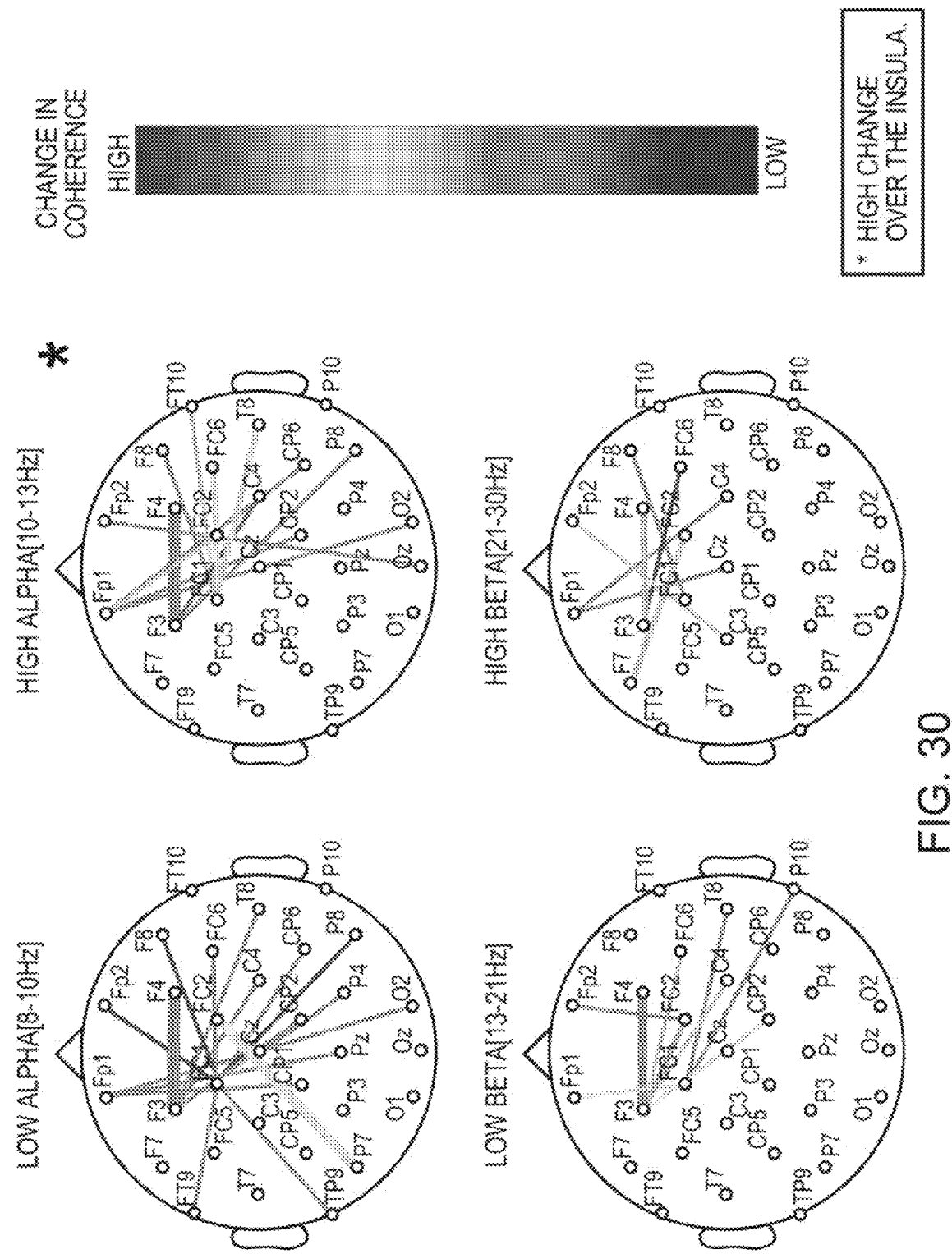
FIG. 30 is a set of graphs showing coherence analysis in EEG data performed for a subject receiving mechanical stimulation in accordance with the devices, systems, and methods described herein.

Turning to FIG. 29 and FIG. 30, coherence analysis of EEG data was also used for validation of treatment efficacy. Coherence is a mathematical technique that quantifies frequency and amplitude of synchronicity of neuronal patterns of oscillating brain activity. Complex connectivity analysis can be executed to target interactions between different brain regions. Coherence provides an understanding of communication (e.g., working together or independently) between different brain regions. Coherence analysis tends to be more meaningful when reviewing functional effects. The coherence data shown in FIG. 30 indicates a high change over the insula when a subject receives mechanical stimulation produced by the isochronic wave of FIG. 4.

Figure 31:
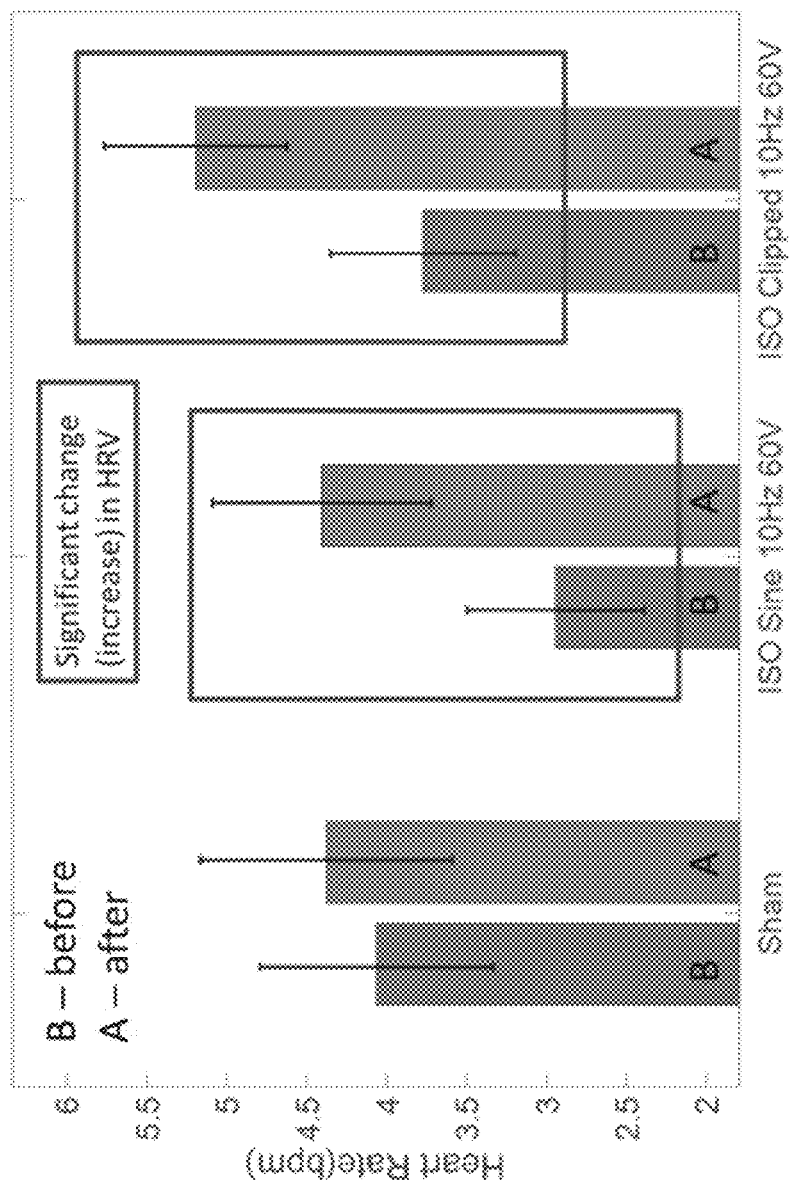
FIG. 31 is a graph comparing heart rate variability (HRV) results for two different types of stimulation used for treatment of anxiety with a control (sham stimulation).

FIG. 31 shows a comparison of two mechanical waveforms tailored for eliciting relaxation in a subject (ISO Sine 10 Hz 60V and ISO Clipped 10 Hz 60V) in comparison with sham stimulation. The figure shows response before (bars labelled "B") and after (bars labelled "A") stimulation for three different types of stimulation—sham (control), a 10 Hz isochronic sine wave, and a 10 Hz clipped isochronic sine wave. As shown in the Figure, a significant increase in HRV of the subjects stimulated with the waveforms relative to those subjected to the sham condition was observed. Increased HRV has been shown to be a measure of parasympathetic and vagal tone, the benefits of which include, without limitation, raising physical recovery, cognitive function, and relaxation.

iii. Controlling Stress Hormone Levels

In certain embodiments, efficacy of anxiety treatment via mechanical stimulation as described herein can be evaluated via measurement of stress hormone levels. For example, a level of cortisol in a subject can be measured following mechanical stimulation. Stimulation that produces a reduction in cortisol levels can be used for treatment of anxiety. Other stress hormones such as oxytocin and serotonin may also be measured. For example, stimulation that increases levels of oxytocin and serotonin may be useful for treatment of anxiety.

In certain embodiments, a length of a telomere of a subject may also be used as a physical measurement for evaluating efficacy of anxiety treatment. In particular, without wishing to be bound to a particular theory, stress is believed to shorten telomeres (see, e.g., Mathur et al., Perceived stress and telomere length: a systematic review, meta-analysis, and methodologic considerations for advancing the field, Brain Behavior, and Immunity, volume 54 (2016), pages 158-159). Accordingly, in certain embodiments, the systems, devices, and methods described herein may reduce a rate of shortening of telomeres.

iv. Case Study Reports

In one case study, a user that typically experienced migraine headaches received mechanical stimulation via an embodiment of the devices described herein. The user reported that while they were typically woken from sleep with a pounding headache, following use of the device they woke from sleep early morning without a pounding headache or any associated nausea. In another case report, a user reported a lack of anxiety in a situation that typically provoked anxiety for them with use of a device as described herein. In particular, the user reported a feeling similar to use of propranolol.

v. Combined Therapy

In certain embodiments, the mechanical stimulation approaches described herein may be combined with a therapy, such as such as psychotherapy, exposure therapy [e.g., for treatment of various phobias (e.g., fear of heights, fear of public speaking, social phobia, panic attack, fear of flying, germ phobia, and the like)], cognitive behavioral therapy (CBT), and acceptance and commitment therapy (ACT). Treating psychological disorders with psychotherapeutic, cognitive, and/or behavioral interventions (of which there are many types) often include developing behavioral and cognitive techniques to alter maladaptive responses. Development of those techniques includes recognizing one's own visceral or emotional responses and acting to mitigate the sequence of events that leads to the maladaptive outcome. In certain embodiments, the devices, systems, and methods described herein enhance EEG activity associated with neural circuits and brain areas associated with evaluating internal bodily responses and integrating those with external stimuli. Combining mechanical stimulation at the time of therapy, and/or when practice techniques and/or when in a situation or environment that can provoke symptoms may improve and/or accelerate the individual's ability to successfully apply therapeutic insights. This form of mechanical stimulation can stimulate neural circuits associated with processing of internal, visceral sensations, improving an individual's ability to respond and more effectively manage maladaptive responses. In practice, individuals may be wearing and using the stimulation immediately prior to, during, or immediately after a therapeutic session. They may also use stimulation when they are practicing techniques to reduce maladaptive responses outside of therapy. They may also use stimulation before, during, or after exposure to some stimulus (such as flooding for phobias) that produces or situation (like public speaking) a maladaptive response.

G. PHYSICAL EMBODIMENTS

Figure 32A:
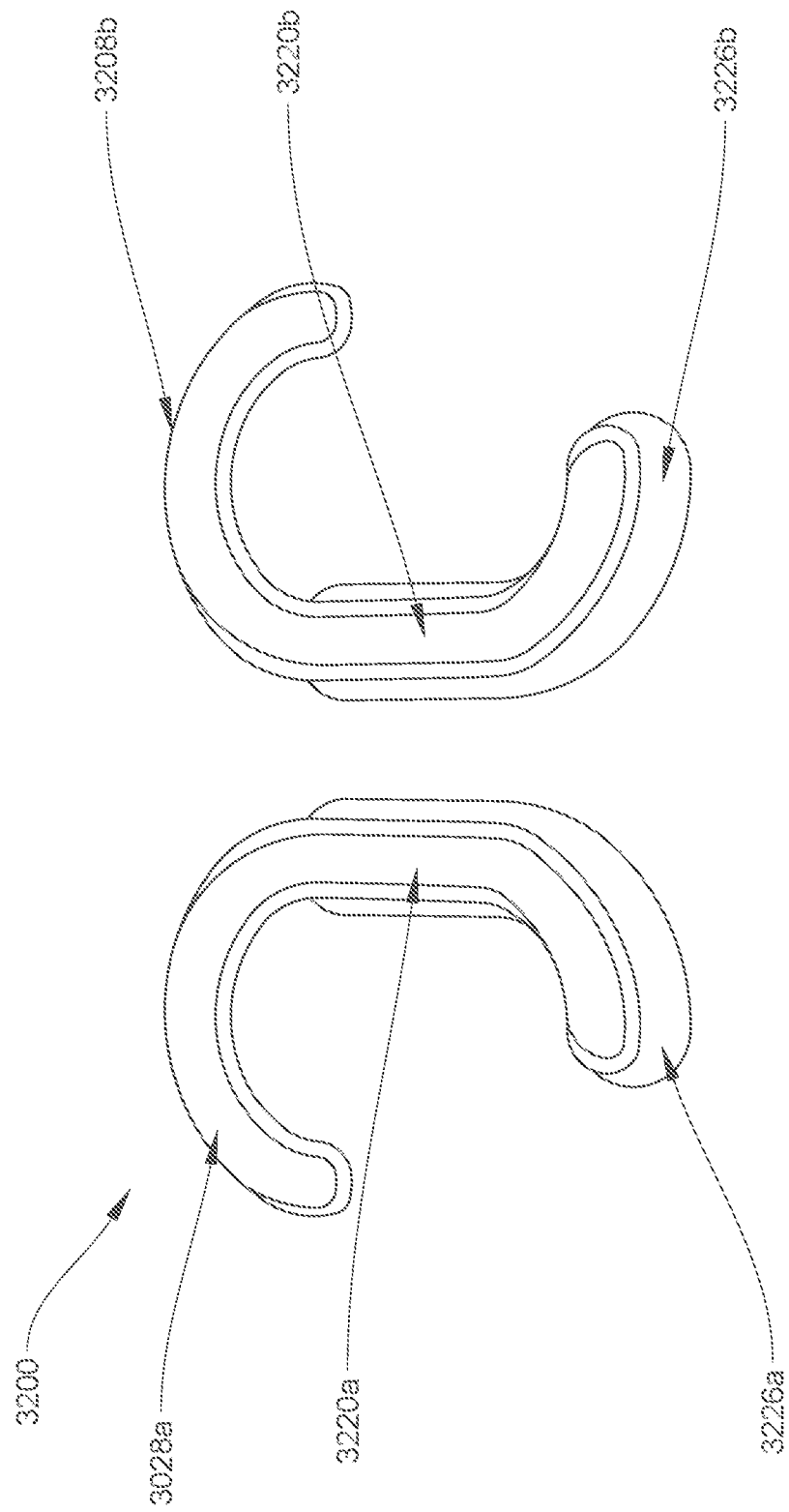
FIG. 32A is a schematic plan view of a transcutaneous neuromodulation device in accordance with one or more embodiments of the invention.

FIG. 32A depicts one embodiment of a transcutaneous neuromodulation device 3200 that includes two separate ergonomic support components 3208a, 3208b (generally, 3208); however, in some applications, the transcutaneous neuromodulation device 3200 includes only a single ergonomic support component 3208. In some embodiments, the transcutaneous neuromodulation device 3200 includes two ergonomic support components 3208, but only one may need to be used to suit a particular application.

As shown in FIG. 32A, each ergonomic support component 3208 includes an elastomeric arm 3220a, 3220b (generally 3220), or similar structure for comfortably engaging with a portion of a human subject 3212. For example, in the embodiment shown, the elastomeric arm 3220 is configured to "hug" or otherwise engage the subject's ear (see, e.g., 3214a in FIG. 32D). In some embodiments, the entire device can be fully supported by the subject's ear via the ergonomic support component.

Each ergonomic support component comprises a housing 3226a, 3226b (generally 3226) for supporting and/or enclosing at least one mechanical transducer. The housings 3226 may also support and/or enclose other components, such as at least one controller board, and at least one battery or other power source (e.g., a photovoltaic cell), as shown in greater detail in FIGS. 34A and 34B, and described in further detail herein. In certain embodiments, controller boards and batteries or other power sources are not enclosed within or supported by the housing, but rather within other portions of the ergonomic support component(s) 3208, for example within the elastomeric arms 3220. The housing(s) 3226 is/are positioned within the ergonomic support component(s) 3208 such that when the ergonomic support component(s) are worn by a human subject, the mechanical transducer(s) within the housing are positioned in proximity to a specific desired body location on the subject, such as a mastoid region. Accordingly, in this manner, mechanical vibration produced by the mechanical transducers is delivered to the specific desired body location.

In certain embodiments, each housing 3326 comprises a window, adjacent to which the mechanical transducers are disposed, and which contacts skin (or other surface) of the subject when the ergonomic support component(s) is/are worn. The window (along with other portions of the housing) may include and be covered with insulating material and/or a tactile fabric so as to prevent direct contact between the transducer surface and skin of the subject. The tactile fabric may be selected to provide a specific sensation (e.g., to mimic touch), and thereby enhance the treatment delivered by the mechanical transducer.

The housing 3226 can also support or include a variety of sensors 3216, controls (e.g., on/off button, indicator light), and/or other interface components (e.g., an external communication interface 3228 (e.g., for charging the device; e.g., for transferring data to and/or from the device)). In various embodiments, at least a portion of each ergonomic support component 3208 can be covered in a conductive fabric or other material that allows the subject 3212 to interface/control the device 3220.

Figure 32B:
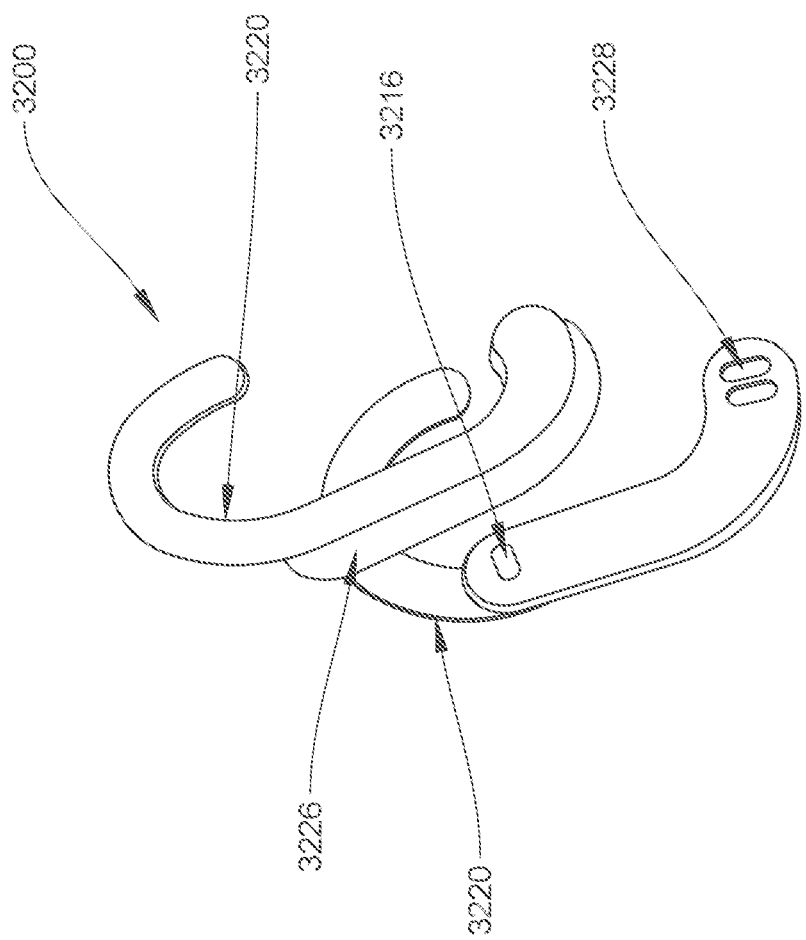
FIG. 32B is a schematic perspective view of the transcutaneous neuromodulation device of FIG. 32A in accordance with one or more embodiments of the invention.

FIG. 32B depicts a perspective view of the device of FIG. 32A. An external communication interface 3228 disposed at a distal end of the elastomeric arm 3220, at least one sensor 3216 are all shown in FIG. 32B.

The sensor(s) 3216 can be mounted within the housing or disposed on an exterior surface thereof, depending on the type of sensor and characteristic to be measured. Typically, the sensor(s) will be monitoring at least one biometric identifier of the human subject 3212, such as galvanic skin response (GSR), pulse, blood pressure (BP), oxygen levels, temperature, or electrical signals (e.g., EEG and EKG). In some embodiments, the sensors include an accelerometer, a pressure transducer for BP, and a conductance sensor for GSR. The sensor(s) can be in communication with the controller so as to provide a signal representative of the biometric identifier (i.e., biofeedback) that the controller board(s) can use to modify a treatment protocol as needed. In some embodiments, the waveform can be adjusted based on user feedback, statistical data, or via machine learning (e.g., artificial intelligence (AI)).

External communication port 3228 can include an interface for use with a wireless or inductive charger or could include a port configured to receive a power cord, for example, a USB port. As can be seen in FIGS. 32A and 32B, the two ergonomic support components 3208 are wireless. In an application where both components 3208 are used, the devices can communicate via Bluetooth®, near-field magnetic induction (NFMI), or similar technology. The components 3208, can communicate wirelessly with one or more peripheral devices, such as a smart phone or watch, a Fitbit® or similar device, a heart rate monitor, a blood pressure monitor, or a personal computer. In some embodiments, the device 3200 may be connected to other devices via a cord.

For example, in various embodiments, the two ergonomic support components 3208 are wirelessly synchronized to deliver a coordinated waveform output; however, not necessarily the same waveform. For example, in some embodiments, each wearable component may deliver the same waveform, but in other embodiments, the wearable components 3208 deliver different, but coordinated waveforms to suit a particular application. In some embodiments, the interface components communicate via NFMI. Communication via NFMI may be advantageous since magnetic field based signals are less likely to be blocked (e.g., scattered and/or attenuated) by a subject's head.

Figure 32C:
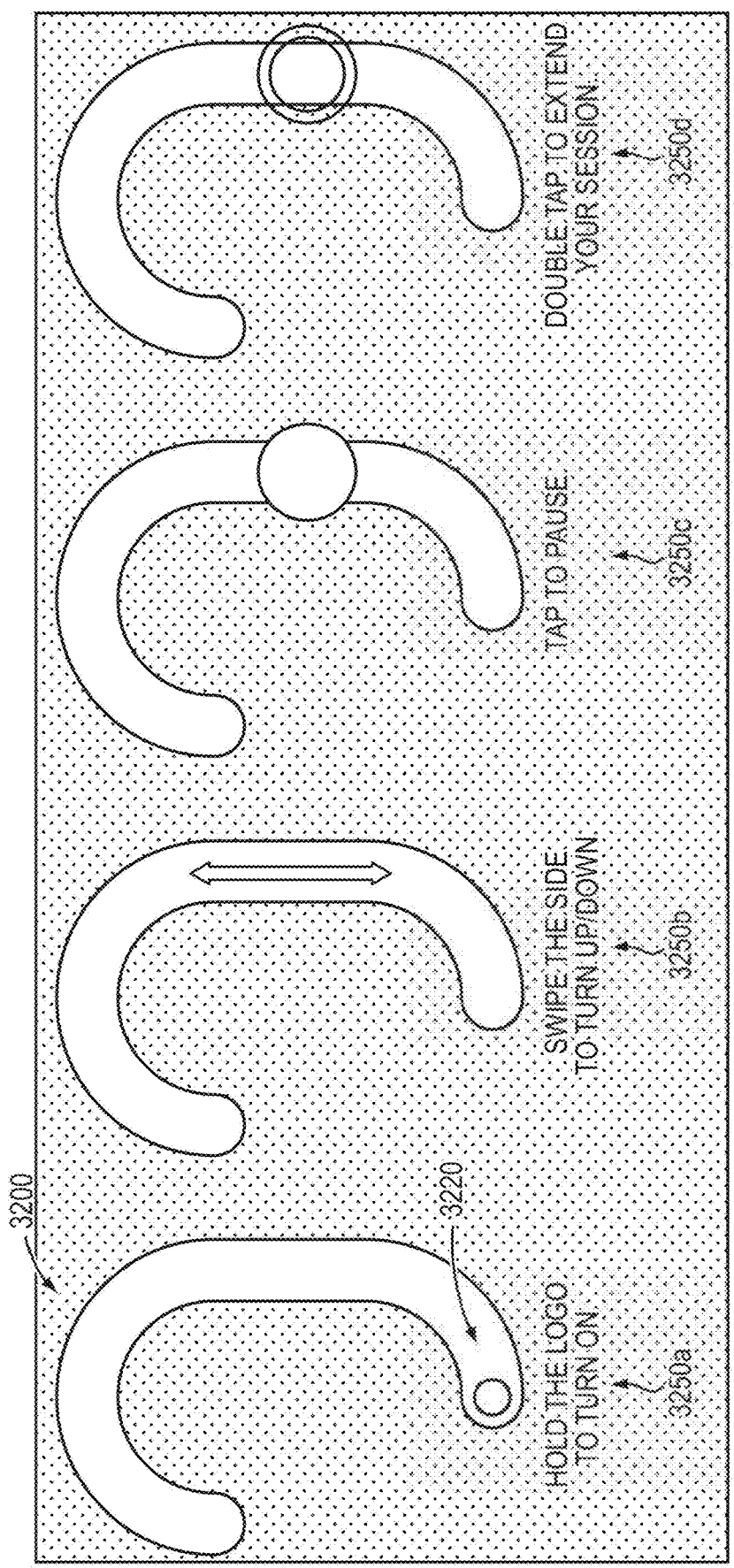
FIG. 32C is a schematic side view of a portion of an ergonomic support device for use with a transcutaneous neuromodulation device depicting a series of control maneuvers for operating the device in accordance with one or more embodiments of the invention.

FIG. 32C depicts the various ways a subject can control the transcutaneous neuromodulation device 3200. For example, the elastomeric arm 3220 can be covered in a conductive fabric or other material that is responsive to human touch. As shown in FIG. 32C, it is possible to turn the device on by touching a specific location (e.g., a logo) on the device (3250a), adjust the intensity of the device output by a swiping motion across the arm (3250b), tap the arm to pause the device (3250c), and double tap to perform other functions, such as extending a treatment session (3250d).

Figure 32D:
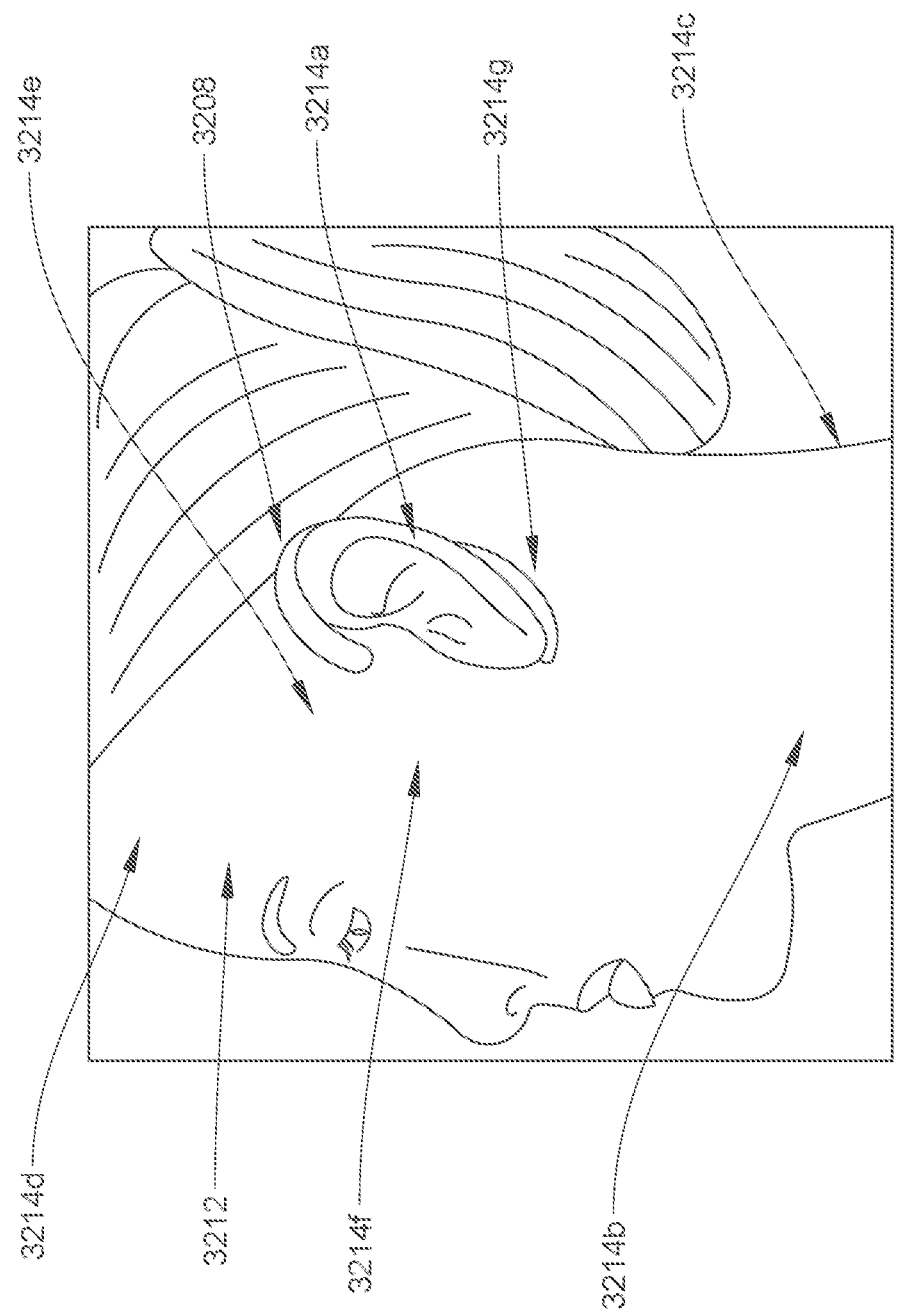
FIG. 32D is a schematic side view of a transcutaneous neuromodulation device positioned on a human subject in accordance with one or more embodiments of the invention.

FIG. 32D depicts an embodiment of the transcutaneous neuromodulation device wherein the ergonomic support component 3208 is secured around the subject's ear 3214a. However, in other embodiments, the ergonomic support component 3208 can be placed on the human subject's neck 3214b, back of neck 3214c, skull 3214d, temples 3214e, face 3214f, or arms (not shown) depending on a specific treatment protocol. In a particular embodiment, the device 3200 is placed on the human subject 3212 to maintain the mechanical transducer substantially proximate the subject's mastoid region 3214g. In some embodiments, the elastomeric arm 3220 has a wire frame core that allows the arm 3220 to be shaped to optimize the fit of the ergonomic support component 3208 to the subject 3212 and to best position the transducer housing 3226 relative to the desired treatment area of the subject 3212. In some embodiments, the frame is made of aluminum wire and covered with a plastic resin to form the arm 3220. In some embodiments, the elastomeric arm includes a resilient material, such that the arm provides a pressing force to hold the transducer against the subject's mastoid or other body part. In some embodiments, the arm 3220 can also be covered in a fabric, such as a conductive, tactile, or haptic fabric to enhance the subject's experience.

Referring back to FIGS. 32A and 32B, the transducer housing 3226 can generally be disposed anywhere on the ergonomic support component; however, in most embodiments, the transducer housing 3226 will be disposed proximate a distal end of the elongate arm, so as to eliminate or reduce any structural resistance (e.g., dampening) of the vibrations. Specifically, the elongate arm acts like a cantilever beam and it is desirable for the transducer to operate as close as possible in a free vibration state, such that the desired treatment is delivered to the subject.

Figure 34B:
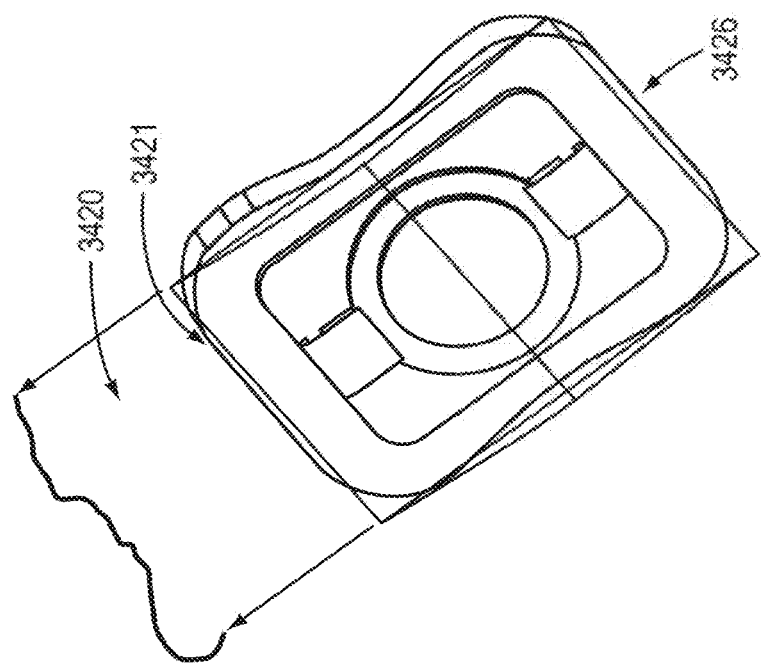
FIG. 34A and FIG. 34B are schematic perspective views of an interface portion of a transcutaneous neuromodulation device in accordance with one or more embodiments of the invention.
Figure 34A:
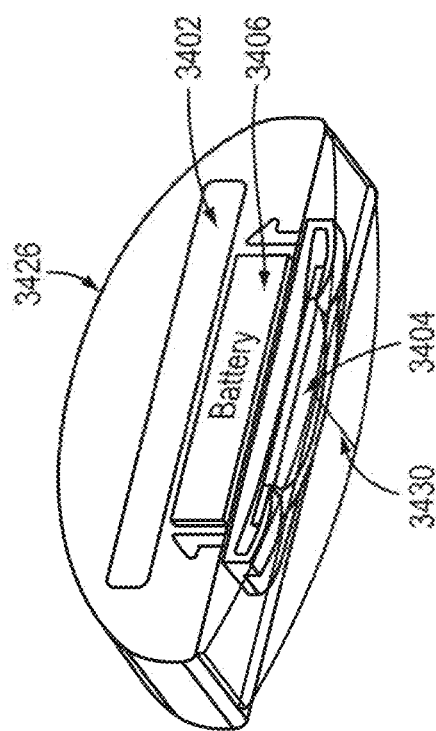

Referring now to FIGS. 34A and 34B, one possible mounting arrangement for the transducer(s) 3404 is shown. Generally, the at least one mechanical transducer should be mounted in an essentially intrinsically safe manner, such that the subject is shielded from electrical shocks or the transfer of excessive heat. For example, the electrical connections between the battery (or other electrical components) and the transducer (e.g., solder joints) can be located within the housing, with the transducer disposed on an exterior surface of the housing and any wires extending therebetween being insulated, potted, or otherwise shielded. In some embodiments, the at least one mechanical transducer itself is encased in an insulated material to prevent direct contact with the human subject. In various embodiments, the mechanical transducers can be covered in a polymeric material, wrapped in a fabric, or encased in an adhesive compound.

As shown in FIG. 34A, the controller 3402, battery 3406, and transducer 3404 are all disposed within the housing 3426 adjacent in an opening or window in the housing 3426. The housing 3426 may comprise an injection molded casing; however, other configurations are contemplated and considered within the scope of the invention. The various components can be secured within the housing 3426 via various approaches. Alternatively or additionally, the mechanical transducer 3404 can be flexibly coupled to the housing 3426. The window and transducer 3404 are covered by an insulating material 3430, as described above. In certain embodiments, the insulating material 3430 is selected to prevent direct contact between the transducer 3404 and the subject's skin, but not impart a dampening effect to the vibrations. Exemplary insulating materials include, without limitation, elastomeric materials such as rubber, silicone, EDTM, nitrile, neoprene, as well as engineered fabrics utilizing blends of nylon, spandex, polyester, and other flexible fibers. Generally, the transducer 3404 can be of any of the types disclosed herein (e.g., piezo).

As shown in FIG. 34B, the housing 3426 and associated components are located at the distal end 3421 of the elongate arm 3420. In some embodiments, the housing is butt mounted to the distal end 3421 to avoid any overlap between the window and the elongate arm 3420. In some embodiments, the housing 3426 can be removably attached to the arm 3420, such that it can be exchanged with a different housing (e.g., to change a treatment protocol, replace a malfunctioning device, or for hygienic reasons.) In some embodiments, the housings 3426 may be disposable.

The overall shape and dimensions of the housing may vary to suit a particular application considering, for example, a treatment area, the nature of the subject (e.g., adult vs. child), and the number of transducers required. The device shown in FIGS. 34A and 34B includes a single transducer 3404 disposed in each housing; however, any number and arrangement of transducers can be selected to suit a particular application. For example, multiple transducers 3404 can be mounted side by side along a length of the housing 3426 and connected electrically in series or parallel depending on the treatment protocol.

Figure 32E:
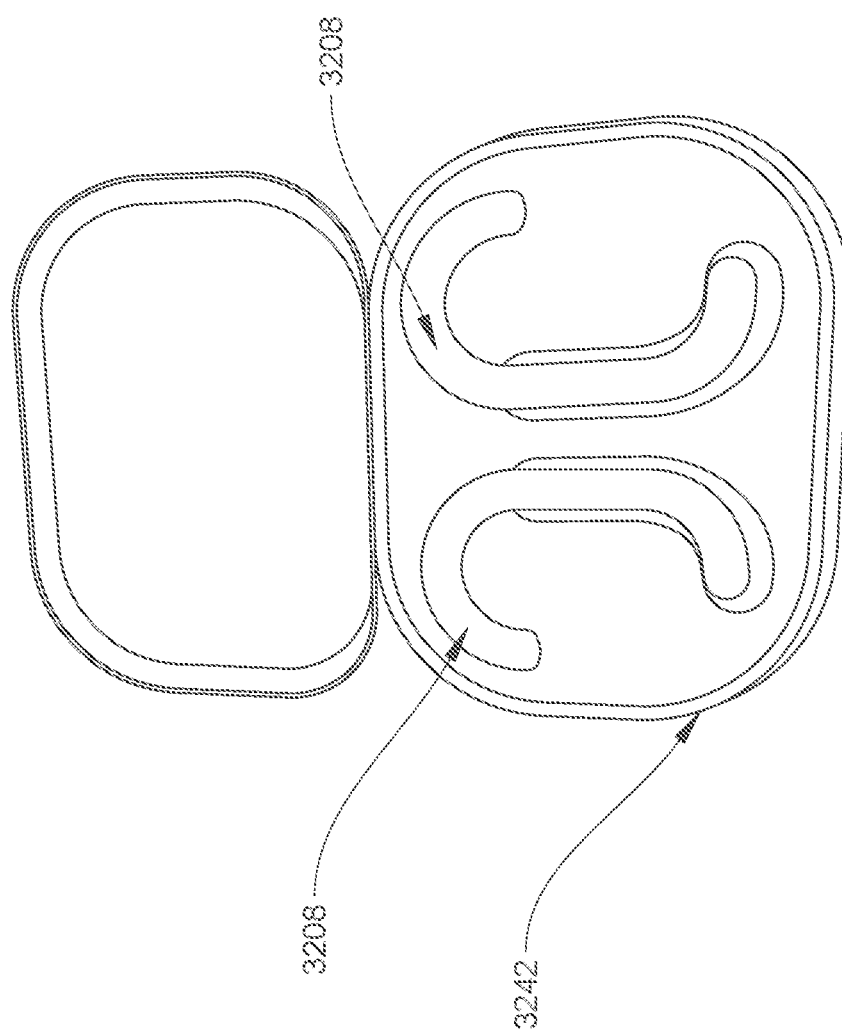
FIG. 32E is a schematic plan view of a transcutaneous neuromodulation device positioned in a storage/charging case in accordance with one or more embodiments of the invention.

FIG. 32E depicts the ergonomic support components disposed within a storage case 3242. In some embodiments, the case 3242 provides a secure, hygienic environment for storing and transporting the device. However, in other embodiments, the case 3242 can include components to provide charging or to even exchange data (e.g., a smart case) that allows the subject to keep track of their usage, such as dates used, time of day used, and duration of use.

Figure 33B:
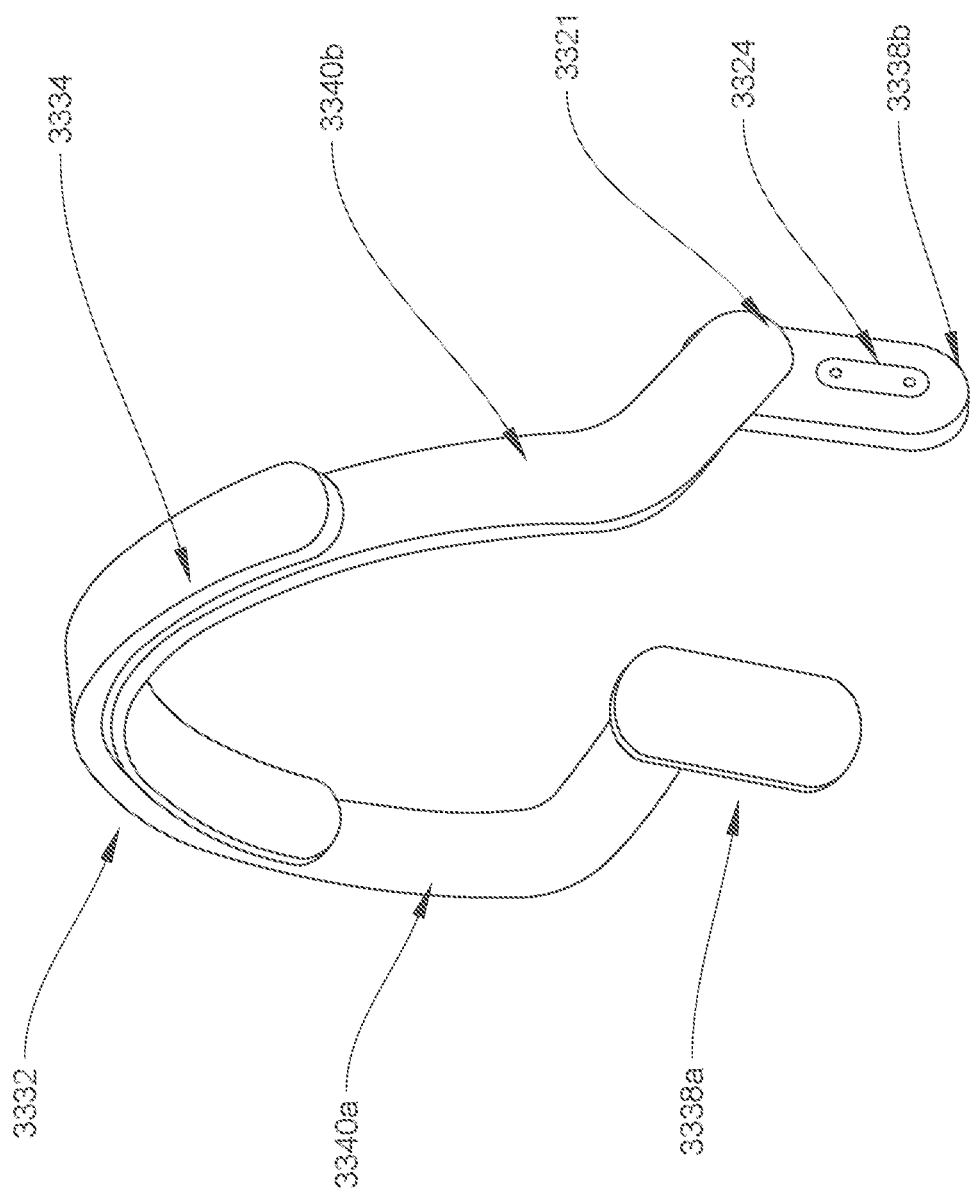
FIG. 33B is a schematic perspective view of the transcutaneous neuromodulation device of FIG. 33A rotated 180 degrees.

FIGS. 33A and 33B depict another embodiment of an ergonomic support component of a transcutaneous neuromodulation device. The ergonomic support component 3300 comprises a linkage component formed to engage (e.g., wrap around) a body part of a subject (e.g., a head). As shown in FIGS. 33A and 33B, two transducer housings are disposed at opposite ends of the linkage component, for example so as to be positioned on opposite sides of the subject's head. Each transducer housing 3338 supports and/or encloses a corresponding transducer set. Each transducer set may comprise one or more transducers, for example arranged in transducer arrays as described herein.

In certain embodiments, the linkage component can be adjusted (e.g., via an adjustment mechanism 3334) to accommodate natural variations the body parts of subjects to which it is formed to engage. For example, in certain embodiments the linkage component is formed to engage (e.g., wrap around) a head of a subject and comprises two interlocking curved arms (e.g., elastomeric arms) 3340a and 3340b. The curved arms are maintained in alignment to form an arc, and can slide with respect to each other so as to vary an amount that the two arms overlap. In this manner, a size of the arc can be adjusted so as to accommodate a variety of sizes of human heads. While described herein with regard to adjustments made to accommodate variations in human heads, similar approaches can be used to provide for adjustable linkage components formed to engage with other parts of the body, for example around arms, wrists, etc.

As shown in FIGS. 33A and 33B, the housings 3338 are flexibly coupled to opposite distal ends 3321a and 3321b of the linkage component 3332. In some embodiments, the housings 3338 are adjustably mounted, such that their relative position can be changed to better interface with the subject and maintained in the position. In some embodiments, the linkage component comprises two curved elastomeric arms 3340a and 3340b similar to those previously described. The curved elastomeric arms 3340a and 3340b can be adjusted to optimize comfort and transducer location and, in some cases, provide a pressing force to hold the transducer against the subject's body.

In certain embodiments, the transducer housing(s) enclose or support at least one mechanical transducer, at least one controller board, and at least one battery or other power source. However, in some embodiments, the controller board(s) and/or power source can be disposed within the linkage mechanism (e.g., within the curved elastomeric arms 3340a and 3340b).

Figure 33F:
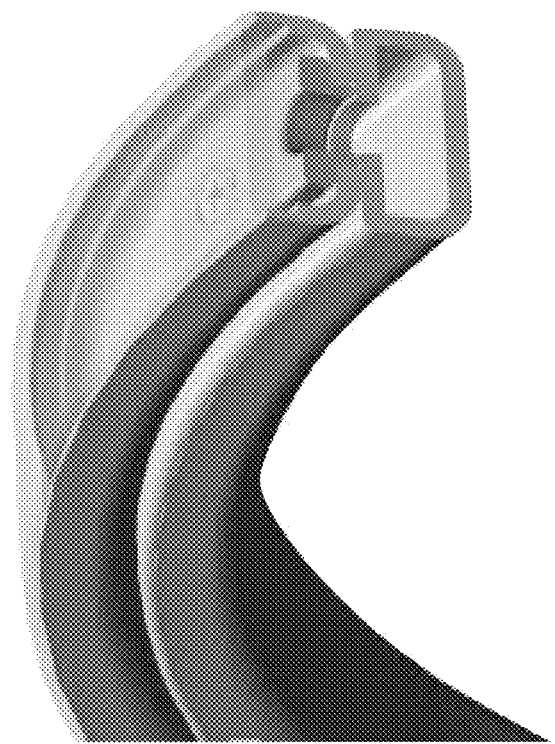
FIG. 33F is a 3D rendered version of the sectional view shown in FIG. 33E.
Figure 33E:
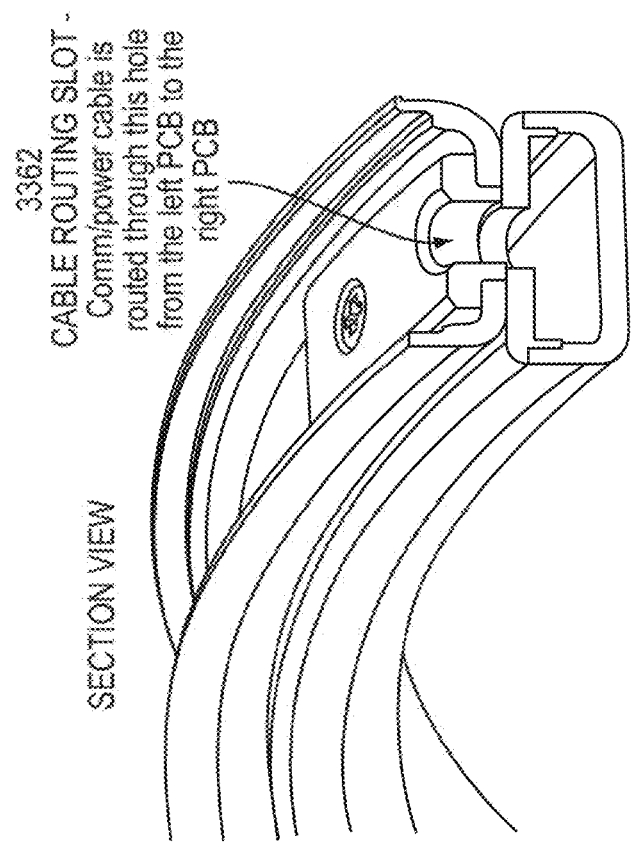
FIG. 33E is schematic showing a sectional view of an adjustment mechanism according to an illustrative embodiment.
Figure 33H:
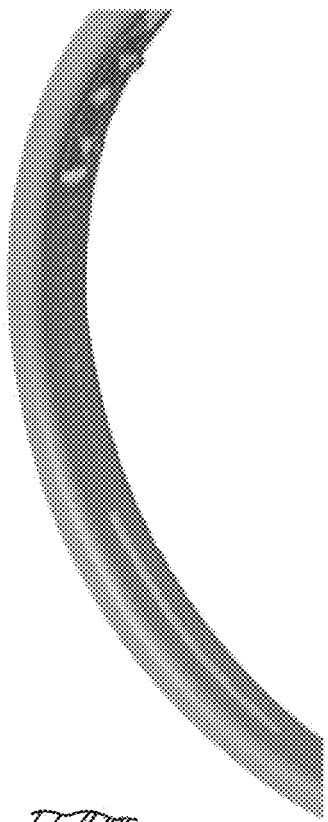
FIG. 33H is a 3D rendered version of the view shown in FIG. 33G.
Figure 33G:
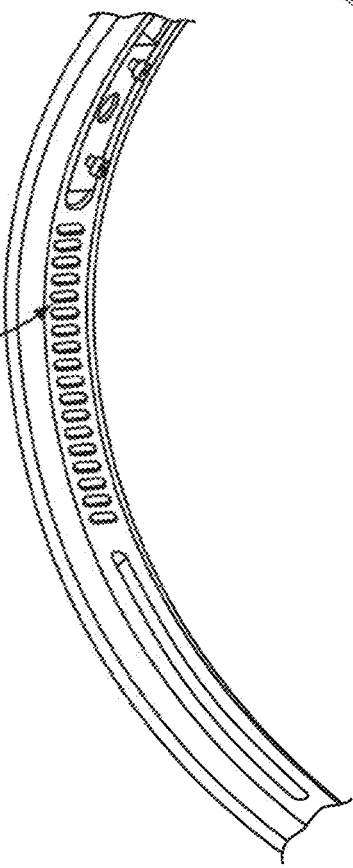
FIG. 33G is schematic showing an underside of a portion of an adjustment mechanism with grooves, according to an illustrative embodiment.

FIGS. 33B-H also depicts the adjustment mechanism 3334 for adjusting a length and/or circumference of the linkage component 3332 as described herein. As shown, the adjustment mechanism 3334 includes two curved arms 3340a, 3340b that are interconnected and slide relative to one another. For example, FIGS. 33C-H show detail of one embodiment of such an adjustment mechanism. As shown in FIG. 33C, a metal slide 3352 bolts into a plastic mate and slides along plastic ramp 3354. Plastic ramp 3354 allows metal slide 3352 to glide and extend headband size. As shown in FIGS. 33E and 33F, the adjustment mechanism may be designed to accommodate electronics included in the support component. For example, metal slide 3352 may include a cable routing slot 3362 through which a communication/power cable is routed to connect controller boards in each of the interface components. As shown in FIGS. 33G and 33H, positioning grooves 3372 may be included as well to allow for controlled extension and positioning of the headband, with a spring insert in mating component 3352 providing for a gentle stopping force as mating component 3352 slides along grooves 3372.

Figure 33I:
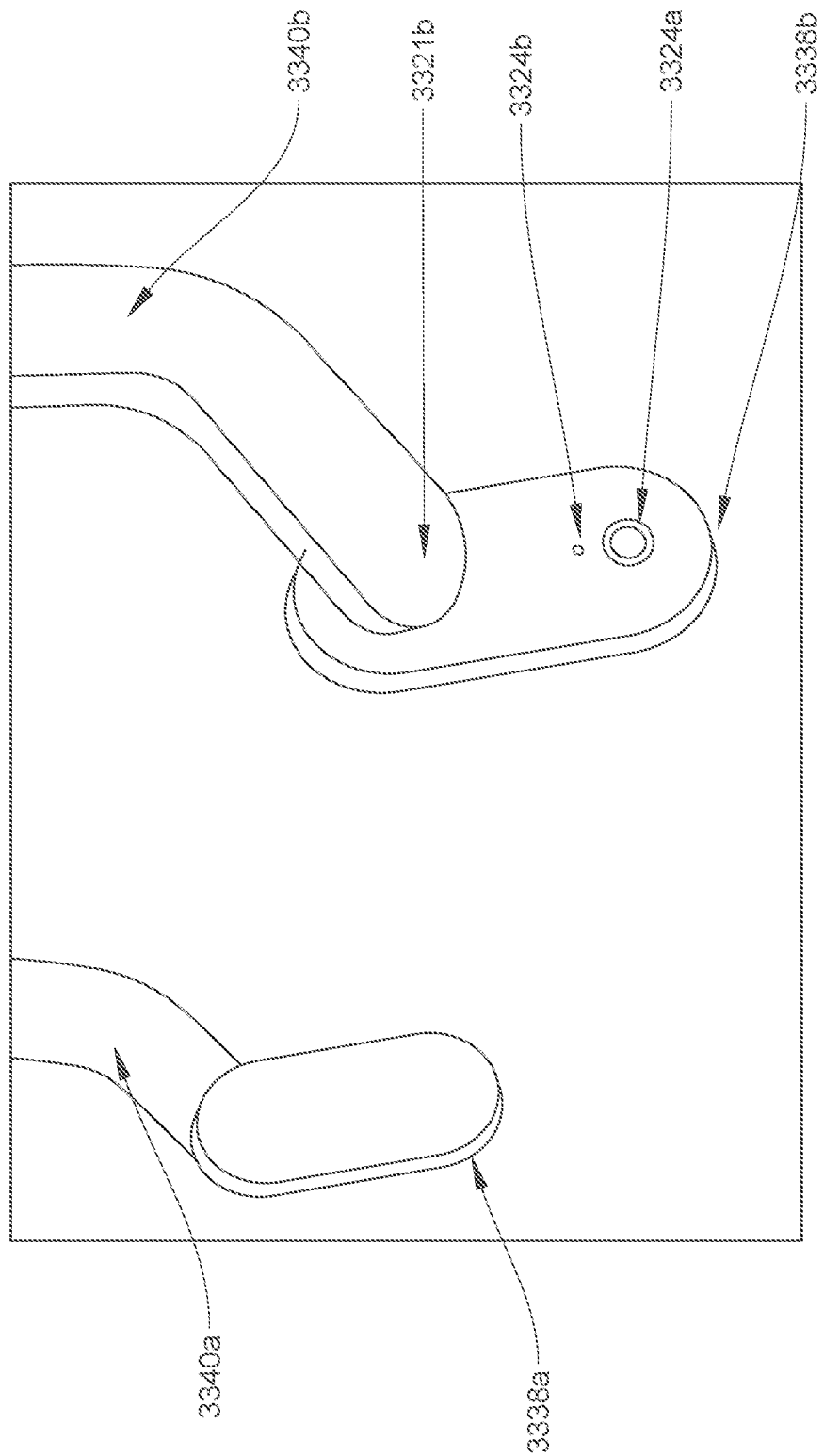
FIG. 33I is an enlarged perspective view of a portion of a transcutaneous neuromodulation device in accordance with one or more embodiments of the invention.
Figure 33J:
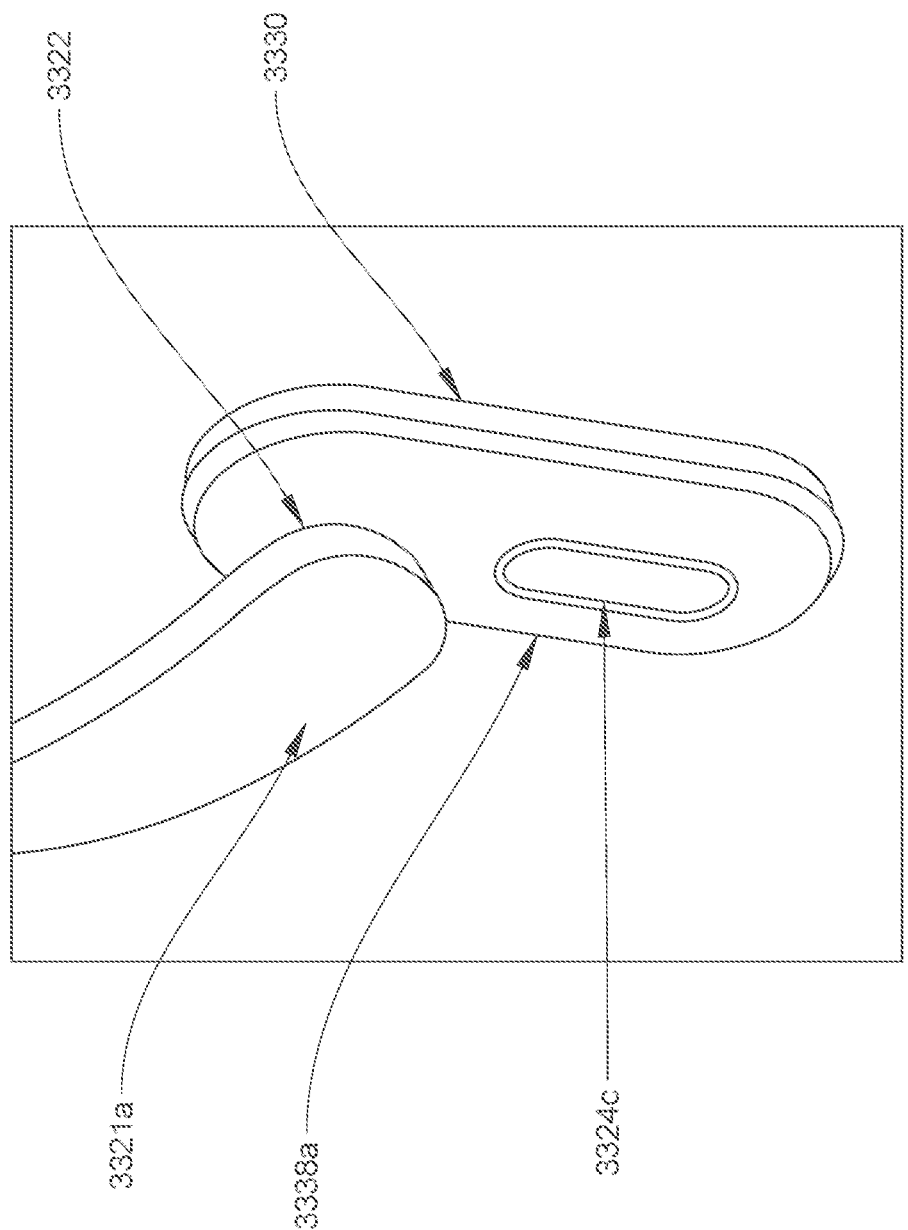
FIG. 33J is an enlarged perspective view of another portion of a transcutaneous neuromodulation device in accordance with one or more embodiments of the invention.

FIGS. 33I and 33J are enlarged views of the devices showing the housings 3338 in greater detail. As shown in FIG. 33I, housing 3338b is coupled to the distal end 3321b of arm 3340b and includes an on/off button 3324a and an LED indicator 3324b to indicate whether the device 3300 is on. In some embodiments, the LED indicator 3324b may change colors to indicate a change in state, such as green for on, red for low charge, yellow for charging, etc. Housing 3338a is coupled to arm 3340a similarly and may include the same controls, or other controls, for example a volume control as described herein.

FIG. 33J depicts a coupling mechanism 3322a used to flexibly couple interface component 3338a to the distal end 3321a of arm 3340a. In certain embodiments, the coupling mechanism is an elastomeric hinge. Generally, an elastomeric hinge is a thinned area of an elastomeric component that allows for flexure at the thinned area, with the thickness of the thinned area determining the stiffness of the hinge. The elastomeric hinge allows the interface portions 3338 to flex relative to the arms 3340a and 3340b of the linkage mechanism 3332 to accommodate the subject's body part and/or provide a pressing force to the transducer. In some embodiments, the hinge may include a wire core to assist in positioning the interface portions 3338 relative to the linkage mechanism 3332. In other embodiments, the coupling mechanism 3322 include a ball and socket joint encased in the elastomeric material or an articulated joint for stepped adjustment of the interface portions' relative position.

FIGS. 33I and 33J also depict an insulating or interface material 3330 (e.g., fabric) disposed on the housing 3338 to prevent direct contact between the transducer surfaces and the subject's skin. Also shown in FIG. 33J are additional controls 3324, in this case a volume button 3324c that is configured to adjust at least one of intensity (i.e., amplitude) or a frequency of the waveform, or the duration of the treatment.

Figure 33K:
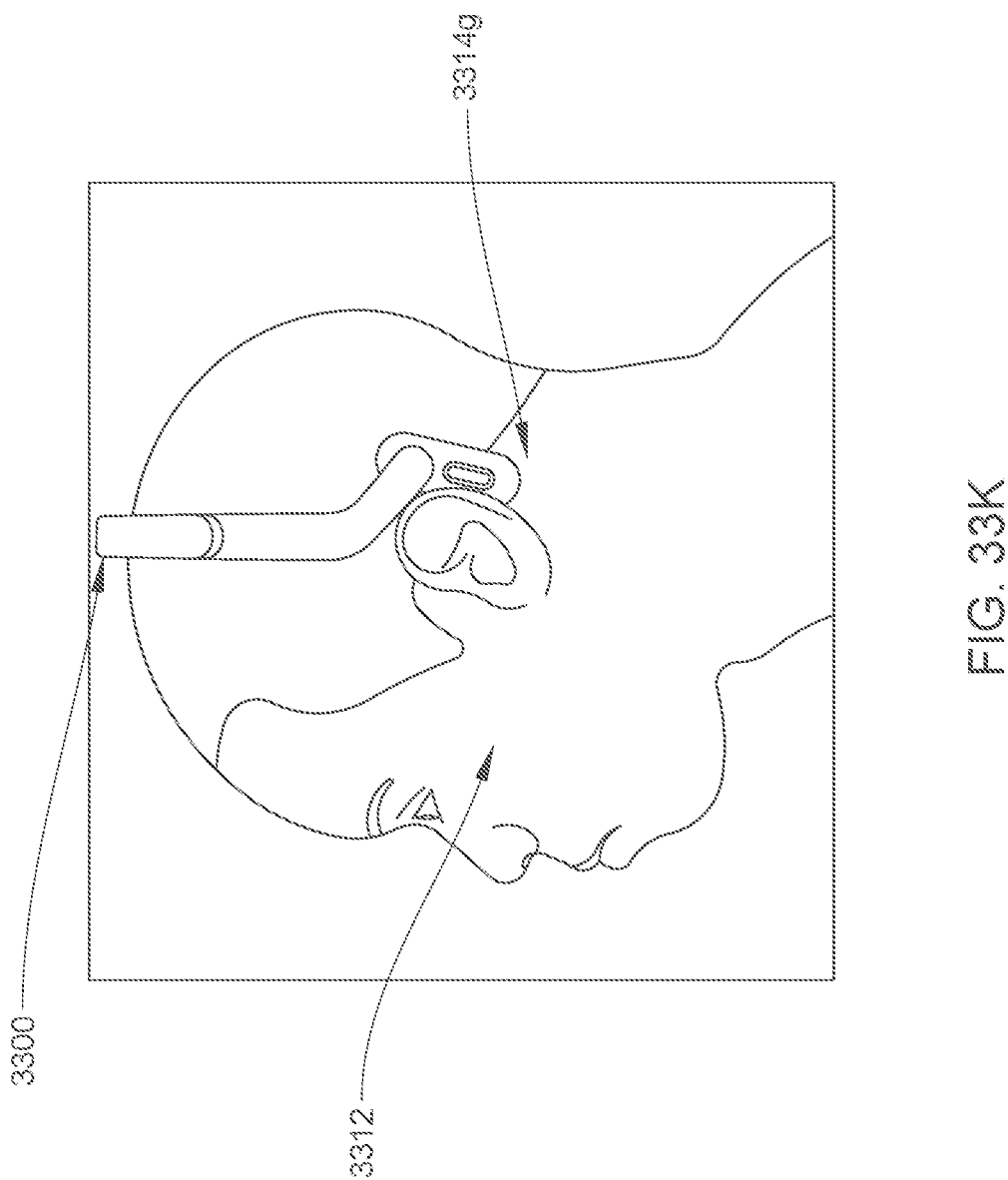
FIG. 33K is a schematic side view of a transcutaneous neuromodulation device positioned on a human subject in accordance with one or more embodiments of the invention.

FIG. 33K depicts an embodiment of the transcutaneous neuromodulation device 3300 positioned on a human subject 3312. As shown, the device 3300 is secured around the subject's head such that the housings 3338, specifically the region where mechanical transducers are positioned substantially proximate the subject's mastoid region 3314g and are held in place via the resilient arm or elastomeric hinge.

H. COMPUTER SYSTEM AND NETWORK ARCHITECTURE

As shown in FIG. 35, an implementation of a network environment 3500 for use in providing systems, methods, and devices described herein is shown and described. In brief overview, referring now to FIG. 35, a block diagram of an exemplary cloud computing environment 3500 is shown and described. The cloud computing environment 3500 may include one or more resource providers 3502a, 3502b, 3502c (collectively, 3502). Each resource provider 3502 may include computing resources. In some implementations, computing resources may include any hardware and/or software used to process data. For example, computing resources may include hardware and/or software capable of executing algorithms, computer programs, and/or computer applications. In some implementations, exemplary computing resources may include application servers and/or databases with storage and retrieval capabilities. Each resource provider 3502 may be connected to any other resource provider 3502 in the cloud computing environment 3500. In some implementations, the resource providers 3502 may be connected over a computer network 3508. Each resource provider 3502 may be connected to one or more computing device 3504a, 3504b, 3504c (collectively, 3504), over the computer network 3508.

The cloud computing environment 3500 may include a resource manager 3506. The resource manager 3506 may be connected to the resource providers 3502 and the computing devices 3504 over the computer network 3508. In some implementations, the resource manager 3506 may facilitate the provision of computing resources by one or more resource providers 3502 to one or more computing devices 3504. The resource manager 3506 may receive a request for a computing resource from a particular computing device 3504. The resource manager 3506 may identify one or more resource providers 3502 capable of providing the computing resource requested by the computing device 3504. The resource manager 3506 may select a resource provider 3502 to provide the computing resource. The resource manager 3506 may facilitate a connection between the resource provider 3502 and a particular computing device 3504. In some implementations, the resource manager 3506 may establish a connection between a particular resource provider 3502 and a particular computing device 3504. In some implementations, the resource manager 3506 may redirect a particular computing device 3504 to a particular resource provider 3502 with the requested computing resource.

Figure 36:
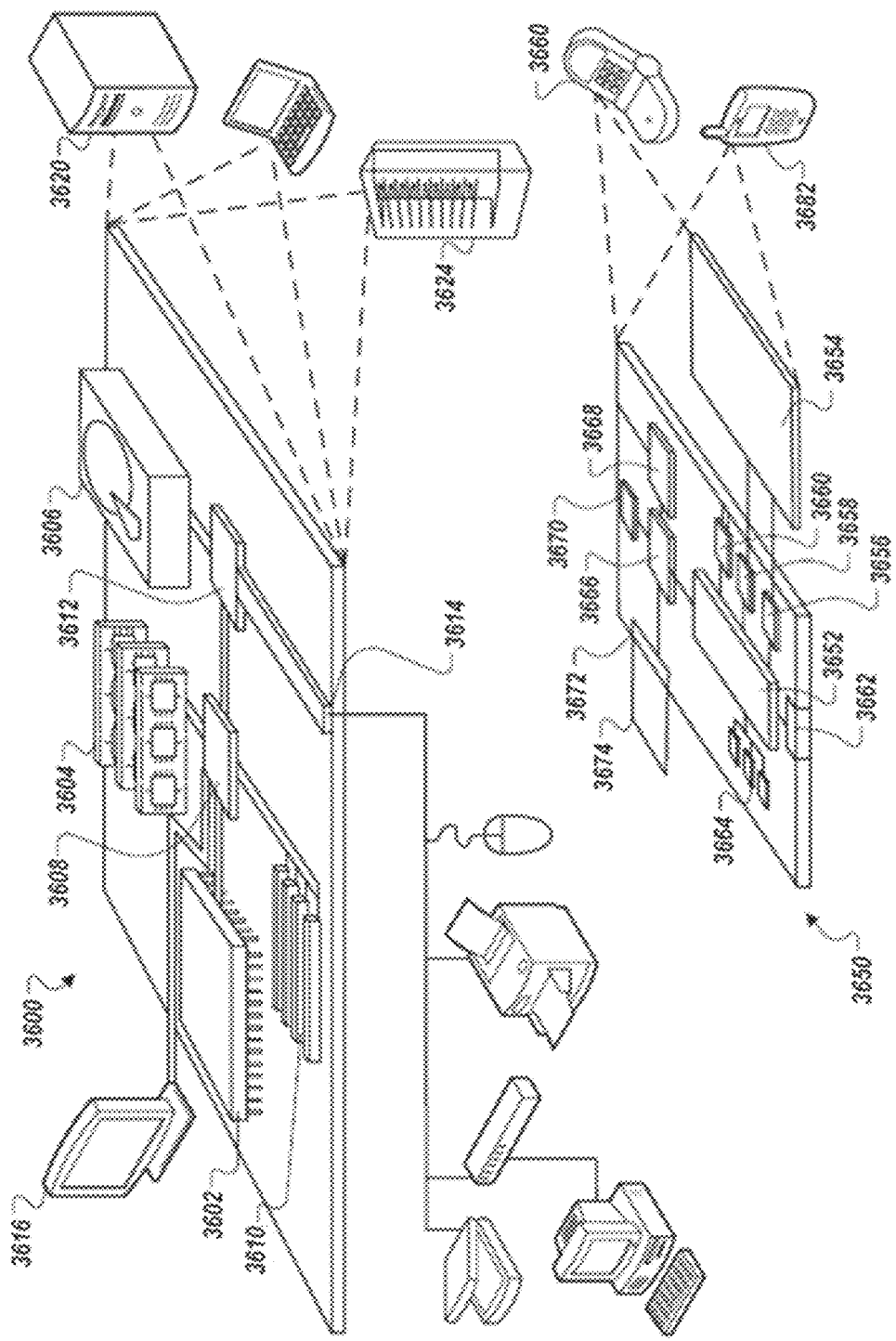
FIG. 36 is a block diagram of an example computing device and an example mobile computing device used in certain embodiments.

FIG. 36 shows an example of a computing device 3600 and a mobile computing device 3650 that can be used to implement the techniques described in this disclosure. The computing device 3600 is intended to represent various forms of digital computers, such as laptops, desktops, workstations, personal digital assistants, servers, blade servers, mainframes, and other appropriate computers. The mobile computing device 3650 is intended to represent various forms of mobile devices, such as personal digital assistants, cellular telephones, smart-phones, and other similar computing devices. The components shown here, their connections and relationships, and their functions, are meant to be examples only, and are not meant to be limiting.

The computing device 3600 includes a processor 3602, a memory 3604, a storage device 3606, a high-speed interface 3608 connecting to the memory 3604 and multiple high-speed expansion ports 3610, and a low-speed interface 3612 connecting to a low-speed expansion port 3614 and the storage device 3606. Each of the processor 3602, the memory 3604, the storage device 3606, the high-speed interface 3608, the high-speed expansion ports 3610, and the low-speed interface 3612, are interconnected using various busses, and may be mounted on a common motherboard or in other manners as appropriate. The processor 3602 can process instructions for execution within the computing device 3600, including instructions stored in the memory 3604 or on the storage device 3606 to display graphical information for a GUI on an external input/output device, such as a display 3616 coupled to the high-speed interface 3608. In other implementations, multiple processors and/or multiple buses may be used, as appropriate, along with multiple memories and types of memory. Also, multiple computing devices may be connected, with each device providing portions of the necessary operations (e.g., as a server bank, a group of blade servers, or a multi-processor system). Thus, as the term is used herein, where a plurality of functions are described as being performed by "a processor", this encompasses embodiments wherein the plurality of functions are performed by any number of processors (one or more) of any number of computing devices (one or more). Furthermore, where a function is described as being performed by "a processor", this encompasses embodiments wherein the function is performed by any number of processors (one or more) of any number of computing devices (one or more) (e.g., in a distributed computing system).

The memory 3604 stores information within the computing device 3600. In some implementations, the memory 3604 is a volatile memory unit or units. In some implementations, the memory 3604 is a non-volatile memory unit or units. The memory 3604 may also be another form of computer-readable medium, such as a magnetic or optical disk.

The storage device 3606 is capable of providing mass storage for the computing device 3600. In some implementations, the storage device 3606 may be or contain a computer-readable medium, such as a floppy disk device, a hard disk device, an optical disk device, or a tape device, a flash memory or other similar solid state memory device, or an array of devices, including devices in a storage area network or other configurations. Instructions can be stored in an information carrier. The instructions, when executed by one or more processing devices (for example, processor 3602), perform one or more methods, such as those described above. The instructions can also be stored by one or more storage devices such as computer- or machine-readable mediums (for example, the memory 3604, the storage device 3606, or memory on the processor 3602).

The high-speed interface 3608 manages bandwidth-intensive operations for the computing device 3600, while the low-speed interface 3612 manages lower bandwidth-intensive operations. Such allocation of functions is an example only. In some implementations, the high-speed interface 3608 is coupled to the memory 3604, the display 3616 (e.g., through a graphics processor or accelerator), and to the high-speed expansion ports 3610, which may accept various expansion cards (not shown). In the implementation, the low-speed interface 3612 is coupled to the storage device 3606 and the low-speed expansion port 3614. The low-speed expansion port 3614, which may include various communication ports (e.g., USB, Bluetooth®, Ethernet, wireless Ethernet) may be coupled to one or more input/output devices, such as a keyboard, a pointing device, a scanner, or a networking device such as a switch or router, e.g., through a network adapter.

The computing device 3600 may be implemented in a number of different forms, as shown in the figure. For example, it may be implemented as a standard server 3620, or multiple times in a group of such servers. In addition, it may be implemented in a personal computer such as a laptop computer 3622. It may also be implemented as part of a rack server system 3624. Alternatively, components from the computing device 3600 may be combined with other components in a mobile device (not shown), such as a mobile computing device 3650. Each of such devices may contain one or more of the computing device 3600 and the mobile computing device 3650, and an entire system may be made up of multiple computing devices communicating with each other.

The mobile computing device 3650 includes a processor 3652, a memory 3664, an input/output device such as a display 3654, a communication interface 3666, and a transceiver 3668, among other components. The mobile computing device 3650 may also be provided with a storage device, such as a micro-drive or other device, to provide additional storage. Each of the processor 3652, the memory 3664, the display 3654, the communication interface 3666, and the transceiver 3668, are interconnected using various buses, and several of the components may be mounted on a common motherboard or in other manners as appropriate.

The processor 3652 can execute instructions within the mobile computing device 3650, including instructions stored in the memory 3664. The processor 3652 may be implemented as a chipset of chips that include separate and multiple analog and digital processors. The processor 3652 may provide, for example, for coordination of the other components of the mobile computing device 3650, such as control of user interfaces, applications run by the mobile computing device 3650, and wireless communication by the mobile computing device 3650.

The processor 3652 may communicate with a user through a control interface 3658 and a display interface 3656 coupled to the display 3654. The display 3654 may be, for example, a TFT (Thin-Film-Transistor Liquid Crystal Display) display or an OLED (Organic Light Emitting Diode) display, or other appropriate display technology. The display interface 3656 may comprise appropriate circuitry for driving the display 3654 to present graphical and other information to a user. The control interface 3658 may receive commands from a user and convert them for submission to the processor 3652. In addition, an external interface 3662 may provide communication with the processor 3652, so as to enable near area communication of the mobile computing device 3650 with other devices. The external interface 3662 may provide, for example, for wired communication in some implementations, or for wireless communication in other implementations, and multiple interfaces may also be used.

The memory 3664 stores information within the mobile computing device 3650. The memory 3664 can be implemented as one or more of a computer-readable medium or media, a volatile memory unit or units, or a non-volatile memory unit or units. An expansion memory 3674 may also be provided and connected to the mobile computing device 3650 through an expansion interface 3672, which may include, for example, a SIMM (Single In Line Memory Module) card interface. The expansion memory 3674 may provide extra storage space for the mobile computing device 3650, or may also store applications or other information for the mobile computing device 3650. Specifically, the expansion memory 3674 may include instructions to carry out or supplement the processes described above, and may include secure information also. Thus, for example, the expansion memory 3674 may be provide as a security module for the mobile computing device 3650, and may be programmed with instructions that permit secure use of the mobile computing device 3650. In addition, secure applications may be provided via the SIMM cards, along with additional information, such as placing identifying information on the SIMM card in a non-hackable manner.

The memory may include, for example, flash memory and/or NVRAM memory (non-volatile random access memory), as discussed below. In some implementations, instructions are stored in an information carrier. that the instructions, when executed by one or more processing devices (for example, processor 3652), perform one or more methods, such as those described above. The instructions can also be stored by one or more storage devices, such as one or more computer- or machine-readable mediums (for example, the memory 3664, the expansion memory 3674, or memory on the processor 3652). In some implementations, the instructions can be received in a propagated signal, for example, over the transceiver 3668 or the external interface 3662.

The mobile computing device 3650 may communicate wirelessly through the communication interface 3666, which may include digital signal processing circuitry where necessary. The communication interface 3666 may provide for communications under various modes or protocols, such as GSM voice calls (Global System for Mobile communications), SMS (Short Message Service), EMS (Enhanced Messaging Service), or MMS messaging (Multimedia Messaging Service), CDMA (code division multiple access), TDMA (time division multiple access), PDC (Personal Digital Cellular), WCDMA (Wideband Code Division Multiple Access), CDMA2000, or GPRS (General Packet Radio Service), among others. Such communication may occur, for example, through the transceiver 3668 using a radio-frequency. In addition, short-range communication may occur, such as using a Bluetooth®, Wi-Fi™, or other such transceiver (not shown). In addition, a GPS (Global Positioning System) receiver module 3670 may provide additional navigation- and location-related wireless data to the mobile computing device 3650, which may be used as appropriate by applications running on the mobile computing device 3650.

The mobile computing device 3650 may also communicate audibly using an audio codec 3660, which may receive spoken information from a user and convert it to usable digital information. The audio codec 3660 may likewise generate audible sound for a user, such as through a speaker, e.g., in a handset of the mobile computing device 3650. Such sound may include sound from voice telephone calls, may include recorded sound (e.g., voice messages, music files, etc.) and may also include sound generated by applications operating on the mobile computing device 3650.

The mobile computing device 3650 may be implemented in a number of different forms, as shown in the figure. For example, it may be implemented as a cellular telephone 3680. It may also be implemented as part of a smart-phone 3682, personal digital assistant, or other similar mobile device.

Various implementations of the systems and techniques described here can be realized in digital electronic circuitry, integrated circuitry, specially designed ASICs (application specific integrated circuits), computer hardware, firmware, software, and/or combinations thereof. These various implementations can include implementation in one or more computer programs that are executable and/or interpretable on a programmable system including at least one programmable processor, which may be special or general purpose, coupled to receive data and instructions from, and to transmit data and instructions to, a storage system, at least one input device, and at least one output device.

These computer programs (also known as programs, software, software applications or code) include machine instructions for a programmable processor, and can be implemented in a high-level procedural and/or object-oriented programming language, and/or in assembly/machine language. As used herein, the terms machine-readable medium and computer-readable medium refer to any computer program product, apparatus and/or device (e.g., magnetic discs, optical disks, memory, Programmable Logic Devices (PLDs)) used to provide machine instructions and/or data to a programmable processor, including a machine-readable medium that receives machine instructions as a machine-readable signal. The term machine-readable signal refers to any signal used to provide machine instructions and/or data to a programmable processor.

To provide for interaction with a user, the systems and techniques described here can be implemented on a computer having a display device (e.g., a CRT (cathode ray tube) or LCD (liquid crystal display) monitor) for displaying information to the user and a keyboard and a pointing device (e.g., a mouse or a trackball) by which the user can provide input to the computer. Other kinds of devices can be used to provide for interaction with a user as well; for example, feedback provided to the user can be any form of sensory feedback (e.g., visual feedback, auditory feedback, or tactile feedback); and input from the user can be received in any form, including acoustic, speech, or tactile input.

The systems and techniques described here can be implemented in a computing system that includes a back end component (e.g., as a data server), or that includes a middleware component (e.g., an application server), or that includes a front end component (e.g., a client computer having a graphical user interface or a Web browser through which a user can interact with an implementation of the systems and techniques described here), or any combination of such back end, middleware, or front end components. The components of the system can be interconnected by any form or medium of digital data communication (e.g., a communication network). Examples of communication networks include a local area network (LAN), a wide area network (WAN), and the Internet.

The computing system can include clients and servers. A client and server are generally remote from each other and typically interact through a communication network. The relationship of client and server arises by virtue of computer programs running on the respective computers and having a client-server relationship to each other.

In some implementations, modules described herein can be separated, combined or incorporated into single or combined modules. Any modules depicted in the figures are not intended to limit the systems described herein to the architectures shown therein.

I. EXAMPLE 1

IRB Approved Randomized and Placebo Controlled Study

Example 1 is a protocol for an IRB-approved, randomized and placebo-controlled study for testing the devices and waveforms (e.g., the transformed time-varying waveform) described herein. In particular, the study tested the whether the devices and waveforms are safe for both episodic and daily use over three weeks. Results and benefits of mechanical nerve stimulation were reported from users and study coordinators and gathered in surveys. Case reports from the study of Example 1 are described in Example 2.

Research participants were subjected to mechanical stimulation comprising acoustic noise, with amplitudes at levels of tactile vibration. Waveforms applied comprised stochastic resonance signals including random noise of various frequencies, standard and modified sine waves, incidentally transformed waves, and multi-scalar modulation of carrier waves.

Devices were placed on locations on the subjects, such as neck, back of neck, ear, skull (e.g. mastoid), temples, face, and arms depending on specific sub-protocol. The device as described herein, included adhesive material to contact transducers to the subjects, helmet or hat like devices, over-the-head bands to site transducers on the subject with or without providing external pressure, a band-like device that goes around the back of the head site transducers on the subject with or without providing external pressure, eyeglass like bands to site transducers on the subject with or without providing external pressure, headphone-like devices to site transducers on the subject with or without providing external pressure among other methods of siting the transducers on the subject or in combination with other devices (e.g. headphones) to site transducers on subject. Stimulation sessions lasted from 10-60 minutes.

A goal of the transcutaneous mechanoacoustic stimulation (TAS) research was to assess the potential to improve productivity, cognition, and quality of life as well as to alleviate symptoms of diseases. To do this, the effects of various TAS parameters on mental state (mood, alertness, relaxation, stress, sleep etc.—as measured by questionnaires and established biomarkers) and cognitive performance (as measured by established tests) were examined. The study included both naturalistic and non-naturalistic settings. Naturalistic settings were useful to determine the relevance of TAS protocols in the daily life of normal healthy individuals. Non-naturalistic settings were useful for the controlled administration of cognitive tests, evoking specific mental states, and the use of biometric sensors.

Device placement, timing, duration, and waveform were varied in a rigorous manner using a common set of dependent variables (including cognitive tasks, questionnaires, and biometrics). One goal was to determine the optimal parameters for improving mental states and to identify and examine the physiological mechanisms and dynamical responses underlying these improvements.

The study tested approximately 2400 subjects over up to 24 months.

i. Stimulation Device

An embodiment of the stimulation device as described herein is used. The device incorporates an amplifier and mechanoelectric vibrating elements that generate and deliver small, gentle vibrations. The amplifier increases output of the signal generator to drive the vibrating elements. The vibrating elements are insulated to avoid skin contact with the transducers delivering the vibratory stimulation. Electrical circuit components for controlling the vibration amplitude are housed in an electronics housing and are attached to the vibrating element via an insulated cable—similar to off-the-shelf headphones. Neither the mechanical transducers nor the circuit housing come into direct contact with the participant, thereby eliminating the risk for electric shock from traditional neurostimulation devices. Furthermore, the circuit board has an included battery safety circuit to protect the participant. The system delivers mechanical stimulation at specified levels of power or within specified modulating levels of power.

ii. Data Collection and Monitoring

Data is collected using paper forms, online survey collection tools, audio or video recordings, or automated software. If software is used, it can coordinate the inputs from biometric testing and behavioral tasks based on both subject Study ID (SID) number and time of day. Electronic data can be saved in a password-protected location only accessible to the research team. Subjects can be monitored intermittently or continuously during data collection to ensure that the automated software remains operational, the biometric assessment devices remain in place, and the subject remains engaged with the task.

Questionnaire data is collected online via an online survey tool. Automated software is used to collect all the biometric information. Audio and video are used for both collecting facial expression data to be analyzed by coders or by automated software and for post stimulation/home test interviews, which will be coded by researchers.

All data are de-identified. Study ID (SID) numbers are used to identify subjects in the study records. Master files linking subject names to SID number are kept separate from the study records, either in a locked drawer or on a password-protected file only accessible to the research team.

In the study records, subjects are identified by SID number only. No personal information such as name or contact information will be included in the study records. The study records are stored in password-protected files only accessible to the research team.

Various biometric assessment that can be performed are listed below:
 a. Blood pressure and respiration rate measurement
   i. Biopatch or Bioharness 3 or similar device
 b. Caloric expenditure measurement:
   i. Metabolic Cart (e.g., http://emedicine.medscape.com/article/2009552-overview) or similar device
 c. Electrophysiology measurement:
   i. EEG: Brain Vision ACTIChamp, Emotiv EEG, B-Alert AT-Series EEG, or similar device
   ii. EMG:
   iii. ECG-EKG:
 d. Facial expression measurement:
   i. iMotions FACET sensor, web camera, or similar device.
 e. GSR measurement:
   i. Shimmer GSR, Affectiva Q-Sensor GSR bracelets, or similar device.
 f. Heart rate measurement:
   i. The device may be attached to the finger, arm, earlobe, chest, or wrist.
   ii. Heart rate monitor: Heart Sensor HRS-07UE, iMotions sensor: Zephyr echo gateway, Polar Chest Strap, Biopatch, or similar device.
 g. Blood and Saliva Testing:
   i. Salivary assays (e.g., cortisol and alpha-amylase)
   ii. Blood assays (e.g. CRP, IL-2, IL-6, TGF-β, TNF, IgA, nitric oxide)
 h. Movement measurement:
   i. Accelerometer such as the Biopatch, Actiwatch, Fitbit®, or similar technology may be used to measure movement
 i. Pupilometry and eye movement measurement (including rate of blinking):
   i. Tobii, web camera or similar eye tracking or pupilometry device.
 j. Temperature measurement:
   i. Evergen TemporalScanner™, infrared thermometer, or similar device iii. Mechanical Stimulation This study includes multiple experimental conditions, which differ in device placement, stimulating device, waveform of stimulation, and timing of stimulation. Each subject is randomly assigned to a condition and experimenters are blinded to conditions where possible. Subjects are blinded to parameter values whenever possible, except in cases where it is necessary for them to control the parameter value to reduce the risk of discomfort. Importantly, in the case that subjects receive both sham and real stimulation within the same session, the ordering is not counterbalanced. This is because real stimulation has expected carry-over effects. Sham and real stimulation are counterbalanced with stimulation sessions occurring on different days.

The following stimulation parameters are among those that may be varied in a controlled manner between experimental groups and/or between sessions over the course of the study:

1. Duration of Stimulation:
   a. Up to 60 min of stimulation per session
   b. Length of stimulation may vary between conditions as the research aims to identify the lowest doses needed to elicit the desired enduring effect.
2. Waveform Parameters:
   a. Categories of Signals:
      i. White noise: Uncorrelated Gaussian noise
      ii. White noise plus signal: Uncorrelated Gaussian noise with an underlying signal
      iii. Plain mechanical signal, no noise
   b. Signal Parameters (within categories):
      i. Frequency (ranges of frequencies (e.g., 0-320 Hz noise))
      ii. Wave type: Sinusoidal, Square, etc.
      iii. Amplitude: Of the noise, the underlying signal, and the ratio between white noise and underlying signal
      iv. Other waveform parameters such as duty cycle and pulse rate
3. Device Placement
   a. Anywhere on the head may be chosen as a location; this will depend on which nerves are targeted. Participants will be randomly assigned to condition.
   b. Upper arm and back of neck may also be chosen as locations. These areas will be tested later in the discovery arm once locations on the head, specifically around the ear, have been optimized.

iv. Sham Stimulation

Much of the stimulation is sub-threshold and is not perceptible to the participants. Accordingly, participants can be suited with a device that shows the power button on, but does not work, as a control. Where stimulation parameters are detectable, participants can be given a waveform that has been demonstrated not to have an effect or placement can be altered so that different nerves are stimulated resulting in a different effect. If the waveform results in sound, participants can wear noise-cancelling headphones or a counter signal can be used to cancel the acoustic wave to mask to condition.

v. Study Arms

There are 3 main arms of this study. Each arm has an in-lab and home component.

a. Discovery

In this arm of testing, participants complete mood questionnaires, use the stimulation device, and wear biometric monitors to capture changes in autonomic arousal. The stimulation parameters and placement may vary depending on results from previous assessments and nerves that are being targeted. In later testing within this arm, learning and memory tasks are paired with the stimulation to assess effects on cognitive abilities.

b. Systematic Validation (Phase I)

In this study arm, there is additional biometric monitoring—eye tracking, EEG, biopatch for respiration rate—with a similar design to discovery: pre-questionnaires, baseline biometric assessment, post-baseline assessment, stimulation (sham versus real), and post-stimulation assessment.

c. Systematic Validation (Phase II)

In the second phase of testing within this arm, participants are subjected to stressors and the stimulation (real versus sham) is examined for attenuating the stress or blunt the response. Participants complete baseline mood questionnaires and mood induction task(s) and receive stimulation (real or sham) followed by post-test mood assessments. A subgroup of participants is yoked to assess hormone levels. This subgroup is random, but only comprises males (at least in the first subset) to avoid female monthly hormonal fluctuations in cortisol.

In later testing within the systematic validation arm, instead of sham stimulation, a positive control is used, such as diaphragmatic breathing, meditation, or electrical stimulation, with the procedures following those described above with regard to the first and second systematic validation phases (Section b. Systematic Validation (Phase I) and Section c. Systematic Validation (Phase II)).

J. EXAMPLE 2

Case Reports from IRB Study of Example 1

Example 2 summarizes case reports from the IRB study of Example 1.

Modulation and practices associated with peripheral nerves and specific neural circuits can produce changes in subjective assessment of mood, which may correlate with enhanced vagal tone (VT) and can be understood as related to improved interoception. Short-term modulation of the cranial nerves with representative waveforms with transducers place on the anatomy in the vicinity of cranial and other peripheral nerves has produced a variety of effects in a general sample of the population. The following case reports have been received:

Alterations in conditions and symptoms that were noted using the present device and methods include: deeper and accelerated relaxation (via improved vagal tone as demonstrated in heart rate variability and mean arterial pressure; improved Alpha wave activity via electroencephalography); improved quality and length of sleep; reduced sleep disturbance and insomnia; lucid dreaming; regulated breathing and improved sleep apnea; spontaneous self-reports of reduced anxieties including, performance anxiety, social anxiety, stage fright, blushing, panic disorder, fear, PTSD, and ADHD; stress-induced tachycardia; calm and receptive during psychotherapy; calming an autistic child; spontaneous and questionnaire based self-reports of focused attention, mental acuity, cognitive performance, improved memory and engagement; reduced chronic pain due to arthritis; reduced perception of pain; reduced inflammation and edema; reduced vertigo and improved balance; reduced menstrual cramping, menstrual headaches; perimenopausal hot flashes, sleep and mood disturbance; stress-induced infertility; prophylaxis and alleviation of migraine and tension headache; reduced tinnitus and ringing in the ears; improved appetite, salivation and gut motility; priming of the limbic system; priming of sexual arousal, libido or desire; enhanced pleasure, climax and orgasm; enhanced vagal tone by heart rate variability; lower stress biomarkers, lower blood pressure as measured.

In multiple cases, users reported a feeling of improved focus or concentration. In multiple cases, users reported a feeling of increased relaxation and increased calmness. In at least one case a user reported increased sexual arousal and/or associated sensation that can occur prior to and concurrent with sexual activity. Concurrent with the reported subjective effects that are similar to those seen in electrical stimulation of the vagus nerve and elsewhere associated with enhancing interoceptive perception, a subgroup of 48 subjects showed specific effects related to heart activity and specifically a derived characteristic called 'heart rate variability' (HRV), which characterizes autonomic nervous system (ANS) activity and control of cardiac function in terms of the components of the ANS, where sympathetic (fight or flight response) activity is characterized by the low frequency power (pLF) of the heart rate variability and parasympathetic (rest and relax) activity is characterized by the high frequency power (pHF). Parasympathetic activation is associated with increased vagal tone and the benefits mentioned about.

In at least one case, a user reported relief from chronic headache and reduction in frequency of same. In at least one case, a user reported a significant reduction in anxiety. In at least one case, a user reported a reduction in social anxiety. In at least one case, a user reported a significant reduction in panic attacks. In multiple cases, users reported a significant reduction in tinnitus. Tinnitus cases for which users have reported reductions through use of embodiments of devices as described herein include noise induced tinnitus as well as tinnitus resulting from ototoxicity. Notably, many chemotherapy drugs are ototoxic. For example, cisplatin is highly ototoxic and often creates ototoxic tinnitus (Frisina, 2016). In one case, a 64 year old female undergoing cisplatin chemotherapy reported a reduction in the majority of ringing through use of the device. In at least one case, a user reported a significant reduction in flushing and fear prior to public speaking. In at least one case, a user reported relief from extreme blushing (idiopathic erythema). In at least one case, a user reported relief from menstrual headaches and cramping. In at least one case, a user reported abatement of arthritic pain. In at least one case, a user reported relief from stress-induced hypertension. In at least one case, a user reported improved sleep and relief from sleep apnea.

Notably, the group using the representative waveform here sustained a lower drop in pHF than either a group using only a sham (no waveform) device as well as one using a distinctly different type of waveform (isochronic 18 Hz: ISO18). This means that there was less parasympathetic inhibition in the representative waveform than in either the sham or ISO18 waveforms. In addition, there was a greater reduction in pLF, consistent with reduced sympathetic activation. These results illustrate the use of a dynamical systems measure for assessing the response to a given waveform (e.g., ISO18) as compared to sham stimulation. Concurrent with these findings, there was a decrease in mean arterial blood pressure compared to sham, another characteristic of decreased sympathetic activation and improved vagal tone.

Taken together, these results show that the representative waveform generates a novel response (as compared with no stimulation and with a second active waveform). pHF remains higher (so less parasympathetic inhibition) and pLF decreases (so less sympathetic activation) which show improved vagal tone. The concurrent finding that mean arterial pressure falls with only the representative wave form (neither with sham nor another active waveform) further supports an increase in relative parasympathetic activation and improved vagal tone.

K. EXAMPLE 3

EEG Measurement of Waveform Effects

Example 3 is an example showing differences in neural activity resulting from different waveforms, as measured via quantitative EEG (qEEG). The results of Example 3 show improved performance via the use of transformed time varying waves as described herein.

Figure 37:
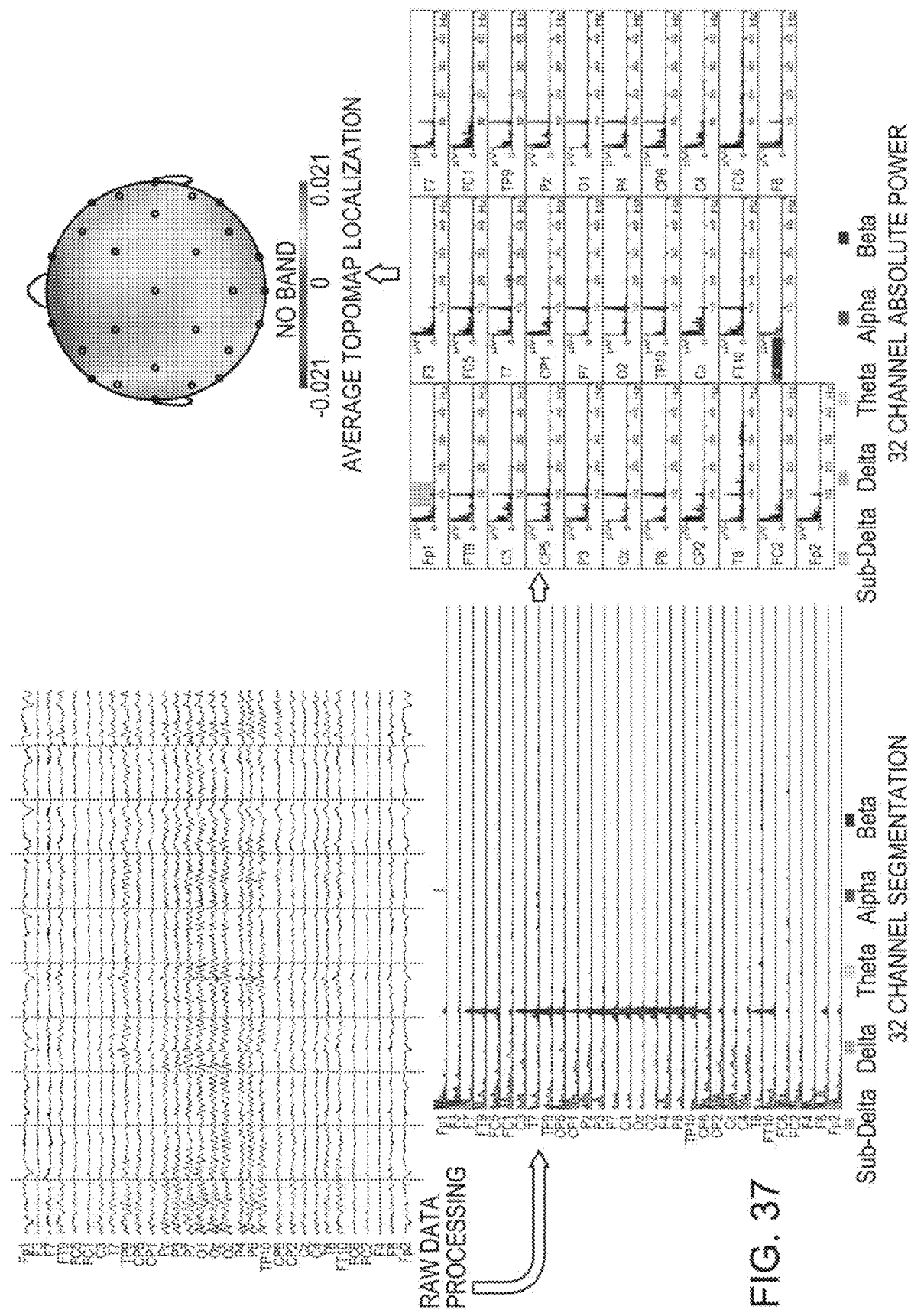
FIG. 37 is a schematic showing an approach for processing qEEG data, used in certain embodiments.

In Example 3, 3 subjects, older than 18 years old were studied. Two subjects were female. Subjects were assessed as follows:

3 minutes of EEG recording at rest in eyes closed (EC) condition
20 minutes of stimulation with simultaneous EEG EC recording (only 2 subjects)
3 minutes post intervention EEG EC recording EEG recording and data processing was as follows. A 32-channel pre-amplified EEG device was used for data acquisition. Data was sampled at a rate of 500 Hz, amplified and filtered using a bandpass of 0.1-45 Hz. EEG was recorded for a total of 9 min per procedure (baseline, intervention, post-intervention). For offline analysis a low-pass cut filter of 35 Hz and high-pass of 1 Hz was used, followed by manual artifact detection and rejection. Power spectra were calculated using BrainAnalizer. Fast Fourier transformation (averaged windows of 5s with 50% overlap) was used to calculate power ($\mu V2$) for the following EEG bands: delta (0.5-4 Hz), theta (4-8 Hz) and alpha (8-13 Hz) and the sub-bands: low-alpha (8-10 Hz), high-alpha (10-13 Hz), low-beta (13-20 Hz) and high beta (21-30 Hz). FIG. 37 illustrates the EEG data processing approach.

Figure 38A:
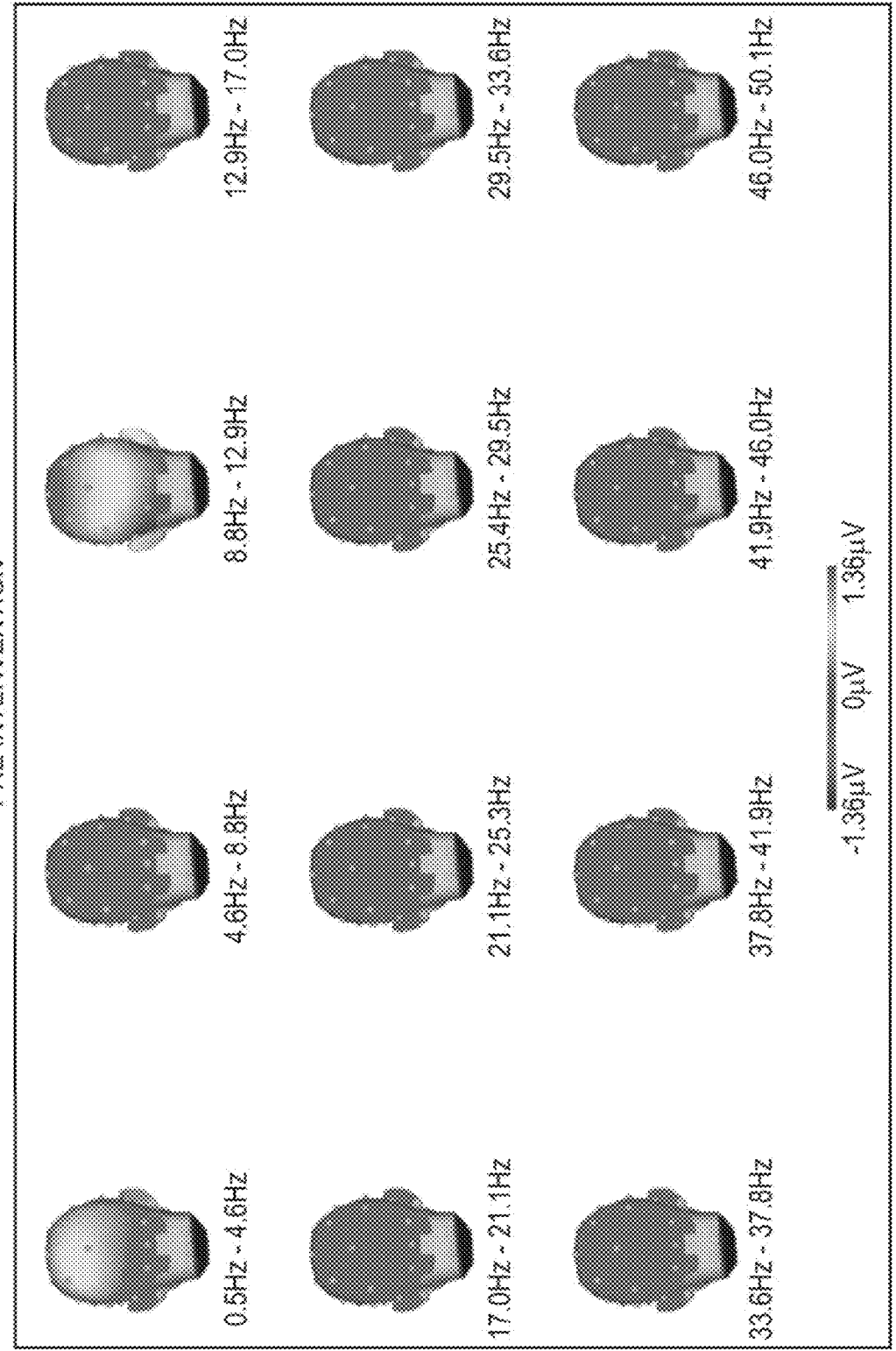
FIG. 38A is visualization of qEEG data for a subject showing a qEEG map for the subject prior to performing an intervention using the mechanical stimulation approaches described herein.
Figure 38B:
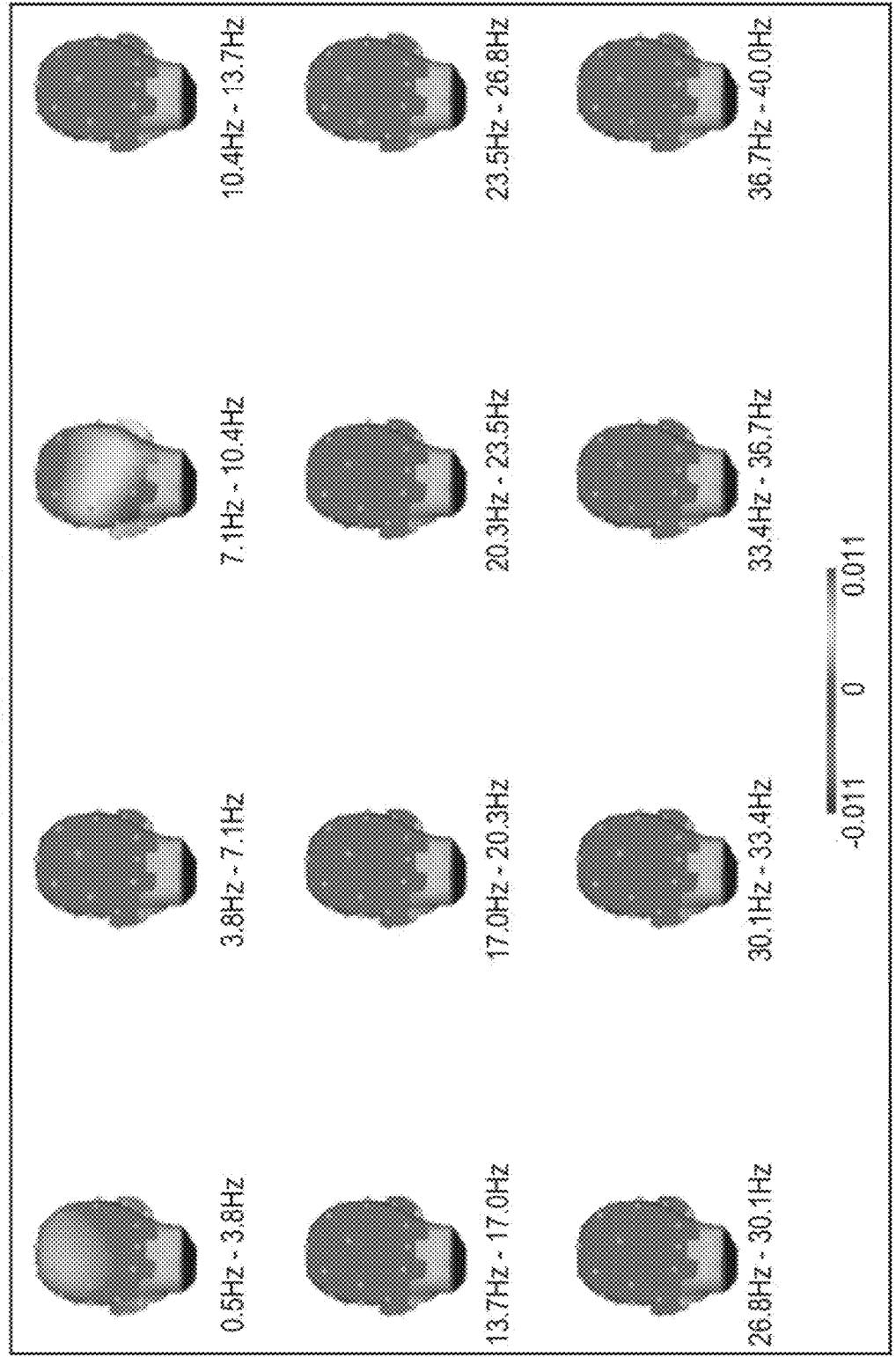
FIG. 38B is visualization of qEEG data for a subject showing a qEEG map for the subject after performing an intervention using the mechanical stimulation approaches described herein.
Figure 39A:
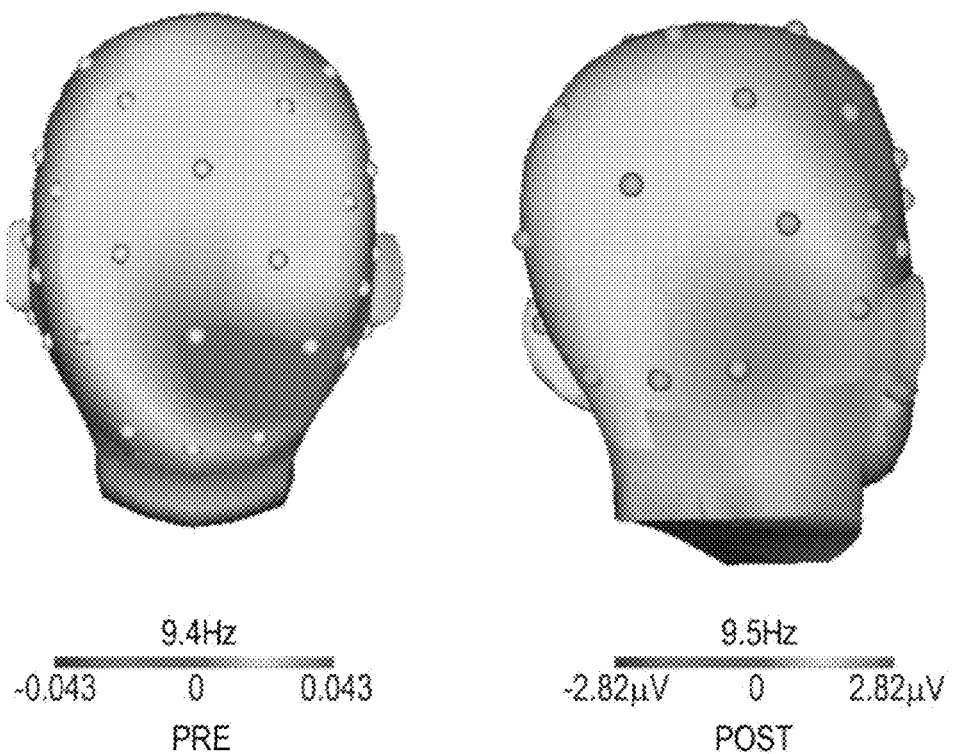
FIG. 39A is a visualization of qEEG data for a subject comparing a pre-intervention and post-intervention qEEG map.
Figure 39B:
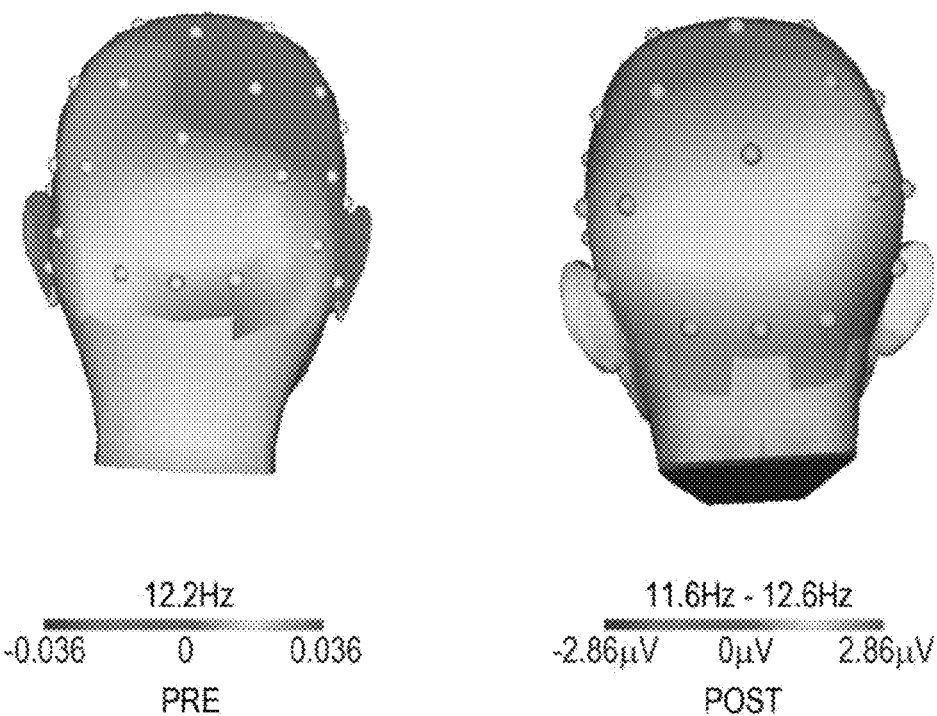
FIG. 39B is a visualization of qEEG data for a subject comparing a pre-intervention and post-intervention qEEG map.

All 3 subjects showed a normoreactive EEG. The EEG architecture was found adequate, with no evidence of abnormal EEG activity. A conventional 50 Hz sine wave was used for stimulation for Subject #1. As demonstrated by the EEG data shown in FIG. 38A and FIG. 38B, Subject #1 did not show significant changes from pre- to post-intervention. Subject #2 and Subject #3 were stimulated via unconventional waveforms. Subject #2 was stimulated using a transformed time varying wave corresponding to a modified version of a 50 Hz sine wave, shown in FIG. 38B. Subject #3 was stimulated using a complex aperiodic waveform (corresponding to the sum of two sines with two different frequencies which ratio equals Phi (the golden ratio—$(1+\sqrt{5})/2)$). EEG data for both Subject #2 and Subject #3 showed near-significant increase in the power of the alpha band in occipital area. It was found that the alpha band increased its power transiently in the areas closer to the stimulation (occipito-temporal) during the stimulation period. EEG data for Subject #2 is shown in FIG. 39A and EEG data for Subject #3 is shown in FIG. 39B.

Accordingly, Example 3 shows that the stimulation was safe and no adverse events were reported. Moreover, the results of Example 3 show dependence of neural stimulation on waveform of the signals used, with particular waveforms such as transformed time varying waves and aperiodic waveforms offering higher levels of stimulation in comparison with a 50 Hz sine wave. As described, two out of the three subjects showed positive EEG modulation after stimulation. As described, two subjects presented transient alpha modulation through the active stimulation period. Post-intervention analysis showed significant increase in the power of the alpha band. The data shows that the main neuromodulatory effect occurred in the occipital area. Increasing alpha power is associated with general improvements in cognition (Hanslmayr, 2005).

L. EXAMPLE 4

Design and Results of Pilot Study for Treatment of Anxiety

Example 4 is an example showing results of a pilot study in which an embodiment of the device described herein was used by participants to manage anxiety.

Figure 40A:
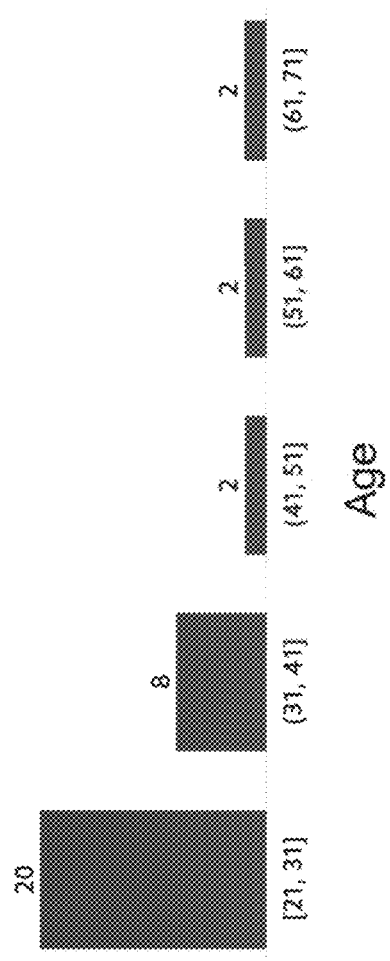
FIG. 40A is a histogram showing age distributions for participants in a pilot study assessing efficacy of embodiments of the devices and methods described herein for treatment of anxiety.
Figure 40B:
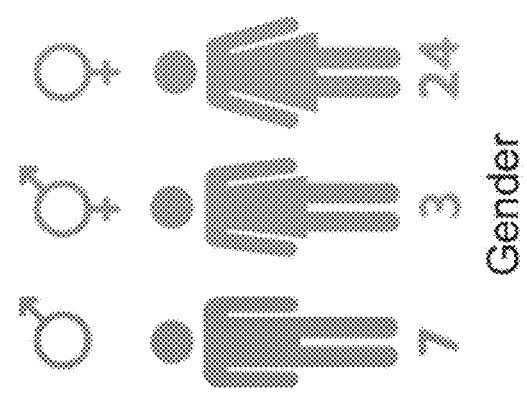
FIG. 40B is an infographic showing gender distribution for participants in a pilot study assessing efficacy of embodiments of the devices and methods described herein for treatment of anxiety.

In the study, 208 potential participants were screened, of which 73 were approved, and 34 ultimately accepted for the study. Nine participants were excluded as non-compliant or unreliable reporters. A histogram showing age distribution of the study participants is shown in FIG. 40A, and a breakdown of gender distribution is shown in FIG. 40B. As shown in the demographic information in FIG. 40B, gender of study participants was predominantly female.

Figure 42:
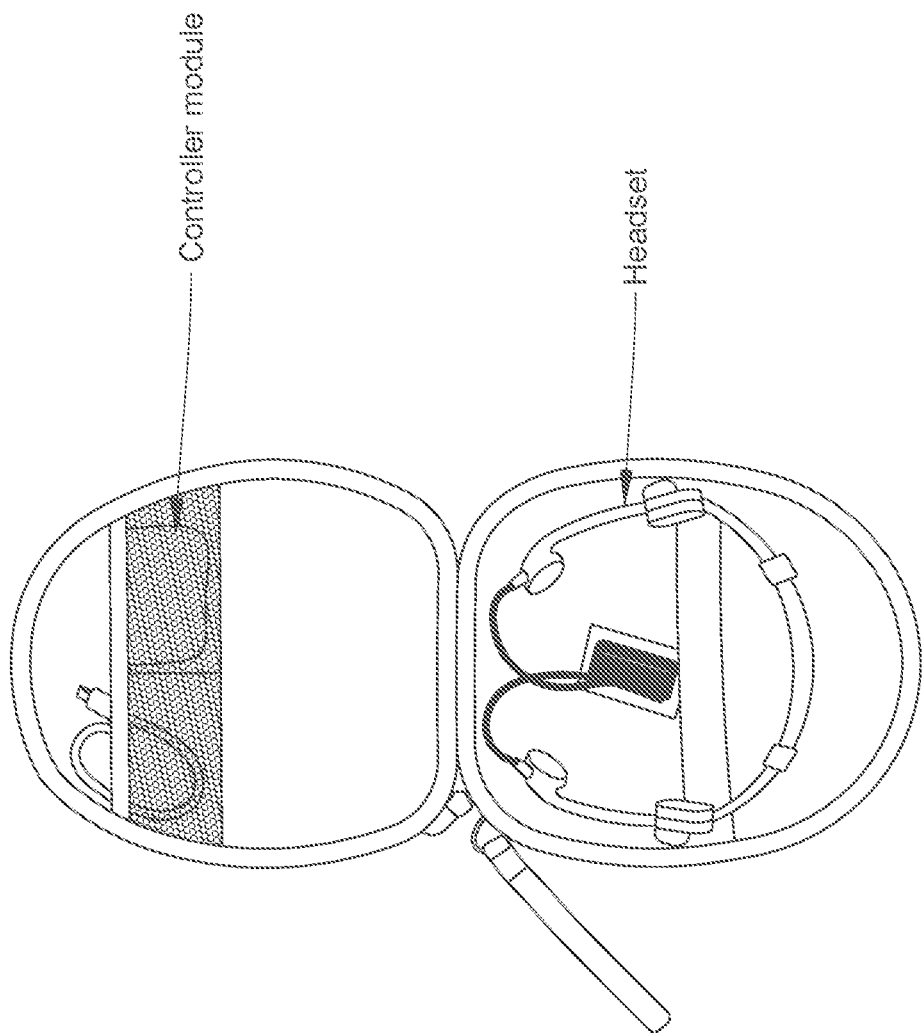
FIG. 42 is a picture of a device used for providing mechanical stimulation to subjects in a pilot study assessing efficacy of embodiments of the devices and methods described herein for treatment of anxiety.
Figure 43A:
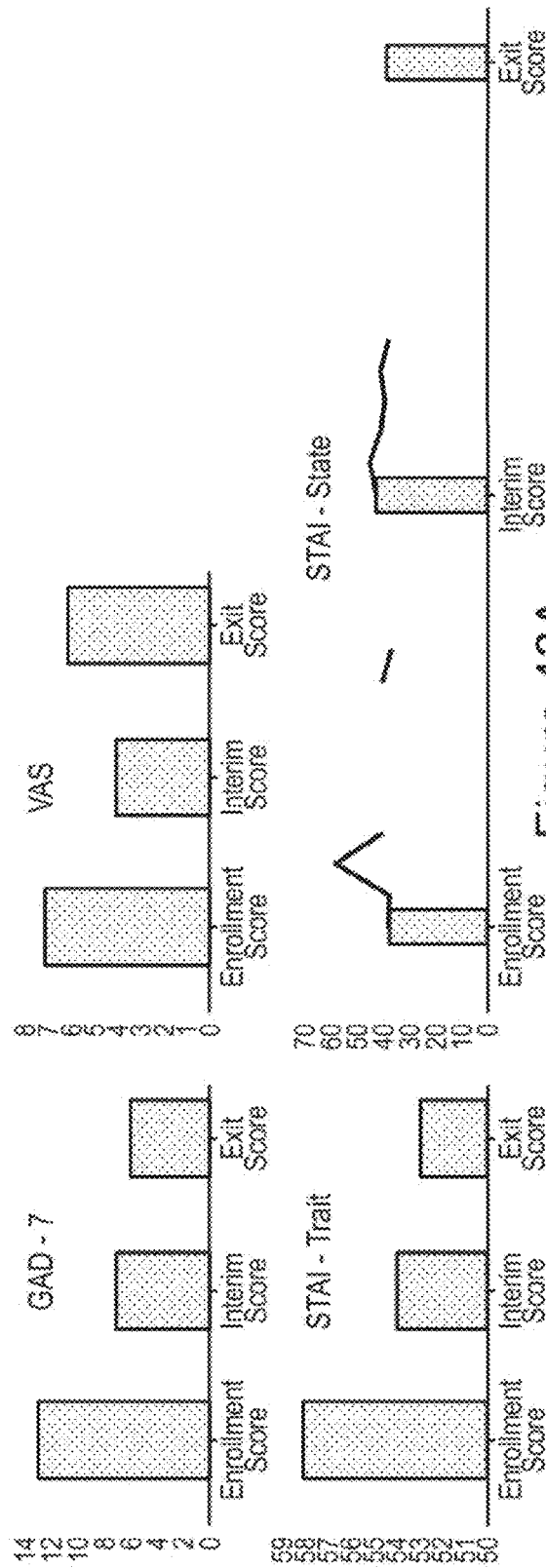
FIG. 43A is a set of graphs showing individual results from a first participant in a pilot study assessing efficacy of embodiments of the devices and methods described herein for treatment of anxiety.
Figure 43B:
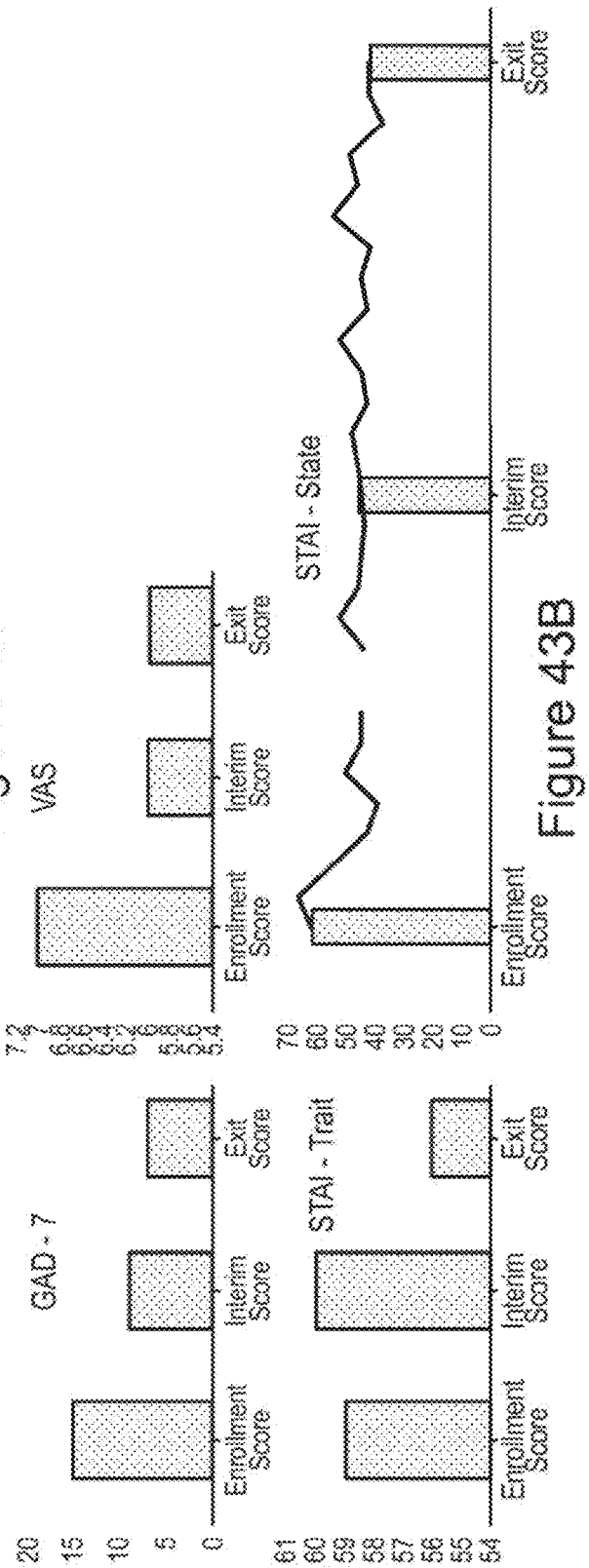
FIG. 43B is a set of graphs showing individual results from a second participant in a pilot study assessing efficacy of embodiments of the devices and methods described herein for treatment of anxiety.
Figure 43E:
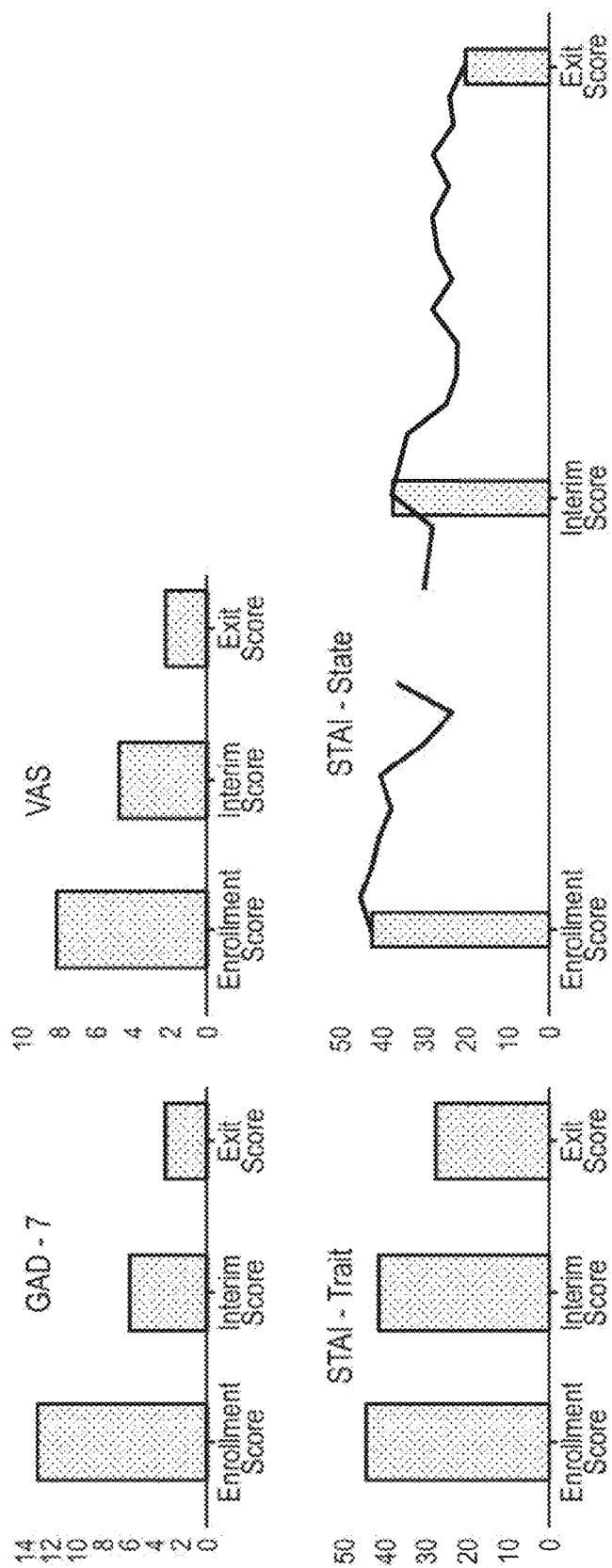
FIG. 43E is a set of graphs showing individual results from a fifth participant in a pilot study assessing efficacy of embodiments of the devices and methods described herein for treatment of anxiety.

Study participants self-administered mechanical stimulation using an embodiment of the device in which mechanical transducers are incorporated into a wearable headset (shown in FIG. 42). The headset positions the mechanical transducers behind a participant's ears (one mechanical transducer behind each ear) allowing for mechanical stimulation to be applied at the skin of the subject near the mastoid. Participants thereby self-administered mechanical stimulation by wearing the headset and turning on a controller module. The controller module comprises a controller board that generates and supplies an electronic signal to drive the mechanical transducers in the headset and provide for generation of mechanical stimulation having a particular waveform designed for treatment of anxiety and anxiety related disorders. In particular, an isochronic sine wave having a 10 Hz carrier frequency was used. An example of such a signal is shown in FIG. 4. As described herein, this signal is tailored supply stimulation that targets Merkel cells and that also accommodates rest periods of Piezo2 proteins, both of which are part of the stimulation pathway for the insula region.

Figure 41:
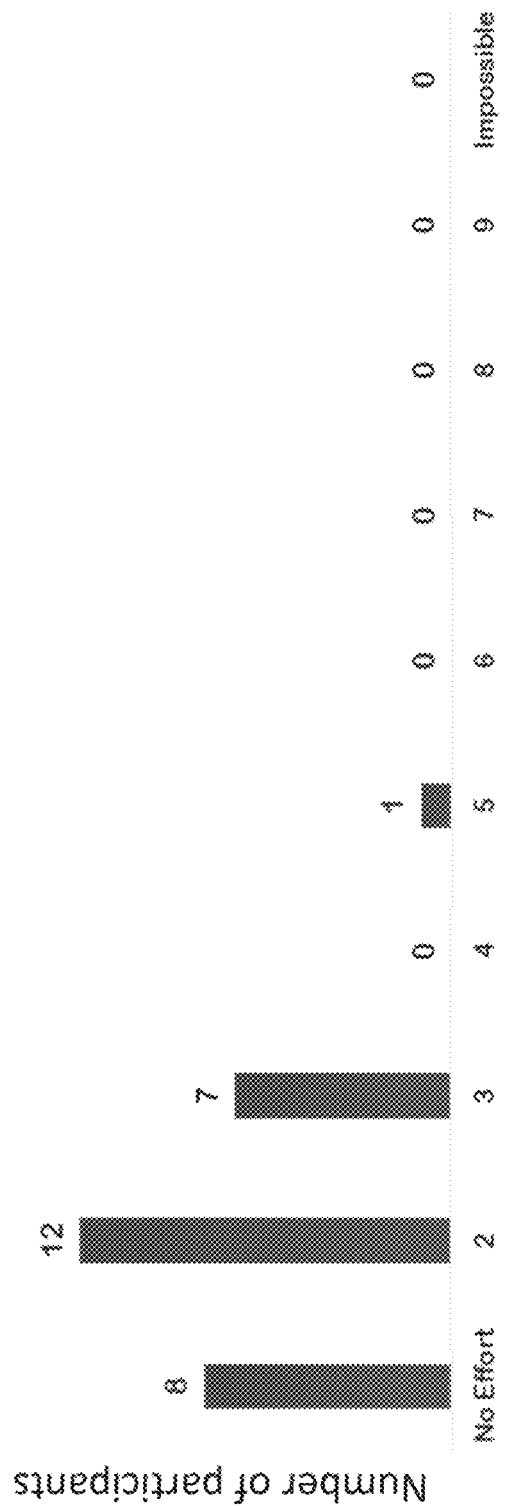
FIG. 41 is a histogram showing feedback regarding ease of use from participants in in a pilot study assessing efficacy of embodiments of the devices and methods described herein for treatment of anxiety.

Participants were instructed to self-administer stimulation for 20 minutes, twice a day, as well as on an as needed basis (e.g., when they felt an onset of anxiety symptoms). Of the study participants, 73% adhered to the prescribed stimulation routine, and 88% reported using the device twice every day for three or more weeks, based on daily surveys. As shown in the survey data in FIG. 41, study participants found the device easy to use, with 96% of the participants reporting none or minimal effort to use. Eighteen headsets and controller modules were used in the study and distributed among participants for use. During the study, three headsets and eight controller modules malfunctioned during a second cycle of use (overall 32% failure rate).

In order to assess efficacy of the device and mechanical stimulation approach for treating and managing anxiety and anxiety related disorders, participants answered questionnaires to evaluate four established anxiety/pain metrics: a Generalized Anxiety Disorder (GAD)-7 score, a Visual Analogue Scale (VAS) score, and a state-trait anxiety inventory (STAI), which comprises two metrics—a state (STAI-State) and a trait (STAI-Trait) anxiety score.

FIGS. 43A-E show case studies (e.g., individual results) for 5 specific participants showing variation in the four aforementioned scores for each individual participant. Feedback provided by each of the 5 participants (along with demographic information, where provided) is shown in Table 1, below.

TABLE 1

Case reports and open-ended feedback

| Participant & demographic information | Open-ended feedback |
| --- | --- |
| 1. Male, 34 years old | "I can definitely report that I feel positive effects from the device. It tends to make me a little more calm than normal and I find I am not worrying as much about things. The worries seem to disappear, at least partially and for a period of time. I would absolutely be using the device on an as needed basis." |
| 2. Other, 26 years old | "Felt like I wasn't being bothered all the time by my anxiety and all that stuff that can make it harder for me like work or whatever. Wasn't getting overwhelmed as much, a lot more self-confident, wow I can do this, all these ideas, more positive. Just overall more positive and happy, everything was good." "I would try to think about things that would make me anxious to see if it was a placebo effect and it didn't make me anxious or stressed." |
| 4. Female, 59 years old | "I felt like it was really in a different realm. I am really going to miss it. This is really saving my life. I feel so awful on the medication, and this makes me feel so much better. I really going to miss it. I don't want to give it back." "I have decreased my usage of anti-anxiety medication almost 90 percent since using the device. The days are going a lot better and my anxiety moods and panic attacks are decreasing." |
| 4. Female, 31 years old | "The device became second nature to use and I didn't notice it on my head as the study continued. It became something that was integrated into my schedule pretty easily." "I dropped a glass container that spilled EVERYWHERE. I think that wearing the device gave me some external cues to remind me to chill out, listen to my body and deal with it without getting stressed/anxious about the huge mess." |
| 5. Female, 66 years old | "Found it pleasant and it helps. Really addresses anxiety." "For the most part I seem to be a little less anxious over the last few days." "Felt more relaxed, didn't experience any physical changes or side effects." |

FIGS. 44A-D show overall results for the study. The data from the study shows that changes in GAD-7, STAI-State and STAI-Trait scores are significant between enrollment and exit. Based on a one-tailed Wilcoxon test, there is enough statistical evidence to conclude that median GAD-7, STAI-State, and STAI-Trait scores are lower at exit than at enrollment. VAS scores appeared inconsistent and insignificant.

Elements of different implementations described herein may be combined to form other implementations not specifically set forth above. Elements may be left out of the processes, computer programs, databases, etc. described herein without adversely affecting their operation. In addition, the logic flows depicted in the figures do not require the particular order shown, or sequential order, to achieve desirable results. Various separate elements may be combined into one or more individual elements to perform the functions described herein.

Throughout the description, where apparatus and systems are described as having, including, or comprising specific components, or where processes and methods are described as having, including, or comprising specific steps, it is contemplated that, additionally, there are apparatus and systems of the present invention that consist essentially of, or consist of, the recited components, and that there are processes and methods according to the present invention that consist essentially of, or consist of, the recited processing steps.

It should be understood that the order of steps or order for performing certain action is immaterial so long as the invention remains operable. Moreover, two or more steps or actions may be conducted simultaneously.

While the invention has been particularly shown and described with reference to specific preferred embodiments, it should be understood by those skilled in the art that various changes in form and detail may be made therein without departing from the spirit and scope of the invention as defined by the appended claims.

REFERENCES

Aaronson S T, Carpenter L L, Conway C R, Reimherr F W, Lisanby S H, Schwartz T L, Moreno F A, Dunner D L, Lesem M D, Thompson P M, Husain M, Vine C J, Banov M D, Bernstein L P, Lehman R B, Brannon G E, Keepers G A, O'Reardon J P, Rudolph R L, Bunker M. Vagus nerve stimulation therapy randomized to different amounts of electrical charge for treatment-resistant depression: acute and chronic effects. Brain Stimul. 2013, Jul. 6(4):631-40.

Ahmadlou M, Adeli H, Adeli A. Fractality and a wavelet-chaos-neural network methodology for EEG-based diagnosis of autistic spectrum disorder. J Clin Neurophysiol. 2010; 27(5):328-33.

Allegrini P, Menicucci D, Bedini R, Fronzoni L, Gemignani A, Grigolini P, et al. Spontaneous brain activity as a source of ideal 1/f noise. Phys Rev E 2009; E80:061914.

Allman J M, Tetreault N A, Hakeem A Y, et al. The von Economo neurons in fronto-insular and anterior cingulate cortex. Ann N Y Acad Sci. 2011; 1225:59-71.

Amaral L A N, Goldberger A L, Ivanov P C, Stanley H E. Scale-independent measures and pathologic cardiac dynamics. Phys Rev Lett. 1998; 81(11):2388-2391.

Baekey D M, Molkov Y I, Paton J F, Rybak I A, Dick T E. Effect of baroreceptor stimulation on the respiratory pattern: insights into respiratory-sympathetic interactions. Respir Physiol Neurobiol. 2010; 174(1-2):135-45.

Balocchi, R. (2011) Fractal Dimension: From Geometry to Physiology, in Advanced Methods of Biomedical Signal Processing (eds S. Cerutti and C. Marchesi), John Wiley & Sons, Inc., Hoboken, N.J., USA.

Bassingthwaighte J B, Liebovitch L S, West B J. (1994) Intraorgan flow heterogeneities, in Fractal Physiology. Methods in Physiology Series. Springer, New York, N.Y.; 236-62.

Bianchi M T, Thomas R J. Technical advances in the characterization of the complexity of sleep and sleep disorders. Prog Neuropsychopharmacol Biol Psychiatry. 2013; 45:277-86.

Brown A G, Iggo A. A quantitative study of cutaneous receptors and afferent fibres in the cat and rabbit. J Physiol. 1967; 193(3):707-33.

Cai P Y, Bodhit A, Derequito R, Ansari S, Abukhalil F, Thenkabail S, Ganji S, Saravanapavan P, Shekar C C, Bidari S, Waters M F, Hedna V S. Vagus nerve stimulation in ischemic stroke: old wine in a new bottle. Front Neurol. 2014; 5:107.

Cessac B. A View Of Neural Networks As Dynamical Systems. Int J Bifurcation Chaos., 2010; 20:1585.

Cerutti S, Signorini MG. Nonlinear advanced methods for biological signal analysis. Engineering in Medicine and Biology, 2002. Proceedings of the Second Joint 24th Annual Conference and the Annual Fall Meeting of the Biomedical Engineering Society.

Chae J H, Jeong J, Peterson B S, Kim D J, Bahk W M, Jun T Y, et al. Dimensional complexity of the EEG in patients with posttraumatic stress disorder. Psychiatry Res 2004; 131(1):79-89.

Cheng W, Law P K, Kwan H C, Cheng R S S. Stimulation Therapies and the Relevance of Fractal Dynamics to the Treatment of Diseases. Open Journal of Regenerative Medicine. 2014; 3:73-94.

Chesler A T, Szczot M, Bharucha-Goebel D, Ceko M, Donkervoort S, Laubacher C, Hayes L H, Alter K, Zampieri C, Stanley C, Innes A M, Mah J K, Grosmann C M, Bradley N, Nguyen D, Foley A R, Le Pichon C E, Bonnemann C G. The Role of PIEZO2 in Human Mechanosensation. N Engl J Med. 2016 Oct. 6; 375(14):1355-1364.

Ciuciu P, Varoquaux G, Abry P, Sadaghiani S, Kleinschmidt A. Scale-Free and Multifractal Time Dynamics of fMRI Signals during Rest and Task. Front Physiol. 2012; 3:186.

Coste B. et al. Piezo proteins are pore-forming subunits of mechanically activated channels. Nature. 2012; 483 (7388): 176-181.

Craig A D. How do you feel—now? The anterior insula and human awareness. Nat Rev Neurosci. 2009; 10(1):59-70.

Craig A D. How do you feel? Interoception: the sense of the physiological condition of the body. Nat Rev Neurosci. 2002; 3(8):655-66.

Delignières D, Fortes M, Ninot G. The fractal dynamics of self-esteem and physical self. Nonlinear Dynamics Psychol Life Sci. 2004; 8(4):479-510.

Di Ieva A, Grizzi F, Jelinek H, Pellionisz A J, Losa G A. Fractals in the Neurosciences, Part I: General Principles and Basic Neurosciences. Neuroscientist. 2014; 20(4): 403-417.

Di Ieva A, Esteban F J, Grizzi F, Klonowski W, Martin-Landrove M. Fractals in the neurosciences, Part II: clinical applications and future perspectives. Neuroscientist. 2015; 21(1):30-43.

Duquette P. Increasing Our Insular World View: Interoception and Psychopathology for Psychotherapists. Front Neurosci. 2017; 11:135.

Engineer C T, Engineer N D, Riley J R, Seale J D, Kilgard M P. Pairing Speech Sounds With Vagus Nerve Stimulation Drives Stimulus-specific Cortical Plasticity. Brain Stimul. 2015; 8(3):637-44.

Esteban F J, Sepulcre J, de Miras J R, Navas J, de Mendizábal NV, Goñi J, et al. Fractal dimension analysis of grey matter in multiple sclerosis. J Neurol Sci 2009; 282(1-2):67-71.

Farb N, Daubenmier J, Price C J, Gard T, Kerr C, Dunn B D, Klein A C, Paulus M P, Mehling W E. Interoception, contemplative practice, and health. Front Psychol. 2015; 6:763.

Fernández A, Andreina M M, Hornero R, Ortiz T, López-Ibor J J. Analysis of brain complexity and mental disorders. Actas Esp Psiquiatr. 2010; 38(4):229-38.

Fernandez A, Gomez C, Hornero R, Lopez-Ibor J J. Complexity and schizophrenia. Prog Neuropsychopharmacol Biol Psychiatry 2013; 45:266-75.

Fernandez A, Quintero J, Hornero R, Zuluaga P, Navas M, Gómez C, Escudero J, Garcia-Campos N, Biederman J, Ortiz T. Complexity analysis of spontaneous brain activity in attention-deficit/hyperactivity disorder: diagnostic implications. Biol Psychiatry. 2009; 65(7):571-7.

Field T. Yoga clinical research review. Complement. Ther Clin Pract. 2011; 17(1):1-8.

Frangos E, Ellrich J, Komisaruk B R. Non-invasive Access to the Vagus Nerve Central Projections via Electrical Stimulation of the External Ear: fMRI Evidence in Humans. Brain Stimul. 2015; 8(3):624-36.

Freeman W J. Vortices in brain activity: their mechanism and significance for perception. Neural Netw. 2009; 22(5-6):491-501.

Frisina R D et al., Comprehensive audiometric analysis of hearing impairment and tinnitus after cisplatin-based chemotherapy in survivors of adult-onset cancer. J. Clin. Oncol. 2016; 34(23): 2712-2720.

Gammaitoni L, Hänggi P, Jung P, Marchesoni F. Stochastic resonance. Rev Mod Phys. 1998; 70:223-287.

Garcia R G, Lin R L, Lee J, Kim J, Barbieri R, Sclocco R, Wasan A D, Edwards R R, Rosen B R, Hadjikhani N, Napadow V. Modulation of brainstem activity and connectivity by respiratory-gated auricular vagal afferent nerve stimulation in migraine patients. Pain. 2017; 158(8):1461-72.

Gavrilov, L. R., et al. The effect of focused ultrasound on the skin and deep nerve structures of man and animal. Progress in brain research 1976; 43:279-92.

Gick B, Derrick D. Aero-tactile integration in speech perception. Nature. 2009; 462(7272):502-4.

Goldberger A L, West B J. Fractals in physiology and medicine. Yale J Biol Med. 1987; 60:421-35.

Gisiger T. Scale invariance in biology: coincidence or footprint of a universal mechanism? Biol Rev Camb Philos Soc. 2001; 76(2):161-209.

Gottlieb P A, Bae C, Sachs F. Gating the mechanical channel Piezo1: a comparison between whole-cell and patch recording. Channels (Austin) 2012; 6(4): 282-9.

Gottschaldt K M, Vahle-Hinz C. Merkel cell receptors: structure and transducer function. Science. 1981; 214(4517):183-6.

Hanslmayr S, Sauseng S, Doppelmayr M, Schabus M, Klimesch W. Increasing individual upper alpha power by neurofeedback improves cognitive performance in human subjects. Applied Psychophysiology and Biofeedback. 2005 30(1)1-10.

Hardstone R, Poil S S, Schiavone G, Jansen R, Nikulin V V, Mansvelder H D, et al. Detrended fluctuation analysis: a scale free view on neuronal oscillations. Front Physiol. 2012; 3:450.

Harry J D, et al. "Method and apparatus for improving human balance and gait and preventing foot injury." U.S. Pat. No. 8,308,665. 13 Nov. 2012.

He W, Wang X, Shi H, Shang H, Li L, Jing X, Zhu B. Auricular acupuncture and vagal regulation. Evid Based Complement Alternat Med. 2012:786839.

Hei W, Jing X H, Zhu B, Zhu X L, Li L, Bai W Z, Ben H. The auriculo-vagal afferent pathway and its role in seizure suppression in rats. BMC Neurosci. 2013; 14:85.

Hein E, Nowak M, Kiess O, Biermann T, Bayerlein K, Kornhuber J, Kraus T. Auricular transcutaneous electrical nerve stimulation in depressed patients: a randomized controlled pilot study. J Neural Transm (Vienna). 2013; 120(5):821-7.

Huang F, Dong J, Kong J, Wang H, Meng H, Spaeth R B, Camhi S, Liao X, Li X, Zhai X, Li S, Zhu B, Rong P. Effect of transcutaneous auricular vagus nerve stimulation on impaired glucose tolerance: a pilot randomized study. BMC Complement Altern Med. 2014; 14:203.

Howland R H. Vagus Nerve Stimulation. Curr Behav Neurosci Rep. 2014; 1(2):64-73.

Huston J M, Gallowitsch-Puerta M, Ochani M, Ochani K, Yuan R, Rosas-Ballina M, Ashok M, Goldstein R S, Chavan S, Pavlov V A, Metz C N, Yang H, Czura C J, Wang H, Tracey K J. Transcutaneous vagus nerve stimulation reduces serum high mobility group box 1 levels and improves survival in murine sepsis. Crit Care Med. 2007; 35(12):2762-8.

Ivanov P C, Rosenblum M G, Peng C K, Mietus J, Havlin S, Stanley H, et al. Scaling behavior of heartbeat intervals obtained by wavelet-based time-series analysis. Nature 1996; 383, 323-327.

Ivanov P C, Amaral L A N, Goldberger A L, Havlin S, Rosenblum M G, Struzik Z R, et al. Multifractality in human heartbeat dynamics. Lett Nat. 1999; 399:461-5.

Ivanov P C, Bunde A, Amaral L A, Havlin S, Fritsch-Yelle J, Baevsky R M, et al. Sleep-wake differences in scaling behavior of the human heartbeat: analysis of terrestrial and long-term space. Europhys Lett. 1999; 48:594.

Jacobs H I, Riphagen J M, Razat C M, Wiese S, Sack A T. Transcutaneous vagus nerve stimulation boosts associative memory in older individuals. Neurobiol Aging. 2015; 36(5):1860-7.

John A M, Elfanagely O, Ayala C A, Cohen M, Prestigiacomo C J. The utility of fractal analysis in clinical neuroscience. Rev Neurosci. 2015; 26(6):633-45.

Kandasamy N, Garfinkel S N, Page L, Hardy B, Critchley H D, Gurnell M, Coates J M. Interoceptive Ability Predicts Survival on a London Trading Floor. Sci Rep. 2016; 6:32986.

Khalsa S S, Lapidus R C. Can Interoception Improve the Pragmatic Search for Biomarkers in Psychiatry? Front Psychiatry. 2016; 7:121.

Klonowski W. Fractal Analysis of Electroencephalographic Time Series (EEG Signals). In: Di Ieva A. (eds) The Fractal Geometry of the Brain. Springer Series in Computational Neuroscience. 2016. Springer, New York, N.Y.

Klonowski W. From conformons to human brains: an informal overview of nonlinear dynamics and its applications in biomedicine. Nonlinear Biomed Phys. 2007; 1:5.

Kok B E, Fredrickson B L. Upward spirals of the heart: autonomic flexibility, as indexed by vagal tone, reciprocally and prospectively predicts positive emotions and social connectedness. Biol Psychol. 2010; 85(3):432-6.

Kreuzer P M, Landgrebe M, Resch M, Husser O, Schecklmann M, Geisreiter F, Poeppl T B, Prasser S J, Hajak G, Rupprecht R, Langguth B. Feasibility, safety and efficacy of transcutaneous vagus nerve stimulation in chronic tinnitus: an open pilot study. Brain Stimul. 2014; 7(5): 740-7.

Kwok T, Smith K A. Optimization via intermittency with a self-organizing neural network. Neural Computation. 2005; 17(11):2454-81.

Legon W, et al. Pulsed ultrasound differentially stimulates somatosensory circuits in humans as indicated by EEG and FMRI. PloS one 7.12 (2012): e51177.

Lesniak D R, Gerling G J. Mimicking the End Organ Architecture of Slowly Adapting Type I Afferents May Increase the Durability of Artificial Touch Sensors. IEEE Haptics Symp. 2014; 2014:361-6.

Levin J E, Miller J P. Broadband neural encoding in the cricket cercal sensory system enhanced by stochastic resonance. Nature. 1996; 165-168.

Li L, Rutlin M, Abraira V E, Cassidy C, Kus L, Gong S, Jankowski M P, Luo W, Heintz N, Koerber H R, Woodbury C J, Ginty D D. The functional organization of cutaneous low-threshold mechanosensory neurons. Cell. 2011; 147(7):1615-27.

Li X, Jiang J, Zhu W, Yu C, Sui M, Wang Y, Jiang T. Asymmetry of prefrontal cortical convolution complexity in males with attention-deficit/hyperactivity disorder using fractal information dimension. Brain Dev 2007; 29(1):649-55.

Linkenkaer-Hansen K, Nikouline V V, Palva J M, Ilmoniemi R J. Long-range temporal correlations and scaling behavior in human brain oscillations. J Neurosci. 2001; 21:1370-7.

Linkenkaer-Hansen K, Nikulin V V, Palva J., Kaila K, Ilmoniemi R J. Stimulus-induced change in long-range temporal correlations and scaling behaviour of sensorimotor oscillations. Eur J Neurosci. 2004; 19:203-11.

Loewenstein W, Altamiranoorrego R. The refractory state of the generator and propagated potentials in a pacinian corpuscle. J Gen Physiol. 1958; 41(4):805-24.

Ma Q. Merkel cells are a touchy subject. Cell. 2014; 157(3):531-3.

Maksimovic S, Baba Y, Lumpkin E A. Neurotransmitters and synaptic components in the Merkel cell-neurite complex, a gentle-touch receptor. Ann N Y Acad Sci. 2013; 1279:13-21.

Mizuno T, Takahashi T, Cho R Y, Kikuchi M, Murata T, Takahashi K, et al. Assessment of EEG dynamical complexity in Alzheimer's disease using multiscale entropy. Clin Neurophysiol. 2010; 121:1438-46.

Morabito F C, Campolo M, Mammone N, Versaci M, Franceschetti S, Tagliavini F, Sofia V, Fatuzzo D, Gambardella A, Labate A, Mumoli L, Tripodi G G, Gasparini S, Cianci V, Sueri C, Ferlazzo E, Aguglia U. Deep Learning Representation from Electroencephalography of Early-Stage Creutzfeldt-Jakob Disease and Features for Differentiation from Rapidly Progressive Dementia. Int J Neural Syst. 2017; 27(2):1650039.

Muehsam D, Lutgendorf S, Mills P J, Rickhi B, Chevalier G, Bat N, Chopra D, Gurfein B. The embodied mind: A review on functional genomic and neurological correlates of mind-body therapies. Neurosci Biobehav Rev. 201773:165-181.

Moss F, Ward L M, Sannita W G. Stochastic resonance and sensory information processing: a tutorial and review of application. Clin Neurophysiol. 2004; 115(2):267-81.

Murthy S E, Dubin A E, Patapoutian A. Piezos thrive under pressure: mechanically activated ion channels in health and disease. Nat Rev Mol Cell Biol. 2017; 18(12):771-783.

Nanni F, Andres D S. Structure Function Revisited: A Simple Tool for Complex Analysis of Neuronal Activity. Front Hum Neurosci. 2017; 11:409.

Oke S L, Tracey K J. The inflammatory reflex and the role of complementary and alternative medical therapies. Ann N Y Acad Sci. 2009; 1172:172-80.

Olson W, Dong P, Fleming M, Luo. The specification and wiring of mammalian cutaneous low-threshold mechanoreceptors. Wiley Interdiscip Rev Dev Biol. 2016; 5(3): 389-404.

Onias H, Viol A, Palhano-Fontes F, Andrade K C, Sturzbecher M, Viswanathan G, de Araujo D B. Brain complex network analysis by means of resting state fMRI and graph analysis: will it be helpful in clinical epilepsy? Epilepsy Behav. 2014; 38:71-80.

Onorati F, Barbieri R, Mauri M, Russo V, Mainardi V. Reconstruction and analysis of the pupil dilation signal: Application to a psychophysiological affective protocol. Engineering in Medicine and Biology Society (EMBC), 2013 35th Annual International Conference of the IEEE.

Peng C K, Havlin S, Hausdorff J J M, Mietus J E, Stanley H E, Goldberger A L. Fractal mechanisms and heart rate dynamics long-range correlations and their breakdown with disease. J Electrocardiol. 1995; 28:59-65.

Pierzchalski M, Stepien R A, Stepien P. New nonlinear methods of heart rate variability analysis in diagnostics of atrial fibrillation. Int J Biol Biomed Eng. 2011; 5:201-8.

Porges S W. Cardiac vagal tone: a physiological index of stress. Neurosci Biobehav Rev. 1995; 19(2):225-233.

Rigoli L M, Holman D, Spivey M J, Kello C T. Spectral convergence in tapping and physiological fluctuations: coupling and independence of 1/f noise in the central and autonomic nervous systems. Front Hum Neurosci. 2014; 8:713.

Riviello, R J. Otolaryngologic Procedures Chapter 63: Otolaryngologic Procedures FIG. 63-14. https://aneskey.com/otolaryngologic-procedures/. Sep. 6, 2016.

Rulkov N F. Modeling of spiking-bursting neural behavior using two dimensional map. Phys Rev E Stat Nonlin Soft Matter Phys. 2002; 65(4 Pt. 1):041922.

Srinivasan K, Ashok M V, Vaz M, Yeragani V K. Decreased chaos of heart rate time series in children of patients with panic disorder. Depress Anxiety 2002; 15:159-67.

Rossi S, et al. Safety, ethical considerations and application guidelines for the use of transcranial magnetic stimulation in clinical practice and research. Clin Neurophysiol 2009 (120) 2008-2039

Sandu A L, Specht K, Beneventi H, Lundervold A, Hugdahl K. Sex differences in grey-white matter structure in normal-reading and dyslexic adolescents. Neurosci Lett 2008b; 438(1):80-4.

Sokunbi M O, Gradin V B, Waiter G D, Cameron G G, Ahearn T S, Murray A D, Steele D J, Staff R T. Nonlinear complexity analysis of brain FMRI signals in schizophrenia. PLoS One. 2014; 9(5):e95146.

Stavrakis S, Humphrey M B, Scherlag B J, Hu Y, Jackman W M, Nakagawa H, Lockwood D, Lazzara R, Po S S. Low-level transcutaneous electrical vagus nerve stimulation suppresses atrial fibrillation. J Am Coll Cardiol. 2005; 65(9):867-75.

Stoléru S, Fonteille V, Cornélis C, Joyal C, Moulier V. Functional neuroimaging studies of sexual arousal and orgasm in healthy men and women: a review and meta-analysis. Neurosci Biobehav Rev. 2012 July; 36(6):1481-509.

Terasawa Y, Moriguchi Y, Tochizawa S, Umeda S. Interoceptive sensitivity predicts sensitivity to the emotions of others, *Cognition and Emotion,* 2014; 28(8):1435-48

Thayer J F, Sternberg E. Beyond heart rate variability: vagal regulation of allostatic systems. Ann N Y Acad Sci. 2006; 1088:361-72.

Tracey K J. Physiology and immunology of the cholinergic anti-inflammatory pathway. J Clin Invest. 2007; 117(2): 289-296.

Tracey K J. The inflammatory reflex. Nature 2002; 420 (6917):853-859.

Triscoli C, Croy I, Steudte-Schmiedgen S, Olausson H, Sailer U. Heart rate variability is enhanced by long-lasting pleasant touch at CT-optimized velocity. Biol Psychol. 2017; 128:71-81.

Tyler R, Cacace A, Stocking C, Tarver B, Engineer N, Martin J, Deshpande A, Stecker N, Pereira M, Kilgard M, Burress C, Pierce D, Rennaker R, Vanneste S. Vagus Nerve Stimulation Paired with Tones for the Treatment of Tinnitus: A Prospective Randomized Double-blind Controlled Pilot Study in Humans. Sci Rep. 2017; 7(1):11960.

Valenza G, Greco A, Citi L, Bianchi M, Barbieri R, Scilingo E P. Inhomogeneous Point-Processes to Instantaneously Assess Affective Haptic Perception through Heartbeat Dynamics Information. Sci Rep. 2016; 6:28567.

Van Orden GC. The fractal picture of health and wellbeing, in Psychological Science Agenda, Vol. 22. Washington, D.C. American Psychological Association. 2007:1-5.

Wang Z, Zhou X, Sheng X, Yu L, Jiang H. Unilateral low-level transcutaneous electrical vagus nerve stimulation: A novel noninvasive treatment for myocardial infarction. Int J Cardiol. 2015; 190:9-10.

Weng G, Bhalla U S, Iyengar R. Complexity in biological signaling systems. Science. 1999; 284(5411):92-6.

Weng W C, Jiang G J, Chang C F, Lu WY, Lin C Y, Lee W T, Shieh J S. Complexity of Multi-Channel Electroencephalogram Signal Analysis in Childhood Absence Epilepsy. PLoS One. 2015; 10(8):e0134083.

Werner G. Fractals in the nervous system: conceptual implications for theoretical neuroscience. Front Physiol. 2010; 1:15.

West, B J, Geneston E L, Grigolini P. Maximizing information exchange between complex networks. Phys Rep. 2008; 468:1-99.

Whipple B, Komisaruk BR. Brain (PET) responses to vaginal-cervical self-stimulation in women with complete spinal cord injury: preliminary findings. J Sex Marital Ther. 2002; 28(1):79-86.

Wiltshire T J, Euler M J, McKinney T L, Butner J E. Changes in Dimensionality and Fractal Scaling Suggest Soft Assembled Dynamics in Human EEG. Front Physiol. 2017; 8:633.

Woo S H, Ranade S, Weyer A D, Dubin A E, Baba Y, Qiu Z, Petrus M, Miyamoto T, Reddy K, Lumpkin E A, Stucky C L, Patapoutian A. Piezo2 is required for Merkel-cell mechanotransduction. Nature. 2014 May 29; 509(7502):622-6.

Wu J, Lewis A H, Grandl J. Touch, Tension, and Transduction—The Function and Regulation of Piezo Ion Channels. Trends Biochem Sci. 2017; 42(1):57-71.

Xu X Z. Demystifying Mechanosensitive Piezo Ion Channels. Neurosci Bull. 2016; 32(3):307-9.

Yakunina N, Kim S S, Nam E C. Optimization of Transcutaneous Vagus Nerve Stimulation Using Functional MRI. Neuromodulation. 2017; 20(3):290-300.

Yu L, Scherlag B J, Li S, Fan Y, Dyer J, Male S, Varma V, Sha Y, Stavrakis S, Po S S. Low-level transcutaneous electrical stimulation of the auricular branch of the vagus nerve: a noninvasive approach to treat the initial phase of atrial fibrillation. Heart Rhythm. 2013; 10(3):428-35.

Yang A C, Tsai S J. Is mental illness complex? From behavior to brain. Prog Neuropsychopharmacol Biol Psychiatry. 2013; 45:253-7.

Yperzeele L, van Hooff R J, Nagels G, De Smedt A, De Keyser J, Brouns R. Heart rate variability and baroreceptor sensitivity in acute stroke: a systematic review. Int J Stroke. 2015; 10(6):796-80.

What is claimed is:

1. A neuromodulation device, the device comprising:
   two or more mechanical transducers, a battery, and one or more controller boards, wherein the two or more mechanical transducers, the battery and the one or more controller boards are in communication;
   wherein the one or more controller boards controls waveform output through each of the two or more mechanical transducers, thereby producing mechanical vibration, and the one or more controller boards modulates the waveform output to introduce particular signals that include active or inactive pulse durations and frequencies configured to accommodate particular mechanoreceptor recovery periods, adaptation times, inactivation times, sensitization and desensitization times, or latencies;
   wherein the waveform output comprises an isochronic wave.

2. The neuromodulation device of claim 1, wherein the isochronic wave of the device-stimulates one or more nerves.

3. The neuromodulation device of claim 2, wherein the one or more nerves comprises the vagus nerve and/or the trigeminal nerve.

4. The neuromodulation device of claim 2, wherein the one or more nerves comprises a C-tactile afferent.

5. The neuromodulation device of claim 1, wherein the isochronic waves are provided as one or more low-amplitude sub-intervals.

6. The neuromodulation device of claim 5, wherein the isochronic waves have a duration of approximately 2 seconds.

7. The neuromodulation device of claim 1, wherein the transducer in substantial proximity to one or more mastoid regions of a human subject.

8. The neuromodulation device of claim 1, wherein the isochronic wave comprises a frequency component ranging from 5 to 15 Hz.

9. The neuromodulation device of claim 1, wherein one or more low-amplitude sub-intervals of the isochronic wave have a duration of greater than or approximately two seconds.

10. The neuromodulation device claim 1, wherein the isochronic wave comprises a carrier wave modulated by an envelope function having-one or more low-amplitude sub-intervals.

11. A neuromodulation device, the device comprising:
    two or more mechanical transducers, a battery, and one or more controller boards;
    wherein the two or more mechanical transducers, the battery and the one or more controller boards are in communication;
    wherein the controller board controls waveform output through each of the two or more mechanical transducers, thereby producing mechanical vibration;
    wherein the waveform output is an isochronic wave that comprises a carrier wave modulated by an envelope function having-one or more low-amplitude sub-intervals.

12. The neuromodulation device of claim 11, wherein the isochronic wave of the device-stimulates one or more nerves.

13. The neuromodulation device of claim 11, wherein the one or more nerves comprises the vagus nerve and/or the trigeminal nerve.

14. The neuromodulation device of claim 11, wherein the one or more nerves comprises a C-tactile afferent.

15. The neuromodulation device of claim 11, wherein the isochronic waves are provided as one or more low-amplitude sub-intervals.

16. The neuromodulation device of claim 11, wherein the isochronic waves have a duration of approximately 2 seconds.

17. The neuromodulation device of claim 11, wherein the transducer in substantial proximity to one or more mastoid regions of a human subject.

18. The neuromodulation device of claim 11, wherein the isochronic wave comprises a frequency component ranging from 5 to 15 Hz.

19. The neuromodulation device of claim 11, wherein one or more low-amplitude sub-intervals of the isochronic wave have a duration of greater than or approximately two seconds.

\* \* \* \* \*